US012404525B2

(12) United States Patent
Joung et al.

(10) Patent No.: US 12,404,525 B2
(45) **Date of Patent: *Sep. 2, 2025**

(54) ENGINEERED HUMAN-ENDOGENOUS VIRUS-LIKE PARTICLES AND METHODS OF USE THEREOF FOR DELIVERY TO CELLS

(71) Applicants: The General Hospital Corporation, Boston, MA (US); President and Fellows of Harvard College, Cambridge, MA (US)

(72) Inventors: J. Keith Joung, Winchester, MA (US); Peter Cabeceiras, Boston, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/351,800

(22) Filed: Jul. 13, 2023

(65) Prior Publication Data

US 2024/0018544 A1 Jan. 18, 2024

Related U.S. Application Data

(63) Continuation of application No. 17/617,490, filed as application No. PCT/US2020/037740 on Jun. 15, 2020.

(60) Provisional application No. 62/861,186, filed on Jun. 13, 2019.

(51) Int. Cl.

*C12N 5/10* (2006.01)
*A61K 48/00* (2006.01)
*C07K 14/005* (2006.01)
*C12N 15/33* (2006.01)
*C12N 15/62* (2006.01)
*C12N 15/86* (2006.01)

(52) U.S. Cl.

CPC ............ *C12N 15/86* (2013.01); *C07K 14/005* (2013.01); *C12N 2740/10023* (2013.01); *C12N 2740/10042* (2013.01); *C12N 2740/10052* (2013.01)

(58) Field of Classification Search

None

See application file for complete search history.

(56) References Cited

U.S. PATENT DOCUMENTS 4,880,635 A 11/1989 Janoff et al.
4,906,477 A 3/1990 Kurono et al.
4,911,928 A 3/1990 Wallach
4,917,951 A 4/1990 Wallach
4,920,016 A 4/1990 Allen et al.
4,921,757 A 5/1990 Wheatley et al.
5,244,797 A 9/1993 Kotewicz et al.
5,892,020 A 4/1999 Mezes et al.
6,054,297 A 4/2000 Carter et al.
6,099,857 A 8/2000 Gross
6,416,997 B1 7/2002 Mir-Shekari et al.
6,453,242 B1 9/2002 Eisenberg et al.
6,479,626 B1 11/2002 Kim et al.
6,534,261 B1 3/2003 Cox, III et al.
6,607,882 B1 8/2003 Cox, III et al.
6,746,838 B1 6/2004 Choo et al.
6,785,613 B2 8/2004 Eisenberg et al.
6,794,136 B1 9/2004 Eisenberg et al.
6,824,978 B1 11/2004 Cox, III et al.
6,866,997 B1 3/2005 Choo et al.
6,903,185 B2 6/2005 Kim et al.
6,933,113 B2 8/2005 Case et al.
6,979,539 B2 12/2005 Cox, III et al.
7,011,966 B2 3/2006 Samuelson et al.
7,013,219 B2 3/2006 Case et al.
7,030,215 B2 4/2006 Liu et al.
7,220,719 B2 5/2007 Case et al.
7,241,573 B2 7/2007 Choo et al.
7,241,574 B2 7/2007 Choo et al.
7,329,807 B2 2/2008 Vadrucci (Continued)

FOREIGN PATENT DOCUMENTS

CA 3079215 A1 5/2019
EP 2134841 12/2009

(Continued)

OTHER PUBLICATIONS

Landgraf et al, Molecular Mechanism of an Oncogenic Mutation That Alters Membrane Targeting: Glu17Lys Modifies the PIP Lipid Specificity of the AKT1 Ph Domain, Biochemistry. Nov. 25, 2008; 47(47): 12260-12269.*

(Continued)

*Primary Examiner* — Maria Marvich

(74) *Attorney, Agent, or Firm* — Fish & Richardson P.C.

(57) ABSTRACT

Human-derived virus-like particles (heVLPs), comprising a membrane comprising a phospholipid bilayer with one or more HERV-derived envelope proteins on the external side; one or more HERV-derived GAG proteins in the heVLP core, and a cargo molecule, e.g., a biomolecule and/or chemical cargo molecule, disposed in the core of the heVLP on the inside of the membrane, wherein the heVLP does not comprise a gag protein, except for gag proteins that are encoded in the human genome or gag proteins that are encoded by a consensus sequence that is derived from gag proteins found in the human genome, and methods of use thereof for delivery of the cargo molecule to cells.

28 Claims, 37 Drawing Sheets

Specification includes a Sequence Listing.

(56) References Cited

U.S. PATENT DOCUMENTS 7,510,706 B2 3/2009 Yonemitsu et al.
7,556,940 B2 7/2009 Galarza et al.
7,585,849 B2 9/2009 Liu et al.
7,595,376 B2 9/2009 Kim et al.
7,842,489 B2 11/2010 Arnould et al.
7,897,372 B2 3/2011 Duchateau et al.
7,998,733 B2 8/2011 Yao et al.
8,021,867 B2 9/2011 Smith et al.
8,119,361 B2 2/2012 Smith et al.
8,119,381 B2 2/2012 Smith et al.
8,124,369 B2 2/2012 Smith et al.
8,129,134 B2 3/2012 Smith et al.
8,133,697 B2 3/2012 Smith et al.
8,163,514 B2 4/2012 Smith et al.
8,420,104 B2 4/2013 Charneau et al.
8,440,431 B2 5/2013 Voytas et al.
8,440,432 B2 5/2013 Voytas et al.
8,450,471 B2 5/2013 Voytas et al.
8,530,441 B2 9/2013 Hall et al.
8,557,971 B2 10/2013 Pedersen et al.
8,586,363 B2 11/2013 Voytas et al.
8,652,460 B2 2/2014 Kasahara et al.
8,663,989 B2 3/2014 Stitz
8,673,612 B2 3/2014 Klatzmann et al.
8,697,359 B1 4/2014 Zhang
8,697,439 B2 4/2014 Mangeot et al.
8,697,853 B2 4/2014 Voytas et al.
8,729,038 B2 5/2014 Gruber et al.
8,741,279 B2 6/2014 Kasahara et al.
9,181,535 B2 11/2015 Liu et al.
9,249,426 B2 2/2016 Girard-Gagnepain et al.
9,296,790 B2 3/2016 Chatterjee et al.
9,347,065 B2 5/2016 Parks et al.
9,393,257 B2 7/2016 Osborn et al.
9,458,484 B2 10/2016 Ma et al.
9,534,201 B2 1/2017 Pitaru
9,580,698 B1 2/2017 Xu et al.
9,593,356 B2 3/2017 Haugwitz et al.
9,695,446 B2 7/2017 Mangeot et al.
9,737,480 B2 8/2017 Lu et al.
9,765,304 B2 9/2017 Klatzmann et al.
9,777,043 B2 10/2017 Anderson et al.
9,783,791 B2 10/2017 Hogrefe et al.
9,791,435 B2 10/2017 Sitbon et al.
9,816,080 B2 11/2017 Lu et al.
9,829,483 B2 11/2017 Balaj et al.
9,840,699 B2 12/2017 Liu et al.
9,932,567 B1 4/2018 Xu et al.
10,010,607 B2 7/2018 Manel et al.
10,040,830 B2 8/2018 Chatterjee et al.
10,047,355 B2 8/2018 Yin et al.
10,072,273 B2 9/2018 Anastasov et al.
10,077,453 B2 9/2018 Liu et al.
10,113,163 B2 10/2018 Liu et al.
10,137,206 B2 11/2018 Angel et al.
10,150,955 B2 12/2018 Lambowitz et al.
10,167,457 B2 1/2019 Liu et al.
10,189,831 B2 1/2019 Arrington et al.
10,202,658 B2 2/2019 Parkin et al.
10,233,445 B2 3/2019 Seow et al.
10,260,055 B2 4/2019 Lu et al.
10,314,906 B2 6/2019 Ogembo et al.
10,316,295 B2 6/2019 Schmitt et al.
10,407,695 B2 9/2019 Charneau et al.
10,442,863 B2 10/2019 Arndt et al.
10,538,570 B2 1/2020 Leonard et al.
10,538,743 B2 1/2020 Kaczmarczyk et al.
10,577,397 B2 * 3/2020 Chatterjee ............... A61P 35/00
10,577,630 B2 3/2020 Zhang et al.
10,583,104 B2 3/2020 Kline et al.
10,584,321 B2 3/2020 Gao et al.
10,624,849 B2 4/2020 Leonard et al.
10,675,244 B2 6/2020 Gho et al.
10,793,828 B2 10/2020 Haugwitz et al.
10,870,865 B2 12/2020 Bouille et al.
10,906,943 B2 2/2021 Carrillo Molina et al.
10,941,395 B2 3/2021 Yin et al.
10,945,954 B2 3/2021 Lu et al.
10,968,253 B2 4/2021 Ohlmann et al.
10,993,967 B2 5/2021 Lu et al.
11,001,817 B2 5/2021 Lu et al.
11,028,383 B2 6/2021 King et al.
11,034,750 B2 6/2021 Puléet al.
11,103,586 B2 8/2021 Wood et al.
11,124,775 B2 9/2021 Bouille et al.
11,129,892 B1 9/2021 Gilbert et al.
11,155,833 B2 10/2021 Nakaishi et al.
11,191,784 B2 12/2021 Gill
11,306,294 B2 4/2022 Bellier et al.
11,351,247 B2 * 6/2022 Holst ...................... A61P 35/04
11,401,530 B2 8/2022 Rao et al.
11,447,527 B2 9/2022 Malone et al.
11,447,770 B1 9/2022 Liu et al.
11,479,767 B2 10/2022 Smith et al.
11,505,578 B2 11/2022 Malone et al.
11,572,556 B2 2/2023 Abudayyeh et al.
11,576,872 B2 2/2023 von Maltzahn et al.
11,576,982 B2 2/2023 Lee et al.
11,608,509 B2 3/2023 Costa Fejoz et al.
11,649,264 B2 5/2023 Ohlmann et al.
11,730,823 B2 8/2023 Lu et al.
11,827,881 B2 11/2023 Abudayyeh et al.
11,834,658 B2 12/2023 Abudayyeh et al.
2003/0232410 A1 12/2003 Liljedahl et al.
2004/0009604 A1 1/2004 Zhang et al.
2004/0028687 A1 2/2004 Waelti
2005/0026157 A1 2/2005 Baltimore et al.
2005/0064474 A1 3/2005 Urnov et al.
2005/0208489 A1 9/2005 Carroll et al.
2006/0063231 A1 3/2006 Li et al.
2006/0172377 A1 8/2006 Padidam
2006/0188987 A1 8/2006 Guschin et al.
2006/0216702 A1 9/2006 Compans et al.
2007/0224176 A1 9/2007 Brink et al.
2007/0298118 A1 12/2007 Lotvall et al.
2008/0171061 A1 7/2008 Nixon et al.
2009/0017543 A1 1/2009 Wilkes et al.
2009/0061010 A1 3/2009 Zale et al.
2009/0202622 A1 8/2009 Fleury et al.
2009/0203140 A1 8/2009 Amacher et al.
2009/0263783 A1 10/2009 Alliel et al.
2009/0305419 A1 12/2009 Miller
2010/0120092 A1 5/2010 Grgacic et al.
2010/0167377 A1 7/2010 Whitt et al.
2011/0059502 A1 3/2011 Chalasani
2011/0206740 A1 8/2011 Karp et al.
2011/0311587 A1 12/2011 Walpita
2011/0311616 A1 12/2011 Smith et al.
2012/0021403 A1 1/2012 Laderoute et al.
2012/0135034 A1 5/2012 Dropulic
2012/0177574 A1 7/2012 Gho et al.
2012/0315335 A1 12/2012 de los Rios et al.
2013/0017210 A1 1/2013 Peabody et al.
2013/0053426 A1 2/2013 Seow et al.
2013/0065296 A1 3/2013 McCray et al.
2013/0202559 A1 8/2013 Skog et al.
2013/0266611 A1 10/2013 Rabinovich et al.
2014/0010885 A1 1/2014 de los Rios et al.
2014/0162329 A1 6/2014 Coppersmith et al.
2014/0255467 A1 9/2014 Bancel et al.
2014/0303232 A1 10/2014 Baryza et al.
2014/0304847 A1 10/2014 Kühn et al.
2014/0348754 A1 11/2014 Wiley et al.
2015/0025127 A1 1/2015 McGarrity
2015/0045417 A1 2/2015 Demina et al.
2015/0166980 A1 6/2015 Liu et al.
2015/0166982 A1 6/2015 Liu et al.
2015/0216998 A1 8/2015 Feinstein et al.
2015/0359879 A1 12/2015 Wellnitz et al.
2016/0051697 A1 2/2016 Pope et al.
2016/0106842 A1 4/2016 Baryza et al.
2016/0137716 A1 5/2016 El Andaloussi et al.
2016/0208221 A1 7/2016 Arhancet et al.
2016/0222409 A1 8/2016 Baltimore et al.

(56) References Cited

U.S. PATENT DOCUMENTS

2016/0311759 A1 10/2016 Brito et al.
2017/0087087 A1 3/2017 Leonard et al.
2017/0112773 A1 4/2017 Stachowiak et al.
2017/0121693 A1 5/2017 Liu et al.
2017/0145492 A1 5/2017 Pham et al.
2017/0173113 A1 6/2017 Besner et al.
2017/0175086 A1 6/2017 Schmitt et al.
2017/0189362 A1 7/2017 Kline et al.
2018/0073012 A1 3/2018 Liu et al.
2018/0085842 A1 3/2018 Lattner et al.
2018/0155789 A1 6/2018 Maeder et al.
2018/0170984 A1 6/2018 Harris et al.
2018/0177727 A1 6/2018 Kalluri et al.
2018/0187185 A1 7/2018 Ostertag et al.
2018/0208976 A1 7/2018 Doudna et al.
2018/0230494 A1 8/2018 Joung et al.
2018/0245065 A1 8/2018 Ihry et al.
2018/0290965 A1 10/2018 Brito et al.
2018/0298359 A1 10/2018 Lee et al.
2018/0312825 A1 11/2018 Liu et al.
2018/0312828 A1 11/2018 Liu et al.
2018/0339166 A1 11/2018 Kraft et al.
2019/0135869 A1 5/2019 Chatterjee et al.
2019/0136231 A1 5/2019 Morrissey et al.
2019/0167810 A1 6/2019 Hean et al.
2019/0203228 A1 7/2019 Bouille et al.
2019/0211361 A1 7/2019 Kahvejian et al.
2019/0224331 A1 7/2019 Wiklander
2019/0225963 A1 7/2019 Khalili et al.
2019/0300902 A1 10/2019 Galy
2019/0345490 A1 11/2019 Cotta-Ramusino et al.
2019/0388347 A1 12/2019 Wiklander et al.
2020/0010835 A1 1/2020 Maianti et al.
2020/0023012 A1 1/2020 Joseph et al.
2020/0060980 A1 2/2020 Von Maltzahn et al.
2020/0062813 A1 2/2020 Nordin et al.
2020/0080112 A1 3/2020 Zhang et al.
2020/0102353 A1 4/2020 Heidmann et al.
2020/0109183 A1* 4/2020 Wiklander ........... G01N 33/554
2020/0109398 A1 4/2020 Rubens et al.
2020/0157570 A1 5/2020 Loiler
2020/0172886 A1 6/2020 Doudna et al.
2020/0172931 A1 6/2020 Liu et al.
2020/0206360 A1 7/2020 Choi et al.
2020/0248156 A1 8/2020 Joung et al.
2020/0283743 A1 9/2020 Zhang et al.
2020/0291072 A1 9/2020 Wang et al.
2020/0330586 A1 10/2020 Holst et al.
2020/0339980 A1 10/2020 Dellinger et al.
2020/0347100 A1 11/2020 Zhang
2020/0392473 A1 12/2020 Zhang et al.
2020/0399626 A1 12/2020 Liu et al.
2020/0405639 A1 12/2020 Zhang et al.
2020/0407418 A1 12/2020 Nordin
2021/0030850 A1 2/2021 Leonard et al.
2021/0040158 A1 2/2021 Parks et al.
2021/0047375 A1 2/2021 Lu et al.
2021/0069254 A1 3/2021 Görgens et al.
2021/0078936 A1 3/2021 Brito et al.
2021/0079389 A1 3/2021 Ryan et al.
2021/0137839 A1 5/2021 Von Maltzahn et al.
2021/0163933 A1 6/2021 Budnik et al.
2021/0187018 A1 6/2021 Von Maltzahn et al.
2021/0188903 A1 6/2021 Wiklander et al.
2021/0189432 A1 6/2021 Shepherd et al.
2021/0198330 A1 7/2021 Liu et al.
2021/0198636 A1 7/2021 Galy et al.
2021/0198698 A1 7/2021 von Maltzahn et al.
2021/0214697 A1 7/2021 Doudna et al.
2021/0228627 A1* 7/2021 von Maltzahn .... A61K 48/0008
2021/0230577 A1 7/2021 Liu et al.
2021/0261930 A1 8/2021 Lu et al.
2021/0261957 A1 8/2021 Petris et al.
2021/0269790 A1 9/2021 Hotta et al.
2021/0277379 A1 9/2021 Gaudelli et al.
2021/0284697 A1 9/2021 Ohlmann et al.
2021/0292769 A1 9/2021 Halperin
2021/0301265 A1 9/2021 Bouille et al.
2021/0301274 A1 9/2021 Bryson
2021/0315814 A1 10/2021 Lu et al.
2021/0324370 A1 10/2021 Yin et al.
2021/0332386 A1 10/2021 Gallego-Perez et al.
2021/0346504 A1 11/2021 Wood et al.
2021/0347829 A1 11/2021 Malone et al.
2021/0353543 A1 11/2021 Trudeau et al.
2021/0371858 A1 12/2021 Evans et al.
2021/0380955 A1 12/2021 Bryson et al.
2021/0403907 A1 12/2021 Malone et al.
2022/0002358 A1 1/2022 Malone et al.
2022/0002718 A1 1/2022 Joung et al.
2022/0008557 A1 1/2022 von Maltzahn et al.
2022/0016032 A1 1/2022 Malone et al.
2022/0025397 A1 1/2022 Morizono
2022/0088224 A1 3/2022 Malone et al.
2022/0090139 A1 3/2022 Rao et al.
2022/0127622 A1 4/2022 Evans et al.
2022/0184225 A1 6/2022 Tilton et al.
2022/0241328 A1 8/2022 Bandoro et al.
2022/0249373 A1 8/2022 Dooley et al.
2022/0249566 A1 8/2022 Culshaw et al.
2022/0259617 A1 8/2022 Joung et al.
2022/0287968 A1 9/2022 Suo et al.
2022/0313799 A1 10/2022 Gehrke et al.
2022/0333132 A1 10/2022 Emmanuel et al.
2022/0333134 A1 10/2022 Cruite et al.
2022/0340889 A1 10/2022 Doudna et al.
2022/0356469 A1 11/2022 Liu et al.
2022/0380740 A1 12/2022 Liu et al.
2022/0389062 A1 12/2022 Zhang et al.
2022/0389451 A1 12/2022 Zhang et al.
2022/0403003 A1 12/2022 Lu et al.
2022/0403379 A1 12/2022 Doudna et al.
2022/0409739 A1 12/2022 Dar et al.
2023/0025039 A1 1/2023 Zhang et al.
2023/0040216 A1 2/2023 Zhang et al.
2023/0043255 A1 2/2023 von Maltzahn et al.
2023/0048166 A1 2/2023 von Maltzahn et al.
2023/0055682 A1 2/2023 Cafferty et al.
2023/0057793 A1 2/2023 Malone et al.
2023/0068547 A1 3/2023 von Maltzahn et al.
2023/0078265 A1 3/2023 Liu et al.
2023/0081117 A1 3/2023 Oakes et al.
2023/0086199 A1 3/2023 Liu et al.
2023/0090221 A1 3/2023 Liu et al.
2023/0140670 A1 5/2023 Wood et al.
2023/0159913 A1 5/2023 Liu et al.
2023/0173094 A1 6/2023 Stice et al.
2023/0174598 A1 6/2023 Smith et al.
2023/0183691 A1 6/2023 Fernandes et al.
2023/0193255 A1 6/2023 Doudna et al.
2023/0201337 A1 6/2023 Gilbert et al.
2023/0220374 A1 7/2023 Liu et al.
2023/0227793 A1 7/2023 Joung et al.
2023/0227852 A1 7/2023 Lu et al.
2023/0270674 A1 8/2023 Verma et al.
2023/0279373 A1 9/2023 Zetsche et al.
2023/0312657 A1 10/2023 Malone et al.
2023/0357766 A1 11/2023 Liu et al.
2023/0365989 A1 11/2023 Zhang et al.
2023/0383282 A1 11/2023 Zhang et al.
2023/0407276 A1 12/2023 Doudna et al.
2024/0011049 A1 1/2024 Joung et al.
2024/0011050 A1 1/2024 Joung et al.
2024/0018544 A1 1/2024 Joung et al.
2024/0052331 A1 2/2024 Liu et al.
2024/0082303 A1 3/2024 Hung et al.
2024/0102052 A1 3/2024 Malone et al.
2024/0132547 A1 4/2024 Ohlmann et al.
2024/0189247 A1 6/2024 Joung et al.
2024/0191208 A1 6/2024 Joung et al.
2024/0191256 A1 6/2024 Joung et al.

(56) References Cited

U.S. PATENT DOCUMENTS

| | | | |
|---|---|---|---|
| 2024/0209359 | A1 | 6/2024 | Zhang et al. |
| 2024/0216523 | A1 | 7/2024 | Parhiz et al. |

FOREIGN PATENT DOCUMENTS

| | | | |
|---|---|---|---|
| EP | 2134841 | B1 | 2/2012 |
| EP | 2450032 | A2 | 5/2012 |
| EP | 2350295 | | 5/2013 |
| EP | 1974043 | B1 | 11/2013 |
| EP | 2371376 | B1 | 4/2014 |
| EP | 2877490 | A2 | 6/2015 |
| EP | 2583974 | | 4/2017 |
| EP | 2788019 | B1 | 4/2017 |
| EP | 3155116 | A2 | 4/2017 |
| EP | 2761010 | B1 | 7/2017 |
| EP | 3192526 | A2 | 7/2017 |
| EP | 3235828 | A1 | 10/2017 |
| EP | 2498823 | B1 | 8/2018 |
| EP | 3365437 | A1 | 8/2018 |
| EP | 3430024 | A1 | 1/2019 |
| EP | 3445862 | A1 | 2/2019 |
| EP | 3454889 | A2 | 3/2019 |
| EP | 3008192 | B1 | 7/2019 |
| EP | 3518981 | A1 | 8/2019 |
| EP | 3079725 | | 10/2019 |
| EP | 3563866 | A1 | 11/2019 |
| EP | 3622079 | A1 | 3/2020 |
| EP | 3635103 | A1 | 4/2020 |
| EP | 3715453 | A1 | 9/2020 |
| EP | 3723732 | A1 | 10/2020 |
| EP | 3727351 | A1 | 10/2020 |
| EP | 3727469 | A1 | 10/2020 |
| EP | 3389700 | | 11/2020 |
| EP | 3294756 | | 12/2020 |
| EP | 3752623 | A1 | 12/2020 |
| EP | 2776567 | B1 | 1/2021 |
| EP | 3788155 | A1 | 3/2021 |
| EP | 3793570 | A2 | 3/2021 |
| EP | 3455239 | | 4/2021 |
| EP | 3820995 | A1 | 5/2021 |
| EP | 3844272 | A1 | 7/2021 |
| EP | 3852813 | A2 | 7/2021 |
| EP | 3880717 | A1 | 9/2021 |
| EP | 3880831 | | 9/2021 |
| EP | 3921432 | A1 | 12/2021 |
| EP | 3971286 | A2 | 3/2022 |
| EP | 4031561 | A1 | 7/2022 |
| EP | 4034088 | A1 | 8/2022 |
| EP | 4061941 | A1 | 9/2022 |
| EP | 4117627 | A1 | 1/2023 |
| EP | 4153245 | A1 | 3/2023 |
| EP | 4164694 | A1 | 4/2023 |
| EP | 4175622 | A1 | 5/2023 |
| EP | 4189096 | A1 | 6/2023 |
| EP | 4228669 | A1 | 8/2023 |
| EP | 4256045 | A1 | 10/2023 |
| EP | 4284813 | A1 | 12/2023 |
| JP | 2003-061694 | A | 3/2003 |
| JP | 2008-521430 | A | 6/2008 |
| JP | 2018-531023 | A | 10/2018 |
| WO | WO 1989/001041 | | 2/1989 |
| WO | WO 1990/012099 | | 10/1990 |
| WO | WO 1994/020621 | | 9/1994 |
| WO | WO 1995/022614 | | 8/1995 |
| WO | WO 1998/050538 | | 11/1998 |
| WO | WO 2001/011042 | A1 | 2/2001 |
| WO | WO 2001/038547 | A2 | 5/2001 |
| WO | WO 2002/102709 | A1 | 12/2002 |
| WO | WO 2004/087748 | A1 | 10/2004 |
| WO | WO 2006/027202 | | 3/2006 |
| WO | WO 2007/014275 | | 2/2007 |
| WO | WO 2007/020965 | | 2/2007 |
| WO | WO 2008/110914 | | 9/2008 |
| WO | WO 2010/040023 | A2 | 4/2010 |
| WO | WO 2013/003555 | A1 | 1/2013 |
| WO | WO 2013/045632 | A1 | 4/2013 |
| WO | WO 2013/074999 | A1 | 5/2013 |
| WO | WO 2014/005219 | | 1/2014 |
| WO | WO 2014/055782 | A1 | 4/2014 |
| WO | WO 2014/093661 | | 6/2014 |
| WO | WO 2014/134412 | | 9/2014 |
| WO | WO 2014/136086 | | 9/2014 |
| WO | WO 2014/168548 | A2 | 10/2014 |
| WO | WO 2015/027134 | A1 | 2/2015 |
| WO | WO 2015/089406 | | 6/2015 |
| WO | WO 2015/095340 | | 6/2015 |
| WO | WO 2015/104376 | A1 | 7/2015 |
| WO | WO 2015/138878 | A1 | 9/2015 |
| WO | WO 2015/167710 | | 11/2015 |
| WO | WO 2015/171543 | A1 | 11/2015 |
| WO | WO 2016/069774 | A1 | 5/2016 |
| WO | WO 2016/149426 | | 9/2016 |
| WO | WO 2017/059241 | | 4/2017 |
| WO | WO 2017/068077 | | 4/2017 |
| WO | WO 2017/070632 | | 4/2017 |
| WO | WO 2017/070633 | A2 | 4/2017 |
| WO | WO 2017/173054 | | 10/2017 |
| WO | WO 2017/182607 | | 10/2017 |
| WO | WO 2017/184786 | | 10/2017 |
| WO | WO 2017/184786 | A8 | 12/2017 |
| WO | WO 2017/212264 | | 12/2017 |
| WO | WO 2018/027078 | | 2/2018 |
| WO | WO 2018/085842 | | 5/2018 |
| WO | WO 2018/165629 | | 9/2018 |
| WO | WO 2018/176009 | A1 | 9/2018 |
| WO | WO 2018/218166 | | 11/2018 |
| WO | WO 2018/218188 | | 11/2018 |
| WO | WO 2018/027078 | A8 | 12/2018 |
| WO | WO 2019/023680 | A1 | 1/2019 |
| WO | WO 2019/043127 | | 3/2019 |
| WO | WO 2019/067992 | | 4/2019 |
| WO | WO 2019/077150 | | 4/2019 |
| WO | WO 2019/118497 | | 6/2019 |
| WO | WO 2019/175428 | A1 | 9/2019 |
| WO | WO 2019/213257 | | 11/2019 |
| WO | WO 2019/217941 | A1 | 11/2019 |
| WO | WO 2019/226953 | A1 | 11/2019 |
| WO | WO 2020/027982 | A1 | 2/2020 |
| WO | WO 2020/041751 | A1 | 2/2020 |
| WO | WO 2020/051360 | A1 | 3/2020 |
| WO | WO 2020/051562 | A2 | 3/2020 |
| WO | WO 2020/086627 | | 4/2020 |
| WO | WO 2020/086908 | | 4/2020 |
| WO | WO 2020/092453 | A1 | 5/2020 |
| WO | WO 2020/102578 | A1 | 5/2020 |
| WO | WO 2020/102659 | A1 | 5/2020 |
| WO | WO 2020/102709 | A1 | 5/2020 |
| WO | WO 2020/160418 | | 8/2020 |
| WO | WO 2020/160481 | A1 | 8/2020 |
| WO | WO 2020/180975 | A1 | 9/2020 |
| WO | WO 2020/191234 | A1 | 9/2020 |
| WO | WO 2020/191239 | A1 | 9/2020 |
| WO | WO 2020/191241 | A1 | 9/2020 |
| WO | WO 2020/191242 | A1 | 9/2020 |
| WO | WO 2020/191248 | A1 | 9/2020 |
| WO | WO 2020/193696 | | 10/2020 |
| WO | WO 2020/205681 | A1 | 10/2020 |
| WO | WO 2020/210751 | A1 | 10/2020 |
| WO | WO 2020/214842 | A1 | 10/2020 |
| WO | WO 2020/219713 | A1 | 10/2020 |
| WO | WO 2020/225287 | | 11/2020 |
| WO | WO 2020/252455 | A1 | 12/2020 |
| WO | WO 2021/041885 | A2 | 3/2021 |
| WO | WO 2021/046143 | | 3/2021 |
| WO | WO 2021/050512 | A1 | 3/2021 |
| WO | WO 2021/050601 | A1 | 3/2021 |
| WO | WO 2021/055855 | A1 | 3/2021 |
| WO | WO 2021/055874 | A1 | 3/2021 |
| WO | WO 2021/072328 | A1 | 4/2021 |
| WO | WO 2021/091974 | A1 | 5/2021 |
| WO | WO 2021/102042 | A1 | 5/2021 |
| WO | WO 2021/113494 | A1 | 6/2021 |
| WO | WO 2021/113772 | | 6/2021 |
| WO | WO 2021/183761 | | 9/2021 |

(56) References Cited

FOREIGN PATENT DOCUMENTS

| | | | |
|---|---|---|---|
| WO | WO 2021/183961 | | 9/2021 |
| WO | WO 2021/188996 | | 9/2021 |
| WO | WO 2021/226077 | A2 | 11/2021 |
| WO | WO 2021/226558 | A1 | 11/2021 |
| WO | WO 2021/252924 | A1 | 12/2021 |
| WO | WO 2021/262788 | | 12/2021 |
| WO | WO 2022/010889 | A1 | 1/2022 |
| WO | WO 2022/020800 | | 1/2022 |
| WO | WO 2022/067130 | A2 | 3/2022 |
| WO | WO 2022/067446 | A1 | 4/2022 |
| WO | WO 2022/081954 | A1 | 4/2022 |
| WO | WO 2022/081957 | A1 | 4/2022 |
| WO | WO 2022/081987 | A1 | 4/2022 |
| WO | WO 2022/109275 | | 5/2022 |
| WO | WO 2022/164942 | | 8/2022 |
| WO | WO 2022/165262 | | 8/2022 |
| WO | WO 2022/173830 | A1 | 8/2022 |
| WO | WO 2022/232514 | A1 | 11/2022 |
| WO | WO 2022/251712 | A1 | 12/2022 |
| WO | WO 2022/261148 | | 12/2022 |
| WO | WO 2022/261149 | | 12/2022 |
| WO | WO 2022/261150 | | 12/2022 |
| WO | WO 2023/015217 | A1 | 2/2023 |
| WO | WO 2023/023055 | A1 | 2/2023 |
| WO | WO 2023/076898 | A1 | 5/2023 |
| WO | WO 2023/077107 | A1 | 5/2023 |
| WO | WO 2023/077148 | A1 | 5/2023 |
| WO | WO 2023/102537 | A2 | 6/2023 |
| WO | WO 2023/102538 | A1 | 6/2023 |
| WO | WO 2023/102550 | A2 | 6/2023 |
| WO | WO 2023/108089 | A1 | 6/2023 |
| WO | WO 2023/114949 | A1 | 6/2023 |
| WO | WO 2023/115039 | A2 | 6/2023 |
| WO | WO 2023/115041 | A1 | 6/2023 |
| WO | WO 2023/117378 | A1 | 6/2023 |
| WO | WO 2023/122764 | A1 | 6/2023 |
| WO | WO 2023/102537 | A3 | 7/2023 |
| WO | WO 2023/115039 | A3 | 7/2023 |
| WO | WO 2023/129993 | A2 | 7/2023 |
| WO | WO 2023/133422 | A1 | 7/2023 |
| WO | WO 2023/133425 | A1 | 7/2023 |
| WO | WO 2023/102550 | A3 | 8/2023 |
| WO | WO 2023/173028 | A2 | 9/2023 |
| WO | WO 2023/173140 | A2 | 9/2023 |
| WO | WO 2023/205708 | A1 | 10/2023 |
| WO | WO 2023/205710 | A1 | 10/2023 |
| WO | WO 2023/205744 | A1 | 10/2023 |
| WO | WO 2023/215831 | A1 | 11/2023 |
| WO | WO 2023/225572 | A2 | 11/2023 |
| WO | WO 2023/225670 | A2 | 11/2023 |
| WO | WO 2023/230498 | A1 | 11/2023 |
| WO | WO 2023/230601 | A1 | 11/2023 |
| WO | WO 2023/240027 | A1 | 12/2023 |
| WO | WO 2023/240124 | A1 | 12/2023 |
| WO | WO 2023/245134 | A2 | 12/2023 |
| WO | WO 2024/006988 | A2 | 1/2024 |
| WO | WO 2024/018003 | A1 | 1/2024 |
| WO | WO 2024/023504 | A1 | 2/2024 |
| WO | WO 2024/026295 | A1 | 2/2024 |
| WO | WO 2024/044655 | A1 | 2/2024 |
| WO | WO 2024/050007 | A1 | 3/2024 |
| WO | WO 2024/081820 | A1 | 4/2024 |
| WO | WO 2024/107959 | A1 | 5/2024 |
| WO | WO 2024/107983 | A1 | 5/2024 |
| WO | WO 2024/108001 | A2 | 5/2024 |
| WO | WO 2024/138033 | A2 | 6/2024 |
| WO | WO 2024/108001 | A3 | 7/2024 |
| WO | WO 2024/138033 | A3 | 9/2024 |

OTHER PUBLICATIONS

Abed et al., "The Gag protein PEG10 binds to RNA and regulates trophoblast stem cell lineage specification," PLoS One, 2019, 14(4):e0214110, 18 pages.

Accola et al., "Efficient particle production by minimal Gag constructs which retain the carboxy-terminal domain of human immunodeficiency virus type 1 capsid-p2 and a late assembly domain, " J Virol, Jun. 2000, 74(12):5395-402.

Aoki et al., "Protein transduction by pseudotyped lentivirus-like nanoparticles," Gene Therapy, Mar. 2011, 18(9):936-941.

Ashley et al., "Retrovirus-like Gag protein Arc1 binds RNA and traffics across synaptic boutons," Cell, Jan. 2018, 172(1-2):262-274.

Bender et al., "Receptor-Targeted Nipah Virus Glycoproteins Improve Cell-Type Selective Gene Delivery and Reveal a Preference for Membrane-Proximal Cell Attachment, " Journals PLoS Pathogens, Jun. 2016, 12(6):e1005641, 19 pages.

Cai et al., "Targeted genome editing by lentiviral protein transduction of zinc-finger and TAL-effector nucleases, " eLife, Apr. 2014, 3:e01911, 47 pages.

Cai, "Abstract OR021: Targeted genome editing by lentiviral protein transduction of ZFN and Cas9 proteins," Abstract, Presented at Proceedings of the ESGCT and NVGCT Collaborative Congress: The Hague, Oct. 23-26, 2014; Human gene therapy, Nov. 2014, 15 pages.

Cai, "Protein Transduction Using Lentiviral Vectors for Transposition and Site-directed Gene Editing," Thesis for the degree of Doctor of Philosophy, Aarhus University, Department of Biomedicine, 2014, 74 pages.

Campbell et al., "Gesicle-Mediated Delivery of CRISPR/Cas9 Ribonucleoprotein Complex for Inactivating the HIV Provirus," Mol Ther, 2019, 27:151-163.

Campillos et al., "Computational characterization of multiple Gag-like human proteins," Trends Genet, 2006, 22(11):585-9.

Castellano et al., "Inducible recruitment of Cdc42 or WASP to a cell-surface receptor triggers actin polymerization and filopodium formation," Cur. Biol., Apr. 1999, 9(7):351-61.

Chandler et al., "Recombinant Adeno-Associated Viral Integration and Genotoxicity: Insights from Animal Models," Hum Gene Ther, 2017, 28:314-322.

Chavez and Calos, "Therapeutic applications of the ΦC31 integrase system," Curr Gene Ther, Oct. 2011, 11(5):375-381.

Chudak et al., "Identification of late assembly domains of the human endogenous retrovirus-K (HML-2), " Retrovirology, 2013, 10:140, 14 pages.

Cronin et al., "Altering the tropism of lentiviral vectors through pseudotyping," Curr Gene Ther., 2005, 5:387-398.

Croyle et al., "PEGylation of a Vesicular Stomatitis Virus G Pseudotyped Lentivirus Vector Prevents Inactivation in Serum," J Virol, 2004, 78(2):912-21.

Dahlman et al., "Barcoded nanoparticles for high throughput in vivo discovery of targeted therapeutics," PNAS, 2017, 114(8):2060-2065.

Dai et al., "Advances and challenges in enveloped virus-like particle (VLP)-based vaccines," Journal of Immunological Sciences, Apr. 2018, 2(2):36-41.

David et al., "Viral Vectors: The Road to Reducing Genotoxicity," Toxicol Sci., 2017, 155:315-325.

De Baar et al., "Subtype-Specific Sequence Variation of the HIV Type 1 Long Terminal Repeat and Primer-Binding Site," AIDS Research and Human Retroviruses, Mar. 2000, 16(5):499-504.

Derakhshankhah and Jafari, "Cell penetrating peptides: A concise review with emphasis on biomedical applications," Biomedicine and Pharmacotherapy, Dec. 2018, 108:1090-1096.

Deverman et al., "Cre-dependent selection yields AAV variants for widespread gene transfer to the adult brain," Nat Biotechnol., 2016, 34:204-209.

Doudna, "The promise and challenge of therapeutic genome editing," Nature, 2020, 578:229-236.

Enkirch et al., "Targeted lentiviral vectors pseudotyped with the Tupaia paramyxovirus glycoproteins," Gene Therapy, Jan. 2013, 20(1):16-23.

ESGCT and FSGT Collaborative Congress Abstracts, Helsinki, Finland, Sep. 17-20, 2015; Hum Gene Ther., Oct. 2015, 26(10):A1-108, 108 pages.

ESGCT and NVGCT Collaborative Congress: The Hague Abstracts, Oct. 23-26, 2014; Human gene therapy, Nov. 2014, 25(11):A1-A121, 121 pages.

(56) References Cited

OTHER PUBLICATIONS

Falkenburger et al., "Phosphoinositides: lipid regulators of membrane proteins," J Physiol., Sep. 2010, 588(Pt 17):3179-85.
Feher et al., "Characterization of the murine leukemia virus protease and its comparison with the human immunodeficiency virus type 1 protease," J Gen Virol, 2006, 87:1321-1330.
Frank et al., "Surface-Engineered Lentiviral Vectors for Selective Gene Transfer into Subtypes of Lymphocytes," Molecular Therapy Methods & Clinical Development, Mar. 2019, 12:19-31.
Freed, "Viral late domains," J Virol., 2002, 76(10):4679-4687.
Gee et al., "Extracellular nanovesicles for packaging of CRISPR-Cas9 protein and sgRNA to induce therapeutic exon skipping, " Nat Commun, 2020, 11:1334.
Gifford et al., "Nomenclature for endogenous retrovirus (ER V) loci," Retrovirology, 2018, 15:59, 11 pages.
Girard-Gagnepain et al., "Baboon envelope pseudotyped LVs outperform VSV-G-LVs for gene transfer into early-cytokine-stimulated and resting HSCs," Blood, Aug. 2014, 124(8):1221-31.
Griffiths, "Endogenous retroviruses in the human genome sequence," Genome Biol., 2001, 2(6):REVIEWS1017, 5 pages.
Guimaraes et al., "Ionizable lipid nanoparticles encapsulating barcoded mRNA for accelerated in vivo delivery screening," J Control Release, 2019, 316:404-417.
Haglund et al., "Expression of human immunodeficiency virus type 1 Gag protein precursor and envelope proteins from a vesicular stomatitis virus recombinant: high-level production of virus-like particles containing HIV envelope," Virology, Mar. 2000, 268:112-121.
Irie et al., "L-domain flanking sequences are important for host interactions and efficient budding of vesicular stomatitis virus recombinants," J Virol., Oct. 2005, 79(20):12617-22.
Jalaguier et al., "Efficient Production of HIV-1 Virus-Like Particles from a Mammalian Expression Vector Requires the N-Terminal Capsid Domain," PLoS One, 20111, 6(11):e28314, 13 pages.
Johnson et al., "Mass spectrometry analysis reveals differences in the host cell protein species found in pseudotyped lentiviral vectors, " Biologicals, 2018, 52:59-66.
Johnson et al., "Nucleic acid-independent retrovirus assembly can be driven by dimerization," J Virol., Nov. 2002, 76(22):11177-85.
Kato et al., "The entire nucleotide sequence of baboon endogenous virus DNA: a chimeric genome structure of murine type C and simian type D retroviruses," The Japanese Journal of Genetics, 1987, 62(2):127-37.
Katoh et al., "Exploitation of the interaction of measles virus fusogenic envelope proteins with the surface receptor CD46 on human cells for microcell-mediated chromosome transfer," BMC Biotechnology, 2010, 10:37, 11 pages.
Kneissl et al., "Measles Virus Glycoprotein-Based Lentiviral Targeting Vectors That Avoid Neutralizing Antibodies, " PLoS One, 2012, 7(10):e46667, 8 pages.
Kozlov et al., "Membrane tension and membrane fusion," Curr Op Struc Bio, Aug. 2015, 33:61-67.
Krebs et al., "Lentiviral LTR-directed expression sequence variation, disease pathogenesis," HIV Sequence Compendium, 2001, 2001:29-70.
Lech et al., "Antibody neutralization of retargeted measles viruses," Virology, 2014, 454-455:237-46.
Lyu et al., "Delivering Cas9/sgRNA ribonucleoprotein (RNP) by lentiviral capsid-based bionanoparticles for efficient 'hit-and-run' genome editing," Nucleic Acids Res, 2019, 47(17):e99, 13 pages.
Martin et al., "Envelope-Targeted Retrovirus Vectors Transduce Melanoma Xenografts but Not Spleen or Liver," Molecular Therapy, Mar. 2002, 5(3):269-274.
Mikkelsen, "Repurposing lentiviral vectors for delivery of genome editing tool kits," Cell Gene Therapy Insights, 2016, 2(5):599-614.
Milone et al., "Clinical use of lentiviral vectors," Leukemia, 2018, 32:1529-1541.
Monde et al., "A Human endogenous retrovirus K Gag coassembles with HIV-1 Gag and reduces the release efficiency and infectivity of HIV-1," J Virol., 2012, 86(20):11194-11208.
Montagna et al., "VSV-G-Enveloped Vesicles for Traceless Delivery of CRISPR-Cas9," Mol Ther Nucleic Acids, 2018, 12:453-462.
Morell et al., "P860: Direct delivery of a Cas9-sgRNA protein complex via cell-derived nanovesicles," Poster, Clontech Labs, 2015, 1 page.
Ostertag et al., "Biology of Mammalian L1 Retrotransposons," Annual Review of Genetics, 2001, 35:501-538.
Pan et al., "Biodistribution and toxicity studies of VSVG-pseudotyped lentiviral vector after intravenous administration in mice with the observation of in vivo transduction of bone marrow," Mol Ther., 2002, 6:19-29.
Parr-Brownlie et al., "Lentiviral vectors as tools to understand central nervous system biology in mammalian model organisms," Front Mol Neurosci., May 2015, 8:14, 12 pages.
Peifang et al., "Enhanced activation of human T cell clones specific for virus-like particles expressing the HIV V3 loop in the presence of HIV V3 loop-specific polyclonal antibodies," Clin Exp Immunol., Sep. 1994, 97(3):361-6.
Perach and Hizi, "Catalytic Features of the Recombinant Reverse Transcriptase of Bovine Leukemia Virus Expressed in Bacteria, " Virology, Jun. 1999, 259(1):176-189.
Peruzzi et al., "Barcoding biological reactions with DNA-functionalized vesicles," Angewandte Chemie, Oct. 2019, 58(51):18683-18690.
Podbilewicz, "Virus and Cell Fusion," Mechanisms Annual Review of Cell and Developmental Biology, 2014, 30:111-139.
Prel et al., "Highly efficient in vitro and in vivo delivery of functional RNAs using new versatile MS2-chimeric retrovirus-like particles," Mol Ther Methods Clin Dev, Oct. 2015, 2:15039, 15 pages.
Presse.Inserm.fr [online], "Press Releases: Nanoblades: shuttles for genome surgery," Mar. 27, 2019, retrieved on Jan. 10, 2023, retrieved from URL<https://presseinsermfr/en/nanoblades-shuttles-for-genome-surgery/34250/>, 10 pages.
Puppo et al., "Retinal transduction profiles by high-capacity viral vectors," Gene Ther., 2014, 21:855-865.
Richard et al., "Intracellular curvature-generating proteins in cell-to-cell fusion," Biochem J., Dec. 2011, 440(Pt 2):185-193.
Rohovie et al., "Virus-like particles: Next-generation nanoparticles for targeted therapeutic delivery," Bioengineering & Translational Medicine, 2017, 2:43-57.
Shaw et al., "Design and Potential of Non-Integrating Lentiviral Vectors," Biomedicines, Janaury 2014, 2(1):14-35.
Shiller et al., "Enhanced Production of Exosome-Associated AAV by Overexpression of the Tetraspanin CD9," Mol Ther Methods Clin Dev., Mar. 2018, 9:278-287.
Skipper and Mikkelsen, "Delivering the Goods for Genome Engineering and Editing," Hum Gene Ther, Aug. 2015, 26(8):486-97.
Stahelin et al., "Cellular and molecular interactions of phosphoinositides and peripheral proteins," Chem Phys Lipids, Sep. 2014, 182:3-18, 37 pages.
Stahelin, "Lipid binding domains: more than simple lipid effectors," Journal of Lipid Research, Apr. 2009, 50 Suppl(Suppl):S299-304.
Takara Bio USA, iDimerize™ Inducible Heterodimer System User Manual, Takara Bio USA, 2017, 16 pages.
Throm et al., "Efficient construction of producer cell lines for a SIN lentiviral vector for SCID-X1 gene therapy by concatemeric array transfection," Blood, May 2009, 113(21):5104-5110.
Van Beveren et al., "Structure of Moloney murine leukemia viral DNA: Nucleotide sequence of the 5' long terminal repeat and adjacent cellular sequences," Proc Natl Acad Sci USA, Jun. 1980, 77(6):3307-3311.
Wang et al., "CRISPR-Based Therapeutic Genome Editing: Strategies and In Vivo Delivery by AAV Vectors," Cell, Apr. 2020, 181(1):136-150.
Wang et al., "Efficient transduction of LEDGF/p75 mutant cells by complementary gain-of-function HIV-1 integrase mutant viruses," Molecular Therapy-Methods & Clinical Development, Jan. 2014, 1:2, 9 pages.
Wanisch et al., "Integration-deficient lentiviral vectors: a slow coming of age," Mol Ther, Aug. 2009, 17(8):1316-1332.

(56) References Cited

OTHER PUBLICATIONS

Wheeler et al., "Proteomics analysis of cellular components in lentiviral vector production using Gel-LC-MS/MS," Proteomics Clin Appl., Feb. 2007, 1(2):224-230.
White et al., "Structures and mechanisms of viral membrane fusion proteins: multiple variations on a common theme," Crit Rev Biochem Mol Biol., May-Jun. 2008, 43(3):189-219, 50 pages.
Wu et al., "MLV based viral-like-particles for delivery of toxic proteins and nuclear transcription factors," Biomaterials, 2014, 35:8416-8426.
Zhadina et al., "Functional interchangeability of late domains, late domain cofactors and ubiquitin in viral budding, " PLoS Pathog., Oct. 2010, 6(10):e1001153, 18 pages.
Zhang et al., "Morphology and ultrastructure of retrovirus particles," AIMS Biophys, 2015, 2(3):343-369.
Zhen et al., "Liposomal delivery of CRISPR/Cas9," Cancer Gene Ther., Nov. 2019, 27(7-8):515-527.
Abounit and Zurzolo, "Wiring through tunneling nanotubes—from electrical signals to organelle transfer," Journal of Cell Science, Mar. 2012, 125(Pt 5):1089-1098.
Abudayyeh et al., "A cytosine deaminase for programmable single-base RNA editing," Science, Jul. 2019, 365(6451):382-386, 9 pages.
Akhoundi et al., "CAR T cell therapy as a promising approach in cancer immunotherapy: challenges and opportunities," Cell Oncol (Dordr)., 2021, 44(3):495-523, 29 pages.
Akishiba et al., "Cytosolic antibody delivery by lipid-sensitive endosomolytic peptide," Nature Chemistry, Aug. 2017, 9(8):751-761, 11 pages.
Anzalone et al., "Search-and-replace genome editing without double-strand breaks or donor DNA," Nature, Dec. 2019, 576(7785):149-157, 30 pages.
Asati et al., "RGD Peptide as a Targeting Moiety for Theranostic Purpose: An Update Study," International Journal of Peptide Research and Therapeutics, 2019, 25:49-65, 17 pages.
Azuma et al., "Controlling leucine-zipper partner recognition in cells through modification of a-g interactions," Chemical Communications, 2014, 50(48):6364-6367.
Babaei et al., "Production of a recombinant anti-human CD4 single-chain variable-fragment antibody using phage display technology and its expression in *Escherichia coli*," J Microbiol Biotechnol., May 2011, 21(5):529-35.
Baeumler et al., "Engineering Synthetic Signaling Pathways with Programmable dCas9-Based Chimeric Receptors," Cell Rep., Sep. 2017, 20(11):2639-2653.
Balla and Várnai, "Visualizing Cellular Phosphoinositide Pools with GFP-Fused Protein-Modules," Sci STKE, Mar. 2002, 2002(125):pl3, 16 pages.
Bannas et al., "Nanobodies and Nanobody-Based Human Heavy Chain Antibodies As Antitumor Therapeutics," Front. Immunol., Nov. 2017, 8:1603, 13 pages.
Banskota et al., "Engineered virus-like particles for efficient in vivo delivery of therapeutic proteins," Cell, Jan. 2022, 185(2):250-265, 33 pages.
Baranov et al., "SWAP70 Organizes the Actin Cytoskeleton and Is Essential for Phagocytosis," Cell Reports, Nov. 2016, 17(6):1518-1531.
Barnea et al., "The genetic design of signaling cascades to record receptor activation," Proc. Natl. Acad. Sci., 2008, 105(1):64-69.
Bastida-Ruiz et al., "The Dark Side of Cell Fusion," Int J Mol Sci., Apr. 2016, 17(5):638, 20 pages.
Bendix Johnsen et al., "Evaluation of electroporation-induced adverse effects on adipose-derived stem cell exosomes," Cytotechnology, Oct. 2016, 68(5):2125-2138.
Benedict et al., "Determination of the binding affinity of an anti-CD34 single-chain antibody using a novel, flow cytometry based assay," J Immunol Methods, Feb. 1997, 201(2):223-31.
Benmebarek et al., "Killing Mechanisms of Chimeric Antigen Receptor (CAR) T Cells," Int J Mol Sci., Mar. 2019, 20(6):1283, 21 pages.
Beskow, "Lessons from HeLa Cells: The Ethics and Policy of Biospecimens," Annu Rev Genomics Hum Genet., Aug. 2016, 17:395-417, 25 pages.
Blanco-Melo et al., "Co-option of an endogenous retrovirus envelope for host defense in hominid ancestors," eLife, Apr. 2017, 6:e22519, 19 pages.
Bluestone et al., "Type 1 diabetes immunotherapy using polyclonal regulatory T cells," Sci. Transl. Med., Nov. 2015, 7(315):315ra189, 15 pages.
Borchardt et al., "Inducing circular RNA formation using the CRISPR endoribonuclease Csy4," RNA, May 2017, 23(5):619-627.
Brenner et al., "Synthetic biology: Sensing with modular receptors," Nature Chemical Biology, 2017, 13:131-132.
Cai et al., "Targeted genome editing by lentiviral protein transduction of zinc finger and TAL-effector nucleases," eLife, Apr. 2014, 3:e01911, 19 pages.
Carpten et al., "A transforming mutation in the pleckstrin homology domain of AKTI in cancer," Nature, Jul. 2007, 448(7152):439-445.
Caussinus et al., "Fluorescent fusion protein knockout mediated by anti-GFP nanobody," Nature Structural & Molecular Biology, Dec. 2011, 19(1):117-121.
Chadwick et al., "Reduced Blood Lipid Levels With In Vivo CRISPR-Cas9 Base Editing of ANGPTL3," Circulation, 2018, 137(9):975-977.
Chang and Chen, "CARs: Synthetic Immunoreceptors for Cancer Therapy and Beyond," Trends in Molecular Medicine, 2017, 23(5):430-450.
Chang et al., "Functional Characterization of the Placental Fusogenic Membrane Protein Syncytin," Biol Reprod., Dec. 2004, 71(6):1956-62.
Charlesworth et al., "Identification of preexisting adaptive immunity to Cas9 proteins in humans," Nature Medicine, Feb. 2019, 25(2):249-254, 18 pages.
Chavez et al., "Comparison of Cas9 Activators in Multiple Species," Nature Methods, Jul. 2016, 13(7):563-567, 7 pages.
Chen et al., "ACE2-targeting monoclonal antibody as potent and broad-spectrum coronavirus blocker," Signal Transduct Target Ther., Aug. 2021, 6(1):315, 9 pages.
Cheynet et al., "Identification of the hASCT2-binding domain of the Env ERVWE1/syncytin-1 fusogenic glycoprotein," Retrovirology, Jul. 2006, 3(41): 7 pages.
Choi et al., "Lentivirus pre-packed with Cas9 protein for safer gene editing," Gene Therapy, 2016, 23(7):627-633.
Chu et al., "Akt Kinase Activation Mechanisms Revealed Using Protein Semisynthesis," Cell, Aug. 2018, 174(4):897-907.e14, 25 pages.
Chu et al., "Rationally Designed Base Editors for Precise Editing of the Sickle Cell Disease Mutation," Crispr J., Apr. 2021, 4(2):169-177.
Ci et al., "Vesicular stomatitis virus G protein transmembrane region is crucial for the hemi-fusion to full fusion transition," Sci Rep., Jul. 2018, 8(1):10669, 11 pages.
Cleverley and Lenard, "The transmembrane domain in viral fusion: Essential role for a conserved glycine residue in vesicular stomatitis virus G protein," Proc Natl Acad Sci U S A, Mar. 1998, 95:3425-3430.
Clift et al., "A Method for the Acute and Rapid Degradation of Endogenous Proteins," Cell, Dec. 2017, 171(7):1692-1706.e18, 34 pages.
Cokol et al., "Finding nuclear localization signals.," EMBO Rep., Nov. 2000, 1(5):411-415.
Colella et al., "Emerging Issues in AAV-Mediated In Vivo Gene Therapy," Molecular Therapy: Methods & Clinical Development, Dec. 2017, 8:87-104.
Cong et al., "Multiplex Genome Engineering Using CRISPR/Cas Systems," Science, Feb. 2013, 339(6121):819-823.
Contreras-Galindo et al., "Human Endogenous Retrovirus Type K (HERV-K) Particles Package and Transmit HERV-K-Related Sequences," J. Virol., Apr. 2015, 89(14):7187-7201.
Coquin et al., "Syncytins enable novel possibilities to transduce human or mouse primary B cells and to achieve well-tolerated in vivo gene transfer," bioRxiv, Oct. 2019, 34 pages.

(56) References Cited

OTHER PUBLICATIONS

Dalton and Rose, "Vesicular Stomatitis Virus Glycoprotein Containing the Entire Green Fluorescent Protein on Its Cytoplasmic Domain Is Incorporated Efficiently into Virus Particles," Virology, Jan. 2001, 279(2):414-21.
Damo et al., "Inducible de novo expression of neoantigens in tumor cells and mice," Nat Biotechnol., Jul. 2020, 39(1):64-73, 26 pages.
Daringer et al., "Modular Extracellular sensor architecture for engineering mammalian cell-based devices," ACS Synth. Biol., 2014, 3(12):892-902.
Davenport et al., "Chimeric antigen receptor T cells form nonclassical and potent immune synapses driving rapid cytotoxicity," Proc Natl Acad Sci U S A, Feb. 2018, 115(9):E2068-E2076; Erratum in: Proc Natl Acad Sci U S A, May 2019, 116(22):11075-11076; 11 pages.
Davis et al., "Membrane nanotubes: dynamic long-distance connections between animal cells," Nature Reviews: Molecular Cell Biology, 2008, 9:431-436.
de Parseval et al., "Survey of human genes of retroviral origin: identification and transcriptome of the genes with coding capacity for complete envelope proteins," Journal of Virology, Oct. 2003, 77(19):10414-10422.
Dehbashi et al., "A Novel CAR Expressing NK Cell Targeting CD25 With the Prospect of Overcoming Immune Escape Mechanism in Cancers," Front Oncol., May 2021, 11:649710, 17 pages.
Del'Guidice et al., "Membrane permeabilizing amphiphilic peptide delivers recombinant transcription factor and CRISPR-Cas9/Cpfl ribonucleoproteins in hard-to-modify cells," PLoS One, Apr. 2018, 13(4):e0195558, 26 pages.
Devanabanda et al., "Immunotoxic effects of gold and silver nanoparticles: Inhibition of mitogen-induced proliferative responses and viability of human and murine lymphocytes in vitro," Journal of Immunotoxicology, 2016, 13(6): 897-902.
Dobbins et al., "Binding of the cytoplasmic domain of CD28 to the plasma membrane inhibits Lck recruitment and signaling," Sci. Signal., Jul. 2016, 9(438):ra75, 13 pages.
Dobson et al., "Antigen identification and high-throughput interaction mapping by reprogramming viral entry, " Nature Methods, Apr. 2022, 19(4):449-460, 25 pages.
Draber et al., "LST1/A is a myeloid leukocyte-specific transmembrane adaptor protein recruiting protein tyrosine phosphatases SHP-1 and SHP-2 to the plasma membrane," Journal of Biological Chemistry, Jun. 2012, 287(27):22812-22821.
Drewlo et al., "C-Terminal truncations of syncytin-1 (ERVWE1 envelope) that increase its fusogenicity," Biol. Chem., Aug. 2006, 387:1113-1120.
Dupont et al., "Tunneling nanotubes: intimate Communication between Myeloid Cells," Frontiers of Immunology, Jan. 2018, 9(43):1-6.
Ebner et al., "PI(3,4,5)P3 Engagement Restricts Akt Activity to Cellular Membranes," Mol Cell, 2017, 65(3):416-431, 23 pages.
Esnault et al., "A placenta-specific receptor for the fusogenic, endogenous retrovirus-derived, human syncytin-2," Proc Natl Acad Sci U S A, Nov. 2008, 105(45):17532-7.
Fan et al., "Secretory expression of human ScFv against keratin in Pichia pastoris and its effects on cultured keratinocytes," Arch Dermatol Res., Jun. 2009, 301(5):367-372.
Feng et al., "Improved split fluorescent proteins for endogenous protein labeling," Nature Communications, 2017, 8:1-11.
Ferdosi et al., "Multifunctional CRISPR-Cas9 with engineered immunosilenced human T cell epitopes," Nature Communications, 2019, 10:1842, 10 pages.
Finn et al., "A single administration of CRISPR/Cas9 lipid nanoparticles achieves robust and persistent in vivo genome editing, " Cell Reports, 2018, 22(9):2227-2235.
Freitas and Cunha, "Mechanisms and signals for the nuclear import of proteins," Curr Genomics, Dec. 2009, 10(8):550-557.
Frejd et al., "Affibody molecules as engineered protein drugs," Experimental & Molecular Medicine, 2017, 49:1-8.
Fuchs et al., "First-in-Human Evaluation of the Safety and Immunogenicity of a Recombinant Vesicular Stomatitis Virus Human Immunodeficiency Virus-1 gag Vaccine (HVTN 090)," Open Forum Infectious Diseases, 2015, 2(3):1-9.
Fujimoto et al., "Selective EGLN Inhibition Enables Ablative Radiotherapy and Improves Survival in Unresectable Pancreatic Cancer," Cancer Research, 2019, 79(9):2327-2338.
Gao et al., "Treatment of autosomal dominant hearing loss by in vivo delivery of genome editing agents," Nature, 2018, 553(7687):217-221, 21 pages.
Gaudelli et al., "Programmable base editing of A•T to G•C in genomic DNA without DNA cleavage," Nature, 2017, 551:464-471.
Gerdes et al., "Tunneling nanotubes: A new route for the exchange of components between animal cells," FEBS Letters, 2007, 581:2194-2201.
Giesecke et al., "Synthetic protein-protein interaction domains created by shuffling Cys2His2 zinc-fingers," Molecular Systems Biology, 2006, 2:1-15.
Gramespacher et al., "Intein Zymogens: Conditional Assembly and Splicing of Split Inteins via Targeted Proteolysis," J Am Chem Soc., Jun. 2017, 139(24):8074-8077.
Gramespacher et al., "Proximity Induced Splicing Utilizing Caged Split Inteins," J Am Chem Soc., Sep. 2019, 141(35):13708-13712.
Grandi and Tramontano, "HERV Envelope Proteins: Physiological Role and Pathogenic Potential in Cancer and Autoimmunity," Front Microbiol., Mar. 2018, 9:462, 26 pages.
Gray et al., "Activation of specific apoptotic caspases with an engineered small-molecule-activated protease, " Cell, Aug. 2010, 142(4):637-46.
Guo et al., "Structural insights into a high fidelity variant of SpCas9," Cell Res., Mar. 2019, 29(3):183-192.
Haimovich et al., "Intercellular mRNA trafficking via membrane nanotube-like extensions in mammalian cells," Proceedings of the National Academy of Sciences, 2017, 114:E9873-E9882.
Hamann et al., "Improved targeting of human $CD4^+$ T cells by nanobody-modified AAV2 gene therapy vectors," PLoS One, Dec. 2021, 16(12):e0261269, 21 pages.
Han et al., "Masked Chimeric Antigen Receptor for Tumor-Specific Activation," Mol. Ther., 2017, 25(1):274-284.
Han et al., "The critical role of AMPK in driving Akt activation under stress, tumorigenesis and drug resistance," Nat Commun, Nov. 2018, 9(1):4728, 16 pages.
Händel et al., "Versatile and efficient genome editing in human cells by combining zinc-finger nucleases with adeno-associated viral vectors," Human Gene Therapy, 2012, 23(3):321-329.
Hanke et al., "Reconstitution of the Ancestral Glycoprotein of Human Endogenous Retrovirus K and Modulation of Its Functional Activity by Truncation of the Cytoplasmic Domain," J Virol., Dec. 2009, 83(24):12790-800.
Hao et al., "A novel therapeutic drug for colon cancer EpCAM scFv-truncated protamine (tp)-siRNA," Cell Biol Int., Aug. 2013, 37(8):860-4.
Harrasser et al., "Inducible localized delivery of an anti-PD-1 scFv enhances anti-tumor activity of ROR1 CAR-T cells in TNBC," Breast Cancer Res., Jun. 2022, 24(1):39, 10 pages.
Harris and Kranz, "Adoptive T Cell Therapies: A Comparison of T Cell Receptors and Chimeric Antigen Receptors," Trends in Pharmacological Sciences, Mar. 2016, 37(3):220-230, 11 pages.
Hase et al., "M-Sec promotes membrane nanotube formation by interacting with Ral and the exocyst complex," Nature Cell Biology, Dec. 2009, 11(12):1427-1432, 18 pages.
Hashimoto et al., "Potential Role of the Formation of Tunneling Nanotubes in HIV-1 Spread in Macrophages," J Immunol., Feb. 2016, 196(4):1832-41, 15 pages.
Heidmann et al., "HEMO, an ancestral endogenous retroviral envelope protein shed in the blood of pregnant women and expressed in pluripotent stem cells and tumors," Proc Natl Acad Sci U S A, Jul. 2017, 114(32):E6642-E6651.
Heim and Tsien, "Engineering green fluorescent protein for improved brightness, longer wavelengths and fluorescence resonance energy transfer," Current Biology, 1996, 6(2):178-182.

(56) References Cited

OTHER PUBLICATIONS

Hosseinzadeh et al., "Production and Evaluation of Specific Single-Chain Antibodies against CTLA-4 for Cancer-Targeted Therapy," Rep Biochem Mol Biol., Oct. 2017, 6(1):8-14.
Inobe and Nukina, "Rapamycin-induced oligomer formation system of FRB-FKBP fusion proteins," Journal of Bioscience and Bioengineering, 2016, 122(1):40-46.
Iordanova et al., "Design and characterization of a chimeric ferritin with enhanced iron loading and transverse NMR relaxation rate, " J. Biol. Inorg. Chem., 2010, 15:957-965.
Jeetendra et al., "The Membrane-Proximal Domain of Vesicular Stomatitis Virus G Protein Functions as a Membrane Fusion Potentiator and Can Induce Hemifusion," Journal of Virology, Dec. 2002, 76(23):12300-12311.
Jeetendra et al., "The Membrane-Proximal Region of Vesicular Stomatitis Virus Glycoprotein G Ectodomain Is Critical for Fusion and Virus Infectivity," Journal of Virology, Dec. 2003, 77(23):12807-12818.
Jiang et al., "Internally inlaid SaCas9 base editors enable window specific base editing," Theranostics, Jun. 2022, 12(10):4767-4778.
Jo et al., "Small molecule-induced cytosolic activation of protein kinase Akt rescues ischemia-elicited neuronal death, " Proc Natl Acad Sci U S A., Jun. 2012, 109(26):10581-10586.
Joseph et al., "The calcium feedback loop and T cell activation: how cytoskeleton networks control intracellular calcium flux," Biochim Biophys Acta., Feb. 2014, 1838(2):557-68.
Kaczmarczyk et al., "Protein delivery using engineered virus-like particles," Proc Natl Acad Sci U S A, 2011, 108(41):16998-17003.
Kennedy et al., "Rapid blue-light-mediated induction of protein interactions in living cells," Nature Methods, 2010, 7(12):973-975.
Kim and Pabo, "Getting a handhold on DNA: Design of poly-zinc finger proteins with femtomolar dissociation constants," PNAS, 1998, 95(6):2812-2817.
Kim et al., "CRISPR RNAs trigger innate immune responses in human cells," Genome Research, 2018, 28:367-373.
Kimizuka et al., "Production and characterization of functional domains of human fibronectin expressed in *Escherichia coli*," J Biochem., Aug. 1991, 110(2):284-91.
Kimura et al., Distinct Roles for the N- and C-terminal Regions of M-Sec in Plasma Membrane Deformation during Tunneling Nanotube Formation, Scientific Reports, 2016, 6:33548, 12 pages.
Kober et al., "Optimized signal peptides for the development of high expressing CHO cell lines," Biotechnol. Bioeng., Apr. 2013, 110(4):1164-1173.
Koide et al., "Chapter six—Target-Binding Proteins Based on the 10th Human Fibronectin Type III Domain ($^{10}$Fn3), " Methods in Enzymology, 2012, 503:135-156.
Komor et al., "Programmable editing of a target base in genomic DNA without double-stranded DNA cleavage, " Nature, 2016, 533(7603):420-424, 17 pages.
Kramer et al., "Combinatorial Control of *Drosophila* Circular RNA Expression by Intronic Repeats, hnRNPs, and SR Proteins," Genes Dev., 2015, 29(20):2168-2182.
Kreiss et al., "Plasmid DNA size does not affect the physicochemical properties of lipoplexes but modulates gene transfer efficiency," Nucleic Acids Research, 1999, 27(19):3792-3798.
Kubala et al., "Structural and Thermodynamic Analysis of the GFP:GFP-nanobody complex," Protein Sci., Dec. 2010, 19(12): 2389-2401.
Lainek et al., "Delivery of an Artificial Transcription Regulator dCas9-VPR by Extracellular Vesicles for Therapeutic Gene Activation," ACS Synthetic Biology, 2018, 7(12):2715-2725.
Leach et al., "Anti-DLL4 VNAR targeted nanoparticles for targeting of both tumour and tumour associated vasculature," Nanoscale, Jul. 2020, 12(27):14751-14763.
Leddon et al., "The CD28 Transmembrane Domain Contains an Essential Dimerization Motif," Front Immunol., Jul. 2020, 11:1519, 15 pages.
Lee and Bieniasz, "Reconstitution of an infectious human endogenous retrovirus," PLoS Pathog., Jan. 2007, 3(1):e10, 12 pages.
Lee et al., "Nanoparticle delivery of Cas9 ribonucleoprotein and donor DNA in vivo induces homology-directed DNA repair," Nature Biomedical Engineering, 2017, 1:889-901, 15 pages.
Levy et al., "Cytosine and adenine base editing of the brain, liver, retina, heart and skeletal muscle of mice via adeno-associated viruses," Nature Biomedical Engineering, 2020, 4:97-110.
Li et al., "A rationally designed semiconducting polymer brush for NIR-II imaging guided light-triggered remote control of CRISPR/Cas9 genome editing," Advanced Materials, 2019, 31(21):1901187, 9 pages.
Li et al., "Autophosphorylation of Akt at Threonine 72 and Serine 246: A potential mechanism of regulation of Akt kinase activity," Journal of Biological Chemistry, May 2006, 281(19):13837-13843.
Liang and Wilusz, "Short intronic repeat sequences facilitate circular RNA production," Genes Dev., Oct. 2014, 28(20):2233-47.
Liao et al., "Peptidyl-prolyl cis/trans isomerase Pin1 is critical for the regulation of PKB/Akt stability and activation phosphorylation," Oncogene, Jul. 2009, 28(26):2436-45.
Liu et al., "Engineering Genetically-Encoded Mineralization and Magnetism via Directed Evolution," Scientific Reports, 2016, 6:38019, 11 pages.
Lu et al., "Delivering SaCas9 mRNA by lentivirus-like bionanoparticles for transient expression and efficient genome editing," Nucleic Acids Research, 2019, 47(8):e44, 13 pages.
Lü et al., "Discovery of an Heparin-Binding Epidermal Growth Factor Domain Antibody from a Phage Library and Analysis of Its Inhibitory Effects in SKOV3 Cells," Cancer Biother Radiopharm, Sep. 2021, 8 pages.
Luan et al., "Engineering exosomes as refined biological nanoplatforms for drug delivery," Acta Pharmacologica Sinica, 2017, 38:754-763, 10 pages.
Lučić et al., "Conformational sampling of membranes by Akt controls its activation and inactivation," Proc Natl Acad Sci U S A, Apr. 2018, 115(17):E3940-E3949.
Lukacs et al., "Size-dependent DNA Mobility in Cytoplasm and Nucleus," Journal of Biological Chemistry, 1999, 275(3):1625-1629.
Lyubchenko et al., "Role of Calcium Influx in Cytotoxic T Lymphocyte Lytic Granule Exocytosis during Target Cell Killing," Immunity, Nov. 2001, 15(5):847-59.
Malecha and Miettinen, "Expression of keratin 13 in human epithelial neoplasms," Virchows Arch A Pathol Anat Histopathol., 1991, 418(3):249-54.
Mangeot et al., "Genome editing in primary cells and in vivo using viral-derived Nanoblades loaded with Cas9-sgRNA ribonucleoproteins, " Nature Communications, 2019, 10:45, 15 pages.
Mangeot et al., "Protein transfer into human cells by VSV-G-induced nanovesicles," Molecular Therapy, 2011, 19(9):1656-1666.
Martínez-Lostao et al., "How Do Cytotoxic Lymphocytes Kill Cancer Cells?," Clin Cancer Res., Nov. 2015, 21(22):5047-56.
Martín-Otal et al., "Targeting the extra domain A of fibronectin for cancer therapy with CAR-T cells," J Immunother Cancer, Aug. 2022, 10(8):e004479, 20 pages.
Maude et al., "Managing cytokine release syndrome associated with novel T cell-engaging therapies," Cancer Journal, 2014, 20(2):119-22.
Meyer et al., "Pseudotyping exosomes for enhanced protein delivery in mammalian cells," International Journal of Nanomedicine, 2017, 12:3153-3170.
Moazen et al., "Selection and Evaluation of Specific Single Chain Antibodies against CD90, a Marker for Mesenchymal and Cancer Stem Cells," Rep Biochem Mol Biol., Oct. 2018, 7(1):45-51.
Moll et al., "Expression of keratin 5 as a distinctive feature of epithelial and biphasic mesotheliomas. An immunohistochemical study using monoclonal antibody AE14," Virchows Arch B Cell Pathol Incl Mol Pathol., 1989, 58(2):129-45.
Momen-Heravi et al., "Exosome-mediated delivery of functionally active miRNA-155 inhibitor to macrophages," Nanomedicine: Nanotechnology, Biology, and Medicine, 2014, 10(7):1517-1527, 12 pages.
Morsut et al., "Engineering Customized Cell Sensing and Response Behaviors Using Synthetic Notch Receptors," Cell, Feb. 2016, 164(4):780-91.

(56) References Cited

OTHER PUBLICATIONS

Mout et al., "Direct cytosolic delivery of CRISPR/Cas9-ribonucleoprotein for efficient gene editing," ACS Nano, Mar. 2017, 11(3):2452-2458.
Münch et al., "Displaying High-affinity Ligands on Adeno-associated Viral Vectors Enables Tumor Cell-specific and Safe Gene Transfer," Molecular Therapy, Jan. 2013, 21(1):109-118.
Nafissi et al., "DNA Ministrings: Highly Safe and Effective Gene Delivery Vectors," Molecular Therapy-Nucleic Acids, May 2014, 3(6):e165, 12 pages.
Naso et al., "Adeno-Associated Virus (AAV) as a Vector for Gene Therapy," BioDrugs, 2017, 31(4):317-334.
Nguyen Tran et al., "Engineering domain-inlaid SaCas9 adenine base editors with reduced RNA off-targets and increased on-target DNA editing," Nat Commun., Sep. 2020, 11(1):4871, 10 pages.
Nikolic et al., "Structural basis for the recognition of LDL-receptor family members by VSV glycoprotein," Nat Commun., Mar. 2018, 9(1):1029, 13 pages.
Nissim et al., "Multiplexed and programmable regulation of gene networks with an integrated RNA and CRISPR/Cas toolkit in human cells," Mol Cell., May 2014, 54(4):698-710.
Oesch-Bartlomowicz et al., "Aryl hydrocarbon receptor activation by cAMP vs. dioxin divergent signaling pathways, " Proc Natl Acad Sci U S A, Jun. 2005, 102(26):9218-23.
Okimoto et al., "VSV-G envelope glycoprotein forms complexes with plasmid DNA and MLV retrovirus-like particles in cell-free conditions and enhances DNA transfection," Molecular Therapy, 2001, 4(3):232-238.
Omsland et al., "Inhibition of Tunneling Nanotube (TNT) Formation and Human T-cell Leukemia Virus Type 1 (HTL V-1) Transmission by Cytarabine," Scientific Reports, 2018, 8(11118 ):1-17.
Orengo et al., "A bichromatic fluorescent reporter for cell-based screens of alternative splicing," Nucleic Acids Res., 2006, 34(22):e148, 10 pages.
Osman et al., "M-CSF inhibits anti-HIV-1 activity of IL-32, but they enhance M2-like phenotypes of macrophages, " J Immunol., Jun. 2014, 192(11):5083-9.
Parikh et al., "Disruption of PH-kinase domain interactions leads to oncogenic activation of AKT in human cancers," PNAS, Nov. 2012, 109(47):19368-19373.
Parrish et al., "A Transmembrane Domain GGxxG Motif in CD4 Contributes to Its Lck-Independent Function but Does Not Mediate CD4 Dimerization," PLoS One, Jul. 2015, 10(7):e0132333, 14 pages.
Pastuzyn et al., "The Neuronal Gene Arc Encodes a Repurposed Retrotransposon Gag Protein that Mediates Intercellular RNA Transfer," Cell, 2018, 172:275-288, 33 pages.
Peralta et al., "Mechanism of Membranous Tunnelling Nanotube Formation in Viral Genome delivery," PLoS Biology, 2013, 11(9):e1001667, 15 pages.
Pinto et al., "An expanded library of orthogonal split inteins enables modular multi-peptide assemblies, " Nat Comm., Mar. 2020, 11:1529, 16 pages.
Qiao et al., "Cytosolic delivery of CRISPR/Cas9 ribonucleoproteins for genome editing using chitosan-coated red fluorescent protein," Chemical Communications, 2019, 55(32):4707-4710.
Rafiq et al., "Targeted delivery of a PD-1-blocking scFv by CAR-T cells enhances anti-tumor efficacy in vivo," Nat Biotechnol., Oct. 2018, 36(9):847-856, 28 pages.
Ran et al., "In vivo genome editing using *Staphylococcus aureus* Cas9," Nature, Apr. 2015, 520(7546):186-191, 18 pages.
Rechavi et al., "Intercellular exchange of proteins: The immune cell habit of sharing," FEBS Letters, 2009, 583(11):1792-1799.
Renteln, "A synthetic mitochondrial-based vector for therapeutic purposes," Medical Hypotheses, Aug. 2018, 117:28-30.
Rittner et al., "New Basic Membrane-Destabilizing Peptides for Plasmid-Based Gene Delivery in Vitro and in Vivo," Molecular Therapy, Mar. 2002, 5(2):104-114.
Robinson-McCarthy et al., "Reconstruction of the cell entry pathway of an extinct virus," PLoS Pathog., Aug. 2018, 14(8):e1007123, 23 pages.
Romano et al., "Treg therapy in transplantation: a general overview," Transplant International, 2017, 30(8):745-753.
Rose et al., "Vesicular stomatitis virus glycoprotein is anchored in the viral membrane by a hydrophobic domain near the COOH terminus, " Proc Natl Acad Sci U S A, Jul. 1980, 77(7):3884-3888.
Roselli et al., "4-1BB and optimized CD28 co-stimulation enhances function of human mono-specific and bi-specific third-generation Car T cells," J Immunother Cancer, Oct. 2021, 9(10):e003354, 15 pages.
Roybal et al., "Engineering T Cells with Customized Therapeutic Response Programs Using Synthetic Notch Receptors, " Cell, 2016, 167(2):419-432, 31 pages.
Ryu et al., "Adenine base editing in mouse embryos and an adult mouse model of Duchenne muscular dystrophy," Nat Biotechnol., Jul. 2018, 36(6):536-539, 7 pages.
Salter et al., "Phosphoproteomic analysis of chimeric antigen receptor signaling reveals kinetic and quantitative differences that affect cell function," Sci. Signal., Aug. 2018, 11(544):eaat6753, 18 pages.
Sanchez and Ting, "Directed evolution improves the catalytic efficiency of TEV protease," Nat Methods, Feb. 2020, 17(2):167-174, 15 pages.
Sanchez et al., "Transcriptional readout of neuronal activity via an engineered $Ca^{2+}$-activated protease," Proc Natl Acad Sci U S A, Dec. 2020, 117(52):33186-96.
Sartori-Rupp et al., "Correlative cryo-electron microscopy reveals the structure of TNTs in neuronal cells," Nature Communications, 2019, 10:1-16.
Sato et al., "Nonspecific binding of common anti-CFTR antibodies in ciliated cells of human airway epithelium," Sci Rep., Dec. 2021, 11(1):23256, 15 pages.
Schenkwein et al., "Production of HIV-1 Integrase Fusion Protein-Carrying Lentiviral Vectors for Gene Therapy and Protein Transduction," Human Gene Therapy, 2010, 21(5):589-602.
Schiller et al., "LST1 promotes the assembly of a molecular machinery responsible for tunneling nanotube formation," Journal of Cell Science, Feb. 2013, 126(3):767-777.
Schwarz et al., "Rewiring human cellular input-output using modular extracellular sensors," Nat. Chem. Biol., 2017, 13:202-209, 9 pages.
Sebollela et al., "A human scFv antibody that targets and neutralizes high molecular weight pathogenic amyloid-β oligomers," J Neurochem., Sep. 2017, 142(6):934-947.
Selgrade et al., "Protein Scaffold-Activated Protein Trans-Splicing in Mammalian Cells," J. Am. Chem. Soc., 2013, 135(20):7713-7719.
Shin et al., "Biomedical applications of nisin," J. Applied Microbial., 2015, 120(6):1449-1465, 17 pages.
Slomovic and Collins, "DNA sense-and-respond protein modules for mammalian cells," Nature Methods, 2015, 12:1085-1089, 8 pages.
Staahl et al., "Efficient genome editing in the mouse brain by local delivery of engineered Cas9 ribonucleoprotein complexes," Nature Biotechnology, May 2017, 35(5):431-433, 7 pages.
Stage et al., "Inhibition of the hammerhead ribozyme by neomycin," RNA, Mar. 1995, 1(1):95-101.
Stains et al., "A general approach for receptor and antibody-targeted detection of native proteins utilizing split-luciferase reassembly," ACS Chem. Biol., 2010, 5(10):943-952, 10 pages.
Stausbøl-Grøn et al., "De novo identification of cell-type specific antibody-antigen pairs by phage display subtraction. Isolation of a human single chain antibody fragment against human keratin 14," Eur J Biochem., May 2001, 268(10):3099-107.
Stein and Alexandrov, "Protease-based synthetic sensing and signal amplification," PNAS, Nov. 2014, 111(45):15934-15939.
Stepanek et al., "Palmitoylated transmembrane adaptor proteins in leukocyte signaling," Cellular Signaling, 2014, 26(5):895-902.
Stevens et al., "A promiscuous split intein with expanded protein engineering applications," PNAS, 2017, 114(32):8538-8543.
Tai et al., "Differential Expression of Metallothionein 1 and 2 Isoforms in Breast Cancer Lines with Different Invasive Potential:

(56) References Cited

OTHER PUBLICATIONS

Identification of a Novel Nonsilent Metallothionein-1H Mutant Variant," American Journal of Pathology, 2003, 163(5):2009-2019.
Tang et al., "Aptazyme-embedded guide RNAs enable ligand-responsive genome editing and transcriptional activation," Nat Commun., Jun. 2017, 8:15939, 8 pages.
Taylor et al., "A DNA-Based T Cell Receptor Reveals a Role for Receptor Clustering in Ligand Discrimination," Cell, 2017, 169(1):108-19.e20, 33 pages.
Tillotson et al., "Engineering an Anti-Transferrin Receptor ScFv for pH-Sensitive Binding Leads to Increased Intracellular Accumulation," PLoS One, Dec. 2015, 10(12):e0145820, 21 pages.
Tiwari et al., "Control of fibrotic changes through the synergistic effects of anti-fibronectin antibody and an RGDS-tagged form of the same antibody," Sci Rep., Aug. 2016, 6:30872, 13 pages.
Toffalini and Demoulin, "The Transmembrane Domain of PDGFR-β Plays An Important Role in ETV6-PDGFR-β Activation," Blood, Nov. 2008, 112(11):5320, 2 pages.
Trahtenherts and Benhar, "An internalizing antibody specific for the human asialoglycoprotein receptor," Hybridoma (Larchmt.), Aug. 2009, 28(4):225-33.
Tsuchiya et al., "Gene design of signal sequence for effective secretion of protein," Nucleic Acids Research, 2003, Supplement No. 3: 261-262.
Urano et al., "Substitution of the myristoylation signal of human immunodeficiency virus type 1 Pr55Gag with the phospholipase C-delta1 pleckstrin homology domain results in infectious pseudovirion production," J. Gen Virology, 2008, 89:3144-3149.
Várnai et al., "Selective cellular effects of overexpressed pleckstrin-homology domains that recognize PtdIns(3,4,5)P3 suggest their interaction with protein binding partners," Journal of Cell Science, Oct. 2005, 118(Pt 20):4879-4888.
Verweij et al., "Quantifying exosome secretion from single cells reveals a modulatory role for GPCR signaling," J Cell Biol., Mar. 2018, 217(3):1129-1142.
Voelkel et al., "Protein transduction from retroviral Gag precursors," Proc Natl Acad Sci USA, 2010, 107(17):7805-7810.
von Heijne, "Signal sequences. The limits of variation," J Mol Biol., Jul. 1985, 184(1):99-105.
Wagner et al., "High prevalence of *Streptococcus pyogenes* Cas9-reactive T cells within the adult human population," Nature Medicine, 2019, 25:242-248, 12 pages.
Wang et al., "Adenovirus-mediated somatic genome editing of Pten by CRISPR/Cas9 in mouse liver in spite of Cas9-specific immune responses," Human Gene Therapy, 2015, 26(7):432-442.
Wang et al., "Antibody fragments directed against different portions of the human neural cell adhesion molecule L1 act as inhibitors or activators of L1 function," PLoS One, Dec. 2012, 7(12):e52404, 13 pages.
Wang et al., "Anti-HER2 scFv-Directed Extracellular Vesicle-Mediated mRNA-Based Gene Delivery Inhibits Growth of HER2-Positive Human Breast Tumor Xenografts by Prodrug Activation," Mol Cancer Ther., May 2018, 17(5):1133-1142.
Wang et al., "ARMMs as a versatile platform for intracellular delivery of macromolecules," Nature Communications, 2018, 9:960, 7 pages.
Wang et al., "Nonviral gene editing via CRISPR/Cas9 delivery by membrane-disruptive and endosomolytic helical polypeptide, " PNAS, 2018, 115:4903-4908.
Wang et al., "Transfer of mitochondria via tunneling nanotubes rescues apoptotic PC12 cells," Cell Death and Differentiation, 2015, 22:1181-1191.
Warrington et al., "Adeno-Associated Virus Type 2 VP2 Capsid Protein Is Nonessential and Can Tolerate Large Peptide Insertions at Its N Terminus," J. Virol., 2004, 78(12):6595-6609.
Watkins et al., "Functional Connectivity between Immune Cells Mediated by Tunneling Nanotubules," Immunity, 2005, 23(3):309-318.
Wehr et al., "Analysis of transient phosphorylation-dependent protein-protein interactions in living mammalian cells using split-TEV," BMC Biotechnol., 2008, 8:55, 15 pages.
Wehr et al., "Monitoring regulated protein-protein interactions using split TEV," Nat Methods., Dec. 2006, 3(12):985-93.
Weidle et al., "LST1: A multifunctional gene encoded in the MHC class III region," Immunobiology, 2018, 223(11):699-708.
Weissman et al., "Molecular cloning and chromosomal localization of the human T-cell receptor zeta chain: distinction from the molecular CD3 complex," Proc. Natl. Acad. Sci., 1988, 85(24):9709-13.
Wildschutte and Coffin, "Pushing the envelope," eLife, Apr. 2017, 6:e26397, 3 pages.
Wong et al., "Engineering a Dual Small Molecule Gated ZAP70 Switch in T Cells," ACS Synth Biol., 2018, 7(4):969-77.
Wroblewska et al., "Mammalian synthetic circuits with RNA binding proteins for RNA-only Delivery," Nature Biotechnology, 2015, 33:839-841, 5 pages.
Xu et al., "Regulation of T cell receptor activation by dynamic membrane binding of the CD3epsilon cytoplasmic tyrosine-based motif," Cell., Nov. 2008, 135(4):702-13.
Yin et al., "Structure-guided chemical modification of guide RNA enables potent non-viral in vivo genome editing," Nature Biotechnology, 2017, 35(12):1179-1187, 22 pages.
Younis et al., "Rapid-response splicing reporter screens identify differential regulators of constitutive and alternative splicing, " Mol Cell Biol., Apr. 2010, 30(7):1718-28.
Zetsche et al., "Cpf1 Is a Single RNA-Guided Endonuclease of a Class 2 CRISPR-Cas System," Cell, 2015, 163(3):759-771.
Zhang et al., "Basic residues in the T-cell receptor ζ cytoplasmic domain mediate membrane association and modulate signaling," Proc Natl Acad Sci U S A, Nov. 2011, 108(48):19323-8.
Zhang et al., "Suppression of p75 neurotrophin receptor surface expression with intrabodies influences Bcl-xL mRNA expression and neurite outgrowth in PC12 cells," PLoS One, 2012, 7(1):e30684, 13 pages.
Zhao et al., "Quantitatively Predictable Control of Cellular Protein Levels through Proteasomal Degradation," ACS Synthetic Biology, 2018, 7(2):540-552.
Zhao et al., "SpyCLIP: an easy-to-use and high-throughput compatible CLIP platform for the characterization of protein-RNA interactions with high accuracy," Nucleic Acids Research, 2019, 47(6):e33, 12 pages.
Zhong et al., "Chimeric antigen receptors combining 4-1BB and CD28 signaling domains augment PI 3 kinase/AKT/Bcl-X L activation and CD8+ T cell-mediated tumor eradication," Mol. Ther., 2010, 18(2):413-420.
Zhuo et al., "Engineered virus-like particles: paving the way for effective somatic genome editing," Signal Transduction and Targeted Therapy, Aug. 2022, 7:279, 3 pages.
Zuris et al., "Cationic lipid-mediated delivery of proteins enables efficient protein-based genome editing in vitro and in vivo," Nature Biotechnology, 2015, 33:73-80, 10 pages.
Hsu et al., "DNA targeting specificity of RNA-guided Cas9 nucleases," Nat Biotechnol., Sep. 2013, 31(9):827-32.
Motsa and Stahelin, "Lipid-protein interactions in virus assembly and budding from the host cell plasma membrane," Biochemical Society Transactions, Aug. 2021, 49(4):1633-1641.
Abe et al., "Enhanced Gene Transfer With Fusogenic Liposomes Containing Vesicular Stomatitis Virus G Glycoprotein," Journal of Virology, Jul. 1998, 72(7):6159-6163.
Abe et al., "In Vitro Cell-free Conversion of Noninfectious Moloney Retrovirus Particles to an Infectious Form by the Addition of the Vesicular Stomatitis Virus Surrogate Envelope G Protein," Journal of Virology, Aug. 1998, 72(8):6356-6361.
Abifadel et al., "Mutations in PCSK9 Cause Autosomal Dominant Hypercholesterolemia," Nature Genetics, Jun. 2003, 34(2):154-156.
Abudayyeh et al., "C2c2 is a single-component programmable RNA-guided RNA-targeting CRISPR effector," Science, 2016, 353(6299):1-17.
Abudu et al., "Murine Retrovirus Escapes From Murine APOBEC3 via Two Distinct Novel Mechanisms," Current Biology, Aug. 2006, 16(15):1565-1570.

(56) References Cited

OTHER PUBLICATIONS

Adamson et al., "Approaches to Maximize sgRNA-barcode Coupling in Perturb-seq Screens," bioRxiv, posted Apr. 11, 2018, 14 pages.
Ahn et al., "Structural and Quantitative Expression Analyses of HERV Gene Family in Human Tissues," Molecular Cells, Aug. 2009, 28(2):99-103.
Aihara et al., "A Conformational Switch Controls the DNA Cleavage Activity of A Integrase," Molecular Cell, Jul. 2003, 12(1):187-198.
Akcakaya et al., "In vivo CRISPR Editing with No. Detectable Genome-wide Off-target Mutations," Nature, 2018, 561(7723):416-419, 27 pages.
Akinc et al., "Targeted Delivery of RNAi Therapeutics With Endogenous and Exogenous Ligand-Based Mechanisms," Molecular Therapy, Jul. 2010, 18(7):1357-1364.
Akopian et al., "Chimeric Recombinases with Designed DNA sequence Recognition," Proceedings of the National Academy of Sciences of the United States of America, Jul. 2003, 100(15):8688-8691.
Alanis-Lobato et al., "Frequent Loss of Heterozygosity in CRISPR-Cas9-edited Early Human Embryos," Proceedings of the National Academy of Sciences of the United States of America, Jun. 2021, 118(22):e2004832117, 9 pages.
Altschul et al., "Basic Local Alignment Search Tool," Journal of Molecular Biology, Oct. 1990, 215(3):403-410.
Altschul et al., "Gapped BLAST and PSI-BLAST: A New Generation Of Protein Database Search Programs," Nucleic Acids Research, Sep. 1997, 25(17):3389-3402.
Álvarez et al., "The Eukaryotic Translation Initiation Factor 4GI is Cleaved by Different Retroviral Proteases," Journal of Virology, Dec. 2003, 77(23):12392-12400.
Amendola et al., "Recent Progress in Genome Editing for Gene Therapy Applications: The French Perspective," Hum Gene Ther., Oct. 2021, 32(19-20):1059-1075.
Amirache et al., "Mystery Solved: VSV-G-LVs Do Not Allow Efficient Gene Transfer into Unstimulated T Cells, B Cells, and HSCs Because They Lack the LDL Receptor," Blood, Feb. 2014, 123(9):1422-1424.
Andersson et al., "Developmental Expression of HERV-R (ERV3) and HERV-K in Human Tissue," Virology, Jun. 2002, 297(2):220-225.
Andrake et al., "Retroviral Integrase: Then and Now," Annual Review of Virology, Nov. 2015, 2(1):241-264.
Annoni et al., "Modulation of Immune Responses in Lentiviral Vector-mediated Gene Transfer," Cellular Immunology, published online Apr. 27, 2018, 342:103802, 8 pages.
Anzalone et al., "Genome editing with CRISPR-Cas nucleases, base editors, transposases and prime editors," Nature Biotechnology, Jul. 2020, 38(7):824-844.
Apolonia et al., "Stable Gene Transfer to Muscle Using Non-integrating Lentiviral Vectors," Molecular Therapy, 2007, 15(11):1947-1954.
Aquino-Jarquin, "CRISPR-Cas14 is now part of the Artillery for Gene Editing and Molecular Diagnostic," Nanomedicine, Jun. 2019, 18:428-431, 15 pages.
Araki et al., "Activation of the thrombopoietin receptor by mutant calreticulin in CALR-mutant myeloproliferative neoplasms," Blood, Mar. 2016, 127(10):1307-1316.
Arezi et al., "Novel mutations in Moloney Murine Leukemia Virus reverse transcriptase increase thermostability through tighter binding to template-primer," Nucleic Acids Research, 2009, 37(2):473-481.
Argaw et al., "In Vivo Targeting Of Lentiviral Vectors Pseudotyped With The Tupaia Paramyxovirus H Glycoprotein Bearing A Cell-specific Ligand," Molecular Therapy Methods & Clinical Development, 2021, 24:21:670-680.
Arnold et al., "Mutants of Tn3 Resolvase which do not Require Accessory Binding sites for Recombination Activity," EMBO Journal, Mar. 1999, 18(5):1407-1414.
Ausubel et al., "Production of CGMP-Grade Lentiviral Vectors," BioProcess International, 2012, 10(2):32-48.
Autieri et al., "IRT-1, a Novel Interferon-γ-responsive Transcript Encoding a Growth-suppressing Basic Leucine Zipper Protein," Journal of Biological Chemistry, Jun. 1998, 273(24):14731-14737.
Avidan et al., "The processivity and fidelity of DNA synthesis exhibited by the reverse transcriptase of bovine leukemia virus," European Journal of Biochemistry, Feb. 2002, 269(3):859-867.
Bacquin et al., "A Cell Fusion-Based Screening Method Identifies Glycosylphosphatidylinositol-Anchored Protein Ly6e as the Receptor for Mouse Endogenous Retroviral Envelope Syncytin-A," Journal of Virology, Aug. 2017, 91(18):e00832-17.
Bae et al., "Design and Testing of Vector-Producing HEK293T Cells Bearing a Genomic Deletion of the SV40 T Antigen Coding Region," Molecular Therapy Methods and Clinical Development, Jul. 2020, 18:631-638.
Bandeira et al., "Downstream Processing of Lentiviral Vectors: Releasing Bottlenecks," Human Gene Therapy Methods, Aug. 2012, 23(4):255-263.
Banerjee et al., "Viral glycoproteins: biological role and application in diagnosis," VirusDisease, Mar. 2016, 27(1):1-11.
Bannert et al., "Retroelements and the Human Genome: New Perspectives on an Old Relation," Proceedings of the National Academy of Sciences of the United States of America, Oct. 2004, 101(Suppl 2):14572-14579.
Baranauskas et al., "Generation and characterization of new highly thermostable and processive M-MuLV reverse transcriptase variants," Protein engineering, design & selection, Oct. 2012, 25(10):657-668.
Barash et al., "Human Secretory Signal Peptide Description by Hidden Markov Model and Generation of a Strong Artificial Signal Peptide for Secreted Protein Expression," Biochemical and Biophysical Research Communications, Jun. 2002, 294(4):835-842.
Barrangou et al., "CRISPR Provides Acquired Resistance Against Viruses in Prokaryotes," Science, Mar. 2007, 315(5819):1709-1712.
Bartel et al., "Directed evolution of novel adeno-associated viruses for therapeutic gene delivery," Gene Therapy, Jun. 2012, 19(6):694-700.
Basel et al., "Designing a Cleavable Cell Surface Protein for Cytotherapy and Drug Delivery Applications," Applied Sciences, 2021, 11(6):2792, 11 pages.
Basyuk et al., "The Packaging Signal of MLV is an Integrated Module That Mediates Intracellular Transport of Genomic RNAs," Journal of molecular biology, Nov. 2005, 354(2):330-339.
Bauler et al., "Production of Lentiviral Vectors Using Suspension Cells Grown in Serum-free Media. Molecular therapy," Methods and Clinical Development, 2020, 17:58-68.
Beal et al., "Model-Driven Engineering Of Gene Expression From RNA Replicons," ACS Synthetic Biology, Jan. 2015, 4(1):48-56.
Becer et al., "Click chemistry beyond metal-catalyzed cycloaddition," Angew Chem Int Ed Engl., 2009, 48(27):4900-4908.
Beerli et al., "Toward controlling gene expression at will: specific regulation of the erbB-2/HER-2 promoter by using polydactyl zinc finger proteins constructed from modular building blocks," Proceedings of the National Academy of Sciences, Dec. 1998, 95(25):14628-14633.
Beilstein et al., "Conditional Control of Mammalian Gene Expression by Tetracycline-dependent Hammerhead Ribozymes," ACS Synthetic Biology, May 2015, 4(5):526-534.
Beilstein et al., "Identification of a pH-Sensitive Switch in VSV-G and a Crystal Structure of the G Pre-fusion State Highlight the VSV-G Structural Transition Pathway," Cell Reports, Aug. 2020, 32(7):108042, 15 pages.
Berens et al., "A Tetracycline-binding RNA Aptamer," Bioorganic & Medicinal Chemistry, Oct. 2001, 9(10):2549-2456.
Berger et al., "Reverse Transcriptase and Its Associated Ribonuclease H: Interplay of Two Enzyme Activities Controls the Yield of Single-Stranded Complementary Deoxyribonucleic Acid," Biochemistry, May 1983, 22(10):2365-2372.
Berkhout et al., "Identification of an Active Reverse Transcriptase Enzyme Encoded by a Human Endogenous HERV-K Retrovirus," Journal of Virology, Mar. 1999, 73(3):2365-2375.

(56) References Cited

OTHER PUBLICATIONS

Beurdeley et al., "Compact Designer TALENs For Efficient Genome Engineering," Nature Communications, 2013, 4(1762):1-8.
Bianchi et al., "Mammalian fertilization: Does sperm IZUMO1 mediate fusion as well as adhesion?," Journal of Cell Biology, Feb. 2023, 222(2):e202301035, 2 pages.
Biswas et al., "A structural basis for allosteric control of DNA recombination by lambda integrase," Nature, Jun. 2005, 435(7045):1059-1066, 16 pages.
Blain et al., "Nuclease Activities of Moloney Murine Leukemia Virus Reverse Transcriptase," The Journal of Biological Chemistry, Nov. 1993, 268(31):23585-23592.
Bleker et al., "Mutational Analysis of Narrow Pores at the Fivefold Symmetry Axes of Adeno-associated Virus Type 2 Capsids Reveals a Dual Role in Genome Packaging and Activation of Phospholipase A2 Activity," Journal of Virology, Feb. 2005, 79(4):2528-2540.
Blond et al., "Molecular Characterization and Placental Expression of HERV-W, a New Human Endogenous Retrovirus Family," Journal of Virology, Feb. 1999, 73(2):1175-1185.
Boch et al., "Breaking the Code of DNA Binding Specificity of TAL-Type III Effectors," Science, Dec. 2009, 3126(5959):1509-1512.
Bogdanove et al., "TAL Effectors: Customizable Proteins for DNA Targeting," Science, Sep. 2011, 333(6051): 1843-1846.
Bojar et al., "Caffeine-inducible Gene Switches Controlling Experimental Diabetes," Nature Communications, Jun. 2018, 9(1):2318, 10 pages.
Böker et al., "The Impact of the CD9 Tetraspanin on Lentivirus Infectivity and Exosome Secretion," Molecular Therapy: the journal of the American Society of Gene Therapy, 2018, 26(2):634-647.
Bokhoven et al., "Insertional Gene Activation by Lentiviral and Gammaretroviral Vectors," Journal of Virology, Jan. 2009, 83(1):283-294.
Boller et al., "Human Endogenous Retrovirus HERV-K113 is Capable of Producing Intact Viral Particles," The Journal of General Virology, Mar. 2008, 89(Pt 2):567-572.
Bonnaud et al., "Evidence of Selection on the Domesticated ERVWEl env Retroviral Element Involved in Placentation," Molecular Biology and Evolution, Oct. 2004, 21(10):1895-1901.
Breakefield et al., "Gesicles: Microvesicle "Cookies" for Transient Information Transfer Between Cells," Molecular Therapy, 2011, 19(9):1574-1576.
Brown et al., "Serine Recombinases as Tools for Genome Engineering," Methods, Apr. 2011, 53(4):372-379.
Brown et al., "Structure-based Mutagenesis of the Human Immunodeficiency Virus Type 1 DNA Attachment Site: Effects on Integration and cDNA Synthesis," Journal of Virology, Nov. 1999, 73(11):9011-9020.
Buchwald et al., "Long-term, continuous intravenous heparin administration by an implantable infusion pump in ambulatory patients with recurrent venous thrombosis," Surgery, Oct. 1980, 88(4):507-516.
Burdick et al., "HIV-1 Uncoats in the Nucleus Near Sites of Integration," Proceedings of the National Academy of Sciences of the United States of America, Mar. 2020, 117(10):5486-5493.
Burke et al., "Activating Mutations of Tn3 Resolvase Marking Interfaces Important in Recombination Catalysis and its Regulation," Molecular Microbiology, 2004, 51:937-948.
Burstein et al., "New CRISPR-Cas systems from uncultivated microbes," Nature, Feb. 2017, 542(7640):237-241, 28 pages.
Byrne et al., "In Vivo-directed Evolution of Adeno-associated Virus in the Primate Retina," JCI Insight, May 2020, 5(10):e135112, 12 pages.
Cabeceiras et al., "Novel Humanized Particles for Efficient Delivery of CRISPR and Other Gene Editors," Poster, Presented at Proceedings of the American Society of Gene and Cell Therapy (ASGCT) 27th Annual Meeting, Nvelop Therapeutics, Baltimore, MD, May 9, 2024, 1 page.
Cabeceiras, Novel Extracellular Vesicle Modalities for Delivery of Genome Editor Ribonucleoprotein Complexes, Thesis for the degree of Doctor of Philosophy, Harvard University Graduate School of Arts and Sciences, Apr. 29, 2022, retrieved on Jun. 6, 2024, retrieved from URL<https://nrs.harvard.edu/URN-3:HUL.INSTREPOS:37372269>, 138 pages.
Cade et al., "Highly efficient generation of heritable zebrafish gene mutations using homo-and heterodimeric TALENs," Nucleic acids research, Sep. 2012, 40(16):8001-8010.
Cai et al., "Lentiviral Delivery of Proteins for Genome Engineering," Current Gene Therapy, 2016, 16:194-206.
Callahan et al., "Link Between Genome Packaging and Rate of Budding for Rous Sarcoma Virus," Journal of Virology, Sep. 2003, 77(17):9388-9398.
Carr et al., "Genome engineering," Nat Biotechnol., Dec. 2009, 27(12):1151-62.
Carroll, "Genome Engineering With Zinc-Finger Nucleases," Genet., Aug. 2011, 188(4):773-782.
Cermak et al., "Efficient Design and Assembly of Custom TALEN and Other TAL Effector-based Constructs for DNA Targeting," Nucleic Acids Research, 2011, 39(12):e82, 11 pages.
Cervera et al., "Generation of HIV-1 Gag VLPs by transient transfection of HEK 293 suspension cell cultures using an optimized animal-derived component free medium," Journal of biotechnology, Jul. 2013, 166(4):152-165.
Cervera-Carrascon et al., "Adenovirus armed with TNFa and IL2 added to aPD-1 regimen mediates antitumor efficacy in tumors refractory to aPD-1," Front. Immunol., 2021, 12:706517, 12 pages.
Chadwick et al., "In Vivo Base Editing of PCSK9 (Proprotein Convertase Subtilisin/Kexin Type 9) as a Therapeutic Alternative to Genome Editing," Arteriosclerosis, Thrombosis, and Vascular Biology, Sep. 2017, 37(9):1741-1747.
Chaikind et al., "A programmable Cas9-serine recombinase fusion protein that operates on DNA sequences in mammalian cells," Nucleic Acids Research, Nov. 2016, 44(20):9758-9770.
Chan et al., "Catalytic domain of restriction endonuclease BmrI as a cleavage module for engineering endonucleases with novel substrate specificities," Nucleic acids research, 2007, 35(18):6238-6248.
Chan et al., "Engineered AAVs for efficient noninvasive gene delivery to the central and peripheral nervous systems," Nature Neuroscience, 2017, 20(8):1172-1179, 27 pages.
Chen et al., "Decorating Chromatin for Enhanced Genome Editing using CRISPR-Cas9," Proceedings of the National Academy of Sciences of the United States of America, 2022, 119(49):1-9.
Chen et al., "Dynamic Imaging of Genomic Loci in Living Human Cells by an Optimized CRISPR/Cas System," Cell, Dec. 2013, 155(7):1479-1491.
Chen et al., "Enhanced Prime Editing Systems by Manipulating Cellular Determinants of Editing Outcomes," Cell, 2021, 184(22):5635-5652.el-e29.
Chen et al., "Enhanced proofreading governs CRISPR-Cas9 targeting accuracy," Nature, 2017, 550(7676):407-410, 25 pages.
Chen et al., "Fastp: an Ultra-Fast All-in-One FASTQ Preprocessor," Bioinformatics, 2018, 34(17):1884-1890.
Cheng et al., "New paradigms on hematopoietic stem cell differentiation," Protein Cell, 2020, 11(1):34-44.
Chua et al., "A novel platform for virus-like particle-display of flaviviral envelope domain III: induction of Dengue and West Nile virus neutralizing antibodies," Virology Journal, Apr. 2013, 10:129, 18 pages.
Chuang et al., "Points of View on the Tools for Genome/Gene Editing," International Journal of Molecular Sciences, 2021, 22(18):9872, 17 pages.
Chylinski et al., "The tracrRNA and Cas9 families of type II CRISPR-Cas immunity systems," RNA Biology, May 2013, 10(5):726-737.
Cideciyan, "Leber Congenital Amaurosis Due to RPE65 Mutations and Its Treatment with Gene Therapy," Progress in Retinal and Eye Research, Sep. 2010, 29(5):398-427.
Ciechonska et al., "Reovirus FAST proteins: virus-encoded cellular fusogens," Trends in Microbiology, 2014, 22(12):715-724.
Clement et al., "CRISPResso2 Provides Accurate and Rapid Genome Editing Sequence Analysis," Nature Biotechnology, Mar. 2019, 37(3):224-226.

(56) References Cited

OTHER PUBLICATIONS

ClinicalTrials.gov [online], "Identifier: NCT03872479. Single Ascending Dose Study in Participants With LCA10," record created Mar. 11, 2019, retrieved on Aug. 8, 2024, retrieved from URL<https://clinicaltrials.gov/study/NCT03872479?cond=NCT03872479&rank=1>, 13 pages.

Cocucci et al., "Ectosomes and Exosomes: Shedding the Confusion Between Extracellular Vesicles," Trends in Cell Biology, Jun. 2015, 25(6):364-372.

Cocucci et al., "Shedding microvesicles: artifacts no more," Trends Cell Biol., 2009, 19(2):43-51.

Cohen et al., "Low LDL Cholesterol in Individuals of African Descent Resulting from Frequent Nonsense Mutations in PCSK9," Nature Genetics, Feb. 2005, 37(2):161-165.

Cohen et al., "Sequence Variations in PCSK9, Low LDL, and Protection Against Coronary Heart Disease," The New England Journal of Medicine, Mar. 2006, 354:1264-1272.

Cooper et al., "Safety-Modified Episomal Vectors For Human Gene Therapy," Proceedings of the National Academy of Sciences of the United States of America, Jun. 1997, 94(12):6450-6455.

Coquin, "Characterization of lentiviral vectors pseudotyped with murine syncytins and their cellular targets in vitro and in vivo," Thesis for the degree of Doctor of Philosophy, University of Évry Val d'Essonne, Defense on Dec. 10, 2019, 238 pages (with English abstract).

Cornelis et al., "Retro-viral envelope gene captures and syncytin exaptation for placentation in marsupials, " PNAS USA, 2015, 112:E487-E496.

Cosset et al., "Retroviral retargeting by envelopes expressing an N-terminal binding domain," Journal of Virology, 1995, 69(10):6314-6322.

Costa et al., "Optimal Design, Anti-tumour Efficacy and Tolerability of Anti-CXCR4 Antibody Drug Conjugates," Scientific Reports, 2019, 9(1):2443, 19 pages.

Craigie, "The Molecular Biology of HIV Integrase," Future Virology, 2012, 7(7):679-686.

Curley et al., "Sequential Deletion of CD63 Identifies Topologically Distinct Scaffolds for Surface Engineering of Exosomes in Living Human Cells," Nanoscale, Jun. 2020, 12(22):12014-12026.

Czechowicz et al., "Selective hematopoietic stem cell ablation using CD117-antibody-drug-conjugates enables safe and effective transplantation with immunity preservation," Nature Communications, 2019, 10(1):617, 12 pages.

Dabrowski et al., "The Human Herpes-Virus Proteases. In: Proteases as Targets for Therapy," Handbook of Experimental Pharmacology, 2000, 140:95-115.

Dalkara et al., "In Vivo-Directed Evolution of a New Adeno-Associated Virus for Therapeutic Outer Retinal Gene Delivery from the Vitreous," Science Translational Medicine, 2013, 5(189): 12 pages.

Das et al., "The Crystal Structure of the Monomeric Reverse Transcriptase from Moloney Murine Leukemia Virus," Structure, May 2004, 12(5):819-29.

Davis et al., "Efficient in Vivo Base Editing via Single Adeno-associated Viruses With Size-optimized Genomes Encoding Compact Adenine Base Editors," Nature biomedical engineering, 2022, 6(11):1272-1283.

Davis et al., "Efficient prime editing in mouse brain, liver and heart with dual AAVs," Nature biotechnology, 2024, 42(2):253-264.

Davis et al., "Small Molecule-triggered Cas9 Protein with Improved Genome-editing Specificity," Nature Chemical Biology, 2015, 11:316-318, 9 pages.

De León Vázquez et al., "A Short Sequence Immediately Upstream Of The Internal Repeat Elements Is Critical For KSHV LANA Mediated DNA Replication And Impacts Episome Persistence," Virology, Jan. 2014, 448:344-355.

Delebecque et al., "Organization of intracellular reactions with rationally designed RNA assemblies," Science, 2011, 333(6041):470-474.

Delenda et al., "Real-time Quantitative PCR for the Design of Lentiviral Vector Analytical Assays," Gene Therapy, 2005, 12(Suppl 1):S36-S50.

Deltcheva et al., CRISPR RNA maturation by trans-encoded small RNA and host factor RNase III, Nature, Mar. 2011, 471(7340):602-607, 19 pages.

den Hollander et al., "Leber Congenital Amaurosis: Genes, Proteins and Disease Mechanisms," Progress in Retinal and Eye Research, 2008, 27(4):391-419.

DePolo et al., "VSV-G Pseudotyped Lentiviral Vector Particles Produced in Human Cells Are Inactivated by Human Serum," Molecular Therapy: the Journal of the American Society of Gene Therapy, 2000, 2(3):218-222.

Desjarlais et al., "Use of a zinc-finger consensus sequence framework and specificity rules to design specific DNA binding proteins," PNAS, Mar. 1993, 90:2256-2260.

Dewannieux et al., "Identification of a Functional Envelope Protein From the HERV-K Family of Human Endogenous Retroviruses," Journal of Virology, Dec. 2005, 79(24):15573-15577.

Dilley et al., "An LYSPL Late Domain in the Gag Protein Contributes to the Efficient Release and Replication of Rous Sarcoma Virus," Journal of Virology, 2010, 84(13):6276-6287.

Dingwall et al., "Nuclear targeting sequences—a consensus?," Trends in biochemical sciences, Dec. 1991, 16(12):478-481.

Doman et al., "Evaluation and Minimization of Cas9-independent off-target DNA Editing by Cytosine base Editors," Nature Biotechnology, 2020, 38:620-628.

Donaldson et al., "ARF family G proteins and their regulators: roles in membrane transport, development and disease," Nat Rev Mol Cell Biol., Jun. 2011, 12(6): 362-75; Erratum in: Nat Rev Mol Cell Biol., 2011, 12(8):533.

Doudna, "Hammering Out the Shape of a Ribozyme," Structure, 1994, 2(12):1271-1272.

Dreja et al., "The Effects of N-terminal Insertion into VSV-G of an scFv Peptide," Virology Journal, 2006, 3:69, 8 pages.

D'Souza et al., "Structural Basis for Packaging the Dimeric Genome of Moloney Murine Leukaemia Virus," Nature, 2004, 431(7008):586-590.

Dubridge et al., "Analysis of Mutation in Human Cells by Using an Epstein-Barr Virus Shuttle System," Molecular and Cellular Biology, 1987, 7(1):379-387.

Duchon et al., "Plasma Membrane Anchoring and Gag:Gag Multimerization on Viral RNA Are Critical Properties of HIV-1 Gag Required to Mediate Efficient Genome Packaging," mBio, 2021, 12(6):e0325421, 17 pages.

Dudek et al., "GPR108 Is a Highly Conserved AAV Entry Factor," Molecular therapy: the journal of the American Society of Gene Therapy, 2020, 28(2):367-381.

Duncan, "Fusogenic Reoviruses and Their Fusion-Associated Small Transmembrane (FAST) Proteins," Annual Review of Virology, 2019, 6(1):341-363.

Durai et al., "Zinc finger nucleases: custom-designed molecular scissors for genome engineering of plant and mammalian cells," Nucleic Acids Research, 2005, 33(18):5978-5990.

During et al., "Controlled release of dopamine from a polymeric brain implant: In vivo characterization," Ann. Neurol., 1989, 25:351-356.

East-Seletsky et al., "Two distinct Rnase activities of CRISPR-C2c2 enable guide-RNA processing and RNA detection," Nature, Oct. 2016, 538(7624):270-273, 26 pages.

Ecker et al., "High-Yield Expression and Purification of Recombinant Influenza Virus Proteins from Stably-Transfected Mammalian Cell Lines," Vaccines, 2020, 8(3):462, 20 pages.

Eidelman et al., "pH-dependent Fusion Induced by Vesicular Stomatitis Virus Glycoprotein Reconstituted Into Phospholipid Vesicles," The Journal of Biological Chemistry, 1984, 259(7):4622-4628.

Evans et al., "Protein trans-Splicing and Cyclization by a Naturally Split Intein from the dnaE Gene of Synechocystis Species PCC6803," Journal of Biological Chemistry, 2000, 275(13):9091-9094.

Evans et al., "Restriction digest screening facilitates efficient detection of site-directed mutations introduced by CRISPR in C. *albicans UME6*," PeerJ, Jun. 2018, 6:e4920, 13 pages.

(56) References Cited

OTHER PUBLICATIONS

Evans, "The Rise of Azide-Alkyne 1,3-Dipolar 'Click' Cycloaddition and its Application to Polymer Science and Surface Modification," Australian Journal of Chemistry, 2007, 60(6):384-395.
Farsani et al., "Identification of a novel human rhinovirus C type by antibody capture VIDISCA-454," Viruses, 2015, 7(1):239-251.
Feldman et al., "Lentiviral Co-packaging Mitigates the Effects of Intermolecular Recombination and Multiple Integrations in Pooled Genetic Screens," bioRxiv, posted Feb. 8, 2018, 6 pages.
Fenard et al., "Vectofusin-1, a New Viral Entry Enhancer, Strongly Promotes Lentiviral Transduction of Human Hematopoietic Stem Cells," Molecular Therapy Nucleic Acids, 2013, 2(5):e90, 10 pages.
Feng et al., "Human L1 Retrotransposon Encodes a Conserved Endonuclease Required for Retrotransposition," Cell, 1996, 87(5):905-916.
Ferré-D'Amaré et al., "Crystal Structure of a Hepatitis Delta Virus Ribozyme," Nature, 1998, 395(6702):567-574.
Ferretti et al., "Complete genome sequence of an M1 strain of *Streptococcus pyogenes*," Proc. Natl. Acad. Sci. USA, 2001, 98(8):4658-4663.
Fielding et al., "Inverse Targeting of Retroviral Vectors: Selective Gene Transfer in a Mixed Population of Hematopoietic and Nonhematopoietic Cells," Blood, 1998, 91(5):1802-1809.
Fitzgerald et al., "Effect of an RNA Interference Drug on the Synthesis of Proprotein Convertase Subtilisin/kexin Type 9 (PCSK9) and the Concentration of Serum LDL Cholesterol in Healthy Volunteers: A Randomised, Single-blind, Placebo-Controlled, Phase 1 Trial," Lancet, 2014, 383:60-68.
Fitzgerald et al., "Exploiting Highly Ordered Subnanoliter Volume Microcapillaries as Microtools for the Analysis of Antibody Producing Cells," Anal Chem., 2014, 87:997-1003.
Flajolet et al., "Woodchuck Hepatitis Virus Enhancer I and Enhancer II Are Both Involved in N-myc2 Activation in Woodchuck Liver Tumors," Journal of Virology, 1998, 72(7):6175-80.
Flockerzi et al., "Expression Patterns of Transcribed Human Endogenous Retrovirus HERV-K(HML-2) Loci in Human Tissues and the Need for a HERV Transcriptome Project," BMC Genomics, 2008, 9:354, 17 pages.
Fontana et al., "Rabies Virus-like Particles Expressed in HEK293 Cells," Vaccine, 2014, 32(24):2799-2804.
Frappier, "The Epstein-Barr Virus EBNA1 Protein," Scientifica, 2012, 2012:438204, 15 pages.
Frietze et al., "Peabody, and Bryce Chackerian Engineering Virus-like Particles as Vaccine Platforms," Current opinion in virology, 2016, 18:44-46.
Fujiwara et al., "Hinge and Transmembrane Domains of Chimeric Antigen Receptor Regulate Receptor Expression and Signaling Threshold," Cells, May 2020, 9(5):1182, 17 pages.
Fung et al., "Structural determinants of nuclear export signal orientation in binding to exportin CRM1," eLife, Sep. 2015, 4:e10034, 19 pages.
Gadok et al., "Connectosomes for Direct Molecular Delivery to the Cellular Cytoplasm," Journal of the American Chemical Society, 2016, 138(39):12833-12840.
Gaj et al., "Structure-guided Reprogramming of Serine Recombinase DNA sequence specificity," Proceedings of the National Academy of Sciences of the United States of America, 2011, 108(2):498-503.
Gaj et al., "Targeted Gene Knockout By Direct Delivery Of Zinc-finger Nuclease Proteins," Nature Methods, 2012, 9(8):805-7, 10 pages.
Gaj et al., "ZFN, TALEN, and CRISPR/CAS-based methods for genome engineering," Trends in Biotechnology, 2013, 31:397-405.
Gallardo et al., "Recombinant Retroviruses Pseudotyped With the Vesicular Stomatitis Virus G Glycoprotein Mediate Both Stable Gene Transfer and Pseudotransduction in Human Peripheral Blood Lymphocytes," Blood, 1997, 90(3):952-957.
Gao et al., "A truncated reverse transcriptase enhances prime editing by split AAV vectors," Molecular Therapy, 2022, 30(9):2942-2951.
Gao et al., "DNA-guided genome editing using the Natronobacterium gregoryi Argonaute," Nature Biotechnology, 2016, 34(7):768-773, 27 pages.
Garneau et al., "The CRISPR/Cas bacterial immune system cleaves bacteriophage and plasmid DNA," Nature, 2010, 468(7320):67-71.
Gasiunas et al., "Cas9-crRNA Ribonucleoprotein complex Mediates specific DNA cleavage for Adaptive Immunity in Bacteria," Proceedings of the National Academy of Sciences of the United States of America, 2012, 109(39):E2579-E2586.
Gaudelli et al., "Directed Evolution of Adenine Base Editors with Increased Activity and Therapeutic Application," Nature Biotechnology, 2020, 38(7):892-900.
Gehrke et al., "An APOBEC3A-Cas9 base Editor with Minimized Bystander and off-target Activities," Nature Biotechnology, 2018, 36(10):977-982.
Gentili et al., "Transmission of Innate Immune Signaling by Packaging of cGAMP in Viral Particles," Science, 2015, 349(6253):1232-1236.
Gerard et al., "Influence on stability in *Escherichia coli* of the carboxy-terminal structure of cloned Moloney murine leukemia virus reverse transcriptase," DNA, 1986, 5(4):271-279.
Gerard, "The role of template-primer in protection of reverse transcriptase from thermal inactivation," Nucleic acids research, 2002, 30(14):3118-3129.
Gerbaud et al., "Review: an Overview of Molecular Events Occurring in Human Trophoblast Fusion," Placenta, 2015, 36(Suppl 1):S35-S42.
Giannoukos et al., "UDiTaS, A Genome Editing Detection Method for Indels and Genome Rearrangements," BMC Genomics, 2018, 19:212, 10 pages.
Gill et al., "Optimized Transgene Delivery Using Third-Generation Lentiviruses," Current Protocols in Molecular Biology, 2020, 133(1):e125, 21 pages.
GitHub.com [online], "CRISPResso2," retrieved on Aug. 9, 2024, retrieved from URL<github.com/pinellolab/CRISPResso2>, 4 pages.
Golczak et al., "Importance of Membrane Structural Integrity for RPE65 Retinoid Isomerization Activity," Journal of Biological Chemistry, 2010, 285(13):9667-9682.
González-Domínguez et al., "A Four-Step Purification Process for Gag VLPs: From Culture Supernatant to High-Purity Lyophilized Particles," Vaccines, 2021, 9(10):1154, 19 pages.
Gordley et al., "Evolution of Programmable Zinc Finger-Recombinases with activity in Human Cells, " Journal of Molecular Biology, 2007, 367:802-813.
Gordley et al., "Synthesis of Programmable Integrases," Proceedings of the National Academy of Sciences of the United States of America, 2009, 106:5053-5058.
Gorelick et al., "Characterization of the Block in Replication of Nucleocapsid Protein Zinc Finger Mutants From Moloney Murine Leukemia Virus," Journal of virology, 1999, 73(10):8185-8195.
Graham et al., "Characteristics of a Human Cell line Transformed by DNA from Human Adenovirus type 5," Journal of General Virology, 1977, 36(1):59-72.
Gray et al., "HIV-1 Rev Interacts with HERV-K RcREs Present in the Human Genome and Promotes Export of Unspliced HERV-K Proviral RNA," Retrovirology, 2019, 16(1):40, 17 pages.
Greig et al., "Integrated Vector Genomes May Contribute to Long-term Expression in Primate Liver After AAV Administration," Nature biotechnology, 2023, 11 pages.
Grieger et al., "Surface-exposed Adeno-associated Virus Vp1-NLS Capsid Fusion Protein Rescues Infectivity of Noninfectious Wild-type Vp2/Vp3 and Vp3-only Capsids but not that of Fivefold Pore Mutant Virions," Journal of Virology, 2007, 81(15):7833-7843.
Grindley et al., "Mechanism of site-specific Recombination," Annual Review of Biochemistry, 2006, 75:567-605.
Gröger et al., "Formation of HERV-K and HERV-Fcl Envelope Family Members is Suppressed on Transcriptional and Translational Level," International Journal of Molecular Sciences, 2020, 21(21):7855, 23 pages.
Groot et al., "The role of Adams in Notch signaling," Adv Exp Med Biol., 2012, 727:15-36, 25 pages.
Groth et al., "Phage Integrases: Biology and Applications," Journal of Molecular Biology, 2004, 335(3):667-678.

(56) References Cited

OTHER PUBLICATIONS

Gruber et al., "The Vienna RNA Websuite," Nucleic Acids Research, 2008, 36(Web Server issue):W70-W74.
Grünewald et al., "A Dual-deaminase CRISPR Base Editor Enables Concurrent Adenine and Cytosine Editing," Nature Biotechnology, 2020, 38(7):861-864, 22 pages.
Grünewald et al., "Transcriptome-wide off-target RNA Editing Induced by CRISPR-guided DNA Base Editors," Nature, 2019, 569(7756):433-437.
Guerrerio et al., "Design of single-stranded nucleic acid binding peptides based on nucleocapsid CCHC-box zinc-binding domains," Journal of the American Chemical Society, 2010, 132(28):9638-9643.
Guha et al., "Programmable genome editing tools and their regulation for efficient genome engineering," Computational and Structural Biotechnology Journal, Jan. 2017, 15:146-160.
Guibinga et al., "Cell Surface Heparan Sulfate is a Receptor for Attachment of Envelope Protein-free Retrovirus-like Particles and VSV-G Pseudotyped M1v-derived Retrovirus Vectors to Target Cells," Molecular Therapy, 2002, 5(5):538-546.
Guilinger et al., "Fusion of catalytically inactive Cas9 to FokI nuclease improves the specificity of genome modification," Nature biotechnology, 2014, 32(6):577-582, 17 pages.
Gulen, "Inside Job: Viruses Transfer cGAMP between Cells," Cell Host Microbe, 2015, 18(3):263-265.
Guo et al., "CXCL12/CXCR4: a symbiotic bridge linking cancer cells and their stromal neighbors in oncogenic communication networks," Oncogene, 2016, 35(7):816-826.
Guo et al., "Structure of Cre Recombinase Complexed with DNA in a Site-specific Recombination Synapse," Nature, 1997, 389(6646):40-46.
Gutierrez-Guerrero et al., "Baboon Envelope Pseudotyped "Nanoblades" Carrying Cas9/gRNA Complexes Allow Efficient Genome Editing in Human T, B, and CD34$^{+}$Cells and Knock-in of AAV6-Encoded Donor DNA in CD34$^{+}$Cells," Front Genome Ed., Feb. 2021, 3:6043, 21 pages.
Gutierrez-Guerrero et al., "Lentiviral vector pseudotypes: precious tools to improve gene modification of hematopoietic cells for research and gene therapy," Viruses, 2020, 12(9):1016, 20 pages.
Gutkin et al., "RNA Delivery with a Human Virus-like Particle," Nature Biotechnology, 2021, 39(12):1514-1515.
György et al., "Extracellular vesicles: nature's nanoparticles for improving gene transfer with adeno-associated virus vectors," WIRES Nanomedicine and Nanobiotechnology, 2018, 10(3):e1488, 13 pages.
Haldrup et al., "Engineered Lentivirus-derived Nanoparticles (LVNPs) for Delivery of CRISPR/Cas Ribonucleoprotein Complexes Supporting Base Editing, Prime Editing and in Vivo Gene Modification," Nucleic acids research, 2023, 51(18):10059-10074.
Halvas et al., "Role of Murine Leukemia Virus Reverse Transcriptase Deoxyribonucleoside Triphosphate-binding Site in Retroviral Replication and in Vivo Fidelity," Journal of Virology, 2000, 74(22):10349-10358.
Hamilton et al., "Cell Type-programmable Genome Editing With Enveloped Delivery Vehicles," bioRxiv, posted Aug. 24, 2022, 22 pages.
Hamilton et al., "Knocking Out Barriers to Engineered Cell Activity," Science, 2020, 367(6481):976-977.
Hamilton et al., "Programmable enveloped delivery vehicles for human genome engineering in vivo," bioRxiv, posted Apr. 2, 2023, 21 pages.
Hamilton et al., "Targeted delivery of CRISPR-Cas9 and transgenes enables complex immune cell engineering," Cell Rep., Jun. 2021, 35(9):109207, 17 pages.
Hanlon et al., "High Levels of AAV Vector Integration into CRISPR-induced DNA Breaks," Nature communications, 2019, 10(1):4439, 11 pages.
Hare et al., "A novel co-crystal structure affords the design of gain-of-function lentiviral integrase mutants in the presence of modified PSIP1/LEDGF/p75," PLoS Pathog., Jan. 2009, 5(1):e1000259, 12 pages.
Harrington et al., "Programmed DNA Destruction by Miniature CRISPR-Cas14 Enzymes," Science, 2018, 362(6416):839-842, 12 pages.
Hartung et al., "Cre Mutants with altered DNA Binding Properties," Journal of Biological Chemistry, 1998, 273:22884-22891.
Havecker et al., "The Diversity of LTR Retrotransposons," Genome Biology, 2004, 5:225, 6 pages.
Hellmund et al., "Coordination of Genomic RNA Packaging With Viral Assembly in HIV-1," Viruses, 2016, 8(7):192, 13 pages.
Henderson et al., "Gag proteins of the highly replicative MN strain of human immunodeficiency virus type 1: posttranslational modifications, proteolytic processings, and complete amino acid sequences," Journal of virology, 1992, 66(4):1856-1865.
Heng et al., "Chromatin Loops are Selectively Anchored using Scaffold/matrix-attachment Regions," Journal of Cell Science, 2004, 117(Pt 7):999-1008.
Herbst-Kralovetz et al., "Norwalk Virus-like Particles as Vaccines," Expert review of vaccines, 2010, 9(3):299-307.
Herschhorn et al., "Retroviral reverse transcriptases," Cellular and molecular life sciences, 2010, 67(16):2717-2747.
Herzig et al., "A Novel Leu92 Mutant of HIV-1 Reverse Transcriptase with a Selective Deficiency in Strand Transfer Causes a Loss of Viral Replication," Journal of virology, 2015, 89(16):8119-8129.
Hindi et al., Enveloped viruses pseudotyped with mammalian myogenic cell fusogens target skeletal muscle for gene delivery, Cell, 2023, 186(10):2062-2077.
Hirano et al., "Highly Efficient Retrograde Gene Transfer Into Motor Neurons by a Lentiviral Vector Pseudotyped With Fusion Glycoprotein," PloS One, 2013, 8(9):e75896, 8 pages.
Hirano et al., "Site-specific Recombinases as Tools for Heterologous Gene Integration," Applied Microbiology and Biotechnology, 2011, 92(2):227-239.
HLA-Ligand-Atlas.org [online], "HLA Ligand Atlas—University of Tübingen. Interface Release 0.9.16," Apr. 23, 2021, retrieved on Mar. 12, 2024, retrieved from URL<https://hla-ligand-atlas.org/welcome>, 2 pages.
Ho et al., "Decoupling the Functional Pleiotropy of Stem Cell Factor by Tuning c-Kit Signaling," Cell, 2017, 168(6):1041-1052.e18.
Hohn et al., "CMV-promoter Driven Codon-optimized Expression Alters the Assembly Type and Morphology of a Reconstituted HERV-k(HML-2)," Viruses, 2014, 6(11):4332-4345.
Hong et al., "Novel Recombinant Hepatitis B Virus Vectors Efficiently Deliver Protein and RNA Encoding Genes Into Primary Hepatocytes," Journal of virology, 2013, 87(12):6615-6624.
Hooper et al., The C679X mutation in PCSK9 is Present and Lowers Blood Cholesterol in a Southern African Population, Atherosclerosis, 2007, 193:445-448.
Hou et al., Lipid nanoparticles for mRNA delivery, Nature Reviews Materials, 2021, 6:1078-1094.
Howard et al., "Intracerebral Drug Delivery in Rats With Lesion-induced Memory Deficits," Journal of Neurosurgery, 1989, 71(1):105-112.
Howe et al., "Insertional Mutagenesis Combined with Acquired Somatic Mutations Causes Leukemogenesis Following Gene Therapy of SCID-X1 Patients," Journal of Clinical Investigation, 2008, 118(9):3143-3150.
Hsu et al., "PrimeDesign Software for Rapid and Simplified Design of Prime Editing Guide RNAs," Nature Communications, 2021, 12:1034, 6 pages.
Hu et al., HIV-1 Reverse Transcription. Cold Spring Harbor Perspectives in Medicine, 2012, 2(10):a006882, 23 pages.
Huang et al., "Circularly Permuted and PAM-modified Cas9 Variants Broaden the Targeting Scope of Base Editors," Nature Biotechnology, 2019, 37(6):626-631.
Huang et al., "Precision genome editing using cytosine and adenine base editors in mammalian cells," Nature Protocols, 2021, 16(2):1089-1128.
Hug et al., "Fusogenic Virosomes Prepared by Partitioning of Vesicular Stomatitis Virus G Protein Into Preformed Vesicles," The Journal of Biological Chemistry, 1994, 269(6):4050-4056.
Humbel et al., "Maximizing lentiviral vector gene transfer in the CNS," Gene Ther, 2021, 28:75-88.

(56) References Cited

OTHER PUBLICATIONS

Humbert et al., "Development of Third-generation Cocal Envelope Producer Cell Lines for Robust Lentiviral Gene Transfer Into Hematopoietic Stem Cells and T-cells," Molecular therapy: the Journal of the American Society of Gene Therapy, 2016, 24(7):1237-1246.
Hwang et al., "Engineering a Serum-resistant and Thermostable Vesicular Stomatitis Virus G Glycoprotein for Pseudotyping Retroviral and Lentiviral Vectors," Gene Therapy, 2013, 20(8):807-815.
Hwang et al., "Lineage tracing using a Cas9-deaminase barcoding system targeting endogenous L1 elements," Nature Communication, 2019, 10:1234, 9 pages.
ICTV.Global [online], "International Committee on Taxonomy of Viruses (ICTV). Genus: Vesiculovirus," accessed Jun. 2023, retrieved from URL<https://ictv.global/report/chapter/rhabdoviridae/rhabdoviridae/vesiculovirus>, 10 pages.
Indikova et al., "Highly efficient 'hit-and-run' genome editing with unconcentrated lentivectors carrying Vpr.Prot. Cas9 protein produced from RRE—containing transcripts," Nucleic Acids Res, 2020, 48:8178-8187.
Ioannidi et al., "Drag-and-drop genome insertion without DNA cleavage with CRISPR-directed integrases," bioRxiv, posted on Nov. 1, 2021, retrieved from URL<https://www.biorxiv.org/content/10.1101/2021.11.01.466786v1>, 61 pages.
Irion et al., "Identification and targeting of the ROSA26 locus in human embryonic stem cells," Nature Biotechnology, 2007, 25:1477-1482.
Iwai et al., "Highly Efficient Protein Trans-splicing by a Naturally Split DnaE Intein From Nostoc Punctiforme," FEBS letters, 2006, 580(7):1853-1858.
Jacobs, "Determination of the base recognition positions of zinc fingers from sequence analysis," EMBO Journal, 1992, 11(12):4507-4517.
Jang et al., "High-purity Production and Precise Editing of DNA base Editing Ribonucleoproteins," Science Advances, 2021, 7(35):eabg2661, 11 pages.
Jenke et al., "Nuclear Scaffold/matrix Attached Region Modules Linked to a Transcription Unit are Sufficient for Replication and Maintenance of a Mammalian Episome," Proc Natl Acad Sci USA, 2004, 101(31):11322-11327.
Jensen et al., "Proteases of human rhinovirus: role in infection," Methods in Molecular Biology, 2015, 1221:129-141.
Jern et al., "Use of Endogenous Retroviral Sequences (ERVs) and Structural Markers for Retroviral Phylogenetic Inference and Taxonomy," Retrovirology, 2005, 2:50, 12 pages.
Jha et al., "Human Endogenous Retrovirus K106 (HERV-K106) Was Infectious After the Emergence of Anatomically Modern Humans, " PLoS One, 2011, 6(5):e20234, 8 pages.
Jiang et al., "An Optimized Method for High-titer Lentivirus Preparations Without Ultracentrifugation," Scientific Reports, 2015, 5:13875, 9 pages.
Jiang et al., "RNA-guided Editing of Bacterial Genomes using CRISPR-Cas Systems," Nature Biotechnology, 2013, 31:233-239.
Jin et al., "Safe Engineering of CAR T Cells for Adoptive Cell Therapy of Cancer Using Long-term Episomal Gene Transfer," EMBO Molecular Medicine, 2016, 8(7):702-711.
Jinek et al., "A Programmable dual-RNA-guided DNA Endonuclease in adaptive Bacterial Immunity," Science, 2012, 337(6096):816-821.
Jo et al., "Deactivation of Akt by a Small Molecule Inhibitor Targeting Pleckstrin Homology Domain and Facilitating Akt Ubiquitination," Proceedings of the National Academy of Sciences of the United States of America, 2011, 108(16):6486-6491.
Jo et al., "Therapeutic Adenine base Editing Corrects Nonsense Mutation and Improves Visual Function in a Mouse Model of Leber Congenital Amaurosis," bioRxiv, posted on Jan. 8, 2021, 19 pages.
Johansson et al., "RNA Recognition by the MS2 Phage Coat Protein," Seminars in Virology, 1997, 8(3):176-185.
Johnson, "Origins and Evolutionary Consequences of Ancient Endogenous Retroviruses," Nature Reviews Microbiology, 2019, 17(6):355-370.
Jorgenson et al., "Foreign Glycoproteins Can Be Actively Recruited to Virus Assembly Sites During Pseudotyping," Journal of Virology, 2009, 83(9):4060-4067.
Joung et al., "TALENs: A Widely Applicable Technology for Targeted Genome Editing," Nature Reviews Molecular Cell Biology, 2013, 14(1):49-55.
June et al., "CAR T Cell Immunotherapy For Human Cancer," Science, 2018, 359(6382):1361-1365.
Kaczorowska et al., "Human Anelloviruses: Diverse, Omnipresent and Commensal Members of the Virome," FEMS Microbiology Reviews, 2020, 44(3):305-313.
Kanai et al., "FAST Proteins: Development and Use of Reverse Genetics Systems for Reoviridae Viruses," Annual Reviews, The Annual Review of Virology, 2021, 8:515-536.
Kang et al., "Chimeric Rabies Virus-like Particles Containing Membrane-anchored GM-CSF Enhances the Immune Response Against Rabies Virus," Viruses, 2015, 7(3):1134-1152.
Kang et al., "Increased Intracellular $Ca^{2+}$ Concentrations Prevent Membrane Localization of Ph Domains Through the Formation of $Ca^{2+}$-phosphoinositides," Proceedings of the National Academy of Sciences of the United States of America, 2017, 114(45):11926-11931.
Kannan et al., "Compact RNA Editors with Small Cas13 Proteins," Nature Biotechnology, 2021, 40(2):194-197.
Karikó et al., "Incorporation of Pseudouridine into mRNA Yields Superior Nonimmunogenic Vector with Increased Translational Capacity and Biological Stability," Molecular therapy, 2008, 16(11):1833-1840.
Karimova et al., "CRISPR/Cas9 nickase-mediated disruption of hepatitis B virus open reading frame S and X," Sci Rep., Sep. 2015, 5:13734, 16 pages.
Karpenshif et al., "From yeast to mammals: Recent Advances in Genetic control of Homologous Recombination," DNA Repair (Amst), 2012, 11(10):781-788, 16 pages.
Katane et al., "Factors Affecting the Direct Targeting of Murine Leukemia Virus Vectors Containing Peptide Ligands in the Envelope Protein," European Molecular Biology Organization Reports, 2002, 3(9):899-904.
Kato et al., "A lentiviral strategy for highly efficient retrograde gene transfer by pseudotyping with fusion envelope glycoprotein," Human gene therapy, 2011, 22(2):197-206.
Kato et al., "Enhancement of the Transduction Efficiency of a Lentiviral Vector for Neuron-specific Retrograde Gene Delivery Through the Point Mutation of Fusion Glycoprotein Type E," Journal of Neuroscience Methods, 2019, 311:147-155.
Kato et al., "Selective Neural Pathway Targeting Reveals Key Roles of Thalamostriatal Projection in the Control of Visual Discrimination," The Journal of Neuroscience, 2011, 31:17169-17179.
Katz et al., "Membrane Assembly in Vitro: Synthesis, Glycosylation, and Asymmetric Insertion of a Transmembrane Protein," Proceedings of the National Academy of Sciences of the United States of America, 1977, 74(8):3278-3282.
Keijzers et al., "Human Exonuclease 1 (EXO1) Activity Characterization and Its Function on Flap Structures," Bioscience reports, 2015, 35(3):e00206, 13 pages.
Kilbride et al., "Determinants of product topology in a hybrid Cre-Tn3 resolvase site-specific recombination system," J Mol Bio, 2006, 355:185-195.
Kim et al., "Enhancement Of Protein Expression By Alphavirus Replicons By Designing Self-replicating Subgenomic RNAs," Proceedings of the National Academy of Sciences of the United States of America, 2014, 111(29):10708-10713.
Kim et al., "Increasing The Genome-targeting Scope And Precision Of Base Editing With Engineered Cas9-cytidine Deaminase Fusions," Nature Biotechnology, 2017, 35(4):371-376, 15 pages.
Kim et al., "Mechanism Of Membrane Fusion Induced By Vesicular Stomatitis Virus G Protein," Proceedings of the National Academy of Sciences of the United States of America, 2017, 114(1):E28-E36.

(56) References Cited

OTHER PUBLICATIONS

Kim et al., "Mutational Analysis of Oncogenic Akt E17K Mutation in Common Solid Cancers and Acute Leukaemias," British Journal of Cancer, 2008, 98(9):1533-1535.
Kim et al., "Precision genome engineering with programmable DNA-nicking enzymes," Genome Res., 2012, 22(7):1327-33.
Kisielow et al., "Deciphering CD4+ T cell specificity using novel MHC-TCR chimeric receptors," Nature Immunology, 2019, 20:652-662.
Kitamura et al., "Human Endogenous Retrovirus K10 Encodes a Functional Integrase," Journal of Virology, 1996, 70(5):3302-3306.
Klehr et al., "Scaffold-attached Regions from the Human Interferon Beta Domain can be used to Enhance the Stable Expression of Genes Under the Control of Various Promoters," Biochemistry, 1991, 30(5):1264-1270.
Kleinstiver et al., "Engineered CRISPR-Cas12a Variants With Increased Activities and Improved Targeting Ranges for Gene, Epigenetic and Base Editing," Nature Biotechnology, 2019, 37(3):276-282.
Kleinstiver et al., "High-fidelity CRISPR-Cas9 Nucleases With No Detectable Genome-wide Off-target Effects," Nature, 2016, 529(7587):490-495.
Klingler et al., "How HIV-1 Gag Manipulates Its Host Cell Proteins: A Focus on Interactors of the Nucleocapsid Domain," Viruses, Aug. 2020, 12(8):888, 42 pages.
Klippel et al., "Isolation and Characterization of Unusual Gin Mutants," The EMBO journal, 1988, 7(12):3983-3989.
Koblan et al., "Improving Cytidine and Adenine Base Editors by Expression Optimization and Ancestral Reconstruction," Nature Biotechnology, 2018, 36(9): 843-846, 4 pages.
Koblan et al., "In vivo Base Editing Rescues Hutchinson-Gilford Progeria Syndrome in Mice," Nature, 2021, 589:608-614.
Kohn et al., "Akt, A Pleckstrin Homology Domain Containing Kinase, is Activated Primarily by Phosphorylation," Journal of Biological Chemistry, 1996, 271(36):21920-21926.
Kolb et al., "Click Chemistry: Diverse Chemical Function from a Few Good Reactions," Angewandte Chemie, 2001, 40(11):2004-2021.
Kolykhalov et al., "Specificity of the hepatitis C virus NS3 serine protease: effects of substitutions at the 3/4A, 4A/4B, 4B/5A, and 5A/5B cleavage sites on polyprotein processing," Journal of Virology, 1994, 68(11):7525-7233.
Komor et al., "Improved Base Excision Repair Inhibition and Bacteriophage Mu Gam Protein Yields C:g-to-t:a Base Editors With Higher Efficiency and Product Purity," Science Advances, 2017, 3(8):eaao4774, 9 pages.
Kosicki et al., "Repair of Double-strand Breaks Induced by CRISPR-Cas9 Leads to Large Deletions and Complex Rearrangements," Nature Biotechnology, 2018, 36(8):765-771, 16 pages.
Kosugi et al., "Nuclear Export Signal Consensus Sequences Defined Using a Localization-based Yeast Selection System," Traffic, 2008, 9(12):2053-2062.
Kotewicz et al., "Cloning and Overexpression of Moloney Murine Leukemia Virus Reverse Transcriptase in *Escherichia Coli*," Gene, 1985, 35(3):249-258.
Kotewicz et al., "Isolation of Cloned Moloney Murine Leukemia Virus Reverse Transcriptase Lacking Ribonuclease H Activity," Nucleic acids research, 1988, 16(1):265-277.
Kronenberg et al., "A Conformational Change in the Adeno-associated Virus Type 2 Capsid Leads to the Exposure of Hidden VP1 N Termini," Journal of Virology, 2005, 79(9):5296-5303.
Kung et al., "The Role of RNA Editing in Cancer Development and Metabolic Disorders," Frontiers in Endocrinology, 2018, 9(762): 21 pages.
Kushnir et al., "Virus-like Particles as a Highly Efficient Vaccine Platform: Diversity of Targets and Production Systems and Advances in Clinical Development," Vaccine, 2012, 31(1):58-83.
Kuzikov et al., "Identification of Inhibitors of SARS-CoV-2 3CL-Pro Enzymatic Activity Using a Small Molecule in Vitro Repurposing Screen," ACS Pharmacology and Translational Science, 2021, 4(3):1096-1110.
la Cour et al., "NESbase Version 1.0: a Database of Nuclear Export Signals," Nucleic Acids Res, 2003, 31(1):393-396.
Lander et al., "Initial Sequencing and Analysis of the Human Genome," Nature, 2001, 409(6822):860-921.
Langer et al., "Chemical and physical structure of polymers as carriers for controlled release of bioactive agents: a review," Journal of Macromolecular Science-Reviews in Macromolecular Chemistry and Physics, 1983, 23(1):61-126.
Langer, "New methods of drug delivery," Science, 1990, 249(4976):1527-1533.
Lapinaite et al., "DNA capture by a CRISPR-Cas9-guided adenine base editor," Science, 2020, 369(6503):566-571, 14 pages.
Latham et al., "Formation of Wild-type and Chimeric Influenza Virus-like Particles Following Simultaneous Expression of Only Four Structural Proteins," Journal of virology, 2001, 75(13):6154-6165.
Lavillette et al., "The envelope glycoprotein of human endogenous retrovirus type W uses a divergent family of amino acid transporters/cell surface receptors," J. Virol., 2002, 76(13):6442-6452.
Lazzarotto et al.: CHANGE-seq Reveals Genetic and Epigenetic Effects on CRISPR-Cas9 Genome-wide Activity, Nature Biotechnology, 2020, 38:1317-1327, 33 pages.
Lee et al., "Adenovirus-Mediated Gene Delivery: Potential Applications for Gene and Cell-Based Therapies in the New Era of Personalized Medicine," Genes Dis., 2017, 4(2):42-63.
Lee et al., "Receptor Mediated Uptake of Peptides That Bind the Human Transferrin Receptor," European journal of biochemistry, 2001, 268(7):2004-2012.
Leibowitz et al., "Chromothripsis as an on-target Consequence of CRISPR-Cas9 genome editing," Nat Genet., 2021, 53:895-905, 26 pages.
LeibundGut-Landmann et al., "Mini-review: Specificity and expression of CIITA, the master regulator of MHC class II genes," Eur. J. Immunol., 2004, 34(6):1513-1525.
Lemmon, "Pleckstrin Homology (PH) Domains and Phosphoinositides," Biochemical Soceity Symposium, 2007, 74:81-93.
Levis et al., "Deletion Mapping Of Sindbis Virus DI RNAs Derived From cDNAs Defines The Sequences Essential For Replication And Packaging, " Cell, 1986, 44(1):137-145.
Levy et al., "Inhibition of Calcification of Bioprosthetic Heart Valves by Local Controlled-release Diphosphonate," Science, 1985, 228(4696):190-192.
Lew et al., "Protein Splicing in Vitro With a Semisynthetic Two-component Minimal Intein," The Journal of biological chemistry, 1998, 273(26):15887-15890.
Li et al., "Directed Evolution of Gold Nanoparticle Delivery to Cells," Chemical communications, 2010, 46(3):392-394.
Li et al., "Expression and Self-Assembly of Empty Virus-Like Particles of Hepatitis E Virus," Journal of Virology, 1997, 71(10):7207-7213.
Li et al., "Safe and Efficient in Vivo Hematopoietic Stem Cell Transduction in Nonhuman Primates Using HDAd5/35++ Vectors. Molecular therapy," Methods & clinical development, 2022, 24:127-141.
Li et al., "Structure and Dynamics of Zika Virus Protease and Its Insights into Inhibitor Design," Biomedicines, 2021, 9(8):1044, 16 pages.
Li et al., "The Importance of Glycans of Viral and Host Proteins in Enveloped Virus Infection," Frontiers in immunology, 2021, 12:638573, 12 pages.
Liao et al., "Physiological Regulation of Akt Activity and Stability," American Journal of Translational Research, 2010, 2(1):19-42.
Lim et al., "Crystal structure of the moloney murine leukemia virus RNase H domain," Journal of virology, 2006, 80(17):8379-8389.
Limberis et al., "AAV6.2: An Efficient and Safe Gene Therapy Clinical Candidate for the Treatment of Cystic Fibrosis Airway Disease," Molecular Therapy, 2007, 15(Suppl 1):S160.
Lin et al., "A Drug-controllable Tag for Visualizing Newly Synthesized Proteins in Cells and Whole Animals," Proceedings of the National Academy of Sciences of the United States of America, 2008, 105(22):7744-7749.

(56) References Cited

OTHER PUBLICATIONS

Lin et al., "Enhanced homology-directed human genome engineering by controlled timing of CRISPR/Cas9 delivery," eLife, 2014, 3:e04766, 13 pages.
Ling et al., "Lentiviral Delivery of Co-packaged Cas9 mRNA and a Vegfa-targeting Guide RNA Prevents Wet Age-related Macular Degeneration in Mice," Nature Biomedical Engineering, 2021, 5(2):144-156.
Litke et al., "Highly Efficient Expression of Circular RNA Aptamers in Cells Using Autocatalytic Transcripts," Nature Biotechnology, 2019, 37(6):667-675.
Liu et al., "A Split Prime Editor With Untethered Reverse Transcriptase and Circular RNA Template," Nature Biotechnology, 2022, 40(9):1388-1393.
Liu et al., "Advanced Genetic Tools For Plant Biotechnology," Nature Reviews Genetics, 2013, 14(11):781-793.
Liu et al., "C2c1-sgRNA Complex Structure Reveals RNA-Guided DNA Cleavage Mechanism," Mol Cell., 2017, 65(2):310-322.
Liu et al., "CasX Enzymes Comprise A Distinct Family Of Rna-guided Genome Editors," Nature, 2019, 566(7743):218-223.
Liu et al., "Reverse Transcriptase-Mediated Tropism Switching in Bordetella Bacteriophage," Science, 2002, 295(5562):2091-2094.
Lokossou et al., "Implication of Human Endogenous Retrovirus Envelope Proteins in Placental Functions," Viruses, 2014, 6(11):4609-4627.
Loughrey et al., "Non-liver mRNA Delivery," Accounts of chemical research, 2022, 55(1):13-23.
Louis et al., "Cloning and Sequencing of the Cellular-viral Junctions From the Human Adenovirus Type 5 Transformed 293 Cell Line, " Virology, 1997, 233(2):423-429.
Lower et al., "The Viruses in All of Us: Characteristics and Biological Significance of Human Endogenous Retrovirus Sequences," Proceedings of the National Academy of Sciences of the United States of America, 1996, 93(11):5177-5184.
Lu et al., "Lentiviral Capsid-Mediated *Streptococcus pyogenes* Cas9 Ribonucleoprotein Delivery for Efficient and Safe Multiplex Genome Editing," The CRISPR journal, 2021, 4(6):914-928.
Lu et al., "Prime Editing: An All-Rounder for Genome Editing," International Journal of Molecular Sciences, 2022, 23(17):9862, 15 pages.
Lu et al., "Types of Nuclear Localization Signals and Mechanisms of Protein Import into the Nucleus," Cell Communication Signal, 2021, 19(1):60, 10 pages.
Luan et al., "Reverse Transcription of R2Bm RNA Is Primed by a Nick at the Chromosomal Target Site: A Mechanism for Non-LTR Retrotransposition," Cell, 1993, 72(4):595-605.
Ludwig et al., "Virus-like Particles-universal Molecular Toolboxes," Current opinion in biotechnology, 2007, 18(6):537-545.
Lufino et al., "Advances in High-capacity Extrachromosomal Vector Technology: Episomal Maintenance, Vector Delivery, and Transgene Expression," Molecular Therapy, 2008, 16(9):1525-1538.
Lundin et al., "Endonuclease specificity and sequence dependence of type IIS restriction enzymes," PLoS One, Jan. 2015, 10(1):e0117059, 14 pages.
Lyu et al., Adenine Base Editor Ribonucleoproteins Delivered by Lentivirus-Like Particles Show High On-Target Base Editing and Undetectable RNA Off-Target Activities, CRISPR J, Feb. 2021, 4(1):69-81.
Lyu et al., "New Advances in Using Virus-like Particles and Related Technologies for Eukaryotic Genome Editing Delivery," International Journal of Molecular Sciences, 2022, 23(15):8750, 17 pages.
Lyu et al., "Virus-Like Particle Mediated CRISPR/Cas9 Delivery for Efficient and Safe Genome Editing, " Life, Dec. 2020, 10(12):366, 16 pages.
Maeder et al., "Development of a Gene-editing Approach to Restore Vision Loss in Leber Congenital Amaurosis Type 10," Nature Medicine, 2019, 25(2):229-233.
Maetzig et al., "Retroviral Protein Transfer: Falling Apart to Make an Impact," Current gene therapy, 2012, 12(5):389-409.
Magin et al., "Corf, the Rev/Rex homologue of HTDV/HERV-K, encodes an arginine-rich nuclear localization signal that exerts a trans-dominant phenotype when mutated," Virology, 2000, 74(1):11-16.
Maguire et al., "Microvesicle-associated AAV Vector as a Novel Gene Delivery System," Molecular Therapy, 2012, 20(5):960-971.
Maheshri et al., "Directed evolution of adeno-associated virus yields enhanced gene delivery vectors", Nature Biotechnology, 2006, 24(2):198-204.
Makarova et al., "An updated evolutionary classification of CRISPR-Cas systems," Nature Reviews Microbiology, 2015, 13:722-736, 31 pages.
Makarova et al., "Evolution and classification of the CRISPR-Cas systems," Nat Rev Microbiol., 2011, 9(6):467-477.
Mali et al., "CAS9 transcriptional activators for target specificity screening and paired nickases for cooperative genome engineering, " Nat Biotech., 2013, 31(9):833-838, 17 pages.
Mangeot et al., "A Universal Transgene Silencing Method Based on RNA Interference," Nucleic Acids Research, 2004, 32(12):e102, 6 pages.
Mangeot et al., "Development of Minimal Lentivirus Vectors Derived from Simian Immunodeficiency Virus (SIVmac251) and Their Use for Gene Transfer into Human Dendritic Cells," J. Virol., 2000, 74(18):8307-8315.
Marcu et al., "HLA Ligand Atlas: a benign reference of HLA-presented peptides to improve T-cell-based cancer immunotherapy," J Immunother Cancer, 2021, 9(4):e002071, 18 pages.
Martinez-Escobar et al., "CRISPR-dCas9-Based Artificial Transcription Factors to Improve Efficacy of Cancer Treatment With Drug Repurposing: Proposal for Future Research," Frontiers In Oncology, 2021, 10:604948, 7 pages.
Martins et al., "Improved Integration Time Estimation of Endogenous Retroviruses With Phylogenetic Data," PLoS One, 2011, 6(3):e14745, 6 pages.
Masuda et al., "Specific and Independent Recognition of U3 and U5 att Sites by Human Immunodeficiency Virus Type 1 Integrase in vivo," Journal of Virology, 1998, 72(10):8396-8402.
Mayer et al., "An Almost-intact Human Endogenous Retrovirus K on Human Chromosome 7," Nature Genetics, 1999, 21(3):257-258.
McCarthy et al., "Structure of the Receptor Binding Domain of EnvP(b)1, an Endogenous Retroviral Envelope Protein Expressed in Human Tissues," MBio®, Nov. 2020, 11(6):e02772-20, 13 pages.
McCullough et al., "Structures, Functions, and Dynamics of ESCRT-III/Vps4 Membrane Remodeling and Fission Complexes," Annual Review of Cell and Developmental Biology, 2018, 34:85-109, 30 pages.
McDonnell et al., "Solution Structure and Dynamics of the Bioactive Retroviral M Domain From Rous Sarcoma Virus," Journal of Molecular Biology, 1998, 279(4):921-928.
Mehta et al., "Immunogenicity of Cas9 Protein," Journal of Pharmaceutical Sciences, 2020, 109(1):62-67.
Meldolesi, "Exosomes and Ectosomes in Intercellular Communication," Current Biology, 2018, 28(8):R435-R444.
Meng et al., "Targeted gene inactivation in zebrafish using engineered zinc finger nucleases," Nat. Biotechnol., Jun. 2008, 26(6):695-701, 17 pages.
Mercuri et al., "Nusinersen versus Sham Control in Later-Onset Spinal Muscular Atrophy," N Engl J Med., 2018, 378:625-635.
Merten et al., "Editorial (Thematic Issue: Proceedings from the EMBO Workshop: "Modern DNA Concepts and Tools for Safe Gene Transfer and Modification")," Curr Gene Ther., 2016, 16(3):153-5.
Merten et al., "Fusoselect: Cell-cell Fusion Activity Engineered by Directed Evolution of a Retroviral Glycoprotein," Nucleic Acids Research, 2006, 34(5):e41, 9 pages.
Metsikkö et al., "Reconstitution of the Fusogenic Activity of Vesicular Stomatitis Virus," The EMBO Journal, 1986, 5(13):3429-3435.
Meunier et al., "Drug-Induced Liver Injury: Biomarkers, Requirements, Candidates, and Validation," Front Pharmacol., 2019, 10:1482, 8 pages.

(56) References Cited

OTHER PUBLICATIONS

Mi et al., "Syncytin is a Captive Retroviral Envelope Protein Involved in Human Placental Morphogenesis," Nature, 2000, 403(6771):785-789.
Milanesi et al., "BK Virus-Plasmid Expression Vector That Persists Episomally In Human Cells And Shuttles Into *Escherichia Coli*," Molecular and Cellular Biology, 1984, 4(8):1551-1560.
Mills et al., "Protein splicing in trans by purified N- and C-terminal fragments of the *Mycobacterium tuberculosis* RecA intein," Proceedings of the National Academy of Sciences of the United States of America, 1998, 95(7):3543-3548.
Mingozzi, "AAV Immunogenicity: A Matter of Sensitivity," Molecular Therapy, 2018, 26(10):2335-2336.
Miyado et al., The fusing ability of sperm is bestowed by CD9-containing vesicles released from eggs in mice, Proceedings of the National Academy of Sciences, 2008, 105(35):12921-12926.
Miyanohara, "Preparation of Vesicular Stomatitis Virus-G (VSV-G) Conjugate and Its Use in Gene Transfer," Cold Spring Harbor Protocols, 2012, 2012(4):453-456.
Mock et al., "Novel Lentiviral Vectors With Mutated Reverse Transcriptase for mRNA Delivery of TALE Nucleases," Scientific Reports, 2014, 4:6409, 8 pages.
Moede et al., "Identification of a nuclear localization signal, RRMKWKK, in the homeodomain transcription factor PDX-1," FEBS Lett, 1999, 461(3):229-234.
Mohr et al., "A reverse transcriptase-Cas1 fusion protein contains a Cas6 domain required for both CRISPR RNA biogenesis and RNA spacer acquisition," Molecular cell, 2018, 72(4):700-714.
Mohr et al., Thermostable group II intron reverse transcriptase fusion proteins and their use in cDNA synthesis and next-generation RNA sequencing, RNA, Jul. 2013, 19(7):958-70.
Monde et al., "Molecular Mechanisms by Which HERV-K Gag Interferes With HIV-1 Gag Assembly and Particle Infectivity, " Retrovirology, 2017, 14(1):27, 16 pages.
Monot et al., "The Specificity and Flexibility of L1 Reverse Transcription Priming at Imperfect T-Tracts," PLoS Genetics, 2013, 9(5):e1003499, 18 pages.
Mselli-Lakhal et al., "Gene Transfer System Derived from The Caprine Arthritis-encephalitis Lentivirus," Journal of Virological Methods, 2006, 136(1-2):177-184.
Murawski et al., "Newcastle Disease Virus-like Particles Containing Respiratory Syncytial Virus G Protein Induced Protection in BALB/c Mice, with no Evidence of Immunopathology," Journal of Virology, 2010, 84(2):1110-1123.
Murphy, "Phage Recombinases and Their Applications," Advances in Virus Research, 2012, 83:367-414.
Musunuru et al., "In vivo CRISPR Base Editing of PCSK9 Durably Lowers Cholesterol in Primates, " Nature, 2021, 593(7859):429-434.
Myers et al., "Optimal alignments in linear space," Comput Appl Biosci., 1988, 4(1):11-7.
Naik et al., "Cellular barcoding: a technical appraisal," Experimental Hematology, 2014, 42(8):598-608.
Naldini et al., "In vivo gene delivery and stable transduction of nondividing cells by a lentiviral vector," Science, 1996, 272:263-7.
Narwade et al., "Mapping of Scaffold/matrix Attachment Regions in Human Genome: a Data Mining Exercise," Nucleic Acids Research, 2019, 47(14):7247-7261.
Naskalska et al., "Virus Like Particles as Immunogens and Universal Nanocarriers," Polish Journal of Microbiology, 2015, 64 (1):3-13.
Nawaz et al., "Extracellular Vesicles, Tunneling Nanotubes, and Cellular Interplay: Synergies and Missing Links," Front Mol Biosci., Jul. 2017, 4:50, 12 pages.
NCBI.NLM.NIH.gov [online], "Engineered virus-like particles for efficient in vivo delivery of therapeutic proteins," registered Oct. 4, 2021, retrieved on Aug. 15, 2024, retrieved from URL<https://www.ncbi.nlm.nih.gov/bioproject/?term=PRJNA768458>, 1 page.
Needleman et al., "A General Method Applicable to the Search for Similarities in the Amino Acid Sequence of Two Proteins," Journal of Molecular Biology, 1970, 48(3):443-453.
Nègre et al., "Characterization of Novel Safe Lentiviral Vectors Derived from Simian Immunodeficiency Virus (SIVmac251) that Efficiently Transduce Mature Human Dendritic Cells," Gene Ther., 2000, 7(19):1613-1623.
Nelson et al., "Engineered pegRNAs Improve Prime Editing Efficiency," Nature Biotechnology, 2022, 40(3):402-410.
Nesbitt, "Targeted Intracellular Therapeutic Delivery Using Liposomes Formulated with Multifunctional FAST proteins," Thesis for the Degree of Master of Science, The University of Western Ontario, 2012; Electronic Thesis and Dissertation Repository, 388, 126 pages.
Newby et al., "Base Editing of Haematopoietic Stem Cells Rescues Sickle Cell Disease in Mice," Nature, 2021, 595(7866):295-302.
Newby et al., "In vivo somatic cell base editing and prime editing," Molecular therapy, 2021, 29(11):3107-3124.
Newman et al., "Comprehensive Identification of Human bZIP Interactions with Coiled-coil Arrays," Science, 2003, 300(5628):2097-2101.
Nightingale et al., "Transient Gene Expression by Nonintegrating Lentiviral Vectors," Molecular Therapy, 2006, 13(6):1121-1132.
Nishida et al., "Targeted Nucelotide Editing Using Hybrid Prokaryotic and Vertebrate Adaptive Immune Systems," Science, 2016, 353(6305):aaf8729, 10 pages.
Nooraei et al., "Virus-like particles: preparation, immunogenicity and their roles as nanovaccines and drug nanocarriers," Journal of Nanobiotechnology, 2021, 19:59, 27 pages.
Norris et al., "A Method for Multiprotein Assembly in Cells Reveals Independent Action of Kinesins in Complex," Journal of Cell Biology, 2014, 207(3):393-406.
Nottingham et al., "RNA-seq of human reference RNA samples using a thermostable group II intron reverse transcriptase," RNA, Apr. 2016, 22(4):597-613.
Noureddine et al., "Engineering of Monosized Lipid-coated Mesoporous Silica Nanoparticles for CRISPR Delivery," Acta Biomaterialia, 2020, 114:358-368.
NovoProLabs.com [online], "Commonly used leader peptide sequences for mammalian cells expression. NovoPro," Apr. 21, 2018, retrieved on Aug. 5, 2024, retrieved from URL<https://www.novoprolabs.com/support/articles/commonly-used-leader-peptide-sequences-for-efficient-secretion-of-a-recombinant-protein-expressed-in-mammalian-cells-201804211337.html>, 3 pages.
Nowak et al., "Structural analysis of monomeric retroviral reverse transcriptase in complex with an RNA/DNA hybrid," Nucleic Acids Res., 2013, 41(6):3874-3887.
Numrych et al., "A comparison of the effects of single-base and triple-base changes in the integrase arm-type binding sites on the site-specific recombination of bacteriophage," Nucleic Acids Res, 1990, 18(13):3953-3959.
O'Carroll et al., "Structural Mimicry Drives HIV-1 Rev-Mediated HERV-K Expression," Journal of Molecular Biology, 2020, 432(24):166711, 43 pages.
Odell et al., "Influence of Membrane Anchoring and Cytoplasmic Domains on the Fusogenic Activity of Vesicular Stomatitis Virus Glycoprotein G," Journal of Virology, 1997, 71(10):7996-8000.
Ogasawara et al., "Recombinant Viral-like Particles of Parvovirus B19 As Antigen Carriers of Anthrax Protective Antigen," In Vivo, 2006, 20(3):319-324.
Ogata et al., "Integrase of Human Endogenous Retrovirus K-10 Supports the Replication of Replication-incompetent Int-Human Immunodeficiency Virus Type 1 Mutant," Japanese Journal of Infectious Diseases, 1999, 52(6):251-252.
Ogden et al., "Comprehensive AAV Capsid Fitness Landscape Reveals a Viral Gene and Enables Machine-guided Design," Science, 2019, 366(6469):1139-1143.
Olorunniji et al., "Synapsis and Catalysis by Activated Tn3 Resolvase Mutants," Nucleic acids research, 2008, 36:7181-7191.
Olsen, "Gene Transfer Vectors Derived from Equine Infectious Anemia Virus," Gene Therapy, 1998, 5(11):1481-1487.

(56) References Cited

OTHER PUBLICATIONS

Oroszlan et al., "Primary structure and processing of gag and env gene products of human T-cell leukemia viruses HTLV-$I_{CR}$ and HTLV-$I_{ATK}$." Current topics in microbiology and immunology, 1985, 115: 221-33.
Ortinski et al., "Integrase-deficient Lentiviral Vector as an All-in-one Platform for Highly Efficient CRISPR/Cas9-mediated Gene Editing," Molecular Therapy Methods & Clinical Development, 2017, 5:153-164, 17 pages (with Supplementary Information).
Osborn et al., "Base Editor Correction of COL7A1 in Recessive Dystrophic Epidermolysis Bullosa Patient-Derived Fibroblasts and iPSCs," J Invest Dermatol., 2020, 140:338-347.e335, 52 pages.
Oshaben et al., "The native GCN4 leucine-zipper domain does not uniquely specify a dimeric oligomerization state," Biochemistry, Nov. 2012, 51(47):9581-91, 27 pages.
Otomo et al., "Improved Segmental Isotope Labeling of Proteins and Application to a Larger Protein," Journal of Biomolecular NMR, 1999, 4(2):105-114.
Otomo et al., "NMR Observation of Selected Segments in A Larger Protein: Central-segment Isotope Labeling Through Intein-mediated Ligation," Biochemistry, 1999, 38(49):16040-16044.
Ou et al., "Quantification of Virus-envelope-mediated Cell Fusion Using a Tetracycline Transcriptional Transactivator: Fusion Does Not Correlate With Syncytium Formation," Virology, 2004, 324(2):263-272.
Paces et al., "HERVd: Database of Human Endogenous Retroviruses," Nucleic Acids Research, 2002, 30(1):205-206.
Packer et al., Methods for the directed evolution of proteins, Nat Rev Genet., 2015, 16(7):379-394.
Pan et al., "Placement of leucine zipper motifs at the carboxyl terminus of HIV-1 protease significantly reduces virion production," PLoS One, 2012, 7(3):e32845, 11 pages.
Pandelakis et al., CRISPR-Based Synthetic Transcription Factors In Vivo: The Future of Therapeutic Cellular Programming, Cell Systems, 2020, 10(1): 14 pages.
Pang et al., "A community-based fitness and mobility exercise program for older adults with chronic stroke: a randomized, controlled trial," J Am Geriatr Soc., 2005, 53(10)1667-1674.
Pang et al., "Retinal degeneration 12 (rd12): a New, Spontaneously Arising Mouse Model for Human Leber Congenital Amaurosis (LCA)," Mol Vis, 2005, 11:152-162, 17 pages.
Park et al., "Sendai Virus, An RNA Virus With No Risk Of Genomic Integration, Delivers CRISPR/Cas9 For Efficient Gene Editing," Molecular Therapy Methods & Clinical Development, 2016, 24(3):16057, 9 pages.
Passos et al., "Retroviral Integrase: Structure, Mechanism, and Inhibition," Enzymes, 2021, 50:249-300, 47 pages.
Patel et al., "Flap endonucleases pass 5'-flaps through a flexible arch using a disorder-thread-order mechanism to confer specificity for free 5'-ends," Nucleic Acids Res., 2012, 40(10):4507-4519.
Paunovska et al., "Drug delivery systems for RNA therapeutics," Nat. Rev. Genet., 2022, 23:(5):265-280.
Pausch et al., "CRISPR-CasΦ from huge phages is a hypercompact genome editor," Science, 2020, 369(6501): 333-337.
Pausch et al., "DNA interference states of the hypercompact CRISPR-CasΦ effector," Nature Structural & Molecular Biology, 2021, 28(8): 652-661.
Pavlicev et al., "Detecting Endogenous Retrovirus-driven Tissue-specific Gene Transcription," Genome Biology and Evolution, 2015, 7(4):1082-1097.
Petri et al., "Reconstitution Into Liposomes of the Glycoprotein of Vesicular Stomatitis Virus by Detergent Dialysis, " Journal of Biological Chemistry, 1979, 254(11):4313-4316.
Petrillo et al., "Cyclosporine H Overcomes Innate Immune Restrictions to Improve Lentiviral Transduction and Gene Editing In Human Hematopoietic Stem Cells," Cell Stem Cell, 2018, 23(6):820-832.
Piccioni et al., "Pooled Lentiviral-Delivery Genetic Screens," Current Protocols in Molecular Biology, 2018, 121:32.1.1-32.1.21.
Pinello et al., "Analyzing CRISPR Genome-editing Experiments With CRISPResso," Nature Biotechnology, 2016, 34(7):695-697.
Pisani et al., "CXCL12-PLGA/Pluronic Nanoparticle Internalization Abrogates CXCR4-Mediated Cell Migration," Nanomaterials (Basel, Switzerland), 2020, 10(11):2304, 19 pages.
Poletti et al., "Designing Lentiviral Vectors for Gene Therapy of Genetic Diseases," Viruses, 2021, 13(8):1526, 14 pages.
Popov et al., "HIV-1 Gag Recruits PACSIN2 to Promote Virus Spreading," Proceedings of the National Academy of Sciences of the United States of America, 2018, 115(27):7093-7098.
ProData.SWMed.edu [online], "NESdb©. [Website] UT Southwestern Medical Center," updated May 2021, retrieved on Mar. 12, 2024, retrieved from URL<http://prodata.swmed.edu/LRNes/index.php>, 1 page.
Proudfoot et al., "Zinc finger Recombinases with Adaptable DNA Sequence Specificity," PLoS One, 2011, 6(4):e19537, 9 pages.
Przybylowski et al., "Production Scale-up and Validation of Packaging Cell Clearance of Clinical-grade Retroviral Vector Stocks Produced in Cell Factories," Gene Therapy, 2006, 13(1):95-100.
Pushko et al., "Development of Virus-like Particle Technology From Small Highly Symmetric to Large Complex Virus-like Particle Structures," Intervirology, 2013, 56(3):141-165.
Pushko et al., "Replicon-Helper Systems From Attenuated Venezuelan Equine Encephalitis Virus: Expression Of Heterologous Genes In Vitro And Immunization Against Heterologous Pathogens In Vivo," Virology, 1997, 239(2):389-401.
Qi et al., "Repurposing CRISPR as an RNA-Guided platform for sequence-specific control of gene expression," Cell, 2013, 152(5):1173-1183, 22 pages.
Qu et al., "Structure and Architecture of Immature and Mature Murine Leukemia Virus Capsids," Proceedings of the National Academy of Sciences of the United States of America, 2018, 115(50):E11751-E11760.
Quan et al., "Influenza M1 VLPs Containing Neuraminidase Induce Heterosubtypic Cross-protection," Virology, 2012, 430(2):127-135.
Raguram et al., "Therapeutic in Vivo Delivery of Gene Editing Agents," Cell, 2022, 185(15):2806-2827.
Ramadan, "Identification and Analysis of the Heparan Sulfate-Binding Domain and Cellular Factors Involved in the Entry of Human Endogenous Retrovirus K HERV-K (HML-2)," Inaugural—Dissertation for the degree of Doctor rerum naturalium, Freie University Berlin, Department of Biology, Chemistry, Pharmacy, Oct. 5, 2022, 156 pages.
Ramirez et al., "Engineered Zinc Finger Nickases Induce Homology-directed Repair With Reduced Mutagenic Effects," Nucleic Acids Research, 2012, 40(12):5560-5568.
Ran et al., "Genome engineering using the CRISPR-Cas9 system," Nature Protocols, 2013, 8(11):2281-2308.
Rao et al., "Large-Scale Phenome-Wide Association Study of PCSK9 Variants Demonstrates Protection Against ISCHEMIC Stroke," Circ Genom Precis Med., 2018, 11:e002162, 8 pages.
Rasmussen et al., "Characterization of Virus-like Particles Produced by a Recombinant Baculovirus Containing the Gag Gene of the Bovine Immunodeficiency-like Virus," Virology, 1990, 178(2):435-451.
Rees et al., "Base editing: precision chemistry on the genome and transcriptome of living cells," Nat Rev Genet., 2018, 19(12):770-788, 41 pages.
Rees et al., "Improving the DNA Specificity and Applicability of Base Editing Through Protein Engineering and Protein Delivery," Nature Communications, 2017, 8:15790, 10 pages.
Renner et al., "A fully automated high-throughput workflow for 3D-based chemical screening in human midbrain organoids," eLife, 2020, 9:e52904, 39 pages.
Renner et al., "Intact Viral Particle Counts Measured by Flow Virometry Provide Insight into the Infectivity and Genome Packaging Efficiency of Moloney Murine Leukemia Virus," J Virol., Jan. 2020, 94(2):e01600-19.
Resh, "A Myristoyl Switch Regulates Membrane Binding of HIV-1 Gag," Proceedings of the National Academy of Sciences of the United States of America, 2004, 101(2):417-418.
Retroviruses, 1st ed., Coffin et al. (eds)., 1997, Chapter 7, 74 pages.

(56) References Cited

OTHER PUBLICATIONS

Reul et al., "Ligand Coupling to the AAV Capsid for Cell-Specific Gene Transfer," Methods in Molecular Biology, 2019, 1950:35-50.
Reynolds et al., "The SARS-CoV-2 SSHHPS Recognized by the Papain-like Protease," ACS Infectious Diseases, 2021, 7(6):1483-1502.
Richter et al., "Phage-assisted Evolution of an Adenine Base Editor with Improved Cas Domain Compatibility and Activity," Nature Biotechnology, 2020, 38(7):883-891.
Robert et al., "Virus-Like Particles Derived from HIV-1 for Delivery of Nuclear Proteins: Improvement of Production and Activity by Protein Engineering," Molecular Biotechnology, 2017, 59(1):9-23.
Robinson et al., "Infectious Entry Pathway Mediated by the Human Endogenous Retrovirus K Envelope Protein," Journal of Virology, 2016, 90(7):3640-3649.
Robison et al., "The Membrane-proximal Stem Region of Vesicular Stomatitis Virus G Protein Confers Efficient Virus Assembly," Journal of Virology, 2000, 74(5):2239-2246.
Rodriguez et al., "Minimal "Self" Peptides That Inhibit Phagocytic Clearance and Enhance Delivery of Nanoparticles," Science, 2013, 339(6122):971-975.
Rohland et al., "Cost-effective, High-throughput DNA Sequencing Libraries for Multiplexed Target Capture," Genome Research, 2012, 22(5):939-946.
Rongrong et al., "Effect of deletion mutation on the recombination activity of Cre recombinase," Acta Biochimica Polonica, 2005, 52(2):541-544.
Rothgangl et al., "In Vivo Adenine Base Editing of Pcsk9 in Macaques Reduces Ldl Cholesterol Levels," Nat Biotechnol., 2021, 39:949-957.
Rouet et al., "Receptor-Mediated Delivery of CRISPR-Cas9 Endonuclease for Cell-Type-Specific Gene Editing," Journal of the American Chemical Society, 2018, 140(21):6596-6603.
Rousseau, "Engineering Virus-Like Particles for the Delivery of Genome Editing Enzymes," Thesis for the degree of Doctor of Philosophy, University of Michigan, Biological Chemistry, 2022, 172 pages.
Rowland et al., "Regulatory Mutations in Sin Recombinase support a structure-based model of the Synaptosome, " Molecular Microbiology, 2009, 74:282-298.
Rust et al., "Envelope-Specific Adaptive Immunity following Transplantation of Hematopoietic Stem Cells Modified with VSV-G Lentivirus," Molecular Therapy Methods & Clinical Development, 2020, 19:438-446.
Sabnis et al., "A Novel Amino Lipid Series for mRNA Delivery: Improved Endosomal Escape and Sustained Pharmacology and Safety in Non-human Primates," Molecular Therapy, 2018, 26:1509-1519.
Sack et al., "Sources of Error in Mammalian Genetic Screens," G3, 2016, 6(9):2781-2790.
Saenz et al., "Feline immunodeficiency virus-based lentiviral vectors," Cold Spring Harbor protocols, 2012, 2012(1):71-76.
Saenz et al., "Production and harvest of feline immunodeficiency virus-based lentiviral vector from cells grown in T75 tissue-culture flasks," Cold Spring Harbor Protocols, 2012, 1:124-125.
Saenz et al., "Production, harvest, and concentration of feline immunodeficiency virus-based lentiviral vector from cells grown in CF10 or CF2 devices," Cold Spring Harbor Protocols, 2011, 1:118-123.
Sago et al., "High-throughput in Vivo Screen of Functional mRNA Delivery Identifies Nanoparticles for Endothelial Cell Gene Editing," Proceedings of the National Academy of Sciences of the United States of America, 2018, 115(42):E9944-E9952.
Sakuma et al., "MMEJ-assisted Gene Knock-in Using TALENs and CRISPR-Cas9 With the PITCh Systems," Nature Protocols, 2016, 11(1):118-133.
Sander et al., "CRISPR-Cas Systems for Editing, Regulating and Targeting Genomes," Nature Biotechnology, 2014, 32(4):347-355.
Sang et al., "A unique uracil-DNA binding protein of the uracil DNA glycosylase superfamily," Nucleic Acids Res., 2015, 43(17):8452-8463.
Sanjana et al., "Improved vectors and genome-wide libraries for CRISPR screening," Nat. Methods, 2014, 11(8):783-784.
Sansbury et al., "Understanding the Diversity of Genetic Outcomes From CRISPR-Cas Generated Homology-directed Repair," Communications Biology, 2019, 2:458, 10 pages.
Sapir et al., Viral and Developmental Cell Fusion Mechanisms: Conservation and Divergence, Developmental Cell, 2008, 14(1): 11-21.
Sapranauskas et al., The *Streptococcus thermophilus* CRISPR/Cas system provides immunity in *Escherichia coli*, Nucleic Acids Res, 2011, 39: 9275-9282.
Sastry et al., "Evaluation of Plasmid DNA Removal From Lentiviral Vectors by Benzonase Treatment," Human Gene Therapy, 2004, 15(2):221-226.
Saudek et al., "A preliminary trial of the programmable implantable medication system for insulin delivery," The New England Journal of Medicine, 1989, 321(9):574-579.
Schäfer et al., "A Novel Siglec-4 Derived Spacer Improves the Functionality of Car T Cells Against Membrane-proximal Epitopes," Frontiers in Immunology, 2020, 11:1704, 18 pages.
Scharenberg et al., Genome engineering with TAL-effector nucleases and alternative modular nuclease technologies, Current Gene Therapy, 2013, 13(4):291-303.
Schauber-Plewa et al., "Complement Regulatory Proteins Are Incorporated Into Lentiviral Vectors and Protect Particles Against Complement Inactivation," Gene Therapy, 2005, 12(3):238-245.
Schellenberger et al., "A recombinant polypeptide extends the in vivo half-life of peptides and proteins in a tunable manner," Nat Biotech., 2009, 27:1186-1190.
Schiller et al., "Tunneling nanotubes enable intercellular transfer of MHC class I molecules," Human Immunology, Apr. 2013, 74(4):412-416.
Scholefield et al., Prime Editing—An Update on the Field, Gene Therapy, 2021, 28(7-8):396-401.
Scholz et al., "Analysis of human immunodeficiency virus matrix domain replacements," Virology, 2008, 371:322-335.
Scott et al., "Production of Cyclic Peptides and Proteins in Vivo," Proceedings of the National Academy of Sciences of the United States of America, 1999, 96(24):13638-13643.
Sefton, "Implantable Pumps," Critical Reviews in Biomedical Engineering, 1987, 14(3):201-240, 41 pages.
Segel et al., "Mammalian Retrovirus-like Protein PEG10 Packages Its Own mRNA and Can Be Pseudotyped for mRNA Delivery," Science, 2021, 373(6557):882-889.
Selyutina et al., "Nuclear Import of the HIV-1 Core Precedes Reverse Transcription and Uncoating," Cell Reports, 2020, 32(13):108201, 17 pages.
Sera, "Zinc-Finger-based Artificial Transcription Factors And Their Applications," Advanced Drug Delivery Reviews, 2009, 61(7-8):513-26.
Serreze et al., "Major histocompatibility complex class I-deficient NOD-$B2m^{null}$ mice are diabetes and insulitis resistant," Diabetes, 1994, 43:505-509.
Services.Health Tech.dtu.dk [online], "NESbase 1.0," retrieved on Mar. 12, 2024, retrieved from URL<https://services.healthtech.dtu.dk/datasets/NESbase-1.0/>, 3 pages.
Sette et al., "The ESCRT-associated protein Alix recruits the ubiquitin ligase Nedd4-1 to facilitate HIV-1 release through the LYPX$_n$L L domain motif," J Virol., Aug. 2010, 84(16):8181-92.
Shah et al., "Protospacer Recognition Motifs: Mixed Identities and Functional Diversity," RNA Biology, 2013, 10(5):891-899.
Shaikh et al., "Chimeras of the Flp and Cre Recombinases: Tests of the mode of cleavage by Flp and Cre," Journal of Molecular Biology, 2000, 302:27-48.
Sharma et al., "Noninfectious Virus-like Particles Produced by Moloney Murine Leukemia Virus-based Retrovirus Packaging Cells Deficient in Viral Envelope Become Infectious in the Presence of Lipofection Reagents," Proceedings of the National Academy of Sciences of the United States of America, 1997, 94(20):10803-10808.

(56) References Cited

OTHER PUBLICATIONS

Shechner et al., "Multiplexable, locus-specific targeting of long RNAs with CRISPR-Display," Nature methods, 2015, 12(7):664-670.
Shen et al., "SeqKit: A Cross-Platform and Ultrafast Toolkit for FASTA/Q File Manipulation," PLoS one, 2016, 11(10):e0163962, 10 pages.
Sheridan et al., "Generation of Retroviral Packaging and Producer Cell Lines for Large-scale Vector Production and Clinical Application: Improved Safety and High Titer," Molecular Therapy, 2000, 2(3):262-275.
Shin et al., "Human-specific HERV-K Insertion Causes Genomic Variations in the Human Genome," PLoS One, 2013, 8(4):e60605, 10 pages.
Shingledecker et al., "Molecular dissection of the *Mycobacterium tuberculosis* RecA intein: design of a minimal intein and of a trans-splicing system involving two intein Fragments," Gene, 1998, 207(2):187-195.
Shirley et al., "Immune Responses to Viral Gene Therapy Vectors," Molecular therapy, 2020, 28(3):709-722.
Shmakov et al., "Discovery and Functional Characterization of Diverse Class 2 CRISPR-Cas Systems," Molecular Cell, 2015, 60:385-397.
Shtyrya et al., "Influenza virus neuraminidase: structure and function," Acta naturae, 2009, 1(2):26-32.
SigmaAldrich.com [online], "Simplicon™Expression System: Designing, Cloning and RNA Synthesis for Expression of Self-Replicative RNA—Catalog No. SCR724, SCR725, SCR726, SCR727, SCR728, SCR729," May 2018, retrieved on Aug. 23, 2024, retrieved from URL<https://www.sigmaaldrich.com/deepweb/assets/sigmaaldrich/product/documents/252/611/scr726-manual.pdf>, 48 pages.
Silva et al., Meganucleases and Other Tools for Targeted Genome Engineering: Perspectives and Challenges for Gene Therapy, Curr Gene Ther., 2011, 11(1):11-27.
Singh et al., "Redefining the specificity of phosphoinositide-binding by human PH domain-containing proteins," Nat Commun., Jul. 2021, 12(1):4339, 13 pages.
Smith et al., "Diversity in the Serine Recombinases," Molecular Microbiology, 2002, 44(2):299-307.
Sockolosky et al., "Fusion of a Short Peptide That Binds Immunoglobulin G to a Recombinant Protein Substantially Increases Its Plasma Half-life in Mice," PLoS One, 2014, 9(7):e102566, 10 pages.
Sodi et al., RPE65-Associated Inherited Retinal Diseases: Consensus Recommendations for Eligibility to Gene Therapy, Orphanet J Rare Dis., 2021, 16:257, 11 pages.
Soldi et al., "Laboratory-Scale Lentiviral Vector Production and Purification for Enhanced Ex Vivo and In Vivo Genetic Engineering," Molecular Therapy Methods & Clinical Development, 2020, 19:411-425.
Song et al., Large-Fragment Deletions Induced by Cas9 Cleavage while Not in the BEs System, Mol Ther Nucleic Acids, 2020, 21:523-526.
Soo et al., "Nanoparticle Tracking Analysis Monitors Microvesicle and Exosome Secretion From Immune Cells," Immunology, 2012, 136(2):192-197.
Southworth et al., "Control of Protein Splicing by Intein Fragment Reassembly," EMBO Journal, 1998, 17(4):918-926.
Spisák et al., "CAUSEL: an epigenome- and genome-editing pipeline for establishing function of noncoding GWAS variants," Nat Med, Nov. 2015, 21(11): 1357-63, 25 pages.
Stadtmauer et al., "CRISPR-engineered T cells in patients with refractory cancer," Science, 2020, 367(6481):eaba7365, 20 pages.
Stahnke et al., "Intrinsic Phospholipase A2 Activity of Adeno-associated Virus is Involved in Endosomal Escape of Incoming Particles," Virology, 2011, 409(1):77-83.
Stamos et al., "Structure of a thermostable group II intron reverse transcriptase with template-primer and its functional and evolutionary implications," Molecular cell, 2017, 68(5): 926-939.
Stavrou et al., "Episomal vectors based on S/MAR and the β-globin Replicator, encoding a synthetic transcriptional activator, mediate efficient γ-globin activation in haematopoietic cells," Scientific Reports, 2019, 9:19765, 16 pages.
Steele-Ogus et al., "Disc and Actin Associated Protein 1 influences attachment in the intestinal parasite Giardia lamblia," PLoS Pathogens, 2022, 18(3):e1010433, 22 pages.
Stein et al., "Human endogenous retroviruses: our genomic fossils and companions," Physiol Genomics, 2023, 55:249-258.
Sternberg et al., "DNA Interrogation by the CRISPR RNA-Guided Endonuclease Cas9," Nature, 2014, 507(7490):62-67, 16 pages.
Strobel et al., "A Small-Molecule-Responsive Riboswitch Enables Conditional Induction of Viral Vector-Mediated Gene Expression in Mice," ACS Synthetic Biology, 2020, 9(6):1292-1305.
Subramanian et al., "Identification, Characterization, and Comparative Genomic Distribution of the HERV-K (HML-2) Group of Human Endogenous Retroviruses," Retrovirology, 2011, 8:90, 22 pages.
Sugita et al., "Screening of peptide ligands that bind to the Fc region of IgG using peptide array and its application to affinity purification of antibody," Biochemical Engineering Journal, 2013, 79:33-40.
Suh et al., Restoration of Visual Function in Adult Mice With an Inherited Retinal Disease via Adenine Base Editing, Nat Biomed Eng, 2021, 5(2):169-178.
Sun et al., "Reconstructed glycosylase base editors GBE2.0 with enhanced C-to-G base editing efficiency and purity," Mol Ther., 2022, 30(7):2452-2463.
Suresh et al., "Bispecific Monoclonal Antibodies From Hybrid Hybridomas," Methods in Enzymology, 1986, 121:210-228.
Swiech et al., "In vivo interrogation of gene function in the mammalian brain using CRISPR-Cas9," Nature biotechnology, 2015, 33(1): 102-106, 22 pages.
Tabebordbar et al., "Directed Evolution of a Family of AAV Capsid Variants Enabling Potent Muscle-directed Gene Delivery Across Species," Cell, 2021, 184(19):4919-4938.
Tague et al., "Chemogenetic Control of Gene Expression and Cell Signaling With Antiviral Drugs," Nature Methods, 2018, 15(7):519-522.
Taha et al., "Real E. Upstream of N-Ras (Unr/CSDE1) Interacts with NCp7 and Gag, Modulating HIV-1 IRES-Mediated Translation Initiation," Viruses, 2022, 14(8):1798, 21 pages.
Takahashi et al., "Induction of Pluripotent Stem Cells From Mouse Embryonic and Adult Fibroblast Cultures by Defined Factors," Cell, 2006, 126(4):663-676.
TakaraBio.com [online], "Guide-it™ CRISPR/Cas9 Gesicle Production System User Manual. Cat. Nos. 632612, 632613, 632616 (053017)," 2017, retrieved on Mar. 13, 2024, retrieved from URL<https://www.takarabio.com/documents/User%20Manual/Guide/Guide-it%20CRISPR-Cas9%20Gesicle%20Production%20System%20User%20Manual_053017.pdf>, 23 pages.
Takematsu et al., "Transmembrane Stem Cell Factor Protein Therapeutics Enhance Revascularization in Ischemia Without Mast Cell Activation," Nature communications, 2022, 13(1):2497, 13 pages.
Takeuchi et al., "Redesign of extensive protein-DNA interfaces of meganucleases using iterative cycles of in vitro compartmentalization," PNAS, Mar. 2014, 111(11):4061-4066.
Taube et al., "Reverse Transcriptase of Mouse Mammary Tumour Virus: Expression In Bacteria, Purification and Biochemical Characterization," The Biochemical Journal, 1998, 329(3):579-587.
Taylor, "Ocular immune privilege, " Eye (Lond)., 2009, 23:1885-1889.
Telesnitsky et al., "RNase H domain mutations affect the interaction between Moloney murine leukemia virus reverse transcriptase and its primer-template," PNAS USA, 1993, 90(4):1276-1280.
Termini et al., Tetraspanins Function as Regulators of Cellular Signaling. Frontiers in Cell and Developmental Biology, 2017, 5:34, 14 pages.
Thomas et al., "CD90-Targeted Cocal-Pseudotyped Lentivirus as a Robust Platform for Human HSC Gene Therapy," Blood, 2023, 142:2254, 2 pages.
Thompson et al., "Long Terminal Repeats: From Parasitic Elements to Building Blocks of the Transcriptional Regulatory Repertoire," Molecular Cell Review, 2016, 62(5):766-776.

(56) References Cited

OTHER PUBLICATIONS

Thompson et al., "SYNZIP Protein Interaction Toolbox: in Vitro and in Vivo Specifications of Heterospecific Coiled-coil Interaction Domains," ACS Synthetic Biology, 2012, 1(4):118-129.
Thorne et al., in Vivo Diffusion Analysis With Quantum Dots and Dextrans Predicts the Width of Brain Extracellular Space, Proc Natl Acad Sci USA, 2006, 103:5567-5572.
Tinland et al., "The T-DNA-linked VirD2 Protein Contains Two Distinct Functional Nuclear Localization Signals," Proceedings of the National Academy of Sciences, 1992, 89(16):7442-7446.
Tirumalai et al., "The recognition of core-type DNA sites by lambda integrase," J Mol Biol., 1998, 279:513-527.
Tomé-Amat et al., "Secreted Production of Assembled Norovirus Virus-like Particles from Pichia Pastoris," Microbial Cell Factories, 2014, 13:134, 9 pages.
Toonen et al., "Intracerebroventricular Administration of a 2'-O-Methyl Phosphorothioate Antisense Oligonucleotide Results in Activation of the Innate Immune System in Mouse Brain," Nucleic Acid Therapeutics, 2018, 28(2):63-73.
Top et al., "Liposome Reconstitution of a Minimal Protein-mediated Membrane Fusion Machine," The EMBO Journal, 2005, 24(17):2980-2988.
Trobridge et al., "Cocal-pseudotyped Lentiviral Vectors Resist Inactivation by Human Serum and Efficiently Transduce Primate Hematopoietic Repopulating Cells," Molecular Therapy, 2010, 18(4):725-733.
Truebestein et al., "Coiled-coils: the Long and Short of It," BioEssays, 2016, 38(9):903-916.
Truong et al., "Development of an Intein-mediated Split-Cas9 System for Gene Therapy," Nucleic Acids Research, 2015, 43(13):6450-6458.
Tsai et al., "Amplification-free, CRISPR-Cas9 Targeted Enrichment and SMRT Sequencing of Repeat-Expansion Disease Causative Genomic Regions," bioRxiv, posted Oct. 16, 2017, 26 pages.
Tsai et al., "CIRCLE-seq: a Highly Sensitive in Vitro Screen for Genome-wide CRISPR-Cas9 nuclease off-targets," Nat Methods, 2017, 14:607-614, 10 pages.
Tsuchida et al., Chimeric CRISPR-CasX enzymes and guide RNAs for improved genome editing activity, Molecular Cell, 2022, 82(6):1199-1209, 28 pages.
Tsutakawa et al., "Human flap endonuclease structures, DNA double-base flipping, and a unified understanding of the FEN1 superfamily," Cell, 2011, 145(2):198-211.
Turan et al., "Site-specific Recombinases: From Tag-and-target—to Tag-and-exchange-based Genomic Modifications," FASEB journal, 2011, 25(12):4088-4107.
Turchiano et al., "Quantitative evaluation of chromosomal rearrangements in gene-edited human stem cells by CAST-Seq," Cell Stem Cell, 2021, 28:1136-1147.e5.
Tycko et al., "High-Throughput Discovery and Characterization of Human Transcriptional Effectors," Cell, 2020, 183(7):2020-2035.
Urnov et al., "Genome editing with engineered zinc finger nucleases," Nature Reviews Genetics, 2010, 11:636-646.
Van Dongen et al., "Extracellular Vesicles Exploit Viral Entry Routes for Cargo Delivery," Microbiology and Molecular Biology Reviews: MMBR, 2016, 80(2):369-386.
Van Duyne, "Teaching Cre to follow directions," Proc Natl Acad Sci USA, 2009, 106(1):4-5.
van Haasteren et al., "The Delivery Challenge: Fulfilling the Promise of Therapeutic Genome Editing," Nature biotechnology, 2020, 38(7):845-855.
Vance et al., "Virus and eukaryote fusogen superfamilies," Current Biology Magazine, Jul. 6, 2020, 30(13):R750-R754.
Vandenberghe et al., "Heparin Binding Directs Activation of T Cells Against Adeno-associated Virus Serotype 2 Capsid," Nature Medicine, 2006, 12(8):967-971.
Várnai et al., "Visualization of Phosphoinositides That Bind Pleckstrin Homology Domains: Calcium- and Agonist-induced Dynamic Changes and Relationship to Myo-[$^3$H]inositol-labeled Phosphoinositide Pools," J Cell Biol., 1998, 143(2):501-510.
Veletanlic et al., "Multiple rotavirus species encode fusion-associated small transmembrane (FAST) proteins with cell type-specific activity," bioRxiv, posted Apr. 8, 2023, 46 pages.
Venken et al., "Genome-wide manipulations of *Drosophila melanogaster* with transposons, Flp recombinase, and ΦC31 integrase," Methods in Molecular Biology, 2012, 859:203-228.
Verghese et al., "S/MAR sequence confers long-term mitotic stability on non-integrating lentiviral vector episomes without selection," Nucleic Acids Res., 2014, 42(7):e53, 13 pages.
Verhoeyen et al., "Novel Lentiviral Vectors Displaying "Early-acting Cytokines" Selectively Promote Survival And Transduction Of NOD/SCID Repopulating Human Hematopoietic Stem Cells," Blood, 2005, 106(10):3386-3395.
Verma, "The reverse transcriptase," Biochim Biophys Acta., 1977, 473: 1-38.
Vijayraghavan et al., "A Protocol for the Production of Integrase-deficient Lentiviral Vectors for CRISPR/Cas9-mediated Gene Knockout in Dividing Cells," J Vis Exp., 2017, 12(130):56915, 8 pages.
Voigtlander et al., "A Novel Adenoviral Hybrid-vector System Carrying a Plasmid Replicon for Safe and Efficient Cell and Gene Therapeutic Applications," Molecular Therapy-Nucleic Acids, 2013, 2(4):e83, 14 pages.
Voisset et al., "Phylogeny of a Novel Family of Human Endogenous Retrovirus Sequences, HERV-W, in Humans and Other Primates," Aids Research and Human Retroviruses, 1999, 15(17):1529-1533.
von Heijne, "A new method for predicting signal sequence cleavage sites," Nucleic Acids Research, 1986, 14(11):4683-4690.
Vonkova et al., "Lipid Cooperativity as a General Membrane-Recruitment Principle for PH Domains," Cell Reports, 2015, 12(9):1519-1530.
Vu et al., "Engineering of a Stable Retroviral Gene Delivery Vector by Directed Evolution," Molecular therapy, 2008, 16(2):308-314.
Wahlfors et al., "Evaluation Of Recombinant Alphaviruses As Vectors In Gene Therapy," Gene Therapy, 2000, 7(6):472-480.
Walpita et al., "Mammalian Cell-derived Respiratory Syncytial Virus-like Particles Protect the Lower as well as the Upper Respiratory Tract," PLoS One, 2015, 10(7):E0130755, 18 pages.
Wang et al., "Anchoring of Actin to the Plasma Membrane Enables Tension Production in the Fission Yeast Cytokinetic Ring," Molecular Biology of the Cell, 2019, 30(16):2053-2064.
Wang et al., "Characterization of an Mps I-h Knock-in Mouse That Carries a Nonsense Mutation Analogous to the Human Idua-w402x Mutation," Mol Genet Metab., 2010, 99:62-71.
Wang et al., "Directed Evolution: Methodologies and Applications," Chemical reviews, 2021, 121(20):12384-12444, 61 pages.
Wang et al., "Shortened nuclear matrix attachment regions are sufficient for replication and maintenance of episomes in mammalian cells," Molecular Biology of the Cell, 2019, 30(22):2737-2857.
Wang et al., "Tangential Flow Microfiltration for Viral Separation and Concentration," Micromachines, 2019, 10(5):320, 13 pages.
Wang et al., "Virus-like Particles for the Prevention of Human Papillomavirus-associated Malignancies," Expert Review of Vaccines, 2013, 12(2):129-141.
Warren et al., "A chimeric cre recombinase with regulated directionality," Proc Natl Acad Sci USA, 2008, 105(47):18278-18283.
Warren et al., "Mutations in the amino-terminal domain of lambda-integrase have differential effects on integrative and excisive recombination," Molecular Microbiology, 2005, 55(4):1104-1112.
Webber et al., "Highly efficient multiplex human T cell engineering without double-strand breaks using Cas9 base editors," Nat Commun., 2019, 10:5222, 10 pages.
Wei et al., "Delivery of Tissue-Targeted Scalpels: Opportunities and Challenges for In Vivo CRISPR/Cas-Based Genome Editing," ACS nano, 2020, 14(8):9243-9262.
Wei et al., "Systemic Nanoparticle Delivery of CRISPR-Cas9 Ribonucleoproteins for Effective Tissue Specific Genome Editing," Nature communications, 2020, 11(1):3232, 12 pages.
Weldon et al., "Characterization of a Small (25-kilodalton) Derivative of the Rous Sarcoma Virus Gag Protein Competent for Particle Release," Journal of Virology, 1993, 67(9):5550-5561.
Welsh et al., "FCMPASS Software Aids Extracellular Vesicle Light Scatter Standardization," Cytometry Part A, 2020, 97(6):569-581.

(56) References Cited

OTHER PUBLICATIONS

Wickramasinghe et al., "Tangential Flow Microfiltration and Ultrafiltration for Human Influenza a Virus Concentration and Purification," Biotechnology and Bioengineering, 2005, 92(2):199-208.
Wildschutte et al., "Discovery of Unfixed Endogenous Retrovirus Insertions in Diverse Human Populations," Proceedings of the National Academy of Sciences of the United States of America, 2016, 113(16):E2326-E2334.
Wolff et al., "Delivering Genes With Human Immunodeficiency Virus-Derived Vehicles: Still State-Of-The-Art After 25 Years," Journal of Biomedical Science, 2022, 29:79, 22 pages.
Wong et al., "Genetic Modification of Dividing Cells Using Episomally Maintained S/MAR DNA Vectors," Molecular Therapy-Nucleic Acids, 2013, 2(8):e115, 12 pages.
Wu et al., "Effect of genome size on AAV vector packaging," Mol Ther., 2010, 18:80-86.
Wu et al., "Protein trans-splicing and functional mini-inteins of a cyanobacterial dnaB intein," Biochim Biophys Acta, 1998, 1387(1-2):422-32.
Xiong et al., "Origin and Evolution of Retroelements Based Upon their Reverse Transcriptase Sequences," The EMBO Journal, 1990, 9(10):3353-3362.
Xu et al., "NESdb: A Database of NES-containing CRMI Cargoes," Molecular Biology of the Cell, 2012, 23(18):3673-3676.
Xu et al., "piggyBac mediates efficient in vivo CRISPR library screening for tumorigenesis in mice," Proceedings of the National Academy of Sciences, 2017, 114(4):722-727.
Xu et al., "Sequence and Structural Analyses of Nuclear Export Signals in the NESdb Database," Molecular Biology of the Cell, 2012, 23(18):3677-3693.
Yamano et al., "Crystal structure of Cpf1 in complex with guide RNA and target DNA," Cell, 2016, 165(4): 949-962.
Yamazaki et al., "Segmental Isotope Labeling for Protein NMR Using Peptide Splicing," Journal of The American Chemical Society, 1998, 120(22):5591-5592.
Yang et al., "HIV-1 Virus-like Particles Produced by Stably Transfected *Drosophila* S2 Cells: a Desirable Vaccine Component," Journal of virology, 2012, 86(14):7662-7676.
Yang et al., "PAM-Dependent Target DNA Recognition and Cleavage by C2c1 CRISPR-Cas Endonuclease," Cell, 2016, 167(7):1814-1828.e12.
Yao et al., "Engineered extracellular vesicles as versatile ribonucleoprotein delivery vehicles for efficient and safe CRISPR genome editing," J Extracell Vesicles, 2021, 10:e12076, 14 pages.
Yarnall et al., "Drag-and-drop genome insertion of large sequences without double-strand DNA cleavage using CRISPR-directed integrases," Nature Biotechnology, 2023, 41:500-512.
Yee et al., "A General Method for the Generation of High-titer, Pantropic Retroviral Vectors: Highly Efficient Infection of Primary Hepatocytes," Proceedings of the National Academy of Sciences, 1994, 91(20):9564-9568.
Yeh et al., "In vivo base editing of post-mitotic sensory cells," Nat Commun., 2018, 9(1):2184, 10 pages.
Yeh et al., "In Vivo Base Editing Restores Sensory Transduction and Transiently Improves Auditory Function in a Mouse Model of Recessive Deafness," Sci Transl Med., 2020, 12(546):eaay9101, 13 pages.
Yi et al., "Expression and Phylogenetic Analyses of Human Endogenous Retrovirus HC2 Belonging to the HERV-T Family in Human Tissues and Cancer Cells," Journal of Human Genetics, 2007, 52(4):285-296.
Yim et al., "Exosome Engineering for Efficient Intracellular Delivery of Soluble Proteins Using Optically Reversible Protein-protein Interaction Module," Nature Communications, 2016, 7:12277, 9 pages.
Yin et al., "Hepatitis A Virus Picornain 3C," Handbook of Proteolytic Enzymes, 2013, Chapter 542:2417-2423.
Yu et al., "Cytosine Base Editors With Minimized Unguided DNA and RNA Off-target Events and High on-target Activity," Nat Commun., 2020, 11:2052, 10 pages.
Yu et al., "Engineered cell entry links receptor biology with single-cell genomics," Cell, 2022, 185:4904-4920.
Yu et al., "The zinc finger of nucleocapsid protein of Friend murine leukemia virus is critical for proviral DNA synthesis in vivo," Journal of virology, 1996, 70(9):5791-5798.
Zábranský et al., "Identification of a Minimal HIV-1 Gag Domain Sufficient for Self-Association," Virology, 2002, 294(1):141-150.
Zalatan et al., "Engineering complex synthetic transcriptional programs with CRISPR RNA scaffolds," Cell, 2015, 160(1-2):339-350.
Zaslavskiy et al., "Efficient Design of Meganucleases Using a Machine Learning Approach," BMC Bioinformatics, 2014, 15 (191): 11 pages.
Závada, "The Pseudotypic Paradox," Journal of General Virology, 1982, 63(Pt 1):15-24.
Zeltins, "Construction and Characterization of Virus-Like Particles: A Review," Mol Biotechnol., 2013, 53:92-107.
Zeng et al., Therapeutic base editing of Human Hematopoietic Stem Cells, Nat Med., 2020, 26:535-541.
Zhang et al., "Conditional Gene Manipulation: Cre-ating a new Biological Era," Journal of Zhejiang University Science B, 2012, 13(7):511-524.
Zhang et al., "Optogenetic Control with a Photocleavable Protein, PhoC1," Nature Methods, 2017, 14(4):391-394.
Zhang et al., "Stabilized plasmid-lipid particles for regional gene therapy: formulation and transfection properties," Gene Therapy, 1999, 6:1438-1447.
Zhang et al., "Transduction of Bone-marrow-derived Mesenchymal Stem Cells by Using Lentivirus Vectors Pseudotyped With Modified Rd114 Envelope Glycoproteins," Journal of Virology, 2004, 78(3):1219-1229.
Zhao et al., "An ultraprocessive, accurate reverse transcriptase encoded by a metazoan group II intron,," RNA, 2018, 24(2):183-195.
Zhao et al., "Crystal structures of a group II intron maturase reveal a missing link in spliceosome evolution," Nature structural & molecular biology, 2016, 23(6):558-565.
Zheng et al., "Development of a flexible split prime editor using truncated reverse transcriptase, " bioRxiv, posted Aug. 29, 2021, 16 pages.
Zhong et al., "Seven Novel Variants Expand the Spectrum of Rpe65-related Leber Congenital Amaurosis in the Chinese Population," Mol Vis., 2019, 25:204-214.
Zhu et al., "An engineered leucine zipper a position mutant with an unusual three-state unfolding pathway," Protein Sci., Jan. 2001, 10(1):24-33.
Zhu et al., "Guide RNAs with embedded barcodes boost CRISPR-pooled screens," Genome Biology, 2019, 20:20, 12 pages.
Zimmerberg et al., How proteins produce cellular membrane curvature, Nature Reviews Molecular Cell Biology, 2006, 7(1):9-19.
Zimmerly et al., "An Unexplored Diversity of Reverse Transcriptases in Bacteria," Microbiology spectrum, 2015, 3(2):MDNA3-0058-2014, 16 pages.
Zimmerly et al., "Group II Intron Mobility Occurs by Target DNA-primed Reverse Transcription," Cell, 1995, 82(4):545-554.
Zincarelli et al., "Analysis of AAV Serotypes 1-9 Mediated Gene Expression and Tropism in Mice After Systemic Injection," Molecular Therapy, 2008, 16(6):1073-1080.
Zufferey et al.: Woodchuck hepatitis virus posttranscriptional regulatory element enhances expression of transgenes delivered by retroviral vectors, Journal of Virology, 1999, 73(4):2886-2892.
Zuker et al., "Optimal computer folding of large RNA sequences using thermodynamics and auxiliary information," Nucleic Acids Res., 1981, 9:133-148.
Zuris et al., "Cationic Lipid-mediated Delivery of Proteins Enables Efficient Protein-based Genome Editing in Vitro and in Vivo," Nature Biotechnology, 2015, 33(1):73-80, 59 pages (with Supplementary Information).
Frietze et al., "Engineering Virus-like Particles as Vaccine Platforms," Current opinion in virology, 2016, 18:44-46.

* cited by examiner

ENGINEERED HUMAN-ENDOGENOUS VIRUS-LIKE PARTICLES AND METHODS OF USE THEREOF FOR DELIVERY TO CELLS

CLAIM OF PRIORITY

This application is a continuation of U.S. patent application Ser. No. 17/617,490, filed Dec. 8, 2021, which is a § 371 National Stage Application of PCT/US2020/037740, filed Jun. 15, 2020, which claims the benefit of U.S. Patent Application Ser. No. 62/861,186, filed on Jun. 13, 2019. The entire contents of the foregoing are hereby incorporated by reference.

FEDERALLY SPONSORED RESEARCH OR DEVELOPMENT

This invention was made with Government support under grant no. GM118158 awarded by the National Institutes of Health. The Government has certain rights in the invention.

SEQUENCE LISTING

This application contains a Sequence Listing that has been submitted electronically as an XML file named '29539-0385004_SL_ST26.xml'. The XML file, created on Jul. 10, 2023, is 136,545 bytes in size. The material in the XML filed is hereby incorporated by reference in its entirety.

TECHNICAL FIELD

Described herein are engineered human-endogenous virus-like particles (heVLPs) comprising a membrane comprising a phospholipid bilayer on the external side; and a cargo, e.g., a biomolecule and/or chemical cargo, disposed in the core of the heVLP on the inside of the membrane, wherein the heVLP does not comprise a protein from non-human gag or pol, and methods of use thereof for delivery of the cargo to cells.

BACKGROUND

Delivery of cargo such as proteins, nucleic acids, and/or chemicals into the cytosol of living cells has been a significant hurdle in the development of biological therapeutics.

SUMMARY

Described herein are heVLPs that are capable of packaging and delivering DNA, RNA, protein, chemical compounds and/or molecules, and any combination of these four entities into eukaryotic cells. The non-viral heVLP systems described herein have the potential to be simpler, more efficient and safer than conventional, artificially-derived lipid/gold nanoparticles and viral particle-based delivery systems because heVLPs are comprised of human-derived components. The cargo inside may or may not be human derived, but the heVLP is entirely comprised from human and synthetic non-immunogenic components. "Synthetic" components include surface scFv/nanobody/darpin peptides that have been demonstrated to not be immunostimulatory and can be used to enhance targeting and cellular uptake of heVLPs. This means that the exterior surface of the particle lacks components that are significantly immunostimulatory, which should minimize immunogenicity and antibody neutralization of these particles. Excluding cargo, the heVLPs do not contain exogenous viral components inherent to other VLPs and this represents a significant and novel advancement in technology. In addition, heVLPs can utilize (but do not require) chemical-based dimerizers, and heVLPs have the ability to package and deliver cargo molecules including therapeutic or diagnostic agents, including biomolecules and chemicals, e.g., specialty single and/or double-stranded DNA molecules (e.g., plasmid, mini circle, closed-ended linear DNA, AAV DNA, episomes, bacteriophage DNA, homology directed repair templates, etc.), single and/or double-stranded RNA molecules (e.g., single guide RNA, prime editing guide RNA, messenger RNA, transfer RNA, long non-coding RNA, circular RNA, RNA replicon, circular or linear splicing RNA, micro RNA, small interfering RNA, short hairpin RNA, piwi-interacting RNA, toehold switch RNA, RNAs that can be bound by RNA binding proteins, bacteriophage RNA, internal ribosomal entry site containing RNA, etc.), proteins, chemical compounds and/or molecules (e.g., small molecules), and combinations of the above listed cargos (e.g. AAV particles).

The heVLPs described herein are different from conventional retroviral particles, virus-like particles (VLPs), exosomes and other previously described extracellular vesicles that can be loaded with cargo, at least because heVLPs can be produced by a strategic overexpression of human-derived components in human cells, heVLPs have a vast diversity of possible cargos and loading strategies, heVLPs lack a limiting DNA/RNA length constraint, heVLPs lack proteins derived from pol and exogenous gag, and heVLPs have unique mechanisms of cellular entry.

Described herein are compositions and methods for cargo delivery that can be used with a diverse array of protein and nucleic acid molecules, including genome editing, epigenome modulation, transcriptome editing and proteome modulation reagents, that are applicable to many disease therapies.

Thus, provided herein are engineered heVLPs, comprising a membrane comprising a phospholipid bilayer with one or more HERV-derived ENV/glycoprotein(s) (e.g., overexpressed from exogenous sources, such as plasmids or stably integrated transgenes, in heVLP production cells) (e.g., as shown in Table 1) on the external side; and a human endogenous GAG protein, other plasma membrane recruitment domain, and/or biomolecule/chemical cargo disposed in the core of the heVLP on the inside of the membrane, wherein the biomolecule cargo may or may not be fused to a human-endogenous GAG or other plasma membrane recruitment domain (e.g., as shown in Table 6), and the heVLP does not comprise a non-human gag and/or pol protein, do not express gag and/or pol proteins except for gag proteins that are encoded in the human genome or gag proteins that are encoded by a consensus sequence that is derived from gag proteins found in the human genome. Human-derived GAG or other plasma membrane recruitment domains fused to biomolecule cargo can be overexpressed from exogenous sources, such as plasmids or stably integrated transgenes, in heVLP production cells.

In some embodiments, the HERV ENV can be truncated or fused to an scFv or other targeting polypeptides.

In some embodiments the HERV GAG can be fused to a plasma membrane recruitment domain (e.g., as shown in Table 6).

In another embodiment, engineered heVLPs comprise a membrane comprising a phospholipid bilayer with one or more HERV-derived ENV/glycoprotein(s) (e.g., overexpressed from exogenous sources, such as plasmids or stably integrated transgenes, in heVLP production cells) (e.g., as shown in Table 1) on the external side; and, if desired, a plasma membrane recruitment domain (e.g., as shown in Table 6); and, if desired a biomolecule/chemical cargo inside the particle.

Also provided are methods of delivering a cargo to a target cell, e.g., a cell in vivo or in vitro, by contacting the cell with the heVLP of claim 1 comprising the biomolecule and/or chemical as cargo.

In addition, provided herein are methods for producing a heVLP comprising a biomolecular cargo. The methods include providing a cell expressing (e.g., engineered to express or overexpress) one or more HERV-derived envelope proteins (e.g., as shown in Table 1), and a cargo, wherein the cell does not express a gag and/or pol protein, except for gag proteins that are encoded in the human genome or gag proteins that are encoded by a consensus sequence that is derived from gag proteins found in the human genome; and maintaining the cell under conditions such that the cells produce heVLPs. In some embodiments, the methods further include harvesting and optionally purifying and/or concentrating the produced heVLPs.

Also provided herein are cells (e.g., isolated cells, preferably mammalian, e.g., human, cells) that express, e.g., that have been induced to overexpress, in combination one or more HERV-derived envelope proteins (e.g., (overexpressed from exogenous sources, such as plasmids or stably integrated transgenes)(e.g., as shown in Table 1), and a cargo fused to a human endogenous GAG or other plasma membrane recruitment domain (e.g., as shown in Table 6), wherein the cell does not express a gag protein except for gag proteins that are encoded in the human genome or gag proteins that are encoded by a consensus sequence that is derived from gag proteins found in the human genome (overexpressed from exogenous sources, such as plasmids or stably integrated transgenes)). In some embodiments, the cells are primary or stable human cell lines, e.g., Human Embryonic Kidney (HEK) 293 cells, HEK293 T cells, or BeWo cells. The cells can be used to produce heVLPs as described herein.

In some embodiments, the methods include using cells that have or have not been manipulated to express any exogenous proteins except for a HERV envelope (e.g., as shown in Table 1), and, if desired, a plasma membrane recruitment domain (e.g., as shown in Table 6). In this embodiment, the "empty" particles that are produced can be loaded with biomolecule or chemical molecule cargo by utilizing nucleofection, lipid, polymer, or $CaCl_2$) transfection, sonication, freeze thaw, and/or heat shock of purified particles mixed with cargo. In all embodiments, producer cells do not express any human exogenous gag protein. This type of loading allows for cargo to be unmodified by fusions to plasma membrane recruitment domains and represents a significant advancement from previous VLP technology.

In another embodiment, heVLPs that contain cargo are produced and isolated can be loaded with additional biomolecule or chemical molecule cargo by utilizing nucleofection, lipid, polymer, or $CaCl_2$) transfection, sonication, freeze thaw, incubation at various temperatures, and/or heat shock of purified particles mixed with cargo.

In some embodiments, the cargo is a therapeutic or diagnostic protein or nucleic acid encoding a therapeutic or diagnostic protein.

In some embodiments, the cargo is a chemical compound or molecule.

In some embodiments, the chemical molecule is a trigger for protein-protein dimerization of multimerization, such as the A/C heterodimerizer or rapamycin.

In some embodiments, the chemical compound is a DNA PK inhibitor, such as M3814, NU7026, or NU7441 which potently enhance homology directed repair gene editing.

In some embodiments, the biomolecule cargo is a gene editing reagent.

In some embodiments, the gene editing reagent comprises a zinc finger (ZF), transcription activator-like effector (TALE), and/or CRISPR-based genome editing or modulating protein; a nucleic acid encoding a zinc finger (ZF), transcription activator-like effector (TALE), and/or CRISPR-based genome editing or modulating protein; or a riboucleoprotein complex (RNP) comprising a CRISPR-based genome editing or modulating protein.

In some embodiments, the gene editing reagent is selected from the proteins listed in Tables 2, 3, 4 & 5.

In some embodiments, the gene editing reagent comprises a CRISPR-based genome editing or modulating protein, and the heVLP further comprises one or more guide RNAs that bind to and direct the CRISPR-based genome editing or modulating protein to a target sequence.

In some embodiments, the cargo comprises a covalent or non-covalent connection to a human-endogenous GAG or other plasma membrane recruitment domain, preferably as shown in Table 6. Covalent connections, for example, can include direct protein-protein fusions generated from a single reading frame, inteins that can form peptide bonds, other proteins that can form covalent connections at R-groups and/or RNA splicing. Non-covalent connections, for example, can include DNA/DNA, DNA/RNA, and/or RNA/RNA hybrids (nucleic acids base pairing to other nucleic acids via hydrogen-bonding interactions), protein domains that dimerize or multimerize with or without the need for a chemical compound/molecule to induce the protein-protein binding, single chain variable fragments, nanobodies, affibodies, proteins that bind to DNA and/or RNA, proteins with quaternary structural interactions, optogenetic protein domains that can dimerize or multimerize in the presence of certain light wavelengths, and/or naturally reconstituting split proteins.

In some embodiments, the cargo comprises a fusion to a dimerization domain or protein-protein binding domain that may or may not require a molecule to trigger dimerization or protein-protein binding.

In some embodiments, the producer cells are FDA-approved cells lines, allogenic cells, and/or autologous cells derived from a donor.

In some embodiments, the full or active peptide domains of human CD47 may be incorporated in the heVLP surface to reduce immunogenicity.

Examples of AAV proteins included here are AAV REP 52, REP 78, and VP1-3. The capsid site where proteins can be inserted is T138 starting from the VP1 amino acid counting. Dimerization domains could be inserted at this point in the capsid, for instance.

Examples of dimerization domains included here that may or may not need a small molecule inducer are dDZF1, dDZF2, DmrA, DmrB, DmrC, FKBP, FRB, GCN4 scFv, 10×/24×GCN4, GFP nanobody and GFP.

Examples of split inteins included here are Npu DnaE, Cfa, Vma, and Ssp DnaE.

Examples of other split proteins included here that make a covalent bond together are Spy Tag and Spy Catcher.

Examples of RNA binding proteins included here are MS2, Com, and PP7.

Examples of synthetic DNA-binding zinc fingers included here are ZF6/10, ZF8/7, ZF9, MK10, Zinc Finger 268, and Zinc Finger 268/NRE.

Examples of proteins that multimerize as a result of quaternary structure included here are *E. coli* ferritin, and the other chimeric forms of ferritin.

Examples of optogenetic "light-inducible proteins" included here are Cry2, CIBN, and Lov2-Ja.

Examples of peptides the enhance transduction included here are L17E, Vectofusin, KALA, and the various forms of nisin.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

This particle was created by producer cells expressing an envelope protein. Cargo was packaged inside the particle either by producer cells expressing cargo or particles being loaded by various particle loading methods described herein, such as electroporation.

Figure 6:
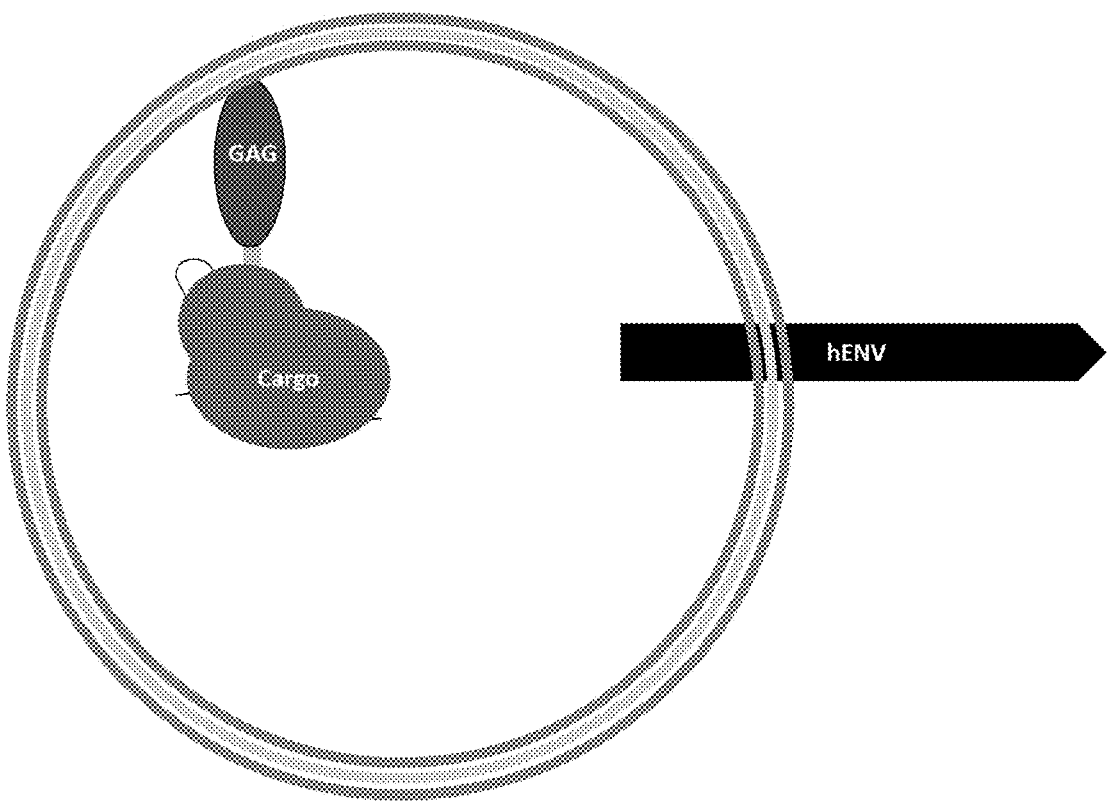

FIG. 6: Depiction of exemplary heVLP and cargo configuration

This particle was created by producer cells expressing an envelope protein. Cargo was packaged inside the particle either by producer cells expressing cargo-gag fusion or particles being loaded by various particle loading methods described herein, such as electroporation.

Figure 7:
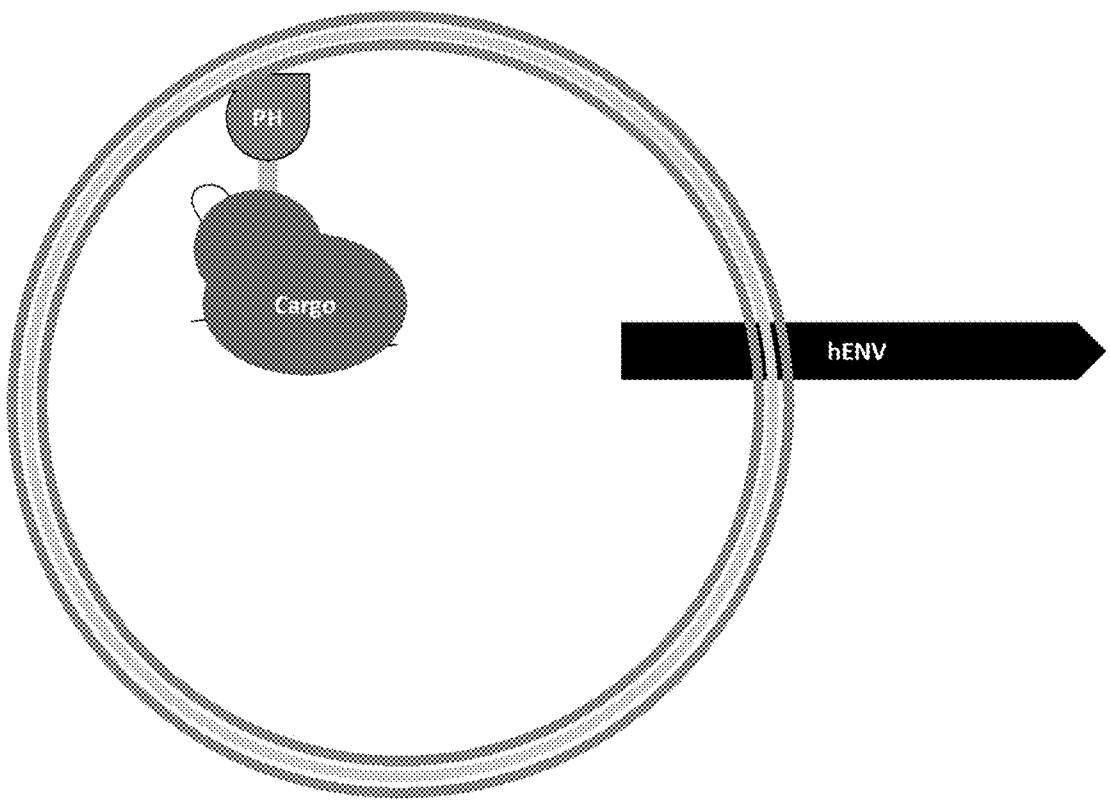

FIG. 7: Depiction of exemplary heVLP and cargo configuration

This particle was created by producer cells expressing an envelope protein. Cargo was packaged inside the particle either by producer cells expressing cargo-PH fusion or particles being loaded by various particle loading methods described herein, such as electroporation.

Figure 8:
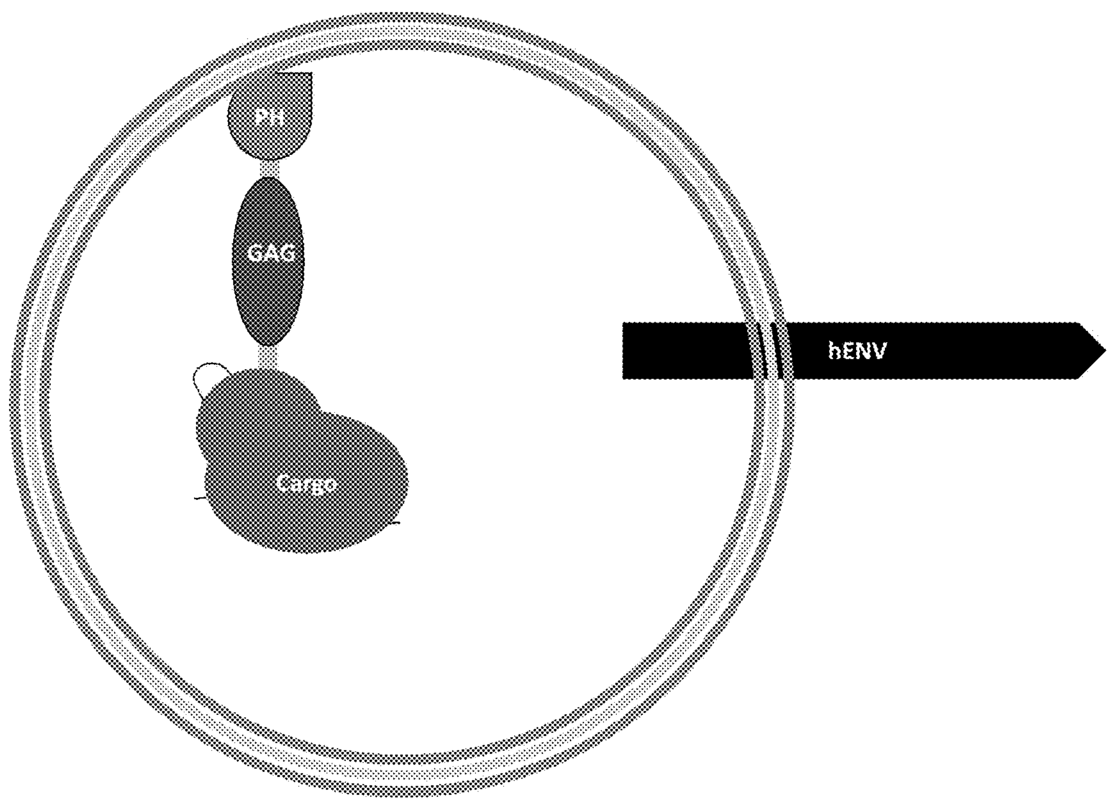

FIG. 8: Depiction of exemplary heVLP and cargo configuration

This particle was created by producer cells expressing an envelope protein. Cargo was packaged inside the particle either by producer cells expressing cargo-gag/PH fusion or particles being loaded by various particle loading methods described herein, such as electroporation.

Figure 9:
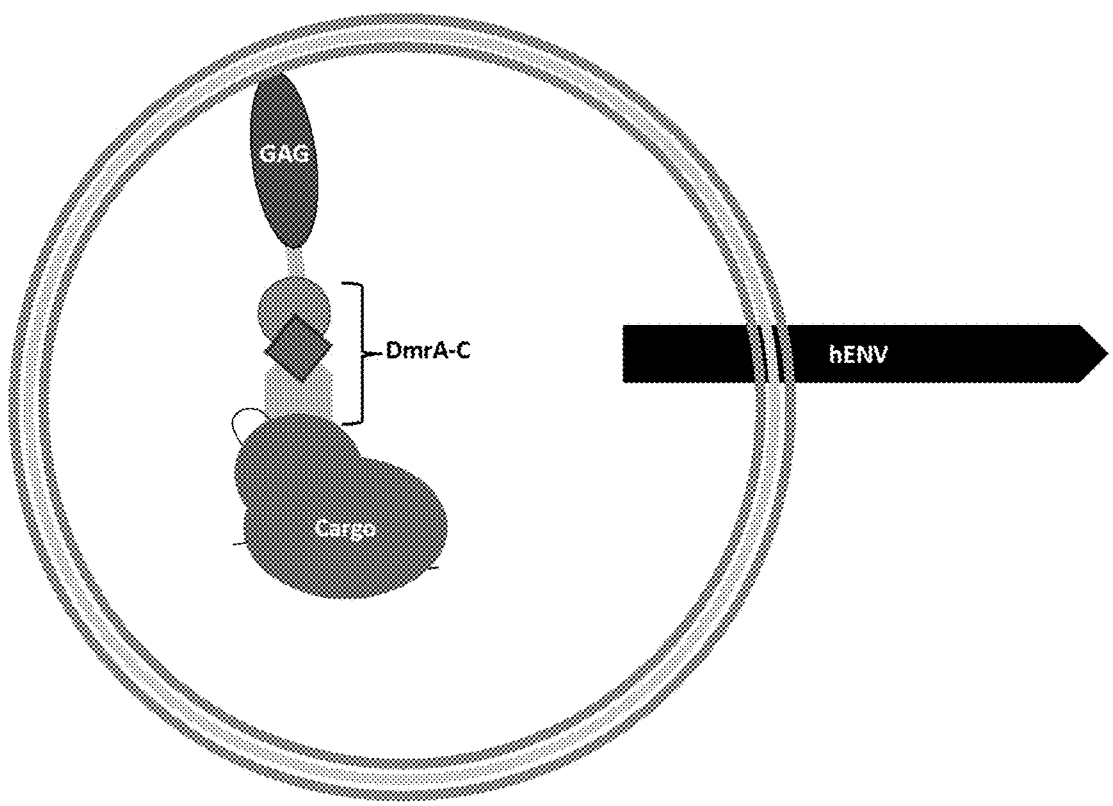

FIG. 9: Depiction of exemplary heVLP and cargo configuration

This particle was created by producer cells expressing an envelope protein. Cargo was packaged inside the particle in the presence of a dimerization molecule (A/C heterodimerizer) either by producer cells expressing cargo and gag fused to DmrA or DmrC or particles being loaded by various particle loading methods described herein, such as electroporation.

Figure 10:
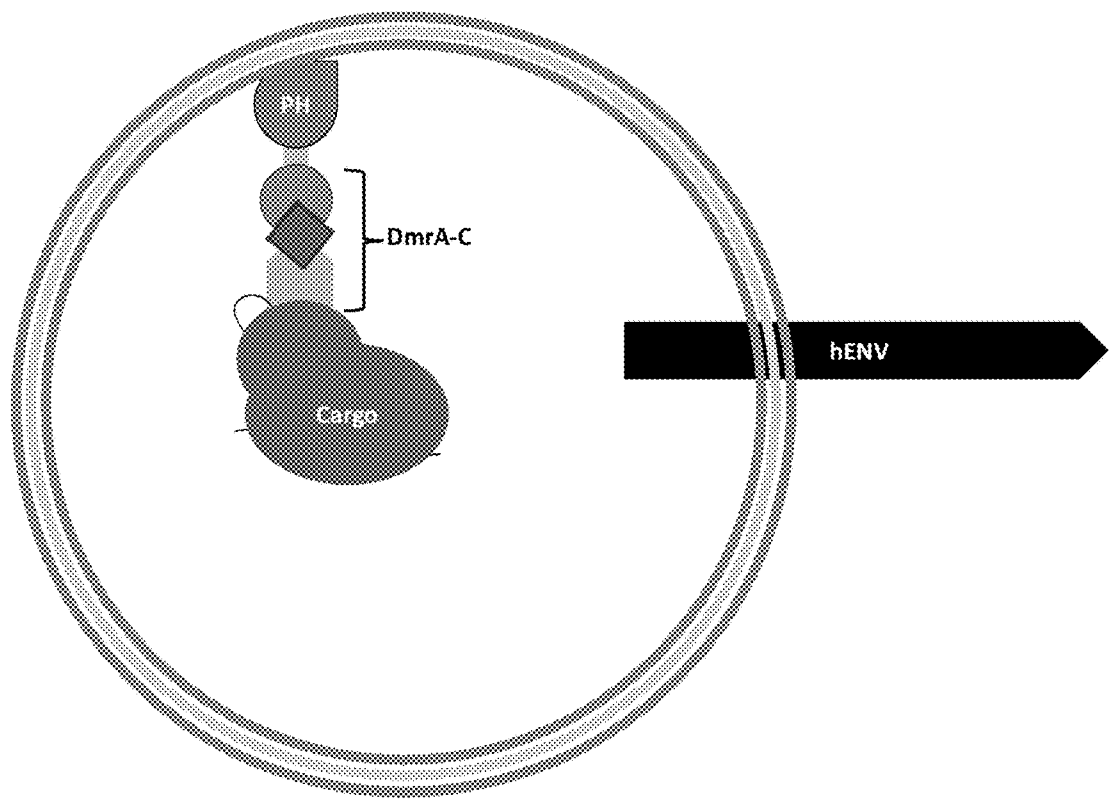

FIG. 10: Depiction of exemplary heVLP and cargo configuration

This particle was created by producer cells expressing an envelope protein. Cargo was packaged inside the particle in the presence of a dimerization molecule (A/C heterodimerizer) either by producer cells expressing cargo and PH fused to DmrA or DmrC or particles being loaded by various particle loading methods described herein, such as electroporation.

Figure 11:
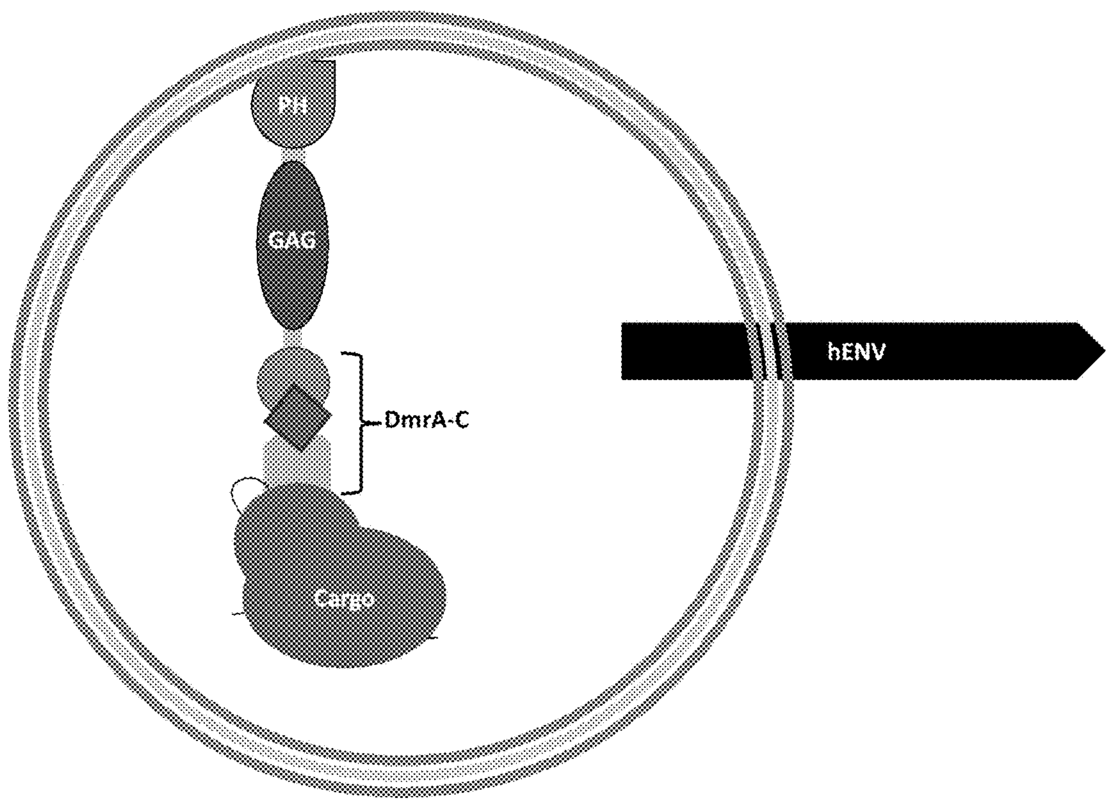

FIG. 11: Depiction of exemplary heVLP and cargo configuration

This particle was created by producer cells expressing an envelope protein. Cargo was packaged inside the particle in the presence of a dimerization molecule (A/C heterodimerizer) either by producer cells expressing cargo and gag/PH fused to DmrA or DmrC or particles being loaded by various particle loading methods described herein, such as electroporation.

Figure 12:
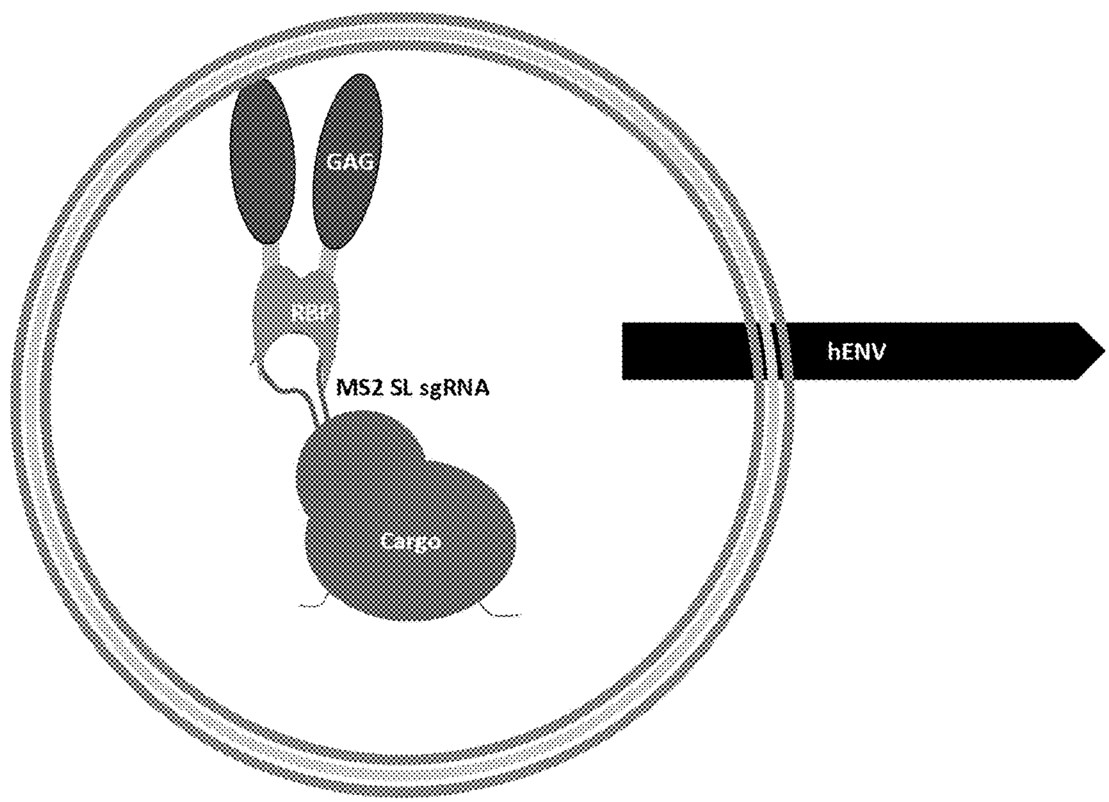

FIG. 12: Depiction of exemplary heVLP and cargo configuration

This particle was created by producer cells expressing an envelope protein. Cargo was packaged inside the particle either by producer cells expressing cargo and gag fused to an RNA binding protein (RBP), MS2, that binds to its MS2 RNA stem loop (MS2 SL) that is complexed with cargo or particles being loaded by various particle loading methods described herein, such as electroporation.

Figure 13:
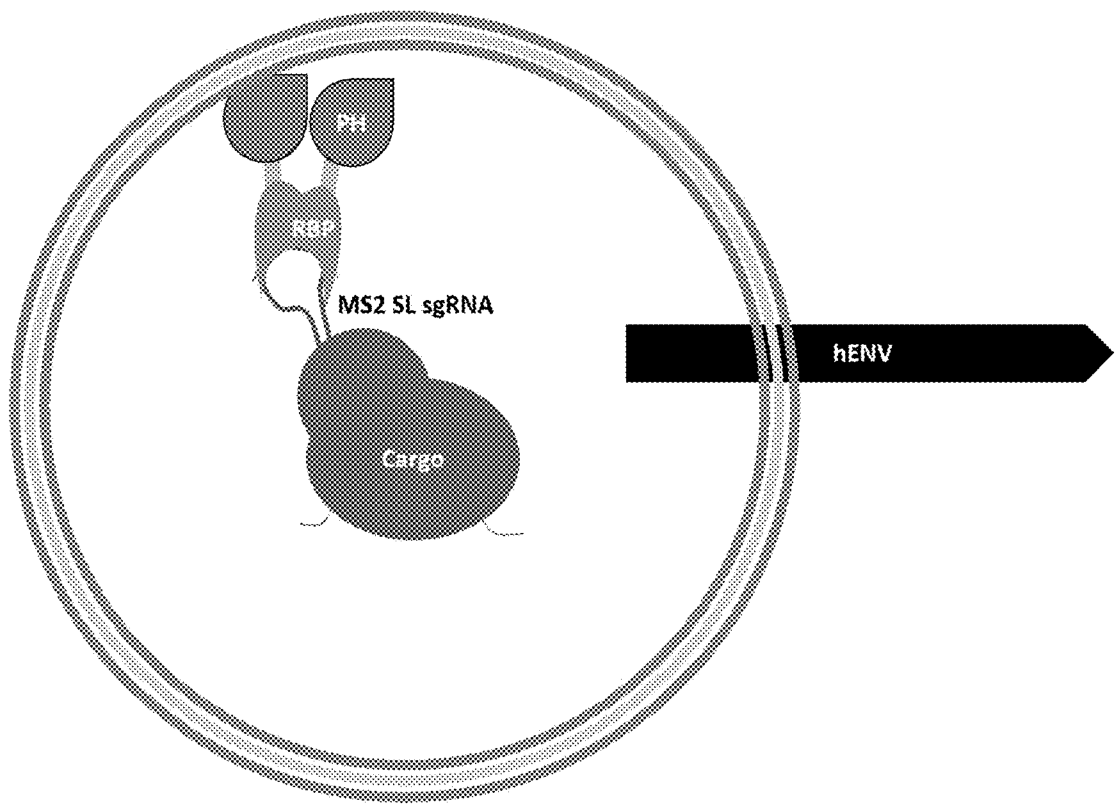

FIG. 13: Depiction of exemplary heVLP and cargo configuration

This particle was created by producer cells expressing an envelope protein. Cargo was packaged inside the particle either by producer cells expressing cargo and PH fused to an RNA binding protein (RBP), MS2, that binds to its RNA stem loop (MS2 SL) that is complexed with cargo or particles being loaded by various particle loading methods described herein, such as electroporation.

Figure 14:
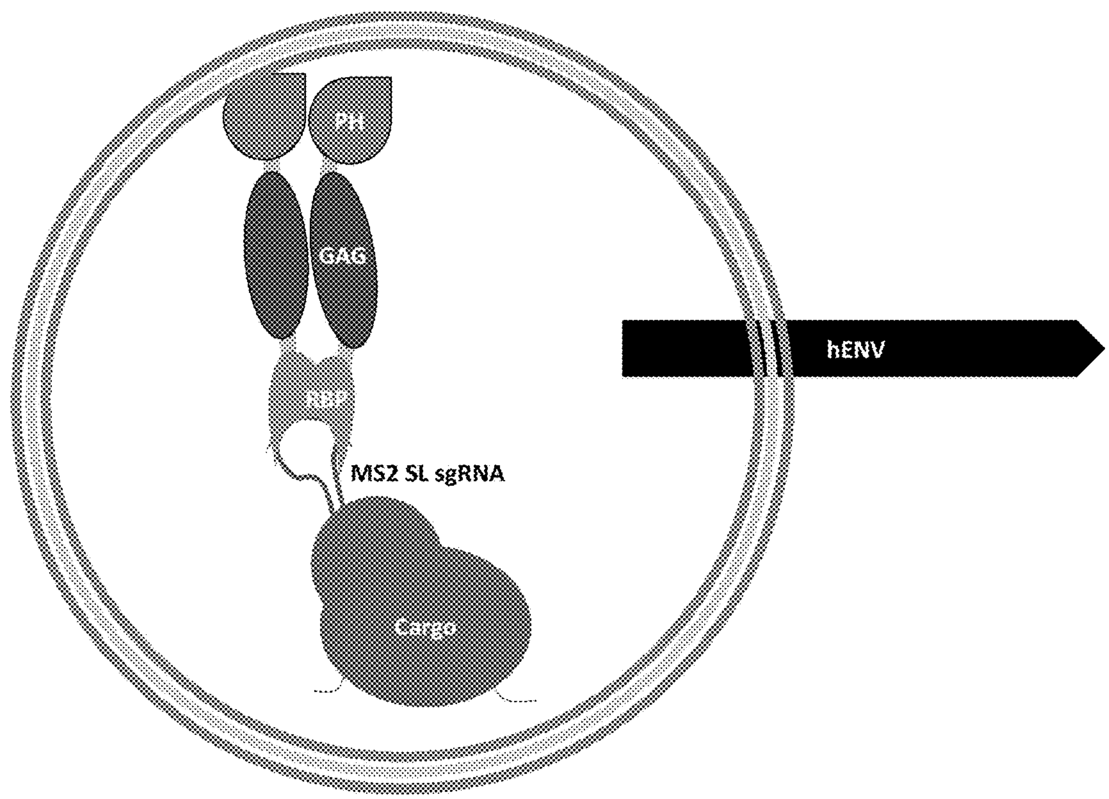

FIG. 14: Depiction of exemplary heVLP and cargo configuration

This particle was created by producer cells expressing an envelope protein. Cargo was packaged inside the particle either by producer cells expressing cargo and gag/PH fused to an RNA binding protein (RBP), MS2, that binds to its RNA stem loop (MS2 SL) that is complexed with cargo or particles being loaded by various particle loading methods described herein, such as electroporation.

Figure 15:
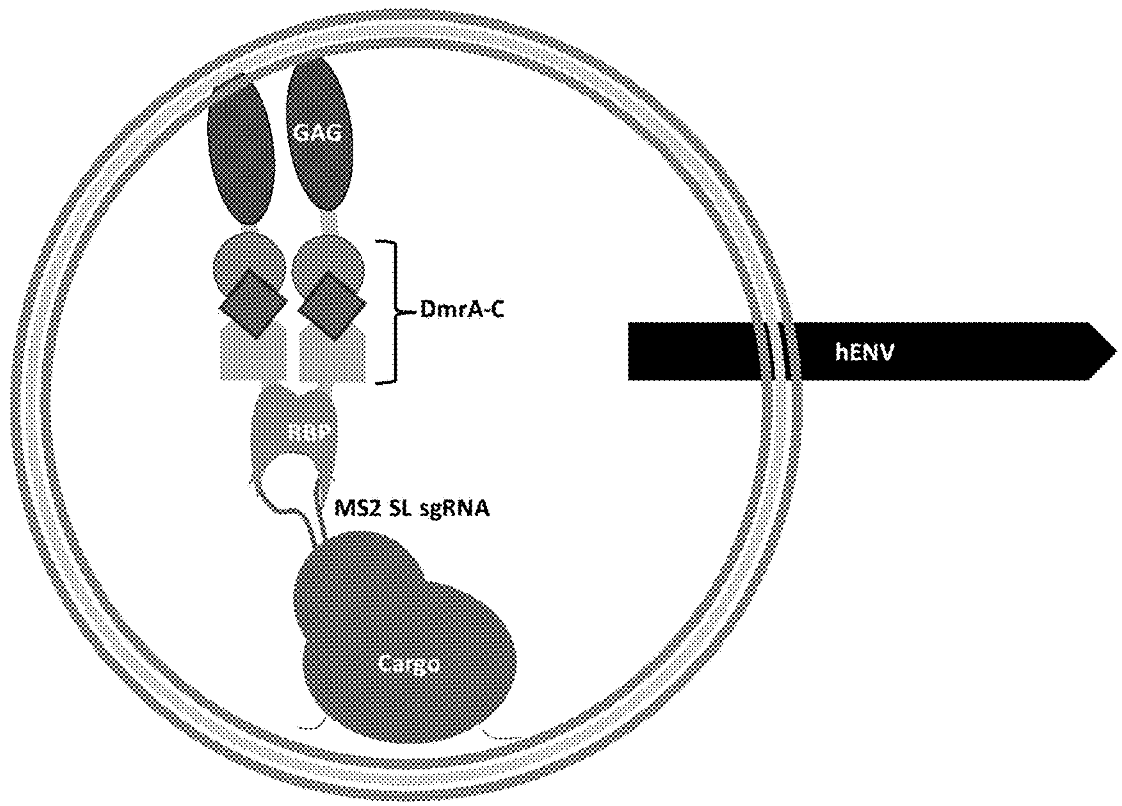

FIG. 15: Depiction of exemplary heVLP and cargo configuration

This particle was created by producer cells expressing an envelope protein. Cargo was packaged inside the particle in the presence of dimerization molecule (A/C Heterodimerizer) either by producer cells expressing cargo and gag and an RNA binding protein (RBP), MS2, fused to DmrA or DmrC that binds to its RNA stem loop (MS2 SL) that is complexed with cargo or particles being loaded by various particle loading methods described herein, such as electroporation.

Figure 16:
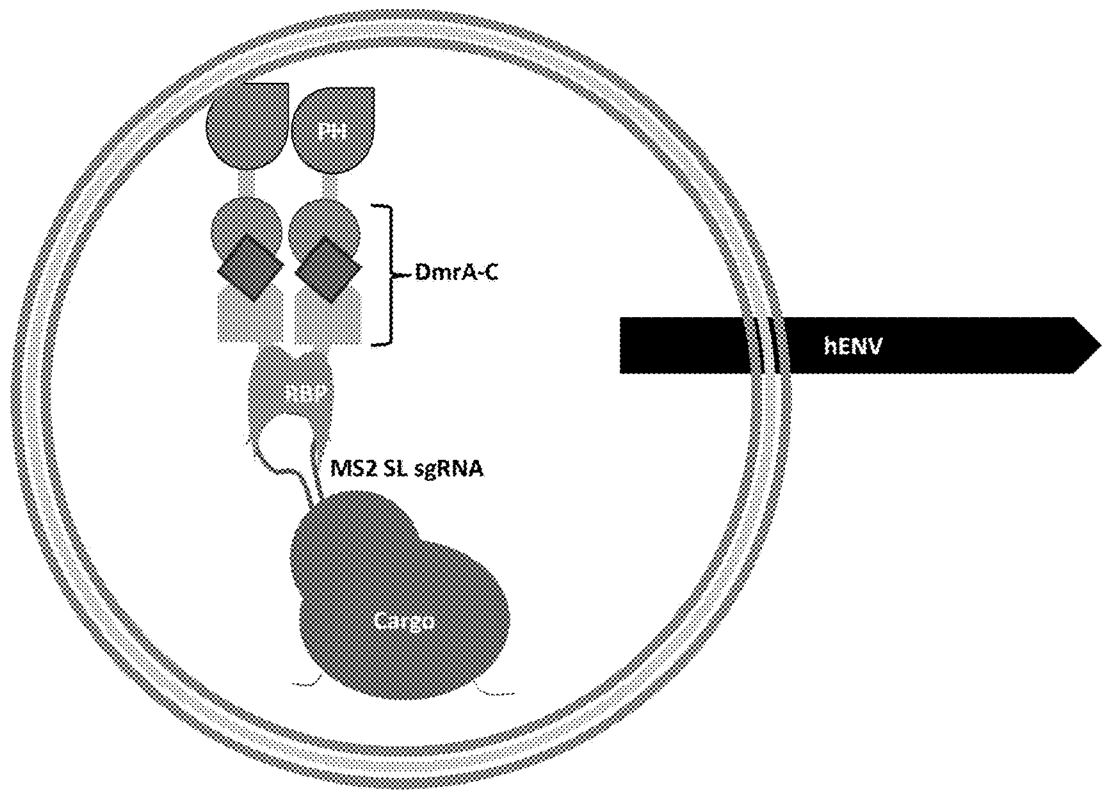

FIG. 16: Depiction of exemplary heVLP and cargo configuration

This particle was created by producer cells expressing an envelope protein. Cargo was packaged inside the particle in the presence of dimerization molecule (A/C Heterodimerizer) either by producer cells expressing cargo and PH and an RNA binding protein (RBP), MS2, fused to DmrA or DmrC that binds to its RNA stem loop (MS2 SL) that is complexed with cargo or particles being loaded by various particle loading methods described herein, such as electroporation.

Figure 17:
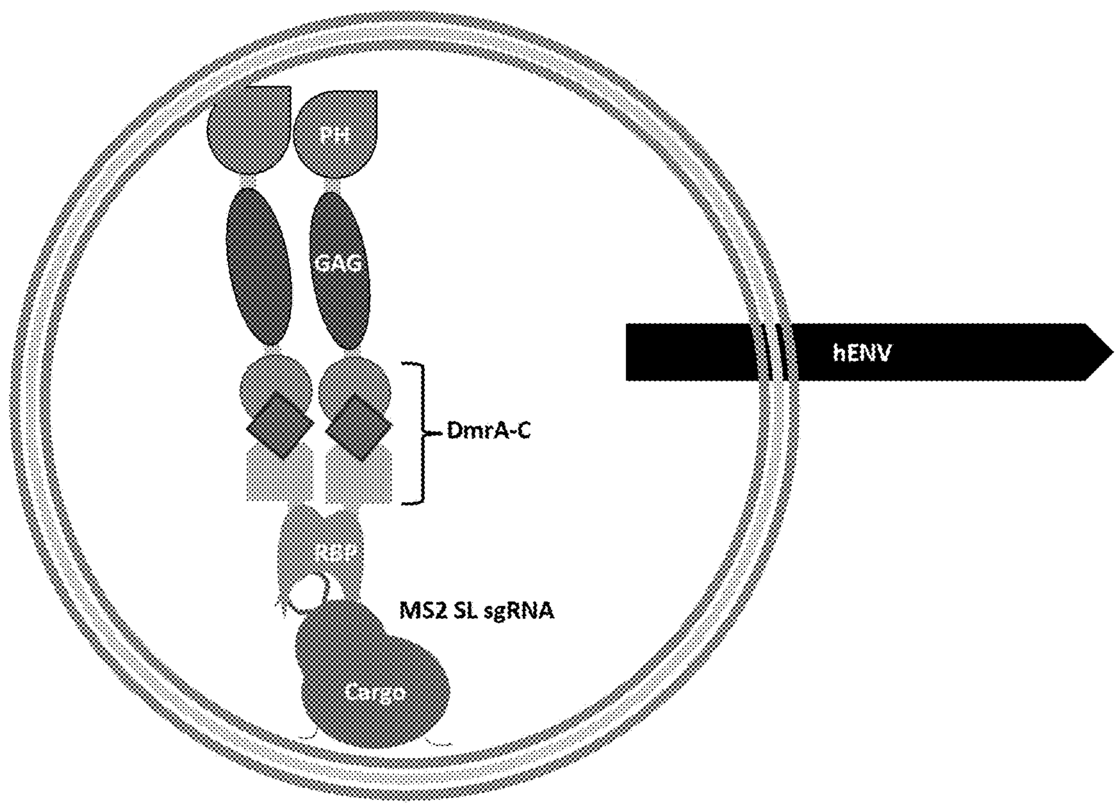

FIG. 17: Depiction of exemplary heVLP and cargo configuration

This particle was created by producer cells expressing an envelope protein. Cargo was packaged inside the particle in the presence of dimerization molecule (A/C Heterodimerizer) either by producer cells expressing cargo and gag/PH and an RNA binding protein (RBP), MS2, fused to DmrA or DmrC that binds to its RNA stem loop (MS2 SL) that is complexed with cargo or particles being loaded by various particle loading methods described herein, such as electroporation.

Figure 18:
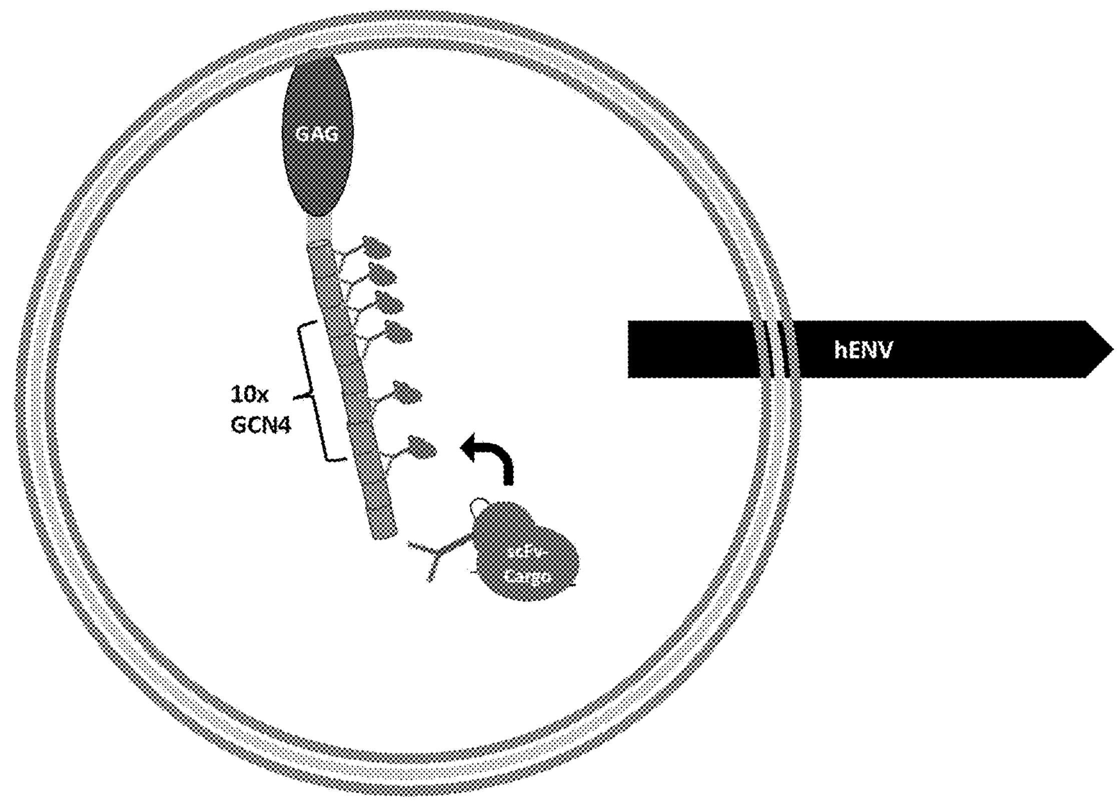

FIG. 18: Depiction of exemplary heVLP and cargo configuration

This particle was created by producer cells expressing an envelope protein. Cargo was packaged inside the particle either by producer cells expressing cargo and gag fused to a repetitive GCN4 domain that is bound by an scFv that is fused with cargo or particles being loaded by various particle loading methods described herein, such as electroporation.

Figure 19:
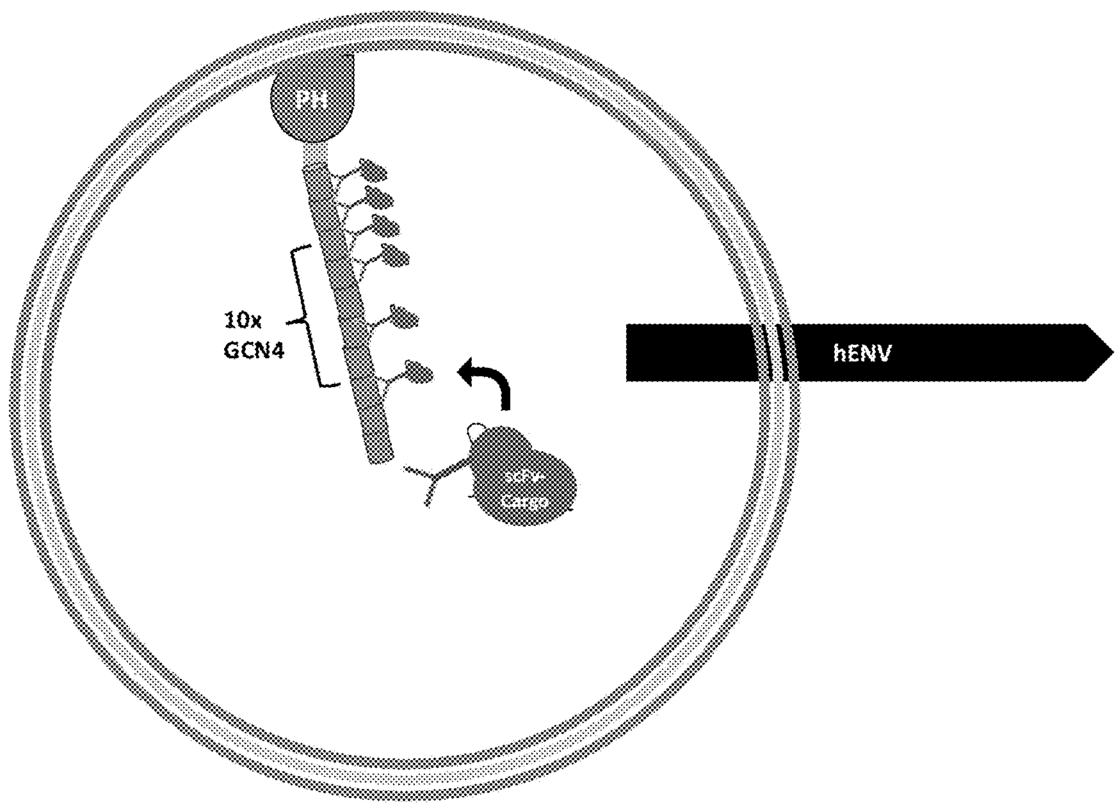

FIG. 19: Depiction of exemplary heVLP and cargo configuration

This particle was created by producer cells expressing an envelope protein. Cargo was packaged inside the particle either by producer cells expressing cargo and PH fused to a repetitive GCN4 domain that is bound by an scFv that is fused with cargo or particles being loaded by various particle loading methods described herein, such as electroporation.

Figure 20:
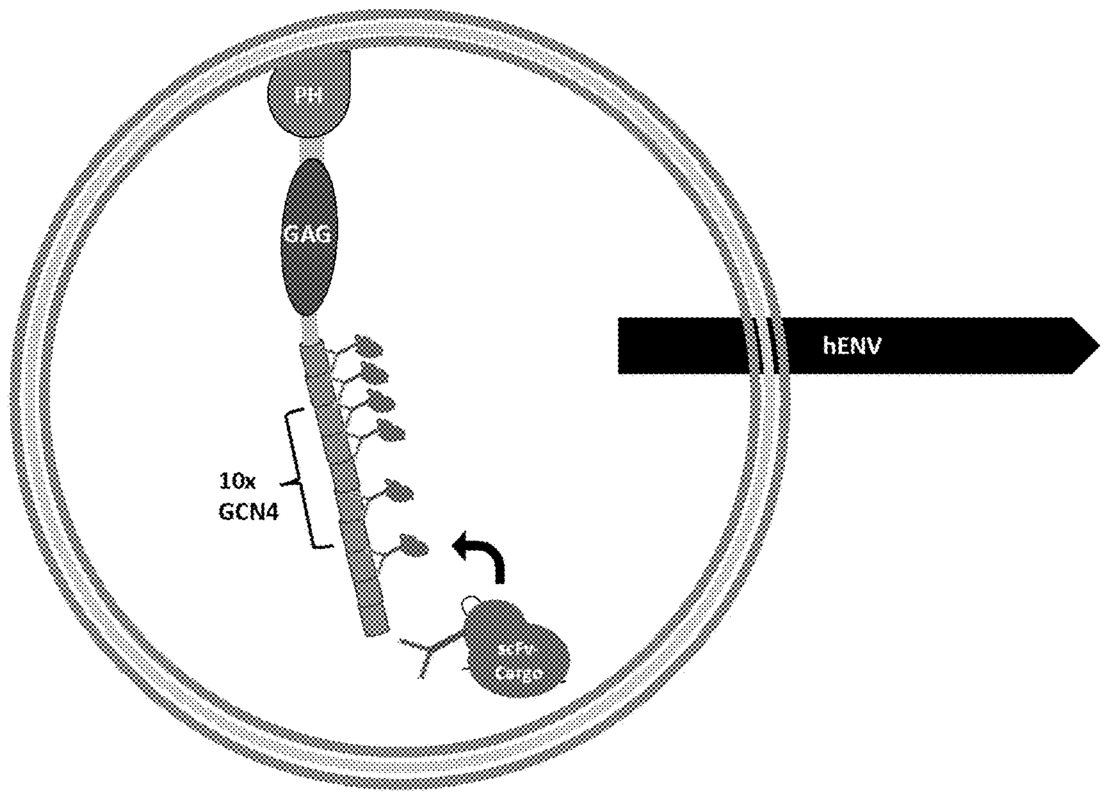

FIG. 20: Depiction of exemplary heVLP and cargo configuration

This particle was created by producer cells expressing an envelope protein. Cargo was packaged inside the particle either by producer cells expressing cargo and gag/PH fused to a repetitive GCN4 domain that is bound by an scFv that is fused with cargo or particles being loaded by various particle loading methods described herein, such as electroporation.

Figure 21:
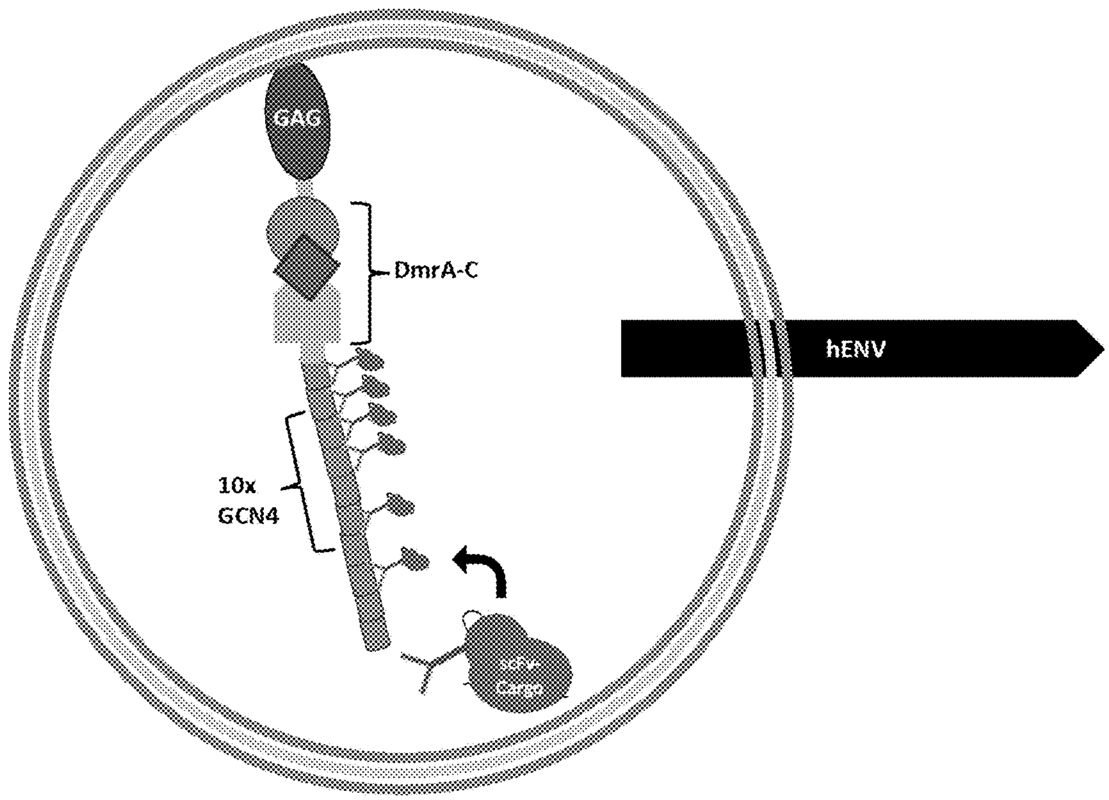

FIG. 21: Depiction of exemplary heVLP and cargo configuration

This particle was created by producer cells expressing an envelope protein. Cargo was packaged inside the particle in the presence of a dimerization molecule (A/C Heterodimerizer) by producer cells expressing gag and a repetitive GCN4 domain that are fused to DmrA or DmrC. GCN4 is bound by an scFv that is fused with cargo that is also being expressed in producer cells. Particles could also be loaded by various particle loading methods described herein, such as electroporation.

Figure 22:
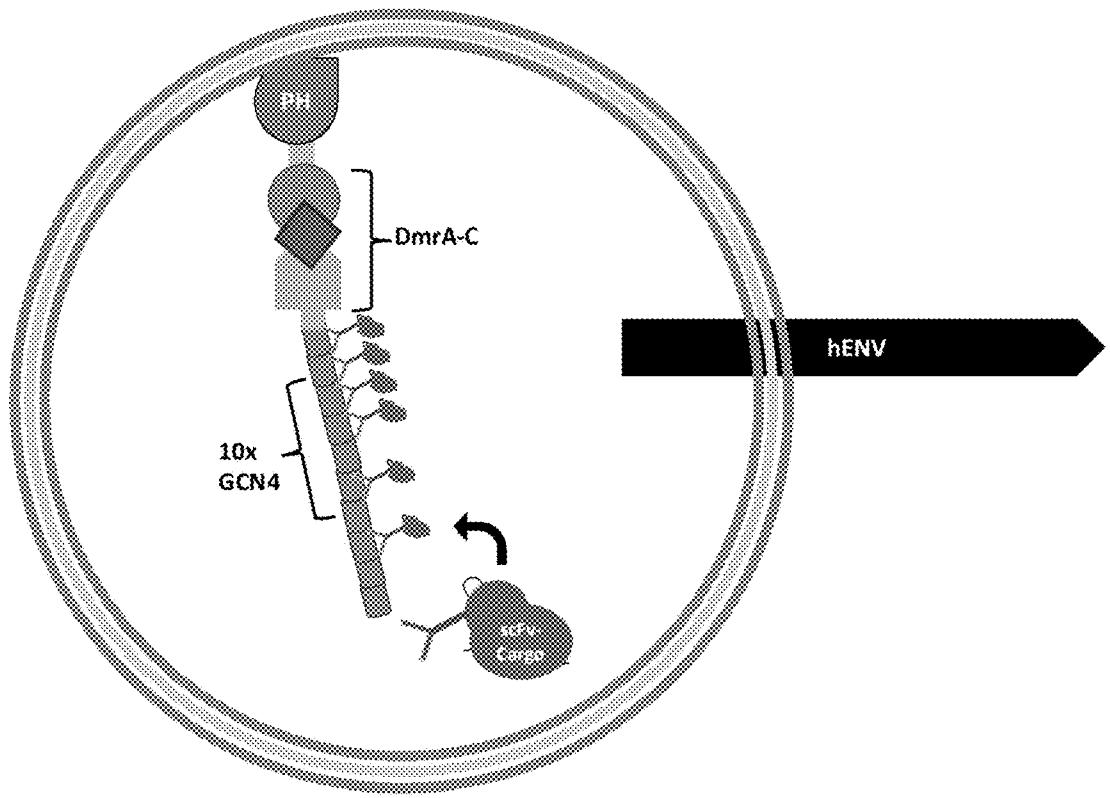

FIG. 22: Depiction of exemplary heVLP and cargo configuration

This particle was created by producer cells expressing an envelope protein. Cargo was packaged inside the particle in the presence of a dimerization molecule (A/C Heterodimerizer) by producer cells expressing PH and a repetitive GCN4 domain that are fused to DmrA or DmrC. GCN4 is bound by an scFv that is fused with cargo that is also being expressed in producer cells. Particles could also be loaded by various particle loading methods described herein, such as electroporation.

Figure 23:
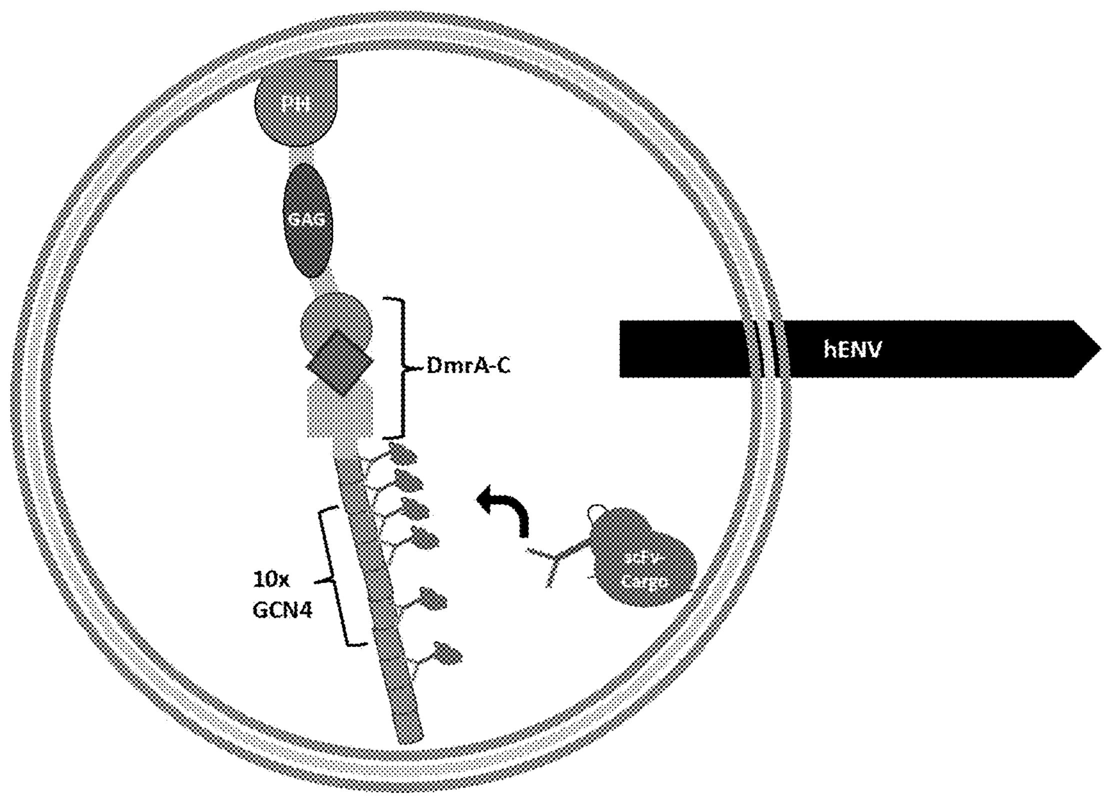

FIG. 23: Depiction of exemplary heVLP and cargo configuration

This particle was created by producer cells expressing an envelope protein. Cargo was packaged inside the particle in the presence of a dimerization molecule (A/C Heterodimerizer) by producer cells expressing gag/PH and a repetitive GCN4 domain that are fused to DmrA or DmrC. GCN4 is bound by an scFv that is fused with cargo that is also being expressed in producer cells. Particles could also be loaded by various particle loading methods described herein, such as electroporation.

Figure 24:
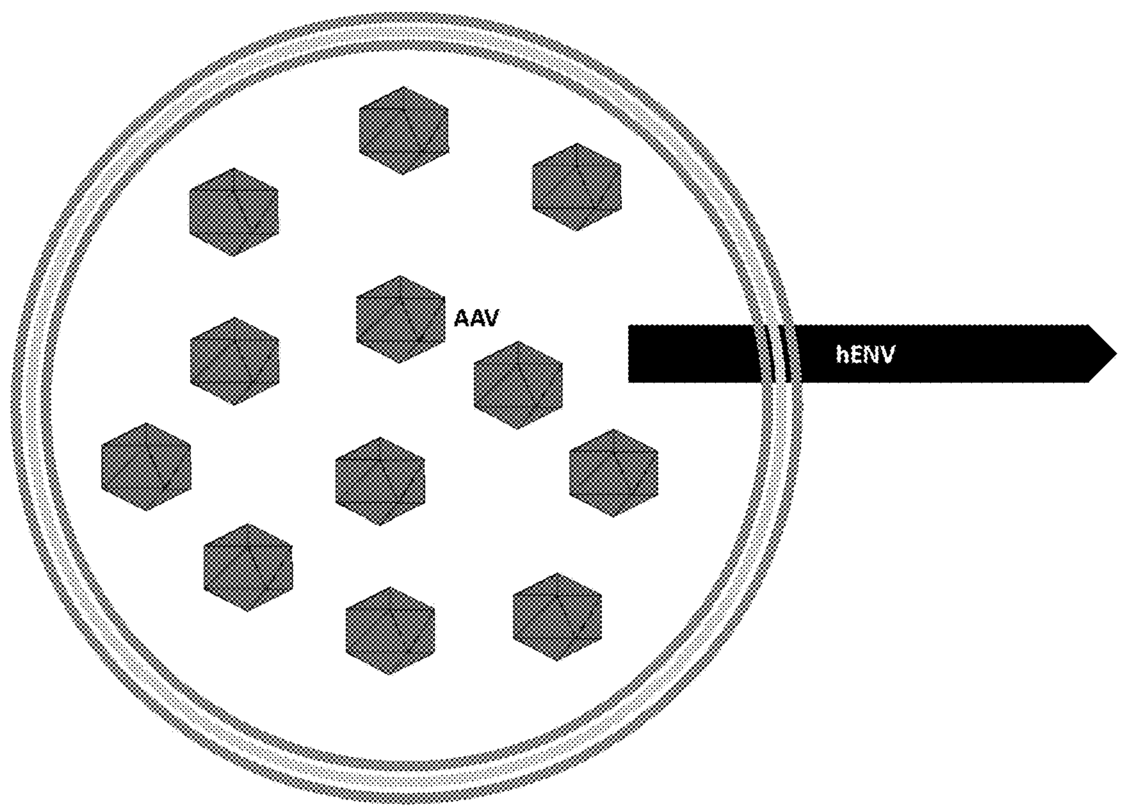

FIG. 24: Depiction of exemplary heVLP and cargo configuration

This particle was created by producer cells expressing an envelope protein. Cargo (AAV particles) was packaged inside the particle either by producer cells expressing cargo or particles being loaded by various particle loading methods described herein, such as electroporation.

Figure 25:
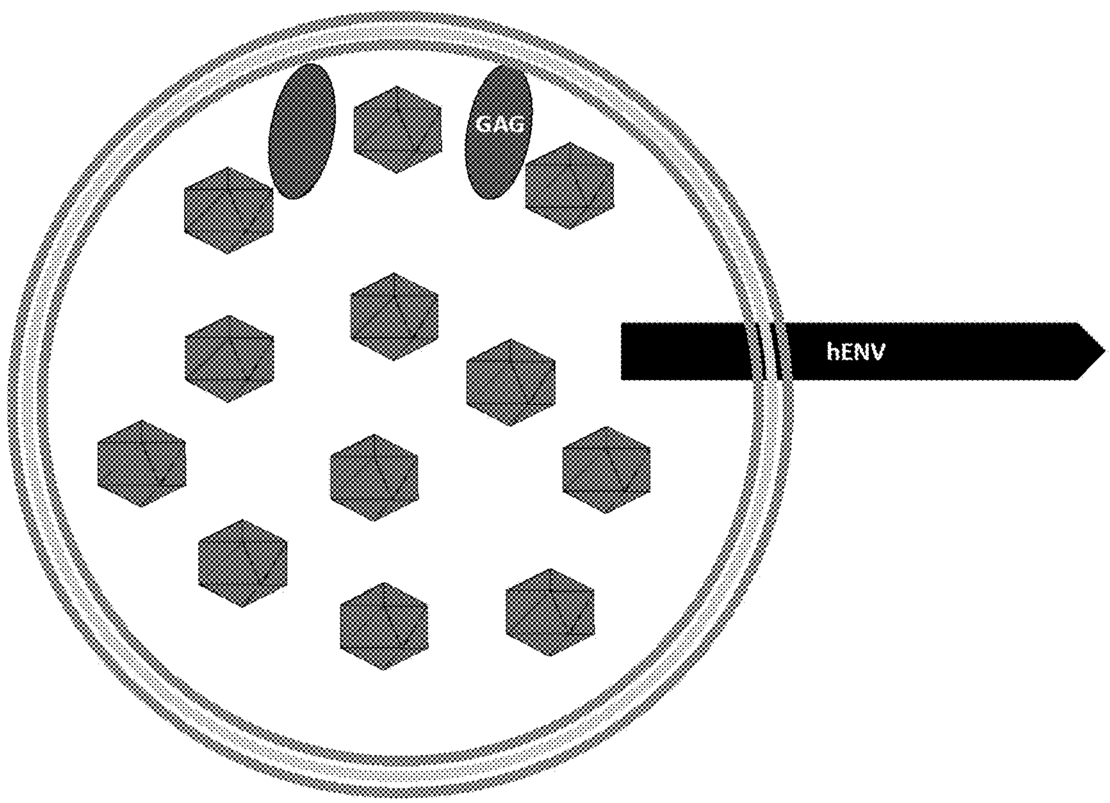

FIG. 25: Depiction of exemplary heVLP and cargo configuration

This particle was created by producer cells expressing an envelope protein. Cargo (AAV particles) was packaged inside the particle either by producer cells expressing cargo and gag or particles being loaded by various particle loading methods described herein, such as electroporation.

Figure 26:
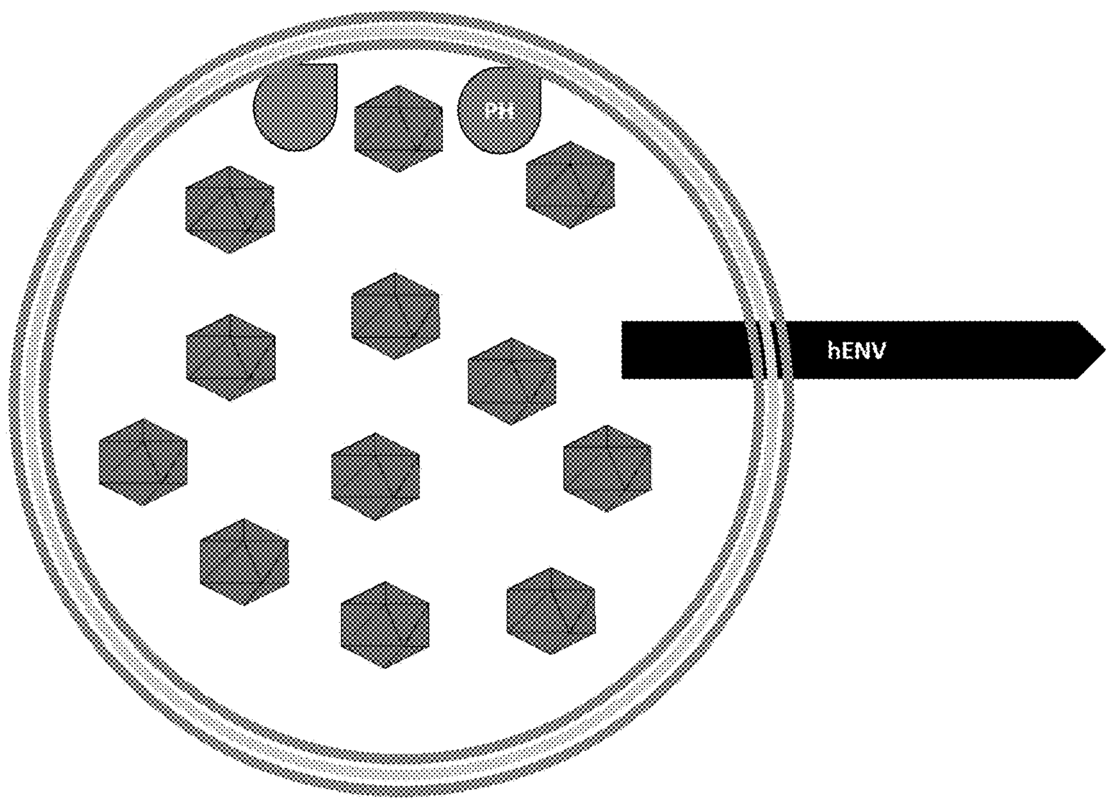

FIG. 26: Depiction of exemplary heVLP and cargo configuration

This particle was created by producer cells expressing an envelope protein. Cargo (AAV particles) was packaged inside the particle either by producer cells expressing cargo and PH or particles being loaded by various particle loading methods described herein, such as electroporation.

Figure 27:
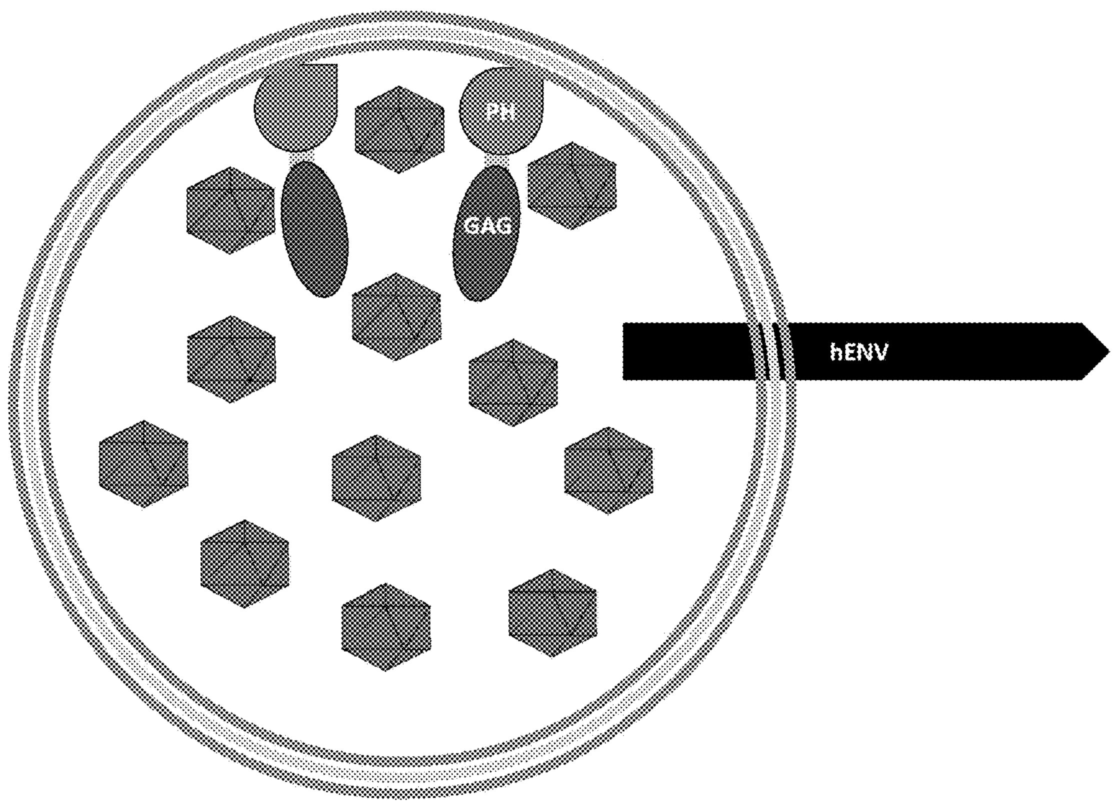

FIG. 27: Depiction of exemplary heVLP and cargo configuration

This particle was created by producer cells expressing an envelope protein. Cargo (AAV particles) was packaged inside the particle either by producer cells expressing cargo and gag/PH or particles being loaded by various particle loading methods described herein, such as electroporation.

Figure 28:
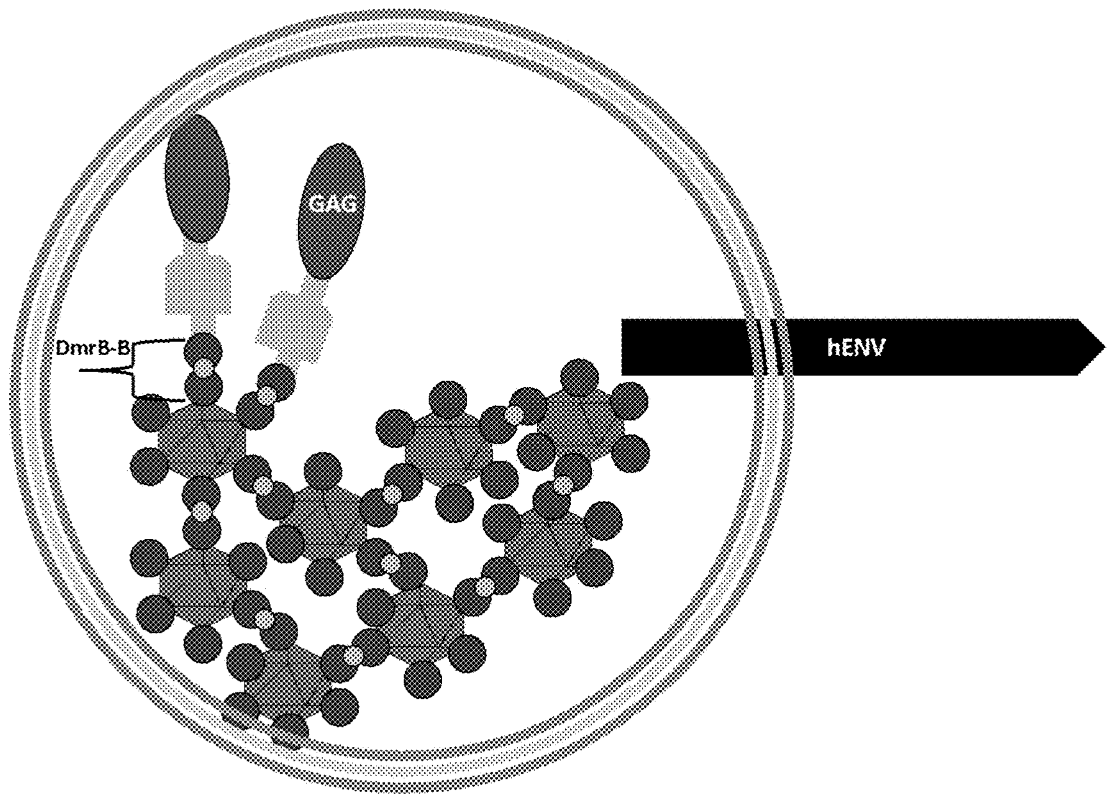

FIG. 28: Depiction of exemplary heVLP and cargo configuration

This particle was created by producer cells expressing an envelope protein. Cargo (AAV particles with DmrB inserted in the Capsid protein, VP2) was packaged inside the particle in the presence of DmrB dimerizer molecule either by producer cells expressing cargo and gag fused to DmrB or particles being loaded by various particle loading methods described herein, such as electroporation.

Figure 29:
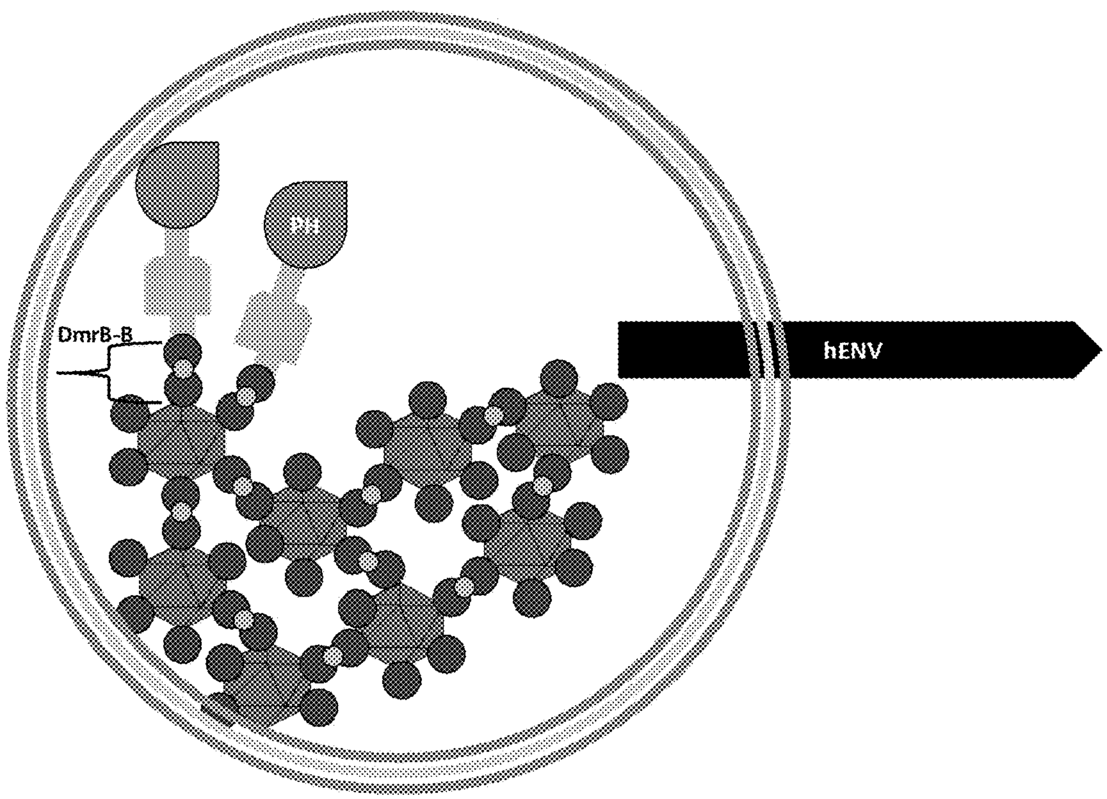

FIG. 29: Depiction of exemplary heVLP and cargo configuration

This particle was created by producer cells expressing an envelope protein. Cargo (AAV particles with DmrB inserted in the Capsid protein, VP2) was packaged inside the particle in the presence of DmrB dimerizer molecule either by producer cells expressing cargo and PH fused to DmrB or particles being loaded by various particle loading methods described herein, such as electroporation.

Figure 30:
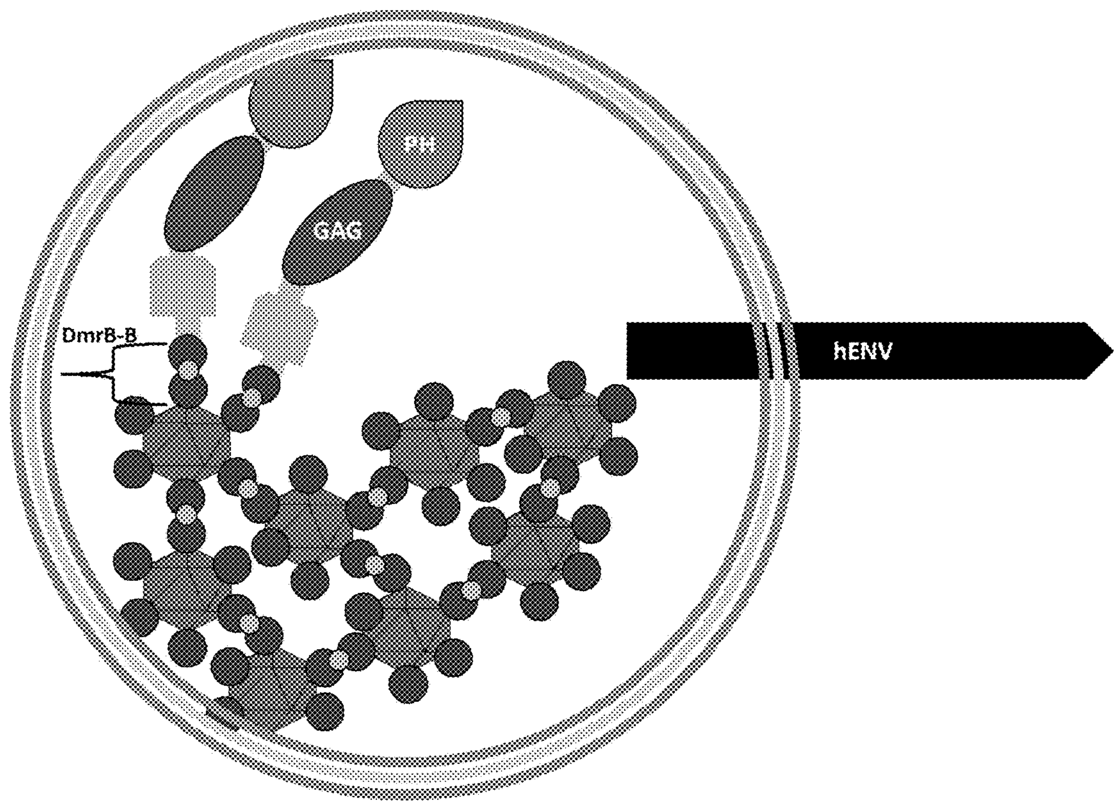

FIG. 30: Depiction of exemplary heVLP and cargo configuration

This particle was created by producer cells expressing an envelope protein. Cargo (AAV particles with DmrB inserted in the Capsid protein, VP2) was packaged inside the particle in the presence of DmrB dimerizer molecule either by producer cells expressing cargo and gag/PH fused to DmrB or particles being loaded by various particle loading methods described herein, such as electroporation.

Figure 31:
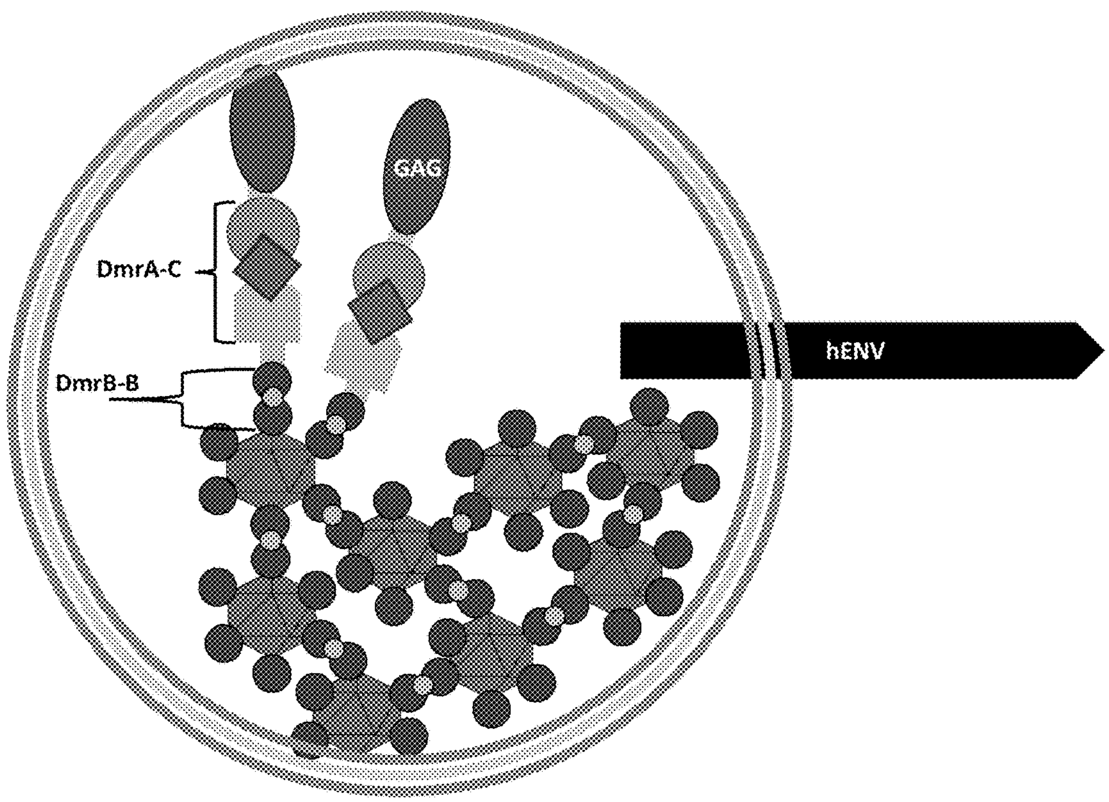

FIG. 31: Depiction of exemplary heVLP and cargo configuration

This particle was created by producer cells expressing an envelope protein. Cargo (AAV particles with DmrB inserted in the Capsid protein, VP2) was packaged inside the particle in the presence of DmrB dimerizer and A/C Heterodimerizer molecules either by producer cells expressing cargo and gag fused to DmrA, DmrB, or DmrC, or particles being loaded by various particle loading methods described herein, such as electroporation.

Figure 32:
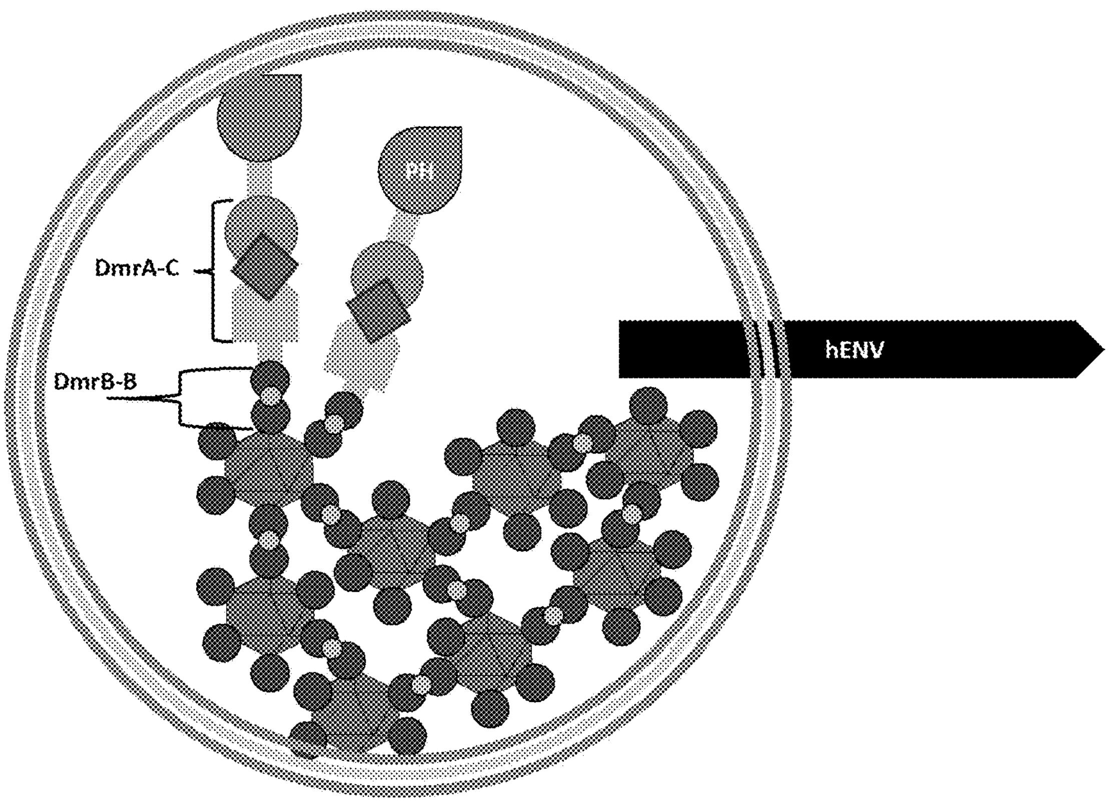

FIG. 32: Depiction of exemplary heVLP and cargo configuration

This particle was created by producer cells expressing an envelope protein. Cargo (AAV particles with DmrB inserted in the Capsid protein, VP2) was packaged inside the particle in the presence of DmrB dimerizer and A/C Heterodimerizer molecules either by producer cells expressing cargo and PH fused to DmrA, DmrB, or DmrC, or particles being loaded by various particle loading methods described herein, such as electroporation.

Figure 33:
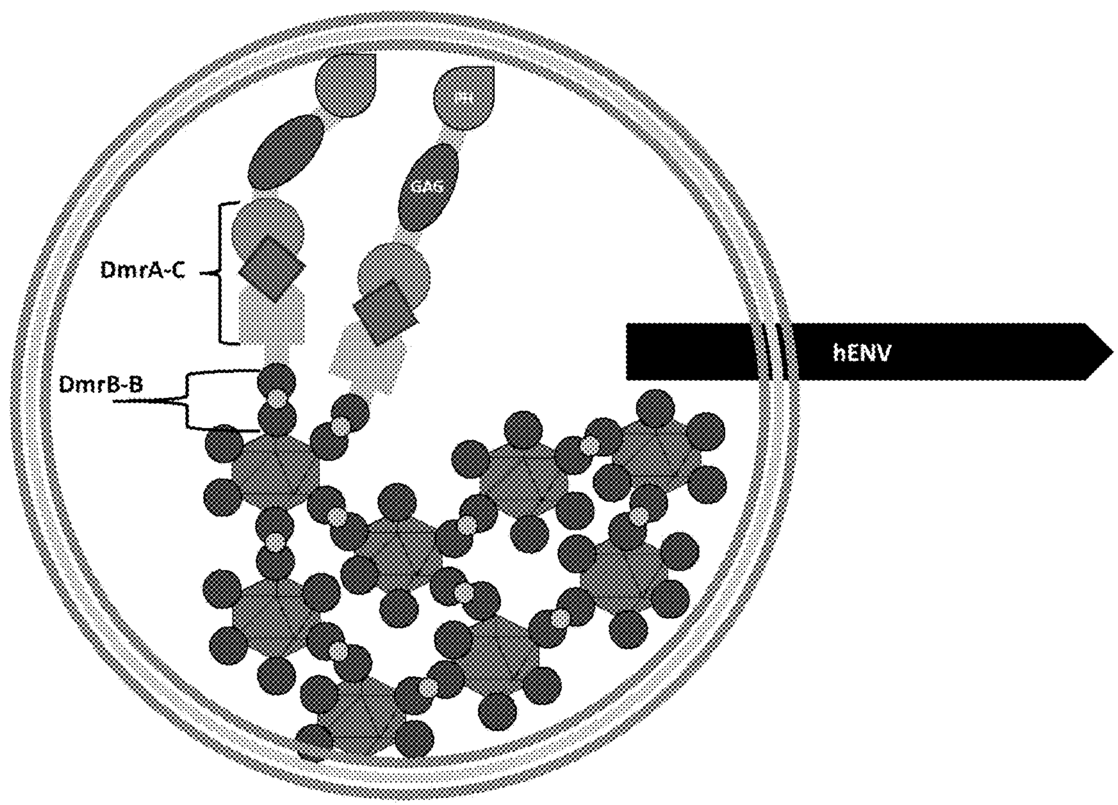

FIG. 33: Depiction of exemplary heVLP and cargo configuration

This particle was created by producer cells expressing an envelope protein. Cargo (AAV particles with DmrB inserted in the Capsid protein, VP2) was packaged inside the particle in the presence of DmrB dimerizer and A/C Heterodimerizer molecules either by producer cells expressing cargo and gag/PH fused to DmrA, DmrB, or DmrC, or particles being loaded by various particle loading methods described herein, such as electroporation.

Figure 34:
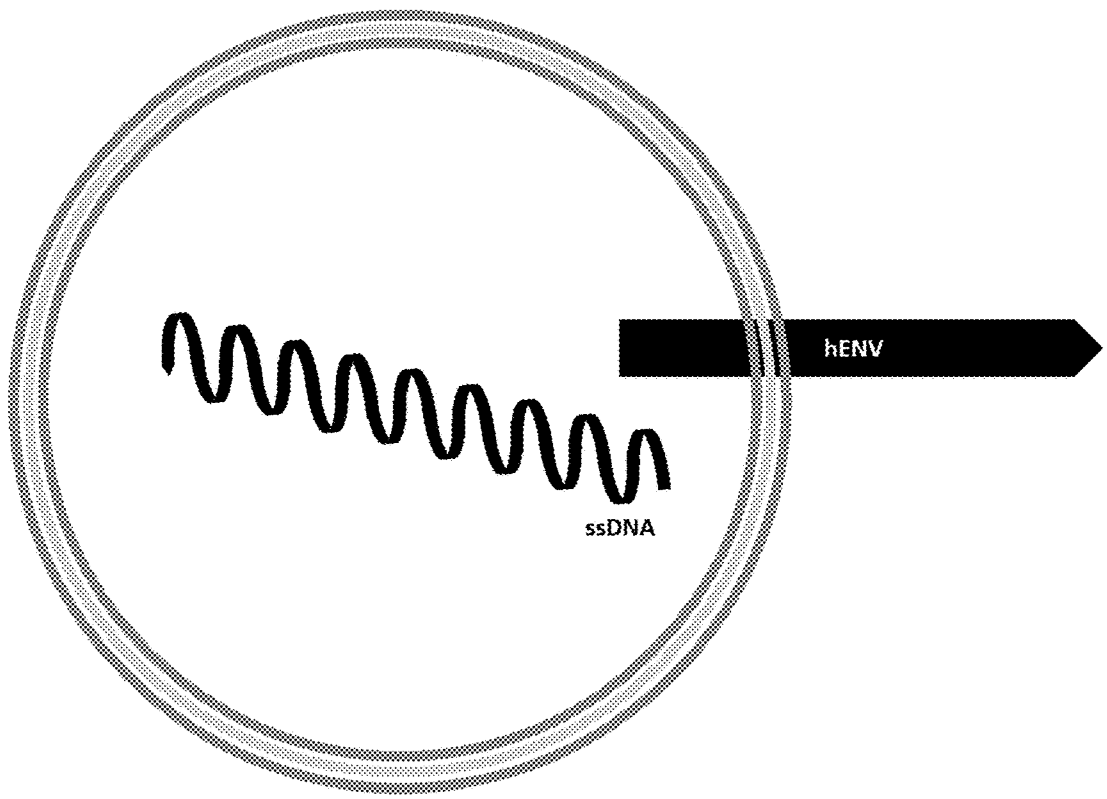

FIG. 34: Depiction of exemplary heVLP and cargo configuration

This particle was created by producer cells expressing an envelope protein. Cargo (single-stranded DNA) can be packaged inside the particle by various particle loading methods described herein, such as electroporation.

Figure 35:
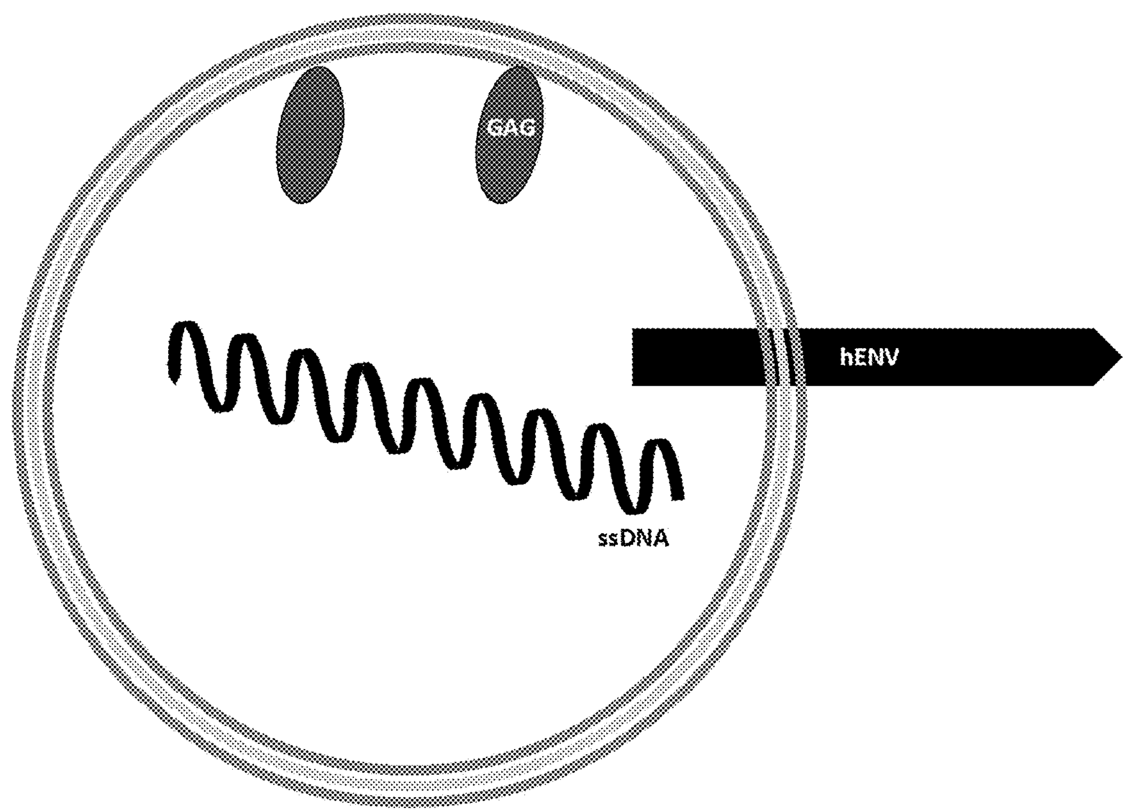

FIG. 35: Depiction of exemplary heVLP and cargo configuration

This particle was created by producer cells expressing an envelope protein and gag. Cargo (single-stranded DNA) can be packaged inside the particle by various particle loading methods described herein, such as electroporation.

Figure 36:
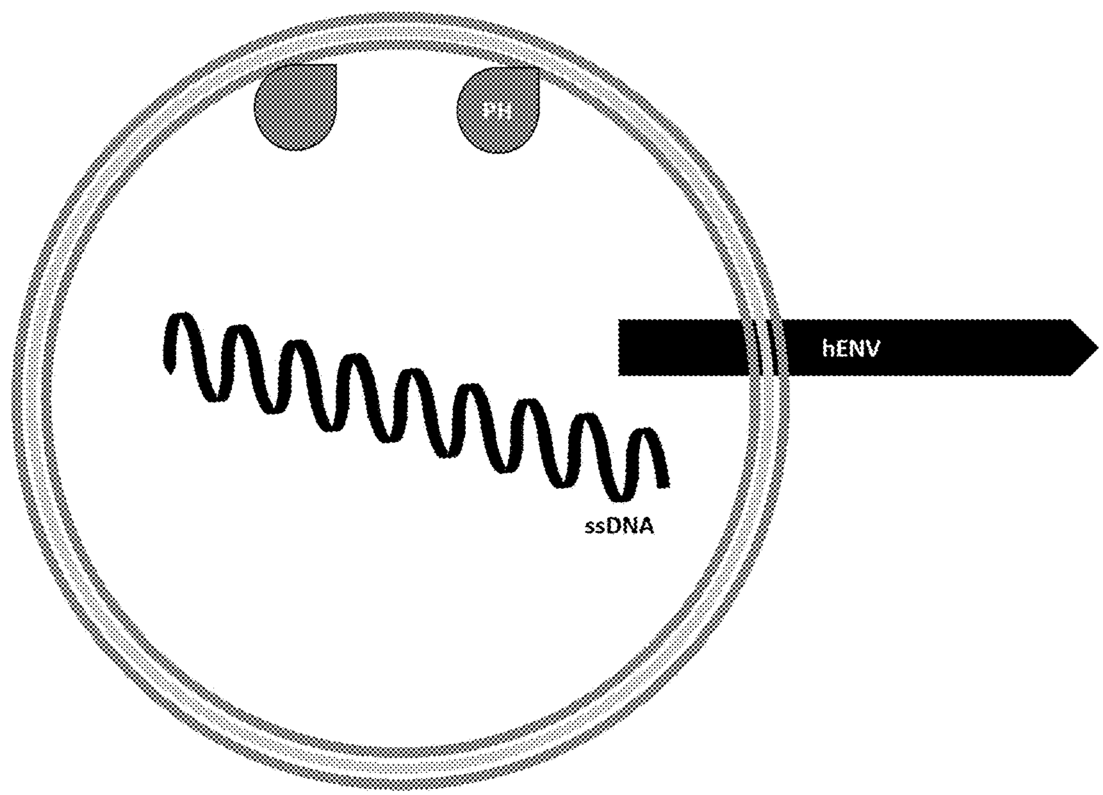

FIG. 36: Depiction of exemplary heVLP and cargo configuration

This particle was created by producer cells expressing an envelope protein and PH. Cargo (single-stranded DNA) can be packaged inside the particle by various particle loading methods described herein, such as electroporation.

Figure 37:
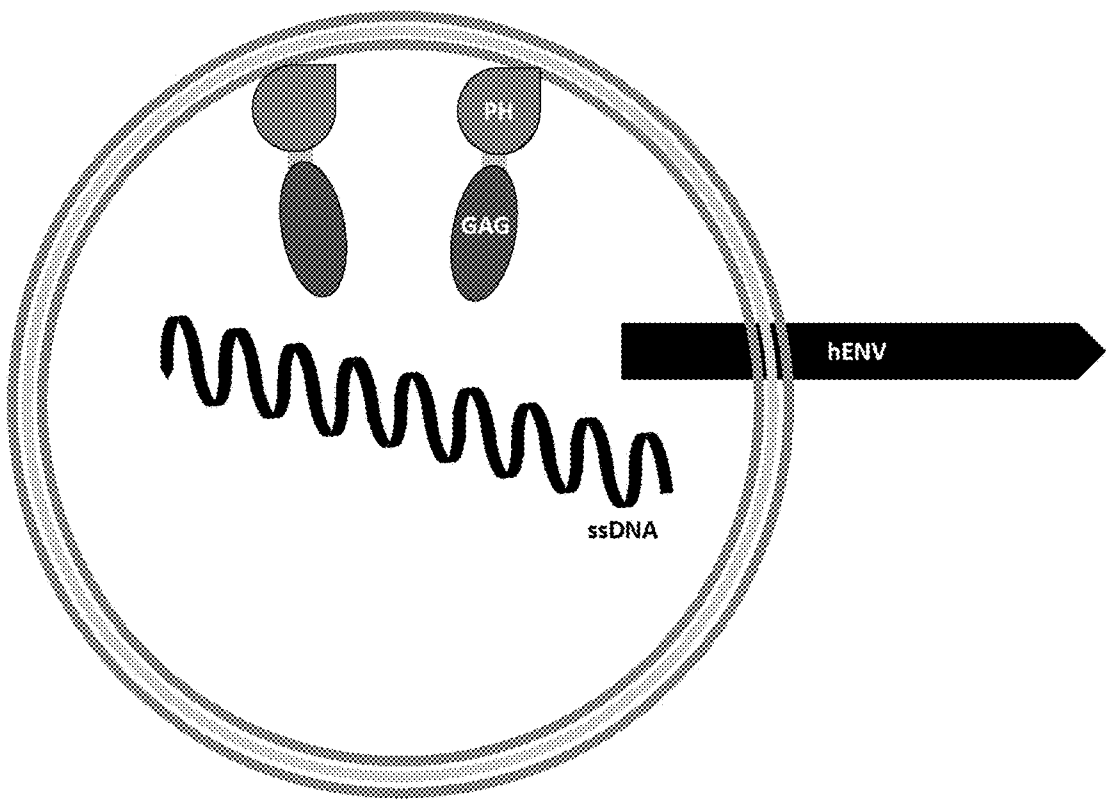

FIG. 37: Depiction of exemplary heVLP and cargo configuration

This particle was created by producer cells expressing an envelope protein and gag/PH. Cargo (single-stranded DNA) can be packaged inside the particle by various particle loading methods described herein, such as electroporation.

Figure 38:
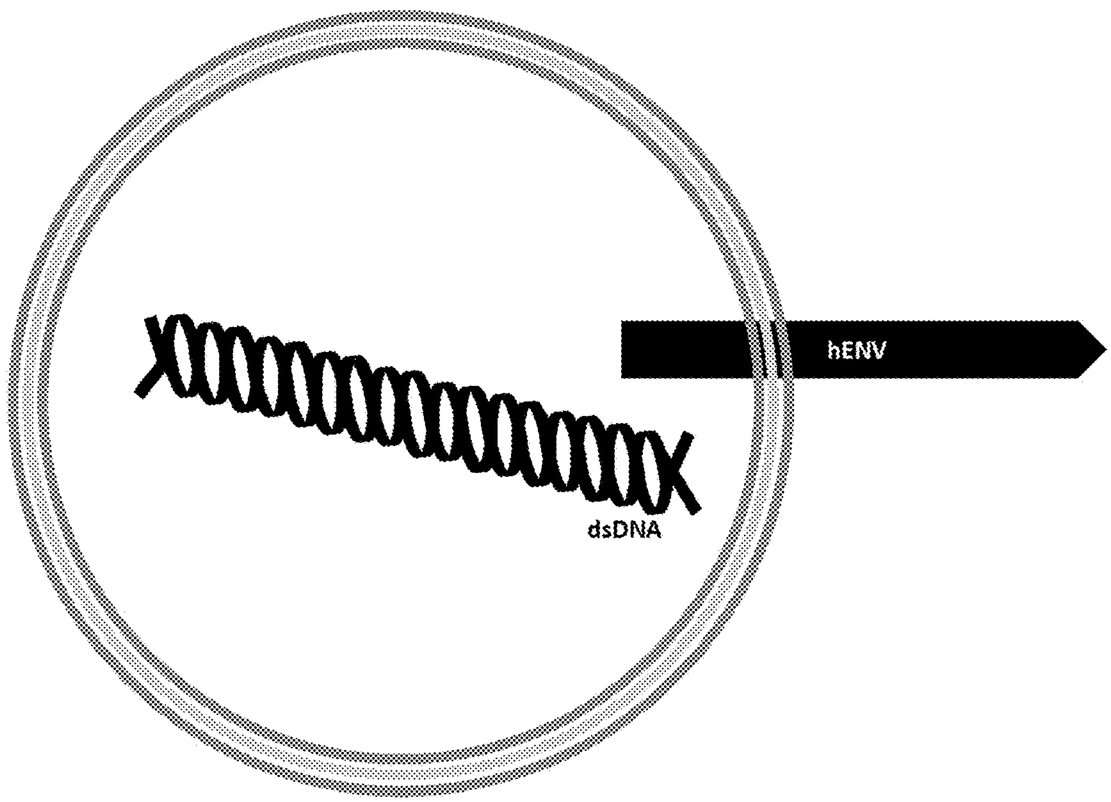

FIG. 38: Depiction of exemplary heVLP and cargo configuration

This particle was created by producer cells expressing an envelope protein. Cargo (double-stranded DNA) can be packaged inside the particle by various particle loading methods described herein, such as electroporation.

Figure 39:
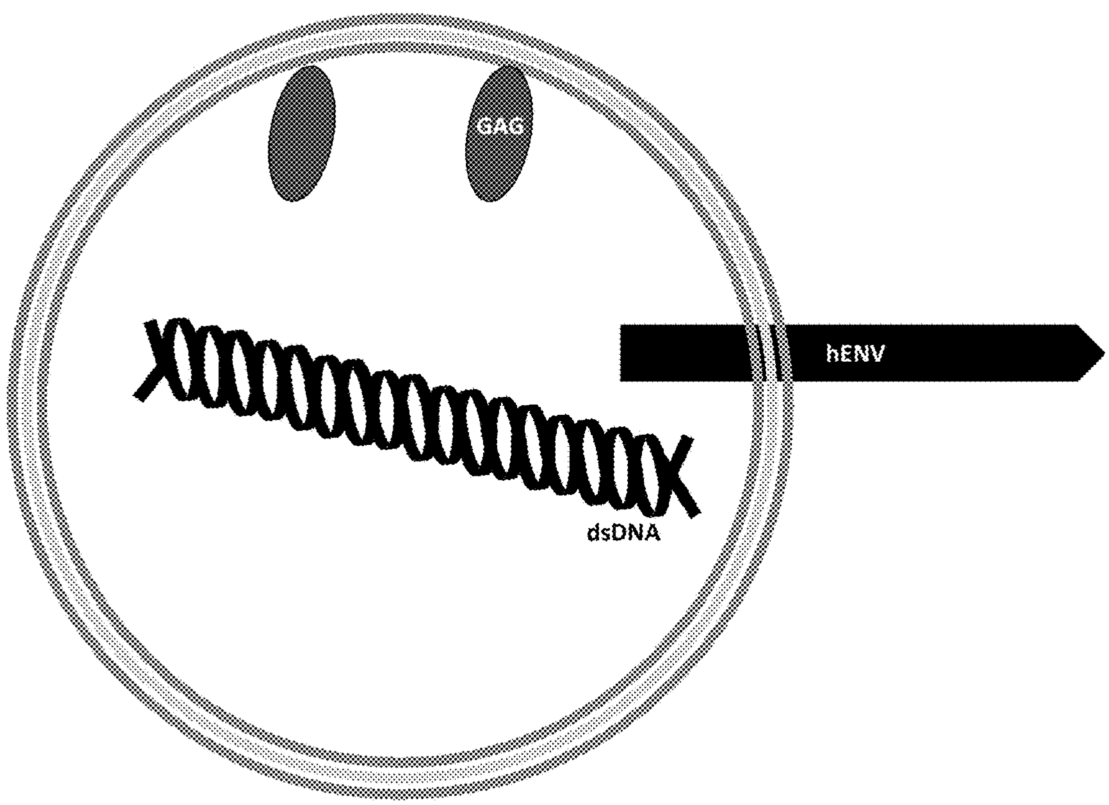

FIG. 39: Depiction of exemplary heVLP and cargo configuration

This particle was created by producer cells expressing an envelope protein and gag. Cargo (double-stranded DNA) can be packaged inside the particle by various particle loading methods described herein, such as electroporation.

Figure 40:
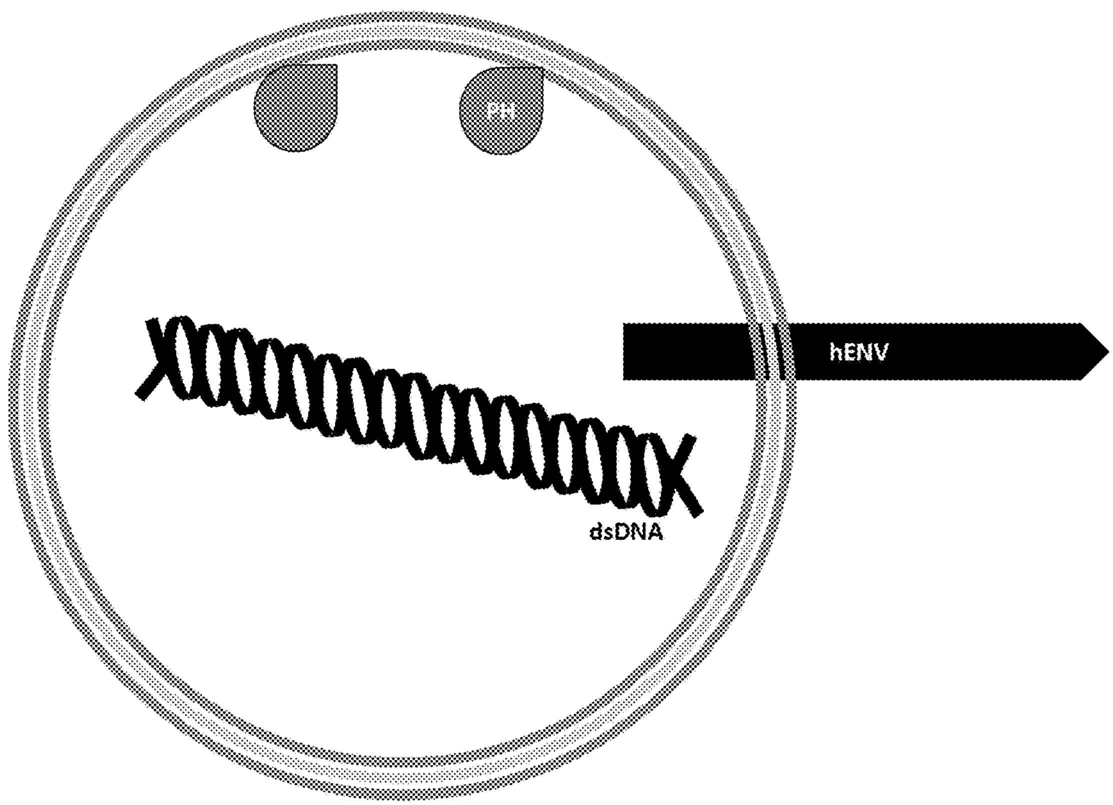

FIG. 40: Depiction of exemplary heVLP and cargo configuration

This particle was created by producer cells expressing an envelope protein and PH. Cargo (double-stranded DNA) can be packaged inside the particle by various particle loading methods described herein, such as electroporation.

Figure 41:
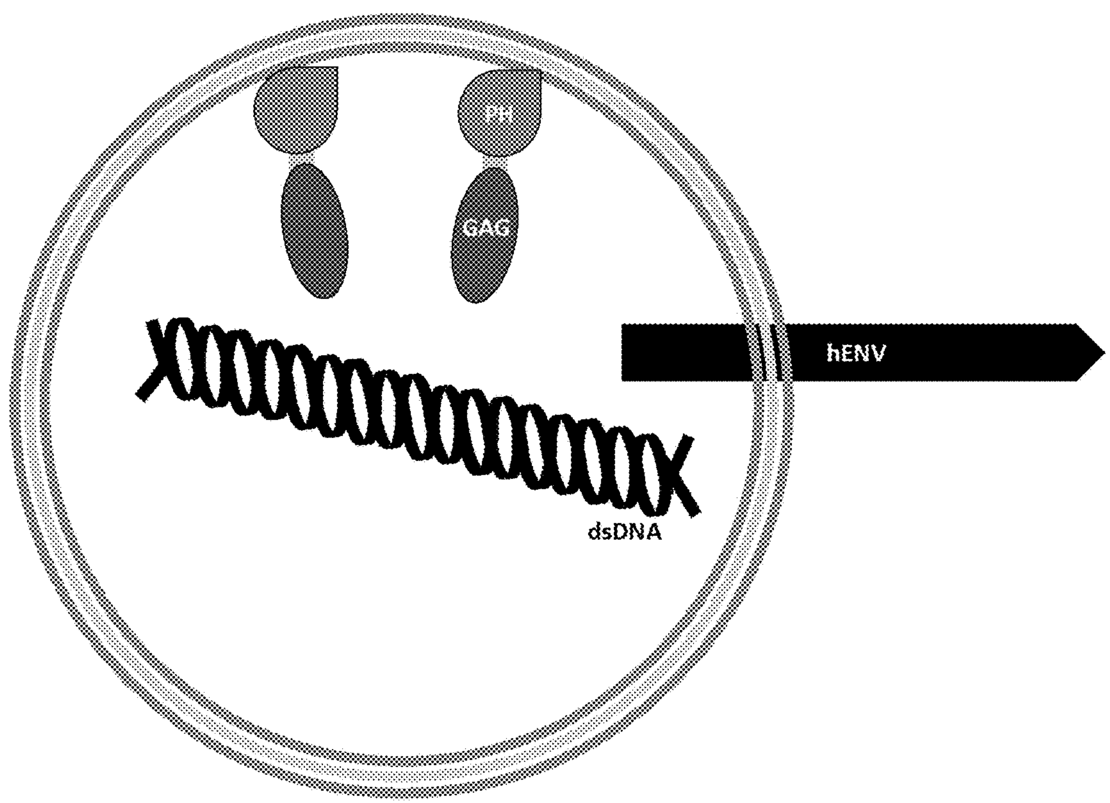

FIG. 41: Depiction of exemplary heVLP and cargo configuration

This particle was created by producer cells expressing an envelope protein and gag/PH. Cargo (double-stranded DNA) can be packaged inside the particle by various particle loading methods described herein, such as electroporation.

Figure 42:
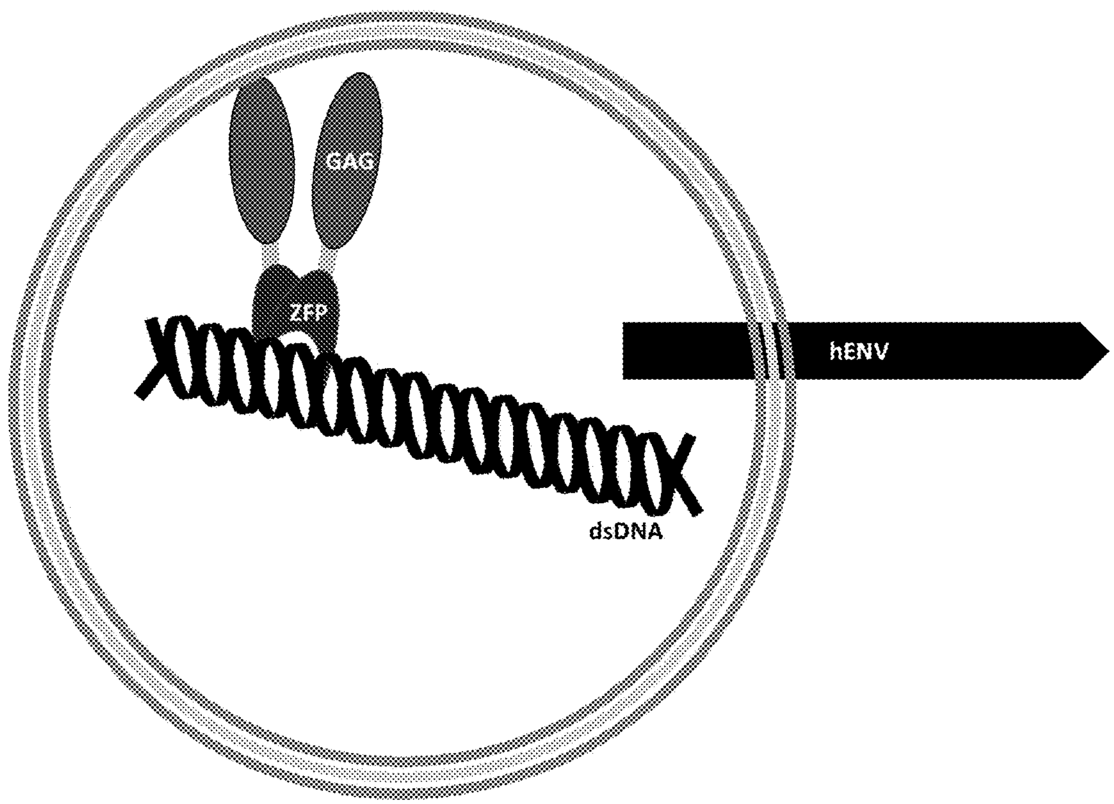

FIG. 42: Depiction of exemplary heVLP and cargo configuration

This particle was created by producer cells expressing an envelope protein and gag fused to a zinc finger protein (ZFP) that will bind a specific sequence in the cargo. Cargo (double-stranded DNA) can be packaged inside the particle by various particle loading methods described herein, such as electroporation.

Figure 43:
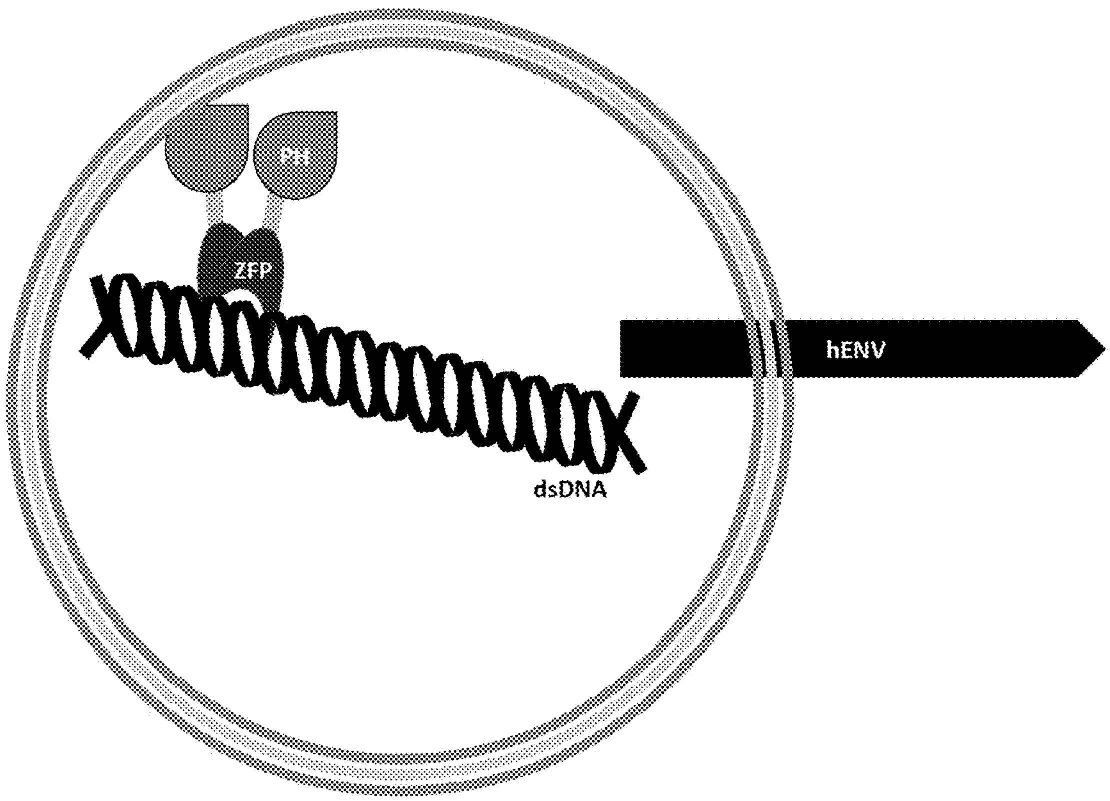

FIG. 43: Depiction of exemplary heVLP and cargo configuration

This particle was created by producer cells expressing an envelope protein and PH fused to a zinc finger protein (ZFP) that will bind a specific sequence in the cargo. Cargo (double-stranded DNA) can be packaged inside the particle by various particle loading methods described herein, such as electroporation.

Figure 44:
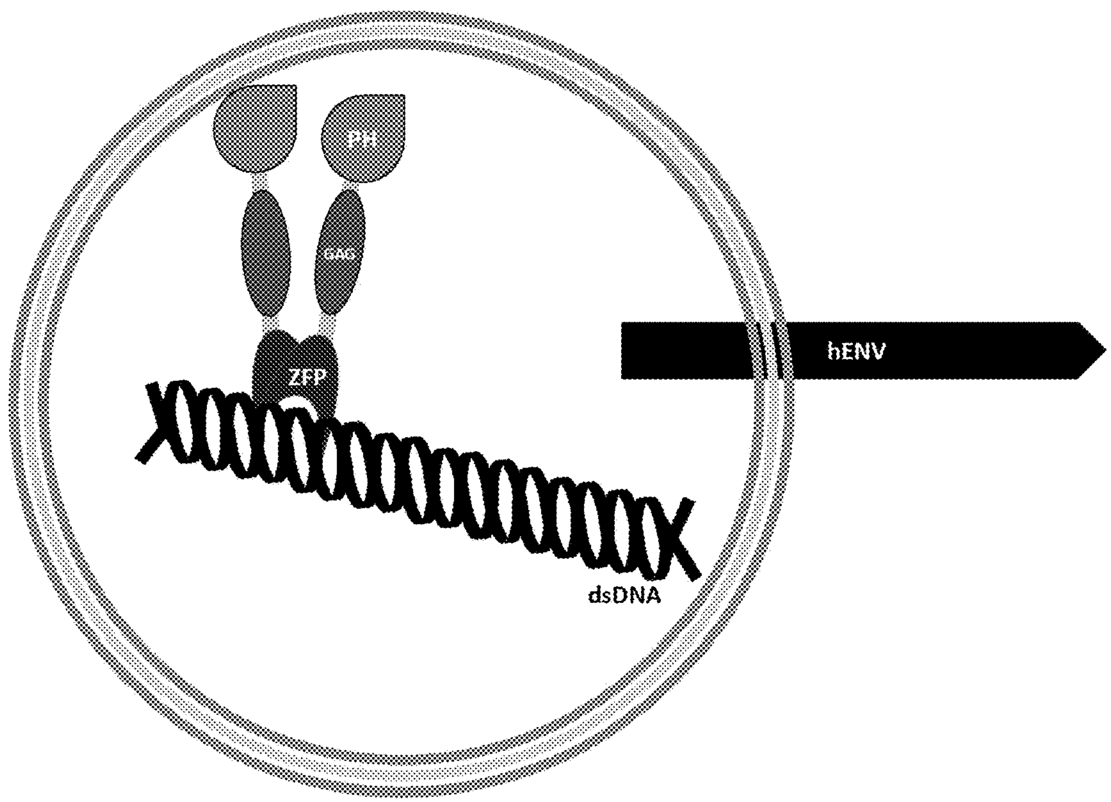

FIG. 44: Depiction of exemplary heVLP and cargo configuration

This particle was created by producer cells expressing an envelope protein and gag/PH fused to a zinc finger protein (ZFP) that will bind a specific sequence in the cargo. Cargo (double-stranded DNA) can be packaged inside the particle by various particle loading methods described herein, such as electroporation.

Figure 45:
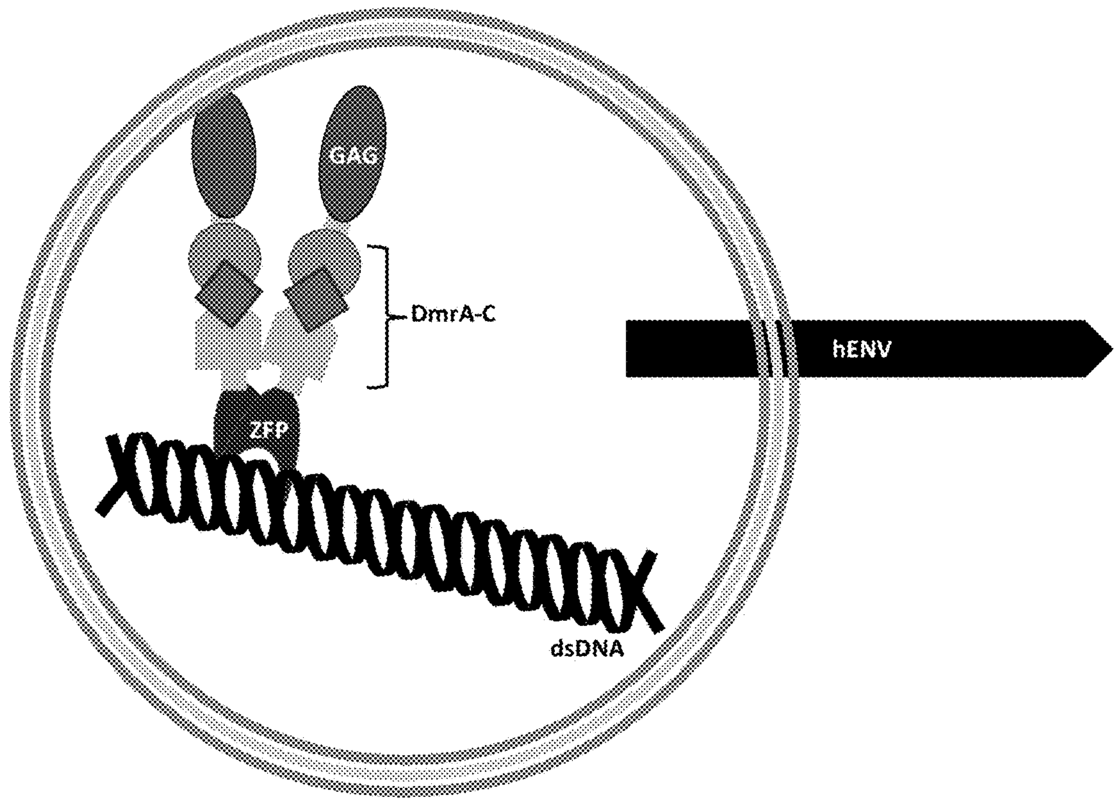

FIG. 45: Depiction of exemplary heVLP and cargo configuration

This particle was created by producer cells expressing an envelope protein and gag and a zinc finger protein (ZFP) that will bind a specific sequence in the cargo fused to DmrA or DmrC in the presence of A/C Heterodimerizer molecule. Cargo (double-stranded DNA) can be packaged inside the particle by various particle loading methods described herein, such as electroporation.

Figure 46:
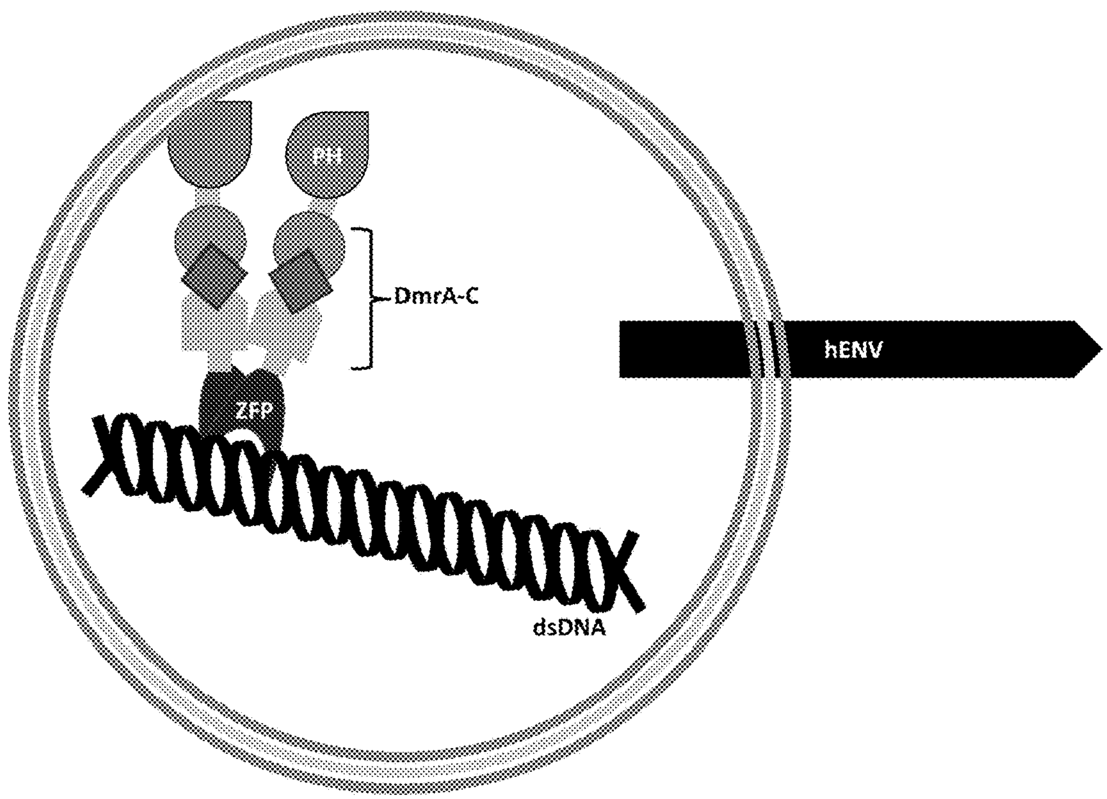

FIG. 46: Depiction of exemplary heVLP and cargo configuration

This particle was created by producer cells expressing an envelope protein and PH and a zinc finger protein (ZFP) that will bind a specific sequence in the cargo fused to DmrA or DmrC in the presence of A/C Heterodimerizer molecule. Cargo (double-stranded DNA) can be packaged inside the particle by various particle loading methods described herein, such as electroporation.

Figure 47:
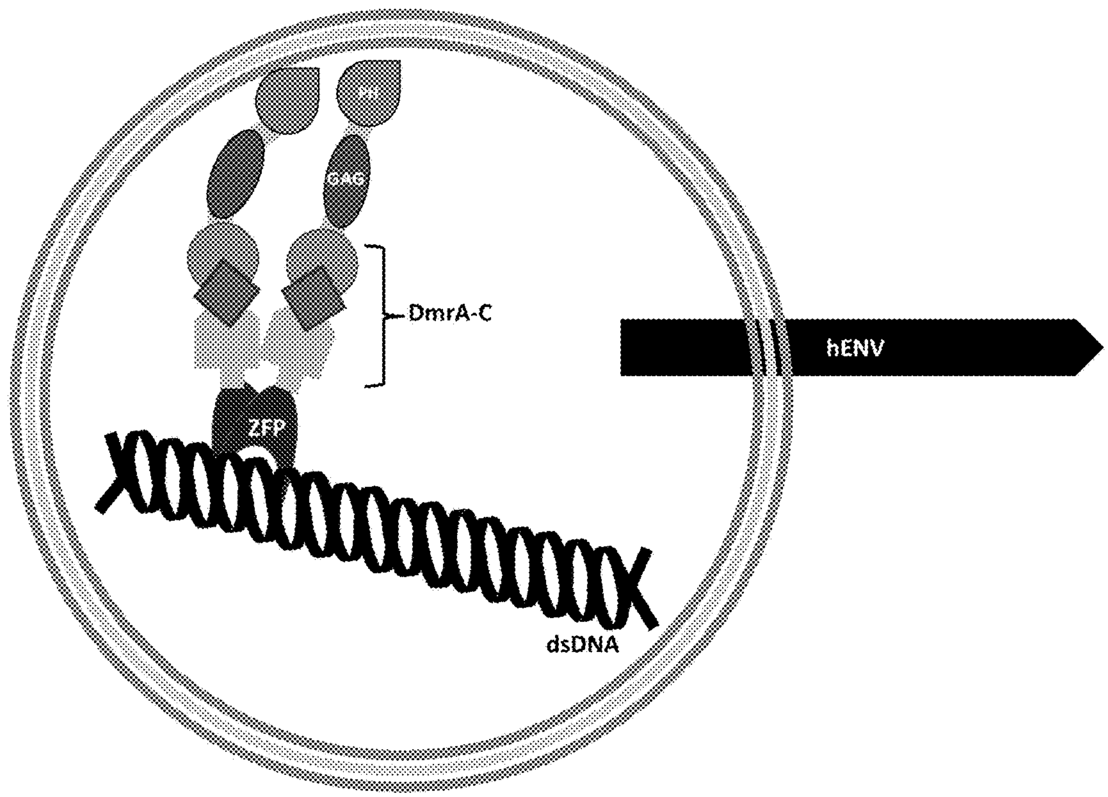

FIG. 47: Depiction of exemplary heVLP and cargo configuration

This particle was created by producer cells expressing an envelope protein and gag/PH and a zinc finger protein (ZFP) that will bind a specific sequence in the cargo fused to DmrA or DmrC in the presence of A/C Heterodimerizer molecule. Cargo (double-stranded DNA) can be packaged inside the particle by various particle loading methods described herein, such as electroporation.

Figure 48:
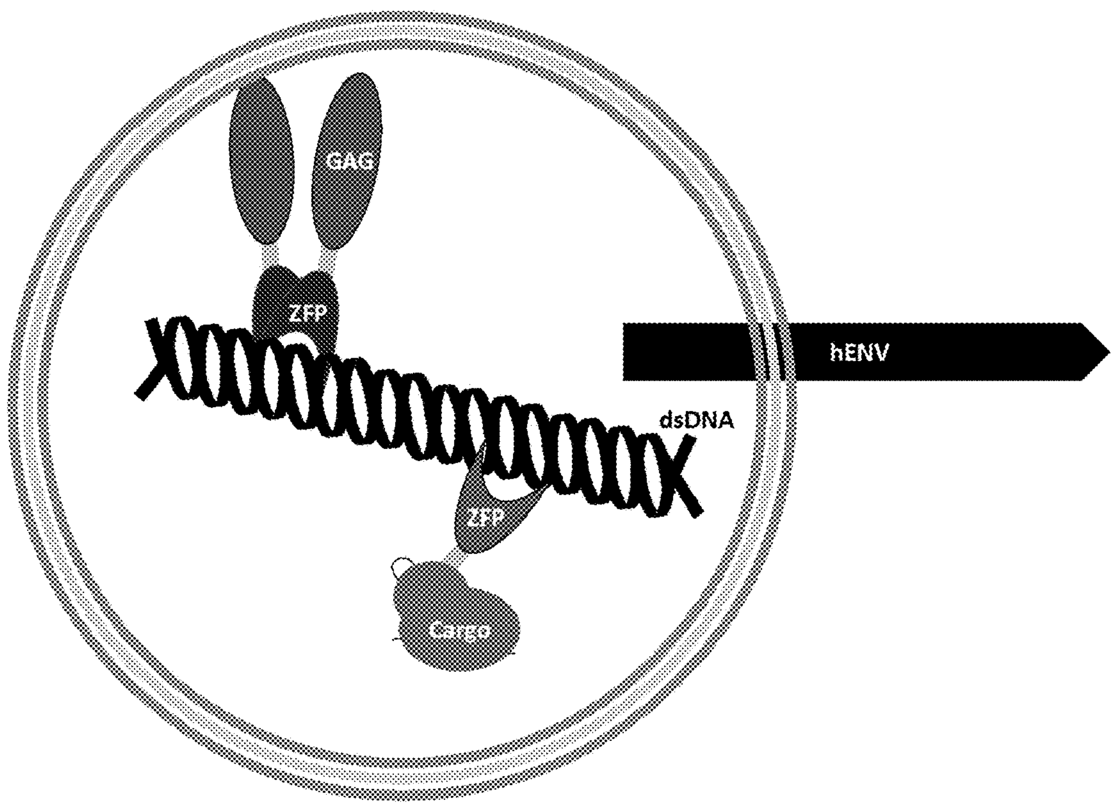

FIG. 48: Depiction of exemplary heVLP and cargo configuration

This particle was created by producer cells expressing an envelope protein and gag fused to a zinc finger protein (ZFP) that will bind a specific sequence in the cargo. Cargo (double-stranded DNA bound by Cas9 RNP-ZFP fusion) can be packaged inside the particle by various particle loading methods described herein, such as electroporation. Alternatively, the Cas9 RNP-ZFP fusion could be expressed by the producer cells and the particles could be loaded by various particle loading methods described herein, such as electroporation.

Figure 49:
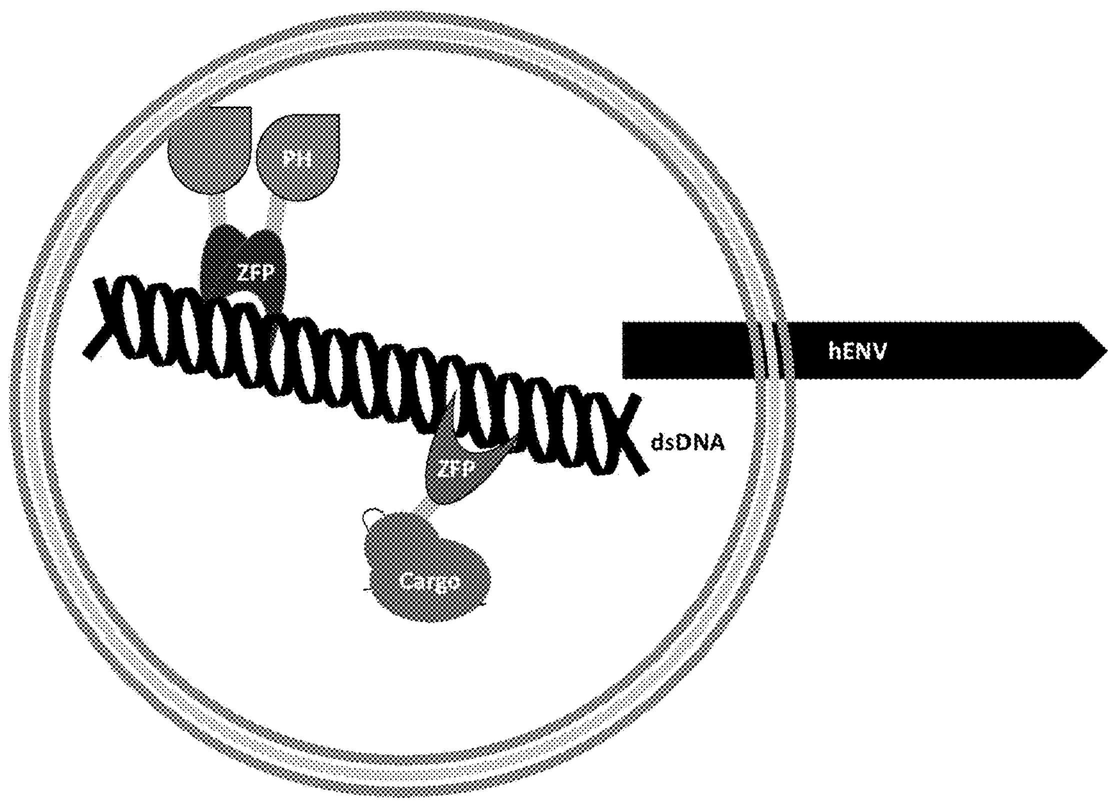

FIG. 49: Depiction of exemplary heVLP and cargo configuration

This particle was created by producer cells expressing an envelope protein and PH fused to a zinc finger protein (ZFP) that will bind a specific sequence in the cargo. Cargo (double-stranded DNA bound by Cas9 RNP-ZFP fusion) can be packaged inside the particle by various particle loading methods described herein, such as electroporation. Alternatively, the Cas9 RNP-ZFP fusion could be expressed by the producer cells and the particles could be loaded by various particle loading methods described herein, such as electroporation.

Figure 50:
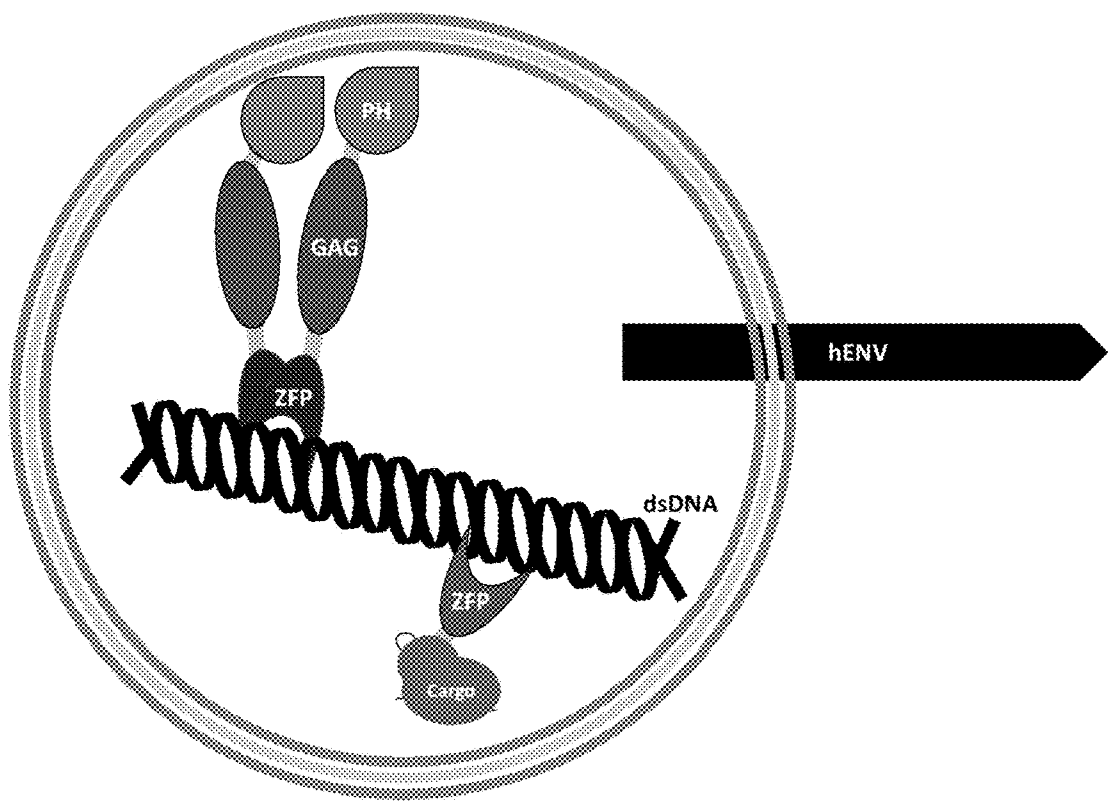

FIG. 50: Depiction of exemplary heVLP and cargo configuration

This particle was created by producer cells expressing an envelope protein and gag/PH fused to a zinc finger protein (ZFP) that will bind a specific sequence in the cargo. Cargo (double-stranded DNA bound by Cas9 RNP-ZFP fusion) can be packaged inside the particle by various particle loading methods described herein, such as electroporation. Alternatively, the Cas9 RNP-ZFP fusion could be expressed by the producer cells and the particles could be loaded by various particle loading methods described herein, such as electroporation.

Figure 51:
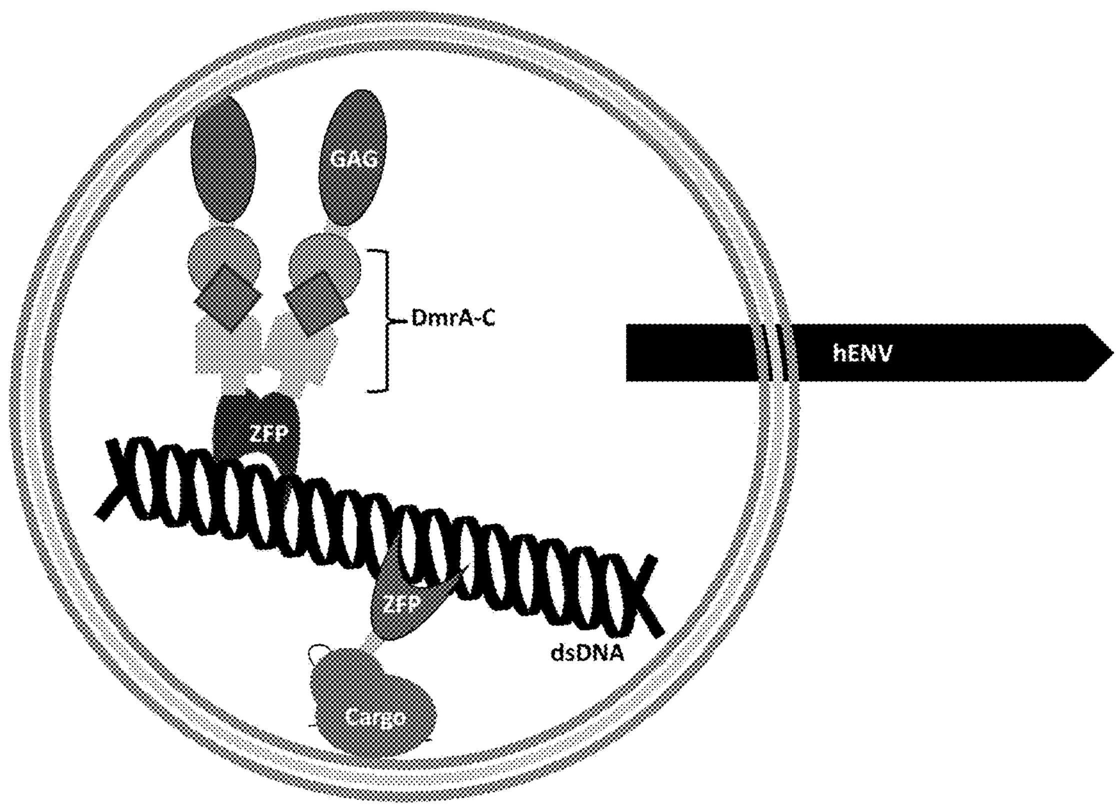

FIG. 51: Depiction of exemplary heVLP and cargo configuration

This particle was created by producer cells expressing an envelope protein and gag fused to a zinc finger protein (ZFP) fused to DmrA or DmrC that will bind a specific sequence in the cargo in the presence of A/C Heterodimerizer molecule. Cargo (double-stranded DNA bound by Cas9 RNP-ZFP fusion) can be packaged inside the particle by various particle loading methods described herein, such as electroporation. Alternatively, the Cas9 RNP-ZFP fusion could be expressed by the producer cells and the particles could be loaded by various particle loading methods described herein, such as electroporation.

Figure 52:
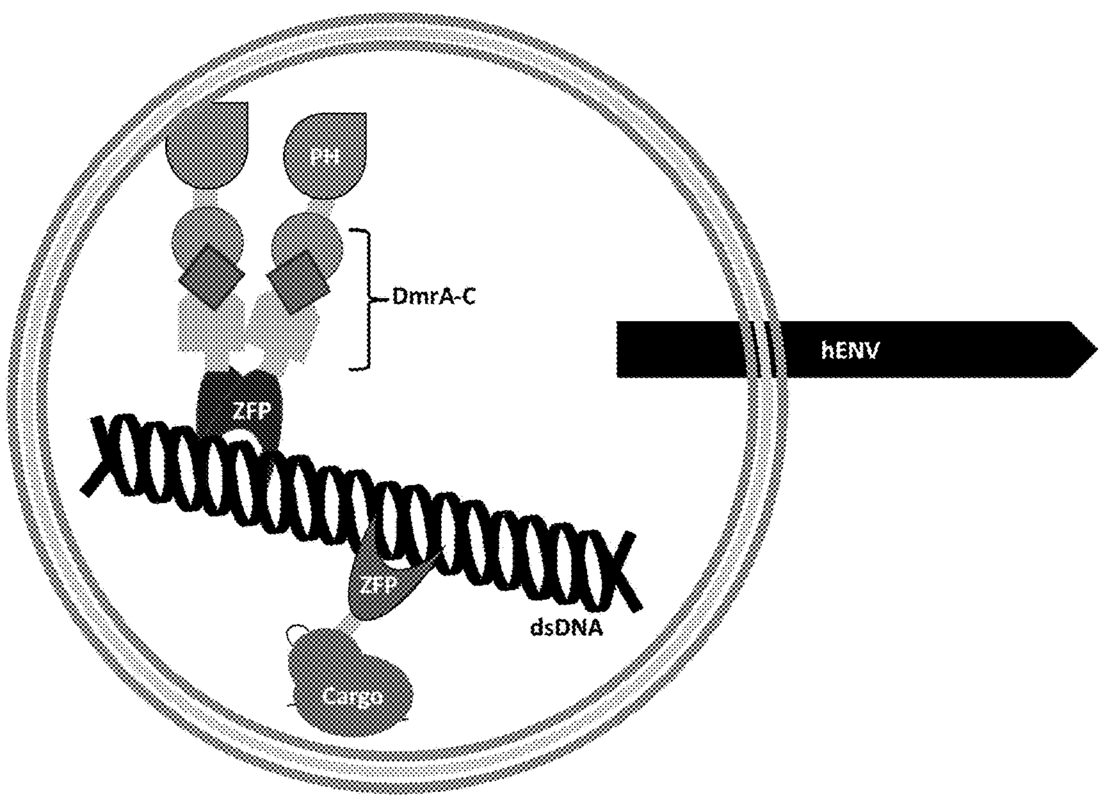

FIG. 52: Depiction of exemplary heVLP and cargo configuration

This particle was created by producer cells expressing an envelope protein and PH fused to a zinc finger protein (ZFP) fused to DmrA or DmrC that will bind a specific sequence in the cargo in the presence of A/C Heterodimerizer molecule. Cargo (double-stranded DNA bound by Cas9 RNP-ZFP fusion) can be packaged inside the particle by various particle loading methods described herein, such as electroporation. Alternatively, the Cas9 RNP-ZFP fusion could be expressed by the producer cells and the particles could be loaded by various particle loading methods described herein, such as electroporation.

Figure 53:
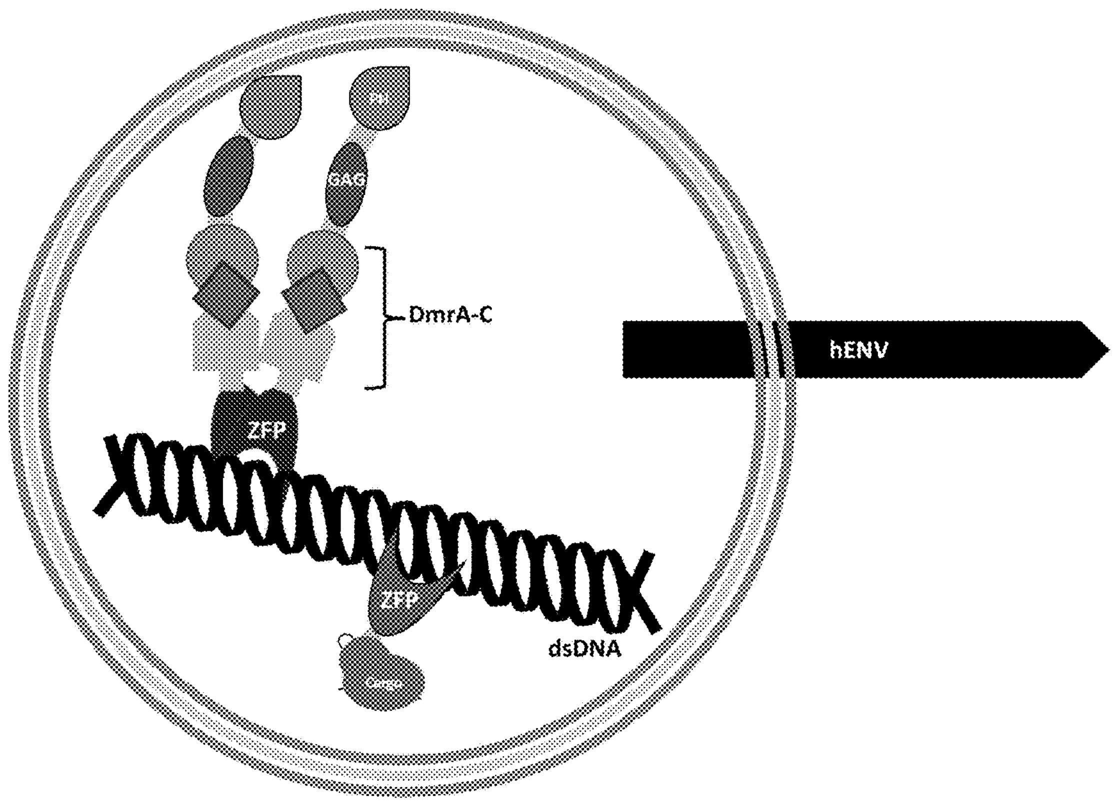

FIG. 53: Depiction of exemplary heVLP and cargo configuration

This particle was created by producer cells expressing an envelope protein and gag/PH fused to a zinc finger protein (ZFP) fused to DmrA or DmrC that will bind a specific sequence in the cargo in the presence of A/C Heterodimerizer molecule. Cargo (double-stranded DNA bound by Cas9 RNP-ZFP fusion) can be packaged inside the particle by various particle loading methods described herein, such as electroporation. Alternatively, the Cas9 RNP-ZFP fusion could be expressed by the producer cells and the particles could be loaded by various particle loading methods described herein, such as electroporation.

Figure 54:
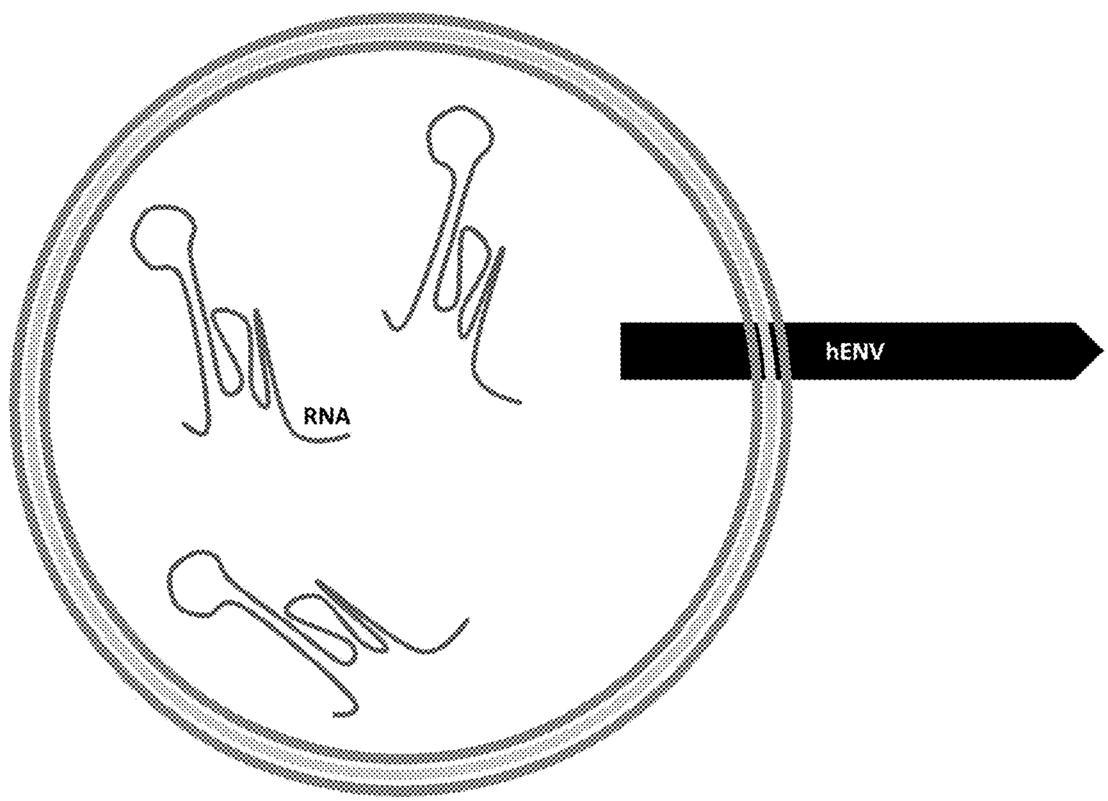

FIG. 54: Depiction of exemplary heVLP and cargo configuration

This particle was created by producer cells expressing an envelope protein. Cargo (RNA) was packaged inside the particle either by producer cells expressing cargo or particles being loaded by various particle loading methods described herein, such as electroporation.

Figure 55:
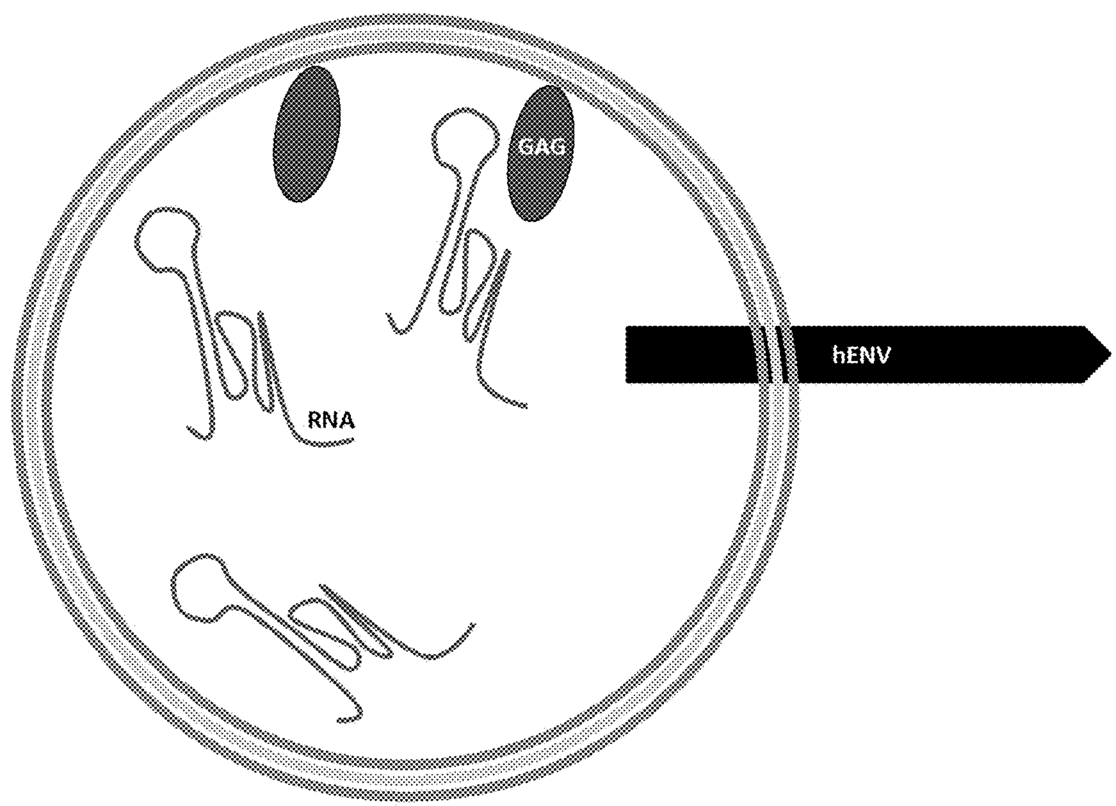

FIG. 55: Depiction of exemplary heVLP and cargo configuration

This particle was created by producer cells expressing an envelope protein. Cargo (RNA) was packaged inside the particle either by producer cells expressing cargo and gag or particles being loaded by various particle loading methods described herein, such as electroporation.

Figure 56:
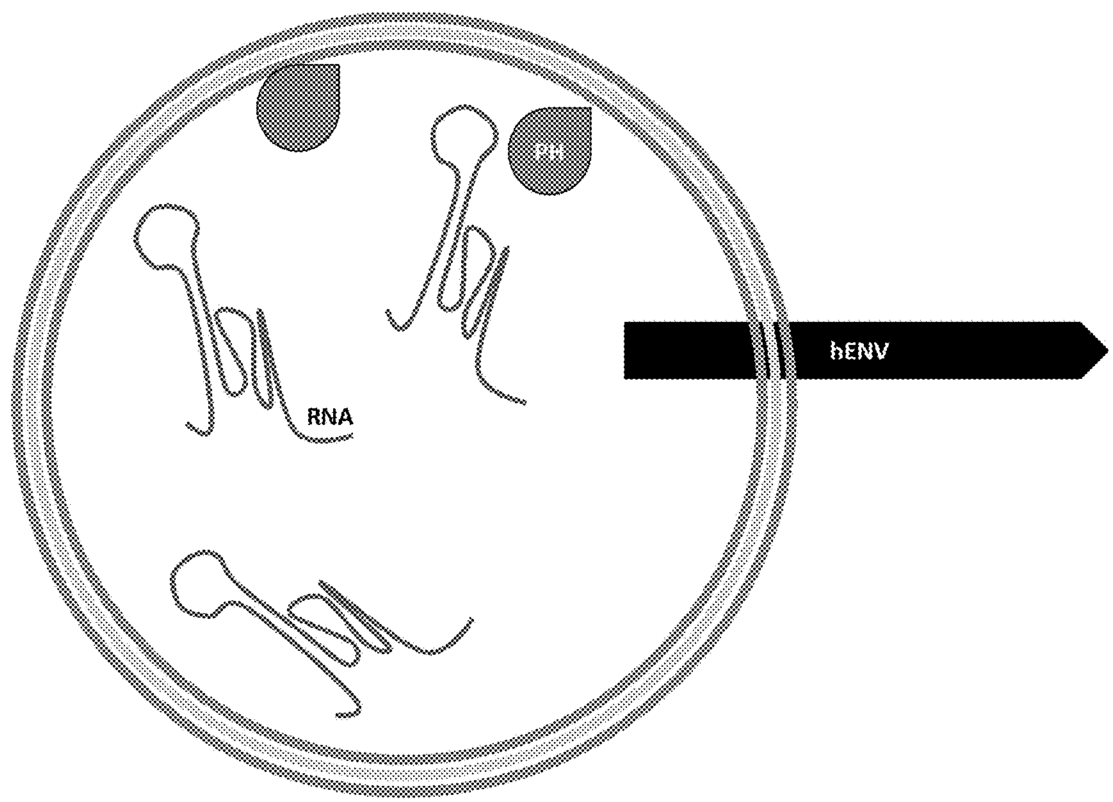

FIG. 56: Depiction of exemplary heVLP and cargo configuration

This particle was created by producer cells expressing an envelope protein. Cargo (RNA) was packaged inside the particle either by producer cells expressing cargo and PH or particles being loaded by various particle loading methods described herein, such as electroporation.

Figure 57:
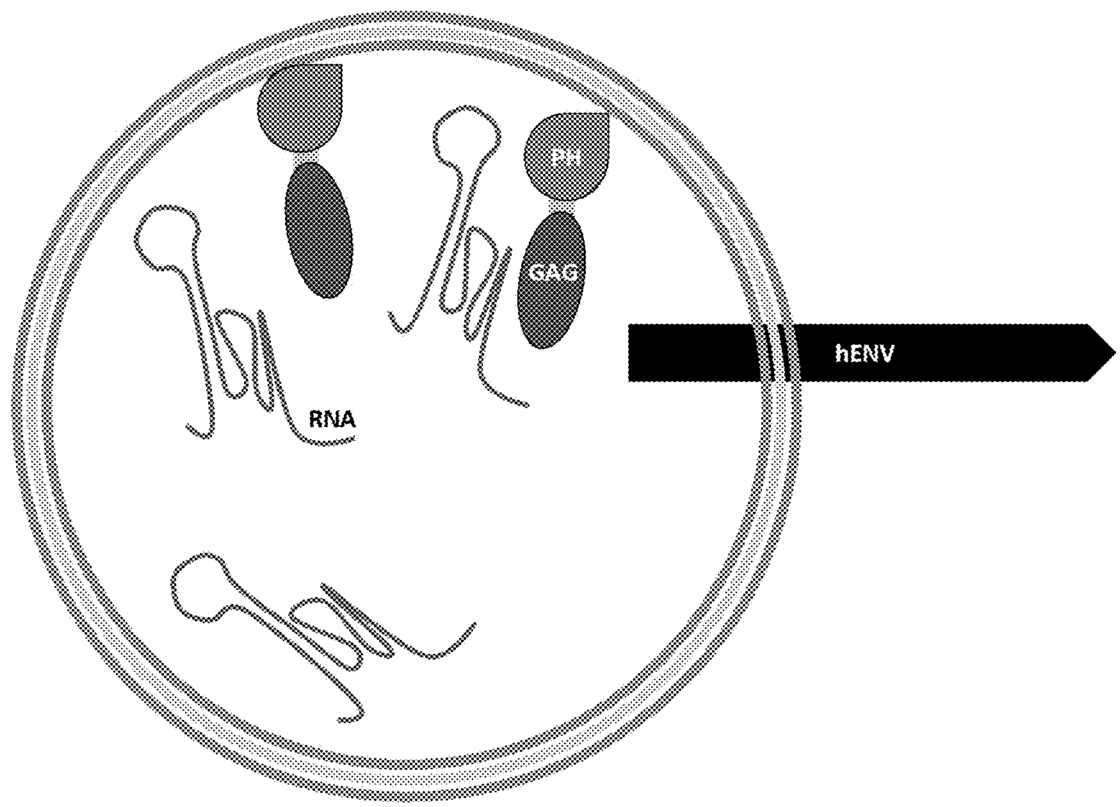

FIG. 57: Depiction of exemplary heVLP and cargo configuration

This particle was created by producer cells expressing an envelope protein. Cargo (RNA) was packaged inside the particle either by producer cells expressing cargo and gag/PH or particles being loaded by various particle loading methods described herein, such as electroporation.

Figure 58:
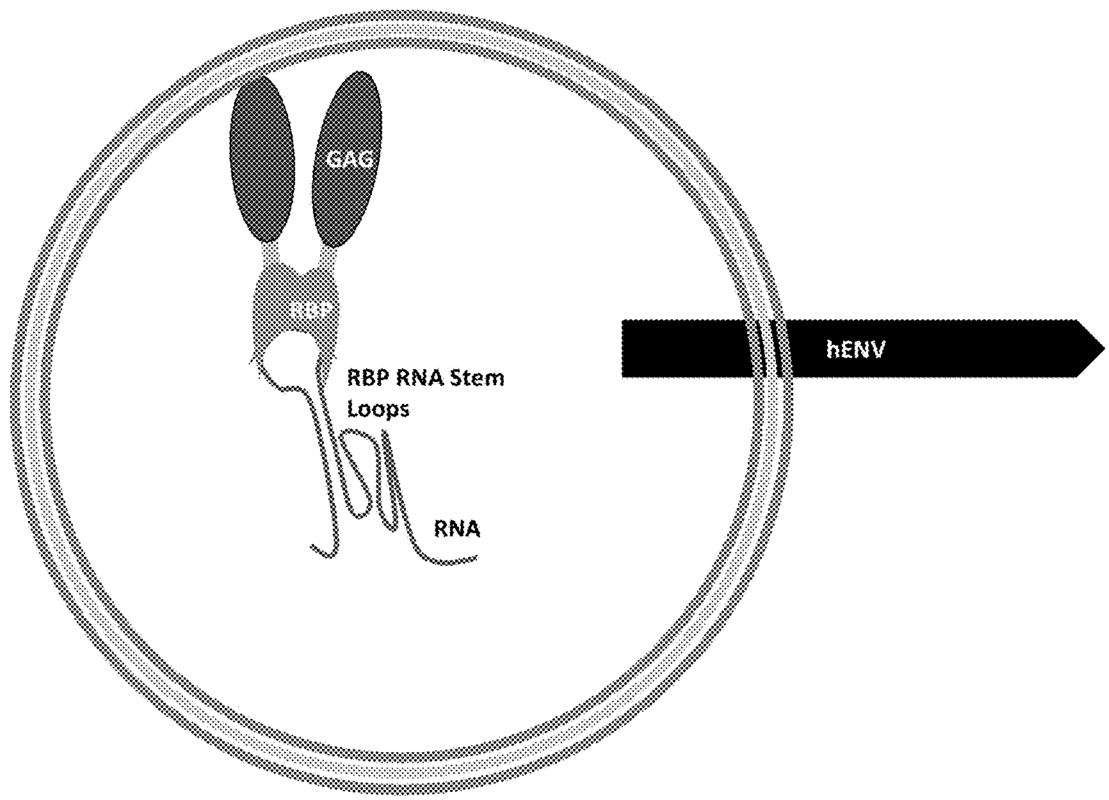

FIG. 58: Depiction of exemplary heVLP and cargo configuration

This particle was created by producer cells expressing an envelope protein. Cargo (RNA with MS2 stem loop(s)) was packaged inside the particle either by producer cells expressing cargo and gag fused to MS2 or particles being loaded by various particle loading methods described herein, such as electroporation.

Figure 59:
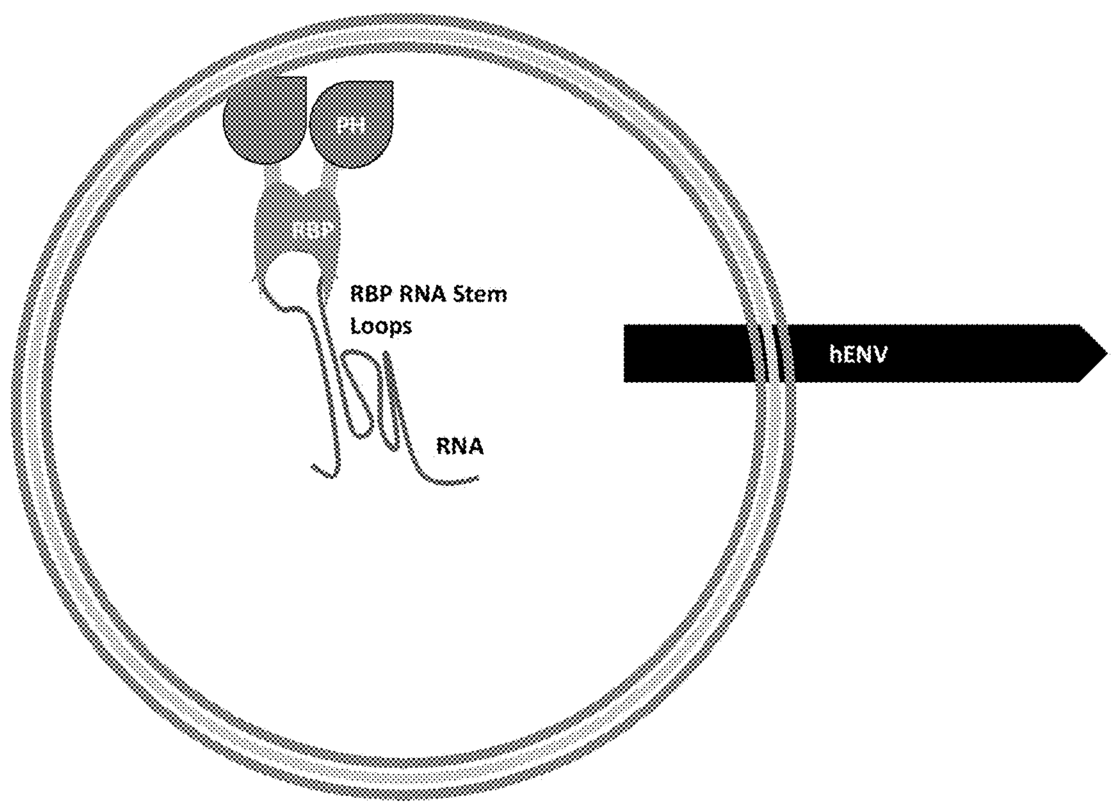

FIG. 59: Depiction of exemplary heVLP and cargo configuration

This particle was created by producer cells expressing an envelope protein. Cargo (RNA with MS2 stem loop(s)) was packaged inside the particle either by producer cells expressing cargo and PH fused to MS2 or particles being loaded by various particle loading methods described herein, such as electroporation.

Figure 60:
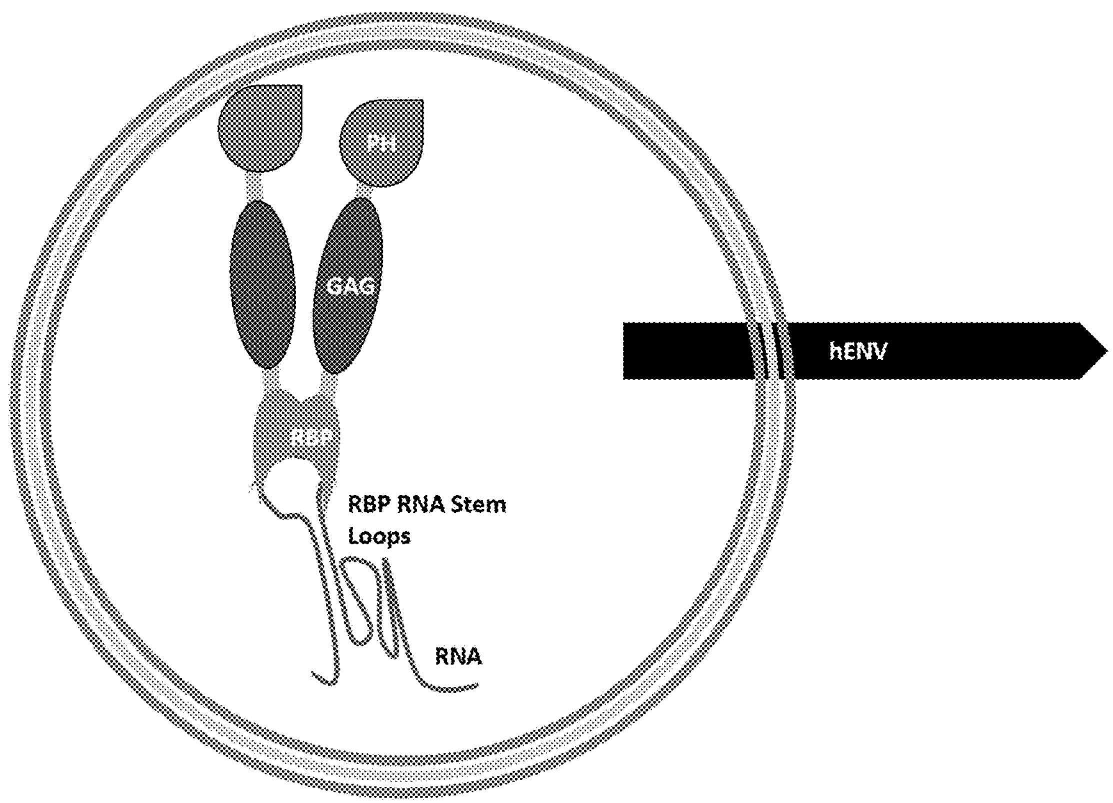

FIG. 60: Depiction of exemplary heVLP and cargo configuration

This particle was created by producer cells expressing an envelope protein. Cargo (RNA with MS2 stem loop(s)) was packaged inside the particle either by producer cells expressing cargo and gag/PH fused to MS2 or particles being loaded by various particle loading methods described herein, such as electroporation.

Figure 61:
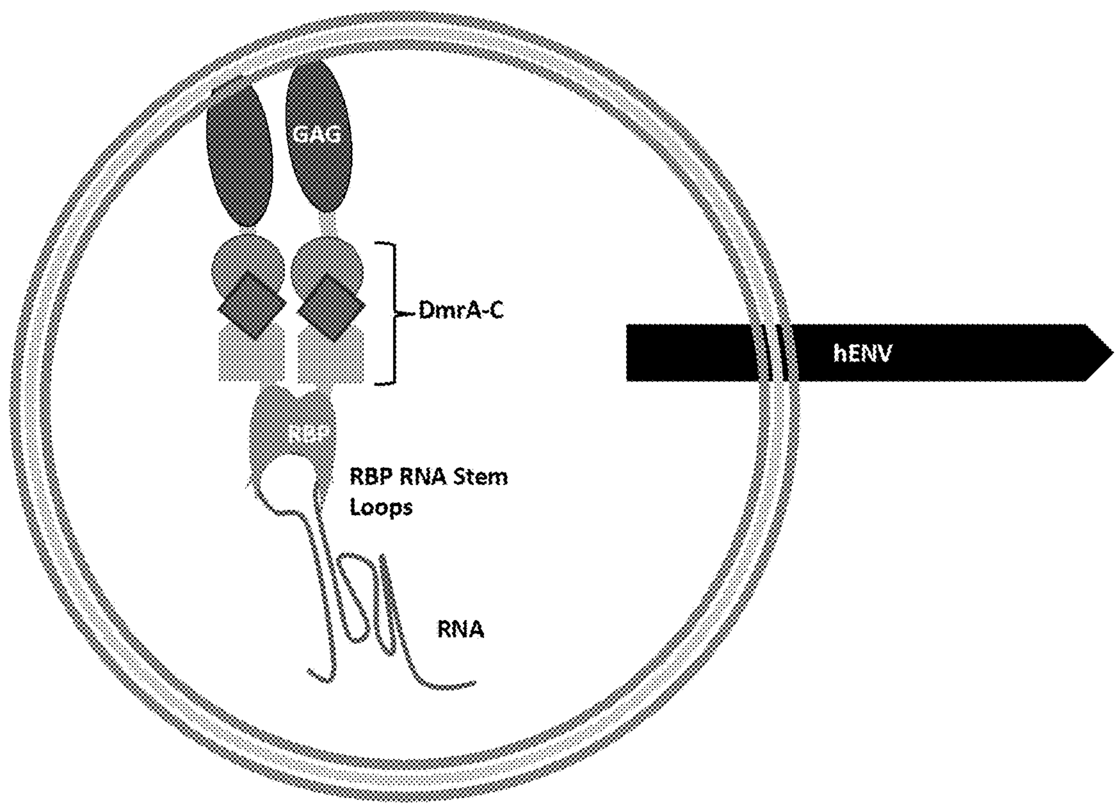

FIG. 61: Depiction of exemplary heVLP and cargo configuration

This particle was created by producer cells expressing an envelope protein. Cargo (RNA with MS2 stem loop(s)) was packaged inside the particle either by producer cells expressing cargo and gag and MS2 fused to DmrA or DmrC in the presence of A/C heterodimerizer, or particles being loaded by various particle loading methods described herein, such as electroporation.

Figure 62:
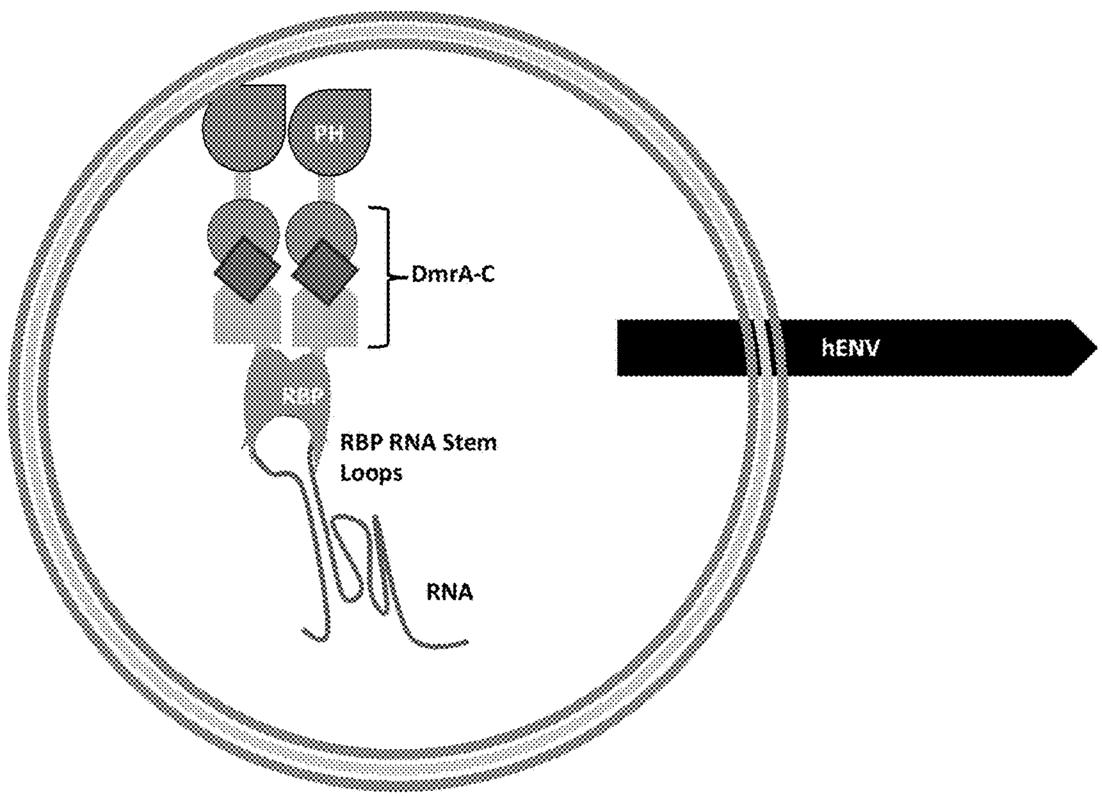

FIG. 62: Depiction of exemplary heVLP and cargo configuration

This particle was created by producer cells expressing an envelope protein. Cargo (RNA with MS2 stem loop(s)) was packaged inside the particle either by producer cells expressing cargo and PH and MS2 fused to DmrA or DmrC in the presence of A/C heterodimerizer, or particles being loaded by various particle loading methods described herein, such as electroporation.

Figure 63:
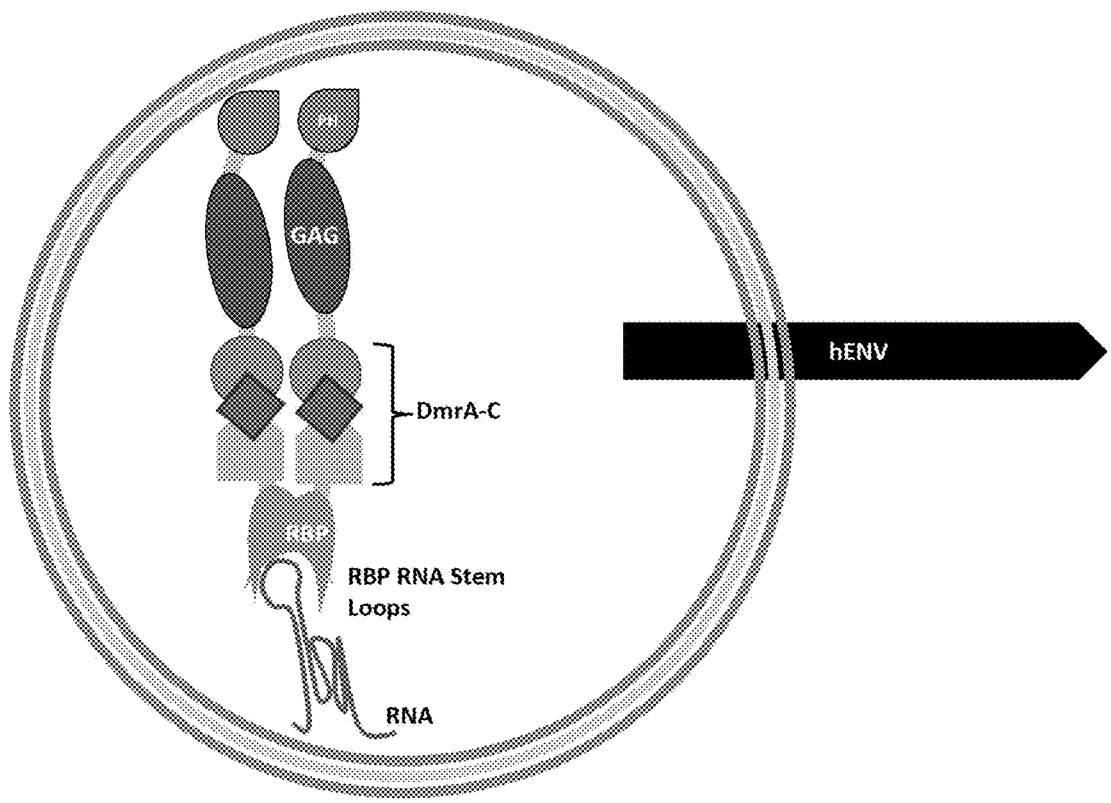

FIG. 63: Depiction of exemplary heVLP and cargo configuration

This particle was created by producer cells expressing an envelope protein. Cargo (RNA with MS2 stem loop(s)) was packaged inside the particle either by producer cells expressing cargo and gag/PH and MS2 fused to DmrA or DmrC in the presence of A/C heterodimerizer, or particles being loaded by various particle loading methods described herein, such as electroporation.

Figure 64:
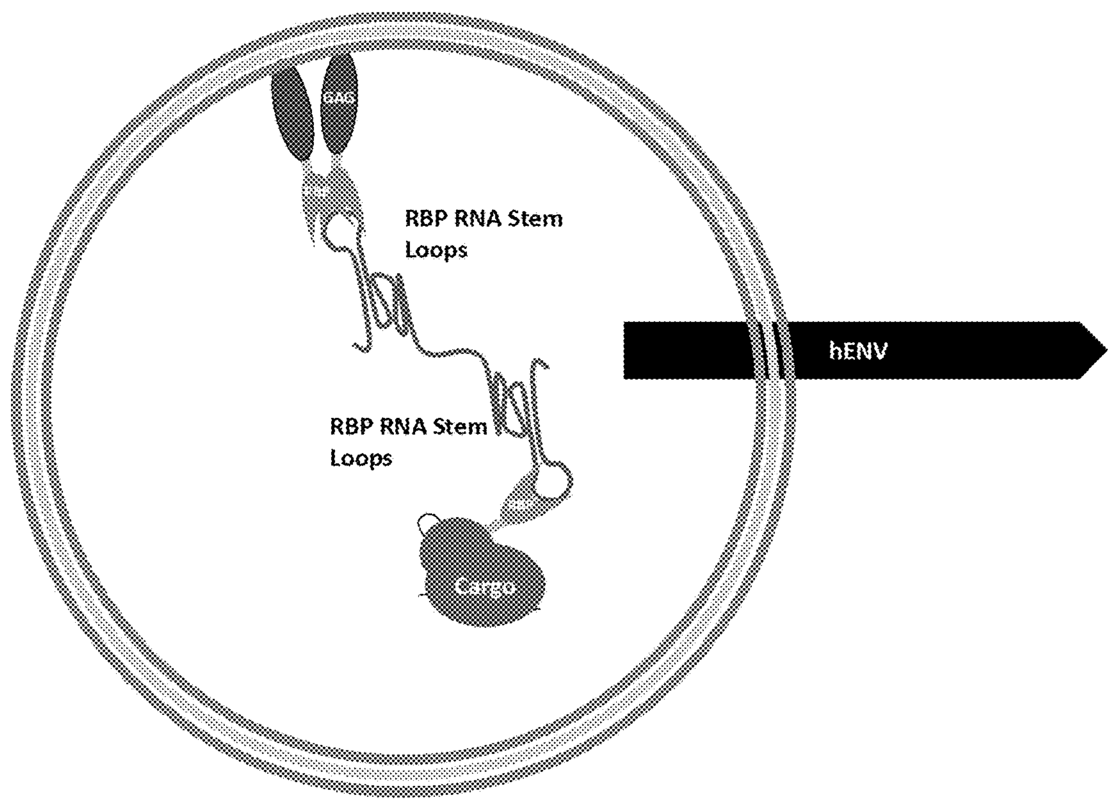

FIG. 64: Depiction of exemplary heVLP and cargo configuration

This particle was created by producer cells expressing an envelope protein. Cargo (RNA with RBP stem loop(s)) was packaged inside the particle either by producer cells expressing cargo fused to an RBP and gag fused to another RBP or particles being loaded by various particle loading methods described herein, such as electroporation.

Figure 65:
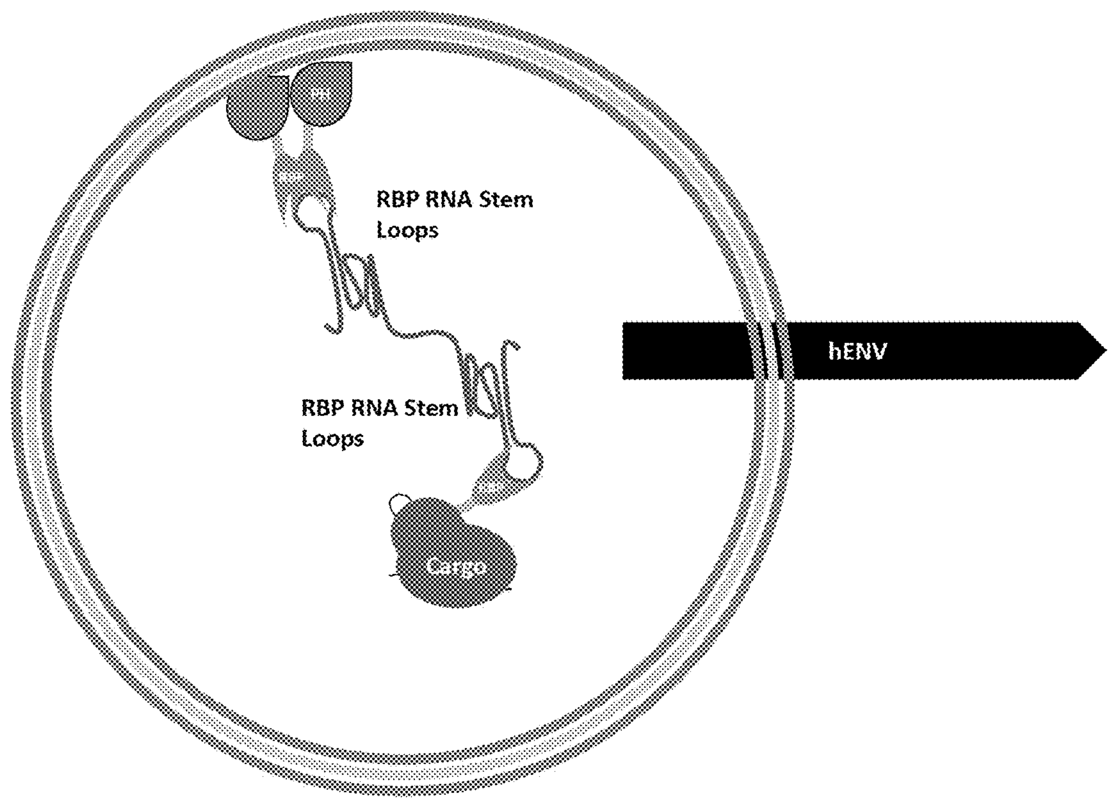

FIG. 65: Depiction of exemplary heVLP and cargo configuration

This particle was created by producer cells expressing an envelope protein. Cargo (RNA with RBP stem loop(s)) was packaged inside the particle either by producer cells expressing cargo fused to an RBP and PH fused to another RBP or particles being loaded by various particle loading methods described herein, such as electroporation.

Figure 66:
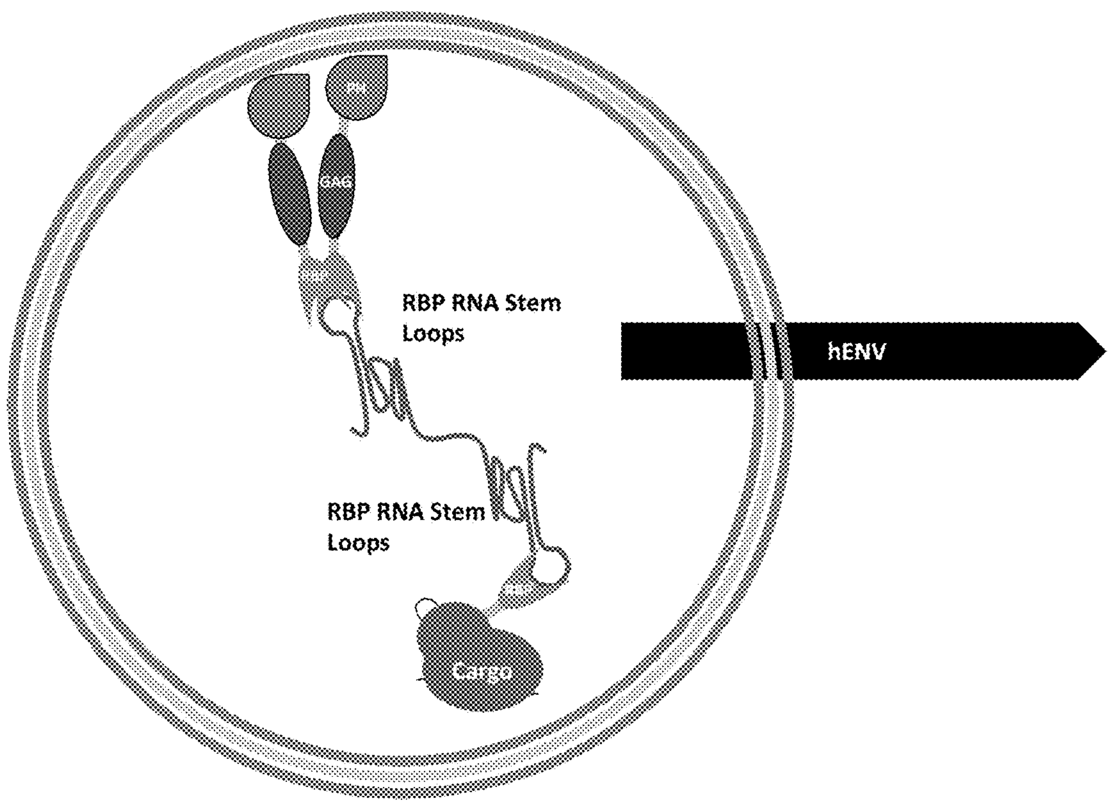

FIG. 66: Depiction of exemplary heVLP and cargo configuration

This particle was created by producer cells expressing an envelope protein. Cargo (RNA with RBP stem loop(s)) was packaged inside the particle either by producer cells expressing cargo fused to an RBP and gag/PH fused to another RBP or particles being loaded by various particle loading methods described herein, such as electroporation.

Figure 67:
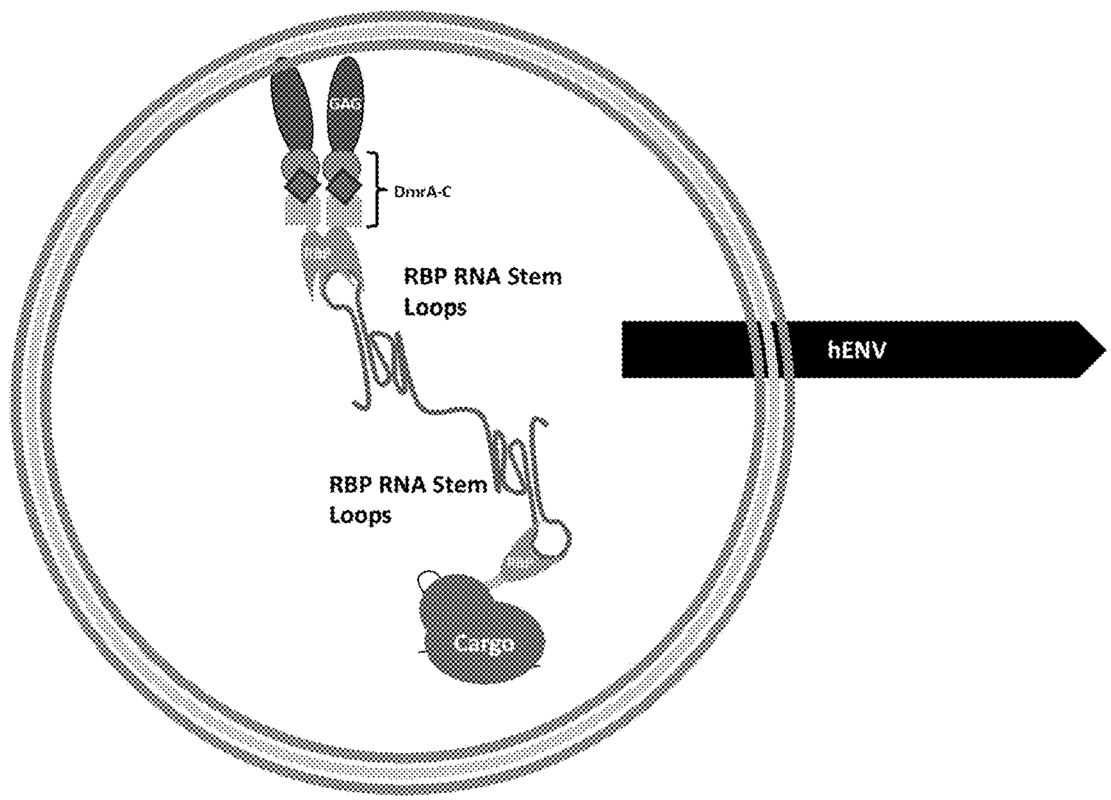

FIG. 67: Depiction of exemplary heVLP and cargo configuration

This particle was created by producer cells expressing an envelope protein. Cargo (RNA with RBP stem loop(s)) was packaged inside the particle either by producer cells expressing cargo fused to an RBP and gag and another RBP fused to DmrA or DmrC in the presence of A/C Heterodimerizer molecule, or particles being loaded by various particle loading methods described herein, such as electroporation.

Figure 68:
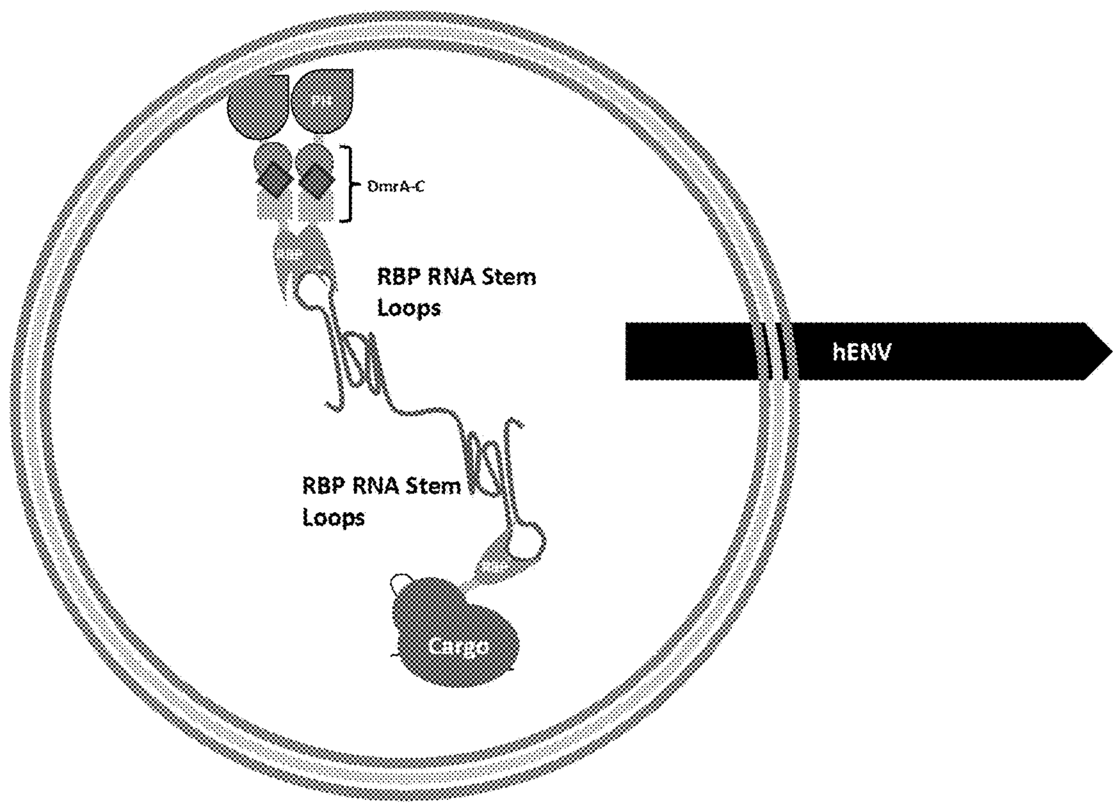

FIG. 68: Depiction of exemplary heVLP and cargo configuration

This particle was created by producer cells expressing an envelope protein. Cargo (RNA with RBP stem loop(s)) was packaged inside the particle either by producer cells expressing cargo fused to an RBP and PH and another RBP fused to DmrA or DmrC in the presence of A/C Heterodimerizer molecule, or particles being loaded by various particle loading methods described herein, such as electroporation.

Figure 69:
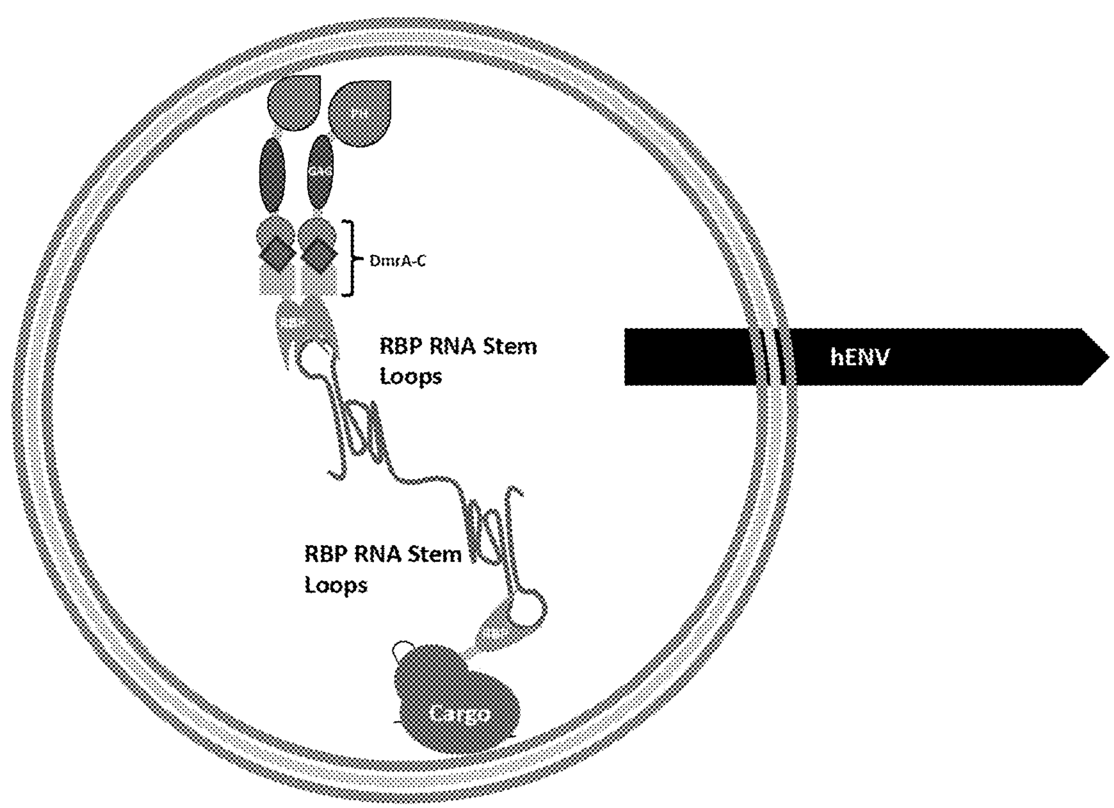

FIG. 69: Depiction of exemplary heVLP and cargo configuration

This particle was created by producer cells expressing an envelope protein. Cargo (RNA with RBP stem loop(s)) was packaged inside the particle either by producer cells expressing cargo fused to an RBP and gag/PH and another RBP fused to DmrA or DmrC in the presence of A/C Heterodimerizer molecule, or particles being loaded by various particle loading methods described herein, such as electroporation.

DETAILED DESCRIPTION

Therapeutic proteins and nucleic acids hold great promise, but for many of these large biomolecules delivery into cells is a hurdle to clinical development. Genome editing reagents such as zinc finger nucleases (ZFNs) or RNA-guided, enzymatically active/inactive DNA binding proteins such as Cas9 have undergone rapid advancements in terms of specificity and the types of edits that can be executed, but the hurdle of safe in vivo delivery still precludes efficacious gene editing therapies. The following details the characteristics of the heVLP that make it a novel and optimal platform for the delivery of genome editing reagents, and contrasts heVLPs with canonical delivery modalities.

Retroviral particles, such as lentivirus, have been developed to deliver RNA that is reverse transcribed to DNA that may or may not be integrated into genomic DNA. VLPs have been developed that mimic virus particles in their ability to self-assemble, but are not infectious as they lack some of the core viral genes. Both lentiviral and VLP vectors are typically produced by transiently transfecting a producer cell line with plasmids that encode all components necessary to produce lentiviral particles or VLP. One major flaw that we have discovered regarding lentiviral particles and VSVG-based VLPs that are produced by this conventional transient transfection method is that, in addition to their conventional cargo, these particles package and deliver plasmid DNA that was used in the initial transient transfection. This unintended plasmid DNA delivery can be immunogenic and cause undesirable effects, such as plasmid DNA being integrated into genomic DNA. It is important to specify the type of biomolecules and/or chemicals that are to be delivered within particles, and heVLPs have been designed to possess this germane capability.

The heVLPs described herein can deliver DNA only, DNA+RNA+protein, or RNA+protein. Importantly, heVLPs are the first VLP delivery modality that leverages select components from human endogenous retroviruses (HERVs) to create particles for customizable cargo delivery into eukaryotic cells. heVLPs are capable of controlling the form of the cargo (DNA, protein, and/or RNA). All other previously described VLPs and viral particles package and deliver unwanted plasmid DNA (or other types of DNA-based gene expression constructs) introduced into particle producer cells via transient transfection in addition to the intended protein and/or RNA cargo(s).

Another non-obvious aspect of heVLPs is the ENV protein on the surface of the heVLP. The ENV protein is responsible for the ability of heVLPs to efficiently deliver cargo into cells. The majority of retroviral ENV proteins require post-translational modifications in the form of proteolytic cleavage of the intracellular domain (ICD) of the ENV protein in order to activate the fusogenicity of the ENV protein; this is essential for infectivity.[1] The envelope proteins described in Table 1 are all derived from HERVs that are expressed to varying levels in healthy human tissues (or HERV ENV consensus sequences). Some of these sequences possess ICD truncations that have been shown to enhance fusogenicity, but most do not require truncation.

heVLPs do not require exogenous, virally-derived GAG for particle formation because heVLPs utilize human-endogenous GAG proteins from HERVs (or HERV GAG consensus sequences).[1] These HERV GAG proteins enable heVLP formation and are expressed to varying levels in healthy human tissues. Importantly, heVLPs are different from previously described viral particles, VLPs, and extracellular vesicles because heVLPs are composed of a novel combination of HERV ENV and GAG components, and heVLPs lack components from exogenous viruses.[2,3] Because of the above mentioned design optimizations, heVLPs are particularly suited for delivery of DNA, RNA, protein, or combinations of biomolecules and/or chemicals, such as DNA-encoded or RNP-based genome editing reagents.

Genome editing reagents, especially CRISPR-CAS, zinc finger, and TAL-nuclease-based reagents have the potential to become in vivo therapeutics for the treatment of genetic diseases, but techniques for delivering genome editing reagents into cells are severely limiting or unsafe for patients. Conventional therapeutic monoclonal antibody delivery is successful at utilizing direct injection for proteins. Unfortunately, strategies for direct injection of gene editing proteins, such as Cas9, are hampered by immunogenicity, degradation, ineffective cell specificity, and inability to cross the plasma membrane or escape endosomes/lysosomes.[4-10] More broad applications of protein therapy and gene editing could be achieved by delivering therapeutic protein cargo to the inside of cells. Cas9, for example, cannot efficiently cross the phospholipid bilayer to enter into cells, and has been shown to have innate and adaptive immunogenic potential.[4-8] Therefore, it is not practical or favorable to deliver Cas9 by direct injection or as an external/internal conjugate to lipid, protein or metal-based nanoparticles that have cytotoxic and immunogenic properties and often yield low levels of desired gene modifications.[9-20]

Nanoparticles that encapsulate cargo are another delivery strategy that can be used to deliver DNA, protein, RNA and RNPs into cells[9-18] Nanoparticles can be engineered for cell specificity and can trigger endocytosis and subsequent endosome lysis. However, nanoparticles can have varying levels of immunogenicity due to an artificially-derived vehicle shell.[9-20] Many nanoparticles rely on strong opposing charge distributions to maintain particle structural integrity, and the electrostatics can make it toxic and unfit for many in vivo therapeutic scenarios.[9] Nanoparticles that deliver RNA have had successes in recent clinical trials, but most have only been used to deliver siRNA or shRNA. Toxicity from such nanoparticles is still a major concern.[9] Nanoparticles that deliver mRNA coding for genome editing RNPs have also been a recent success, but these create a higher number of off-target effects compared to protein delivery and RNA stability is lower than that of protein.[17] Nanoparticles that deliver genome editing RNPs and DNA have been a significant breakthrough because they can leverage both homology directed repair (HDR) and non-homologous end joining (NHEJ), but exhibit prohibitively low gene modification frequencies in vitro and in vivo, and therefore currently have limited applications in vivo as a gene editing therapeutic.[15]

Currently, the clinical standard vehicles for delivering genome editing therapeutics are adeno-associated virus (AAV). Although AAV vectors are a promising delivery modality that can successfully deliver DNA into eukaryotic cells, AAV cannot efficiently package and deliver DNA constructs larger than 4.5 kb and this precludes delivery of many CRISPR-based gene editing reagents that require larger DNA expression constructs. CRISPR-based gene editing reagents can be split into multiple different AAV particles, but this strategy drastically reduces delivery and editing efficiency. Depending on the dose required, AAV and adenoviral vectors can have varying levels of immunogenicity. In addition, inverted-terminal repeats (ITRs) in the AAV DNA construct can promote the formation of spontaneous episomes leading to prolonged expression of genome editing reagents and increased off-target effects. ITRs can also promote the undesired integration of AAV DNA into genomic DNA.[21-24] Recently, VLPs have been utilized to deliver mRNA and protein cargo into the cytosol of cells.[2,3,25-30] VLPs have emerged as a substitute delivery modality for retroviral particles. VLPs can be designed to lack the ability to integrate retroviral DNA, and to package and deliver protein/RNP/DNA. However, most VLPs, including recently conceived VLPs that deliver genome editing reagents known to date, utilize HIV or other virally-derived gag-pol protein fusions and viral proteases to generate retroviral-like particles.[25-27,29,30] Secondly, some VLPs containing RGNs also must package and express guide RNAs from a lentiviral DNA transcript.[27] Thirdly, some VLPs require a viral protease in order to form functional particles and release genome editing cargo.[25-27,29] Since this viral protease recognizes and cleaves at multiple amino acid motifs, it can cause damage to the protein cargo which could be hazardous for therapeutic applications. Fourthly, most published VLP modalities that deliver genome editing proteins to date exhibit low in vitro and in vivo gene modification efficiencies due to low packaging and transduction efficiency.[25-27] Fifthly, the complex viral genomes utilized for these VLP components possess multiple reading frames and employ RNA splicing that could result in spurious fusion protein products being delivered.[25-27,29,30] Sixthly, the presence of reverse transcriptase, integrase, capsid and a virally-derived envelope protein in these VLPs is not ideal for most therapeutic applications because of immunogenicity and off target editing concerns. Lastly, most retroviral particles, such as lentiviral particles, are pseudotyped with VSVG and nearly all described VLPs that deliver genome editing reagents hitherto possess and rely upon VSVG.[2,3,]

25-30 We have discovered that VSVG-based particles that are formed by transiently transfecting producer cells package and deliver DNA that was transfected. The current versions of VSVG-based VLPs cannot prevent this inadvertent delivery of DNA and this impedes the use of VLPs in scenarios that necessitate minimal immunogenicity and off target effects.

Extracellular vesicles are another delivery modality that can package and deliver cargo within exosomes and ectosomes.[31,32] Similar to VLPs, extracellular vesicles are comprised of a phospholipid bilayer from a mammalian cell. Unlike VLPs, extracellular vesicles lack viral components and therefore have limited immunogenicity. Whereas VLPs have a great ability to enter cells due to external fusogenic glycoproteins (VSVG) extracellular vesicles mainly rely on cellular uptake via micropinocytosis and this limits the delivery efficiency of extracellular vesicles.

heVLPs try to leverage the delivery benefits of extracellular vesicles and VLPs. heVLPs are the first VLP modality to eliminate all the potentially harmful exogenous, virally-derived components. heVLP components are known to be involved in extracellular vesicle biogenesis, they are known to possess local immunosuppressive properties, and their expression in healthy human tissues minimizes the chance of eliciting an immune response because of central tolerance.[1] heVLPs are a safer and more effective alternative than previously described VLPs, extracellular vesicles, AAVs and nanoparticles-especially for delivery of genome editing reagents-because heVLPs are comprised of all human-derived components, heVLPs have the ability to deliver DNA+ RNP, or RNP alone while other previously described VLPs cannot prevent transient transfection DNA from being unintentionally packaged and delivered, heVLPs can deliver specialty DNA molecules while previously described VLPs, nanoparticles and AAVs cannot or do not, and heVLPs can be produced with cells that have been derived from patients (autologous heVLPs) and other FDA-approved cell lines (allogenic heVLPs) to further reduce the risks of adverse immune reactions. Here, we describe methods and compositions for producing, purifying, and administering heVLPs for in vitro and in vivo applications of genome editing, epigenome modulation, transcriptome editing and proteome modulation. The desired editing outcome depends on the therapeutic context and will require different gene editing reagents. *Streptococcus pyogenes* Cas9 (spCas9) and *acidaminococcus sp*. Cas12a (functionalize) are two of the most popular RNA-guided enzymes for editing that leverages NHEJ for introducing stop codons or deletions, or HDR for causing insertions.[34-36] Cas9-deaminase fusions, also known as base editors, are the current standard for precise editing of a single nucleotide without double stranded DNA cleavage.[37,38] Importantly, this invention provides a novel way of packaging and delivering reagents for applications of genome editing, epigenome modulation, transcriptome editing and proteome modulation. Importantly, this invention is also the first to address the phenomenon of inadvertent DNA delivery in VLPs and the first to control for the type of biomolecule to be delivered (DNA, RNA, and/or protein) thereby increasing the types of therapeutic in vivo genome modifications that are possible and minimizing deleterious off target effects.

Section 1: heVLP-Mediated Delivery of Cargo Including DNAs, Proteins, Compounds, and RNAs Conventional VLPs that have been engineered to encapsulate and deliver protein-based cargo commonly fuse cargo to the INT or GAG polyprotein[25-27,29,30,39,40] After transient transfection of production plasmid DNA constructs, these protein fusions are translated in the cytosol of conventional VLP production cell lines, the gag matrix is acetylated and recruited to the cell membrane, and the gag fusions are encapsulated (transient transfection DNA is also unintentionally encapsulated) within VLPs as VLPs bud off of the membrane into extracellular space.

Figure 1:
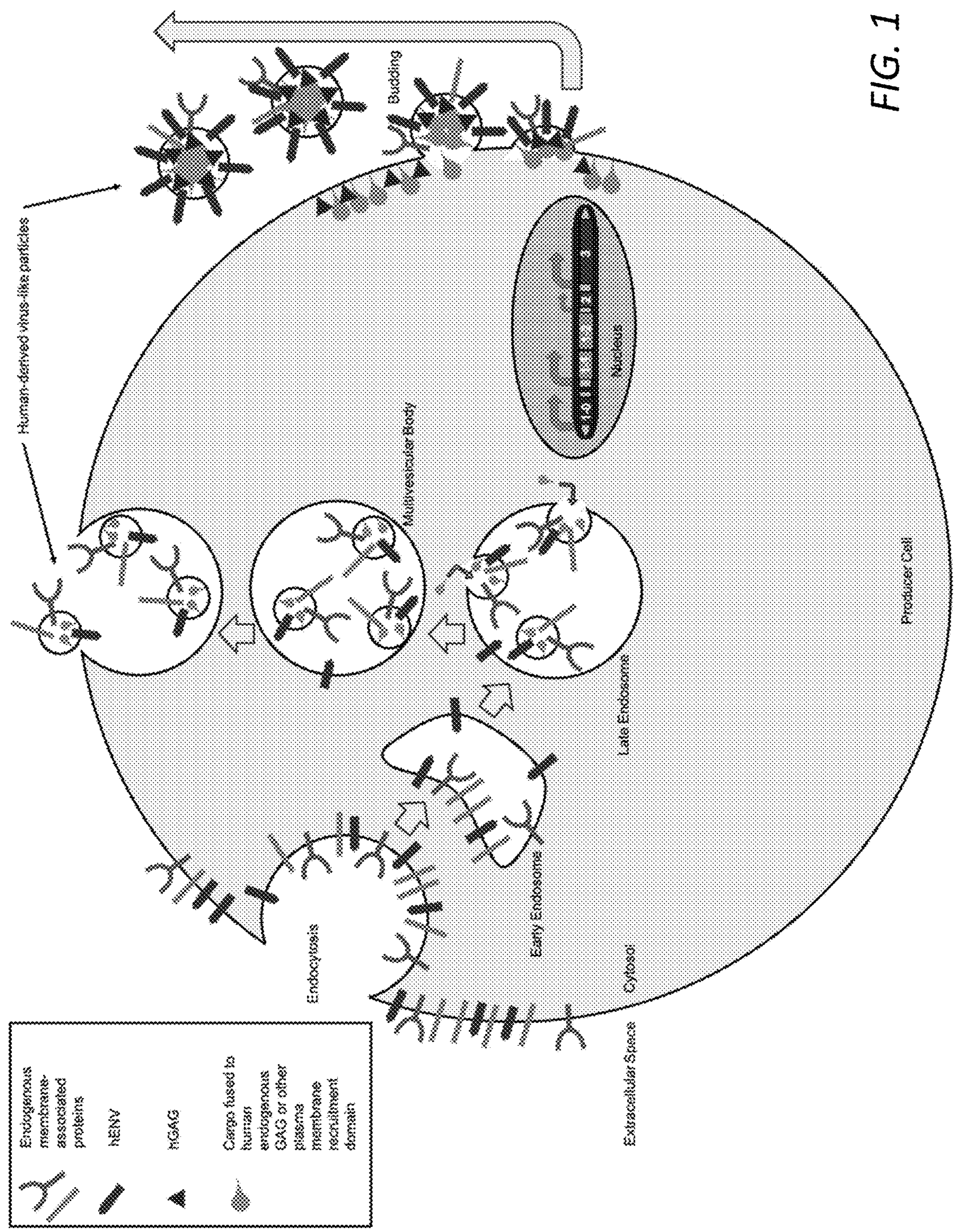
FIG. 1: Depiction of exemplary T2heVLP/T4heVLP production and transduction for RNP/protein delivery. All heVLP expression constructs are stably integrated in the genome of the producer cell. Construct 1-0 corresponds to the human-endogenous GAG (hGAG). Construct 1-1 corresponds to the human-endogenous GAG or other phospholipid bilayer recruitment domain. 1-2 corresponds to the cargo. 2 corresponds to an optional guide RNA. 1-0, 1-1 and 1-2 are translated in the cytosol where the fusion of 1-1 and 1-2 complexes with guide RNA before it is recruited to the phospholipid bilayer. 3 corresponds to a HERV-derived glycoprotein (hENV). The HERV-derived glycoprotein is expressed as a transmembrane protein on the plasma membrane. hGAG drives budding of cargo-containing heVLPs from the plasma membrane to extracellular space. These particles are purified and are able to fuse with target cells and deliver cargo by interacting with surface receptors at the target cell surface.
Figure 2:
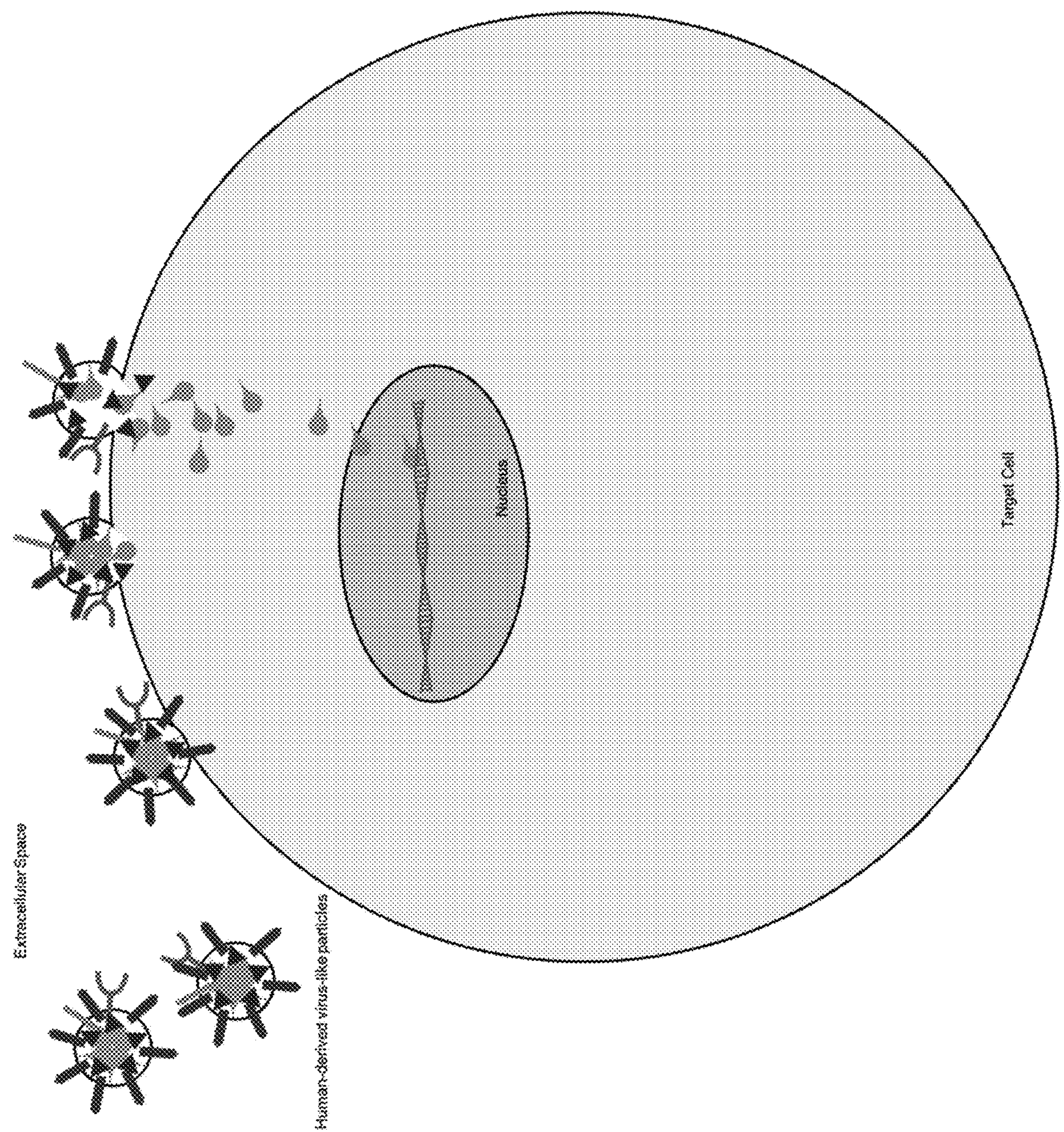
FIG. 2: Depiction of purified heVLPs entering a target cell and delivering cargo to the cytosol. Importantly, the human-endogenous GAG or other phospholipid bilayer recruitment domain allows cargo to enter the target cell nucleus as long as cargo possesses a nuclear localization sequence.
Figure 3:
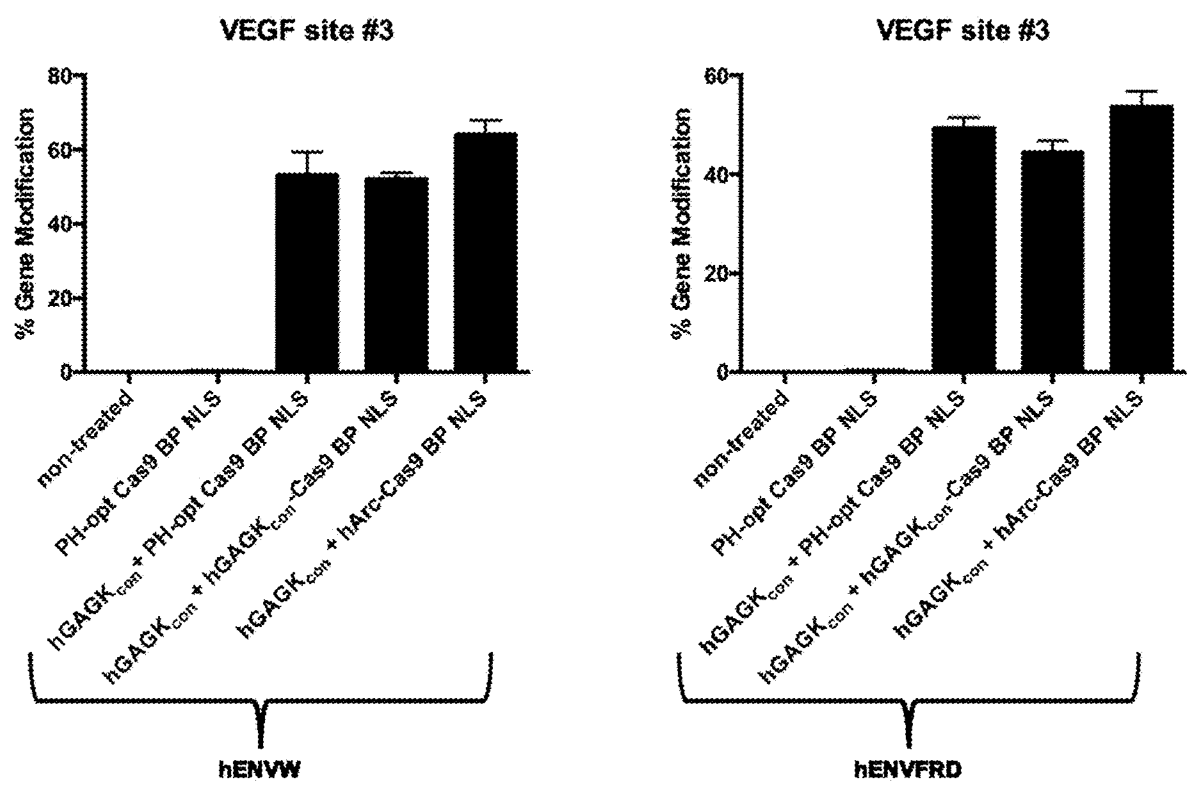
FIG. 3: Exemplary T1heVLP-delivered spCas9 genome editing in vitro. HEK 293T cells transduced with T1heVLPs containing PLC PH fused to spCas9, hGAGK$_{con}$ fused to spCas9, or human Activity-regulated cytoskeleton-associated protein (hArc) fused to spCas9 targeted to VEGF site #3. heVLPs are pseudotyped with either hENVW (left chart) or hENVFRD (right chart). Gene modification is measured by amplicon sequencing.
Figure 4:
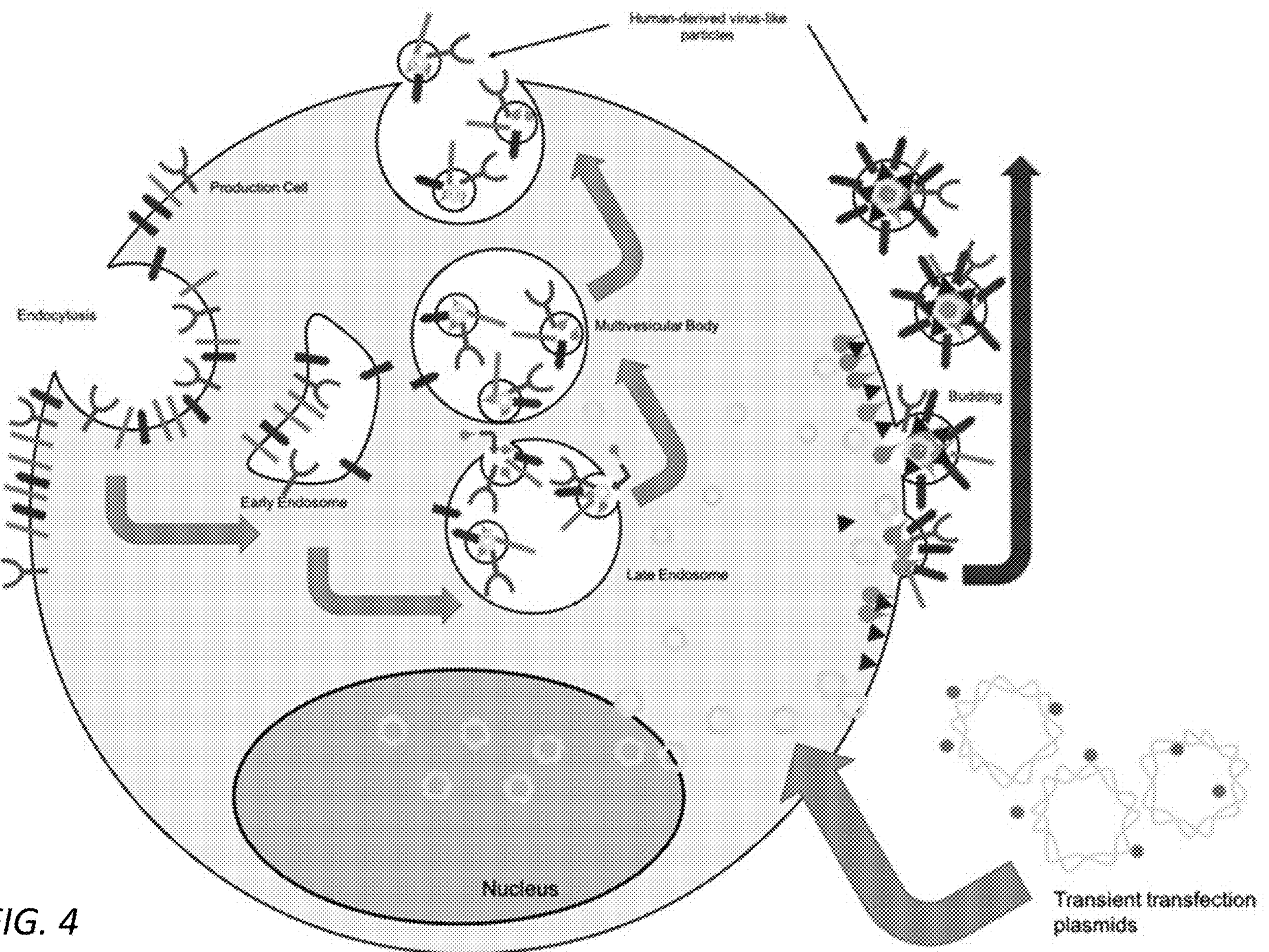
FIG. 4: Depiction of T1heVLP/T3heVLP production. Plasmid DNA constructs involved in the transfection encode cargo, an optional guide RNA, hGAG and a HERV-derived glycoprotein. Plasmids, or other types of DNA molecules, will be distributed throughout the production cell, so constructs located in the nucleus will express heVLP components and cargo, and constructs located near the plasma membrane or endosomes will be encapsulated within budding heVLPs.

In contrast, the heVLPs described herein can package protein-based cargo by integrating all production DNA into the genomic DNA of production cell lines. Once cell lines are created, protein delivery heVLPs can be produced in a constitutive or inducible fashion. Proteins are packaged into heVLP by fusing select human-endogenous GAG proteins or other plasma membrane recruitment domains to protein-based cargo (e.g., as shown in Table 6). Human-endogenous GAG proteins and human pleckstrin homology (PH) domains localize to biological membranes. PH domains interact with phosphatidylinositol lipids and proteins within biological membranes, such as PIP2, PIP3, βγ-subunits of GPCRs, and PKC.[41,42] However, in addition to localizing to phospholipid bilayers, human-endogenous GAG proteins drive budding and particle formation.[42] This dual functionality of human-endogenous GAG enables packaging of cargo and budding/formation of particles. One such human-endogenous GAG protein used for this purpose is the human Arc protein, which can be fused to protein-based cargo to recruit cargo to the cytosolic side of the phospholipid bilayer.[43] These human-endogenous GAG phospholipid bilayer recruitment domains can be fused to the N-terminus or C-terminus of protein-based cargo via polypeptide linkers of variable length regardless of the location or locations of one or more nuclear localization sequence(s) (NLS) within the cargo. Preferably, the linker between protein-based cargo and the human-endogenous GAG phospholipid bilayer recruitment domain is a polypeptide linker 5-20, e.g., 8-12, e.g., 10, amino acids in length primarily composed of glycines and serines. The human-endogenous GAG or other phospholipid bilayer recruitment domain localizes the cargo to the phospholipid bilayer and this protein cargo is packaged within heVLPs that bud off from the producer cell into extracellular space (FIG. 1). In this application, the use of these human-endogenous GAG and other phospholipid bilayer recruitment domains is novel and unique in that these human-endogenous GAG and other proteins can facilitate for localization of cargo to the cytosolic face of the plasma membrane within the heVLP production cells, and they also allow for cargo to localize to the nucleus of heVLP-transduced cells without the utilization of exogenous retroviral GAG or chemical and/or light-based dimerization systems (FIG. 2). The heVLP delivery of Cas9, for example, is significantly more efficient with a fusion to a human-endogenous GAG protein compared to a fusion to a PH plasma membrane recruitment domain or no fusion at all (FIG. 3).

heVLPs can also package and deliver a combination of DNA and RNA if heVLPs are produced via transient transfection of a production cell line. DNA that is transfected into cells will possess size-dependent mobility such that a fraction of the transfected DNA will remain in the cytosol while another fraction of the transfected DNA will localize to the nucleus.[44-46] One fraction of the transfected DNA in the nucleus will expressed components needed to create heVLPs and the other fraction in the cytosol/near the plasma membrane will be encapsulated and delivered in heVLPs (FIG. 4).

heVLP "Cargo" as used herein can refer to a one or more of chemicals, e.g., small molecule compounds, combination of DNA, RNA, and protein, a combination of RNA and protein, a combination of DNA and protein, or protein, e.g., for therapeutic or diagnostic use, or for the applications of genome editing, epigenome modulation, and/or transcriptome modulation. In addition, endogenous RNA and protein from the producer cells get packaged and/or incorporated into heVLPs. In order to simplify these distinctions, a combination of exogenous DNA, exogenous RNA, and protein (exogenous and/or endogenous protein) will be referred to as type 1 cargo (T1heVLPs), exogenous RNA and protein (exogenous and/or endogenous protein) will be referred to as type 2 cargo (T2heVLPs), a combination of exogenous DNA and proteins (exogenous and/or endogenous protein) will be referred to as type 3 cargo (T3heVLPs), proteins (exogenous and/or endogenous protein) will be referred to as type 4 cargo (T4heVLPs). Therefore, T1 contains DNA, RNA, +/−exogenous protein, T2 contains RNA+/−exogenous protein, T3 contains DNA+/−exogenous protein, and T4 is a particle with or without exogenous protein cargo. Hence, T4 without exogenous protein is considered an “empty particle” because there is no “exogenous cargo.” “Exogenous cargo” is cargo not endogenous to the producer cells that can be packaged and/or incorporated into heVLPs. In addition, T1-T4heVLPs can package exogenous chemical molecules in addition to the types of cargoes present in T1-T4heVLPs. RNA in this context, for example, could be single guide RNA (sgRNA), Clustered Regularly Interspaced Palindromic Repeat (CRISPR) RNA (crRNA), and/or mRNA coding for cargo.

As used herein, “small molecules” refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The cargo is limited by the diameter of the particles, e.g., which in some embodiments range from 150 nm to 500 nm. Cargo developed for applications of genome editing also includes nucleases and base editors. Nucleases include FokI and AcuI ZFNs and Transcription activator-like effector nucleases (TALENs) and CRISPR based nucleases or a functional derivative thereof (e.g., as shown in Table 2) (ZFNs are described, for example, in United States Patent Publications 20030232410; 20050208489; 20050026157; 20050064474; 20060188987; 20060063231; and International Publication WO 07/014275) (TALENs are described, for example, in United States Patent Publication U.S. Pat. No. 9,393,257B2; and International Publication WO2014134412A1) (CRISPR based nucleases are described, for example, in United States Patent Publications U.S. Pat. No. 8,697,359B1; US20180208976A1; and International Publications WO2014093661A2; WO2017184786A8).[34-36] Base editors that are described by this work include any CRISPR based nuclease orthologs (wt, nickase, or catalytically inactive (CI)), e.g., as shown in Table 2, fused at the N-terminus to a deaminase or a functional derivative thereof (e.g., as shown in Table 3) with or without a fusion at the C-terminus to one or multiple uracil glycosylase inhibitors (UGIs) using polypeptide linkers of variable length (Base editors are described, for example, in United States Patent Publications US20150166982A1; US20180312825A1; U.S. Ser. No. 10/113,163B2; and International Publications WO2015089406A1; WO2018218188A2; WO2017070632A2; WO2018027078A8; WO2018165629A1).[37,38] In addition, prime editors are also compatible with heVLP delivery modalities (Prime editors are described, for example, in Anzalone et al., Nature. 2019 December; 576(7785):149-157).

sgRNAs complex with genome editing reagents during the packaging process and are co-delivered within heVLPs. To date, this concept has been validated in vitro by experiments that demonstrate the T2heVLP delivery of RGN RNP for the purposes of site specific editing of an endogenous site (FIG. 3). For example, T2heVLPs have been used to deliver Cas9 RNP to HEK 293T cells for the purposes of editing endogenous VEGF site #3 (FIG. 3).

Cargo designed for the purposes of epigenome modulation includes the CI CRISPR based nucleases, zinc fingers (ZFs) and TALEs fused to an epigenome modulator or combination of epigenome modulators or a functional derivative thereof connected together by one or more variable length polypeptide linkers (Tables 2 & 4). T1-T4 cargo designed for the purposes of transcriptome editing includes CRISPR based nucleases or any functional derivatives thereof in Table 5 or CI CRISPR based nucleases or any functional derivatives thereof in Table 5 fused to deaminases in Table 3 by one or more variable length polypeptide linkers.

The cargo can also include any therapeutically or diagnostically useful protein, DNA, RNP, or combination of DNA, protein and/or RNP. See, e.g., WO2014005219; U.S. Ser. No. 10/137,206; US20180339166; U.S. Pat. No. 5,892,020A; EP2134841B1; WO2007020965A1. For example, cargo encoding or composed of nuclease or base editor proteins or RNPs or derivatives thereof can be delivered to retinal cells for the purposes of correcting a splice site defect responsible for Leber Congenital Amaurosis type 10. In the mammalian inner ear, heVLP delivery of base editing reagents or HDR promoting cargo to sensory cells such as cochlear supporting cells and hair cells for the purposes of editing β-catenin (β-catenin Ser 33 edited to Tyr, Pro, or Cys) in order to better stabilize β-catenin could help reverse hearing loss.

In another application, heVLP delivery of RNA editing reagents or proteome perturbing reagents could cause a transitory reduction in cellular levels of one or more specific proteins of interest (potentially at a systemic level, in a specific organ or a specific subset of cells, such as a tumor), and this could create a therapeutically actionable window when secondary drug(s) could be administered (this secondary drug is more effective in the absence of the protein of interest or in the presence of lower levels of the protein of interest). For example, heVLP delivery of RNA editing reagents or proteome perturbing reagents could trigger targeted degradation of MAPK and PI3K/AKT proteins and related mRNAs in vemurafenib/dabrafenib-resistant BRAF-driven tumor cells, and this could open a window for the administration of vemurafenib/dabrafenib because BRAF inhibitor resistance is temporarily abolished (resistance mechanisms based in the MAPK/PI3K/AKT pathways are temporarily downregulated by heVLP cargo). This example is especially pertinent when combined with heVLPs that are antigen inducible and therefore specific for tumor cells.

In another application, heVLPs could deliver Yamanaka factors Oct3/4, Sox2, Klf4, and c-Myc to human or mouse fibroblasts in order to generate induced pluripotent stem cells.

In another application, heVLPs could deliver dominant-negative forms of proteins in order to elicit a therapeutic effect.

heVLPs that are antigen-specific could be targeted to cancer cells in order to deliver proapoptotic proteins BIM, BID, PUMA, NOXA, BAD, BIK, BAX, BAK and/or HRK in order to trigger apoptosis of cancer cells.

90% of pancreatic cancer patients present with unresectable disease. Around 30% of patients with unresectable pancreatic tumors will die from local disease progression, so it is desirable to treat locally advanced pancreatic tumors with ablative radiation, but the intestinal tract cannot tolerate high doses of radiation needed to cause tumor ablation. Selective radioprotection of the intestinal tract enables ablative radiation therapy of pancreatic tumors while minimizing damage done to the surrounding gastrointestinal tract. To this end, heVLPs could be loaded with dCas9 fused to the transcriptional repressor KRAB and guide RNA targeting EGLN. EGLN inhibition has been shown to significantly reduce gastrointestinal toxicity from ablative radiation treatments because it causes selective radioprotection of the gastrointestinal tract but not the pancreatic tumor.[47]

Unbound steroid receptors reside in the cytosol. After binding to ligands, these receptors will translocate to the nucleus and initiate transcription of response genes. heVLPs could deliver single chain variable fragment (scFv) antibodies to the cytosol of cells that bind to and disrupt cytosolic steroid receptors. For example, the scFv could bind to the glucocorticoid receptor and prevent it from binding dexamethasone, and this would prevent transcription of response genes, such as metallothionein 1E which has been linked to tumorigenesis.[48]

heVLPs can be indicated for treatments that involve targeted disruption of proteins. For example, heVLPs can be utilized for targeting and disrupting proteins in the cytosol of cells by delivering antibodies/scFvs to the cytosol of cells. Classically, delivery of antibodies through the plasma membrane to the cytosol of cells has been notoriously difficult and inefficient. This mode of protein inhibition is similar to how a targeted small molecule binds to and disrupts proteins in the cytosol and could be useful for the treatment of a diverse array of diseases.[49-51]

In addition, the targeting of targeted small molecules is limited to proteins of a certain size that contain binding pockets which are relevant to catalytic function or protein-protein interactions. scFvs are not hampered by these limitations because scFvs can be generated that bind to many different moieties of a protein in order to disrupt catalysis and interactions with other proteins. For example, RAS oncoproteins are implicated across a multitude of cancer subtypes, and RAS is one of the most frequently observed oncogenes in cancer. For instance, the International Cancer Genome Consortium found KRAS to be mutated in 95% of their Pancreatic Adenocarcinoma samples. RAS isoforms are known to activate a variety of pathways that are dysregulated in human cancers, like the PI3K and MAPK pathways. Despite the aberrant roles RAS plays in cancer, no efficacious pharmacologic direct or indirect small molecule inhibitors of RAS have been developed and approved for clinical use. One strategy for targeting RAS could be heVLPs that can deliver specifically to cancer cells scFvs that bind to and disrupt the function of multiple RAS isoforms.[49-51]

Figure 5:
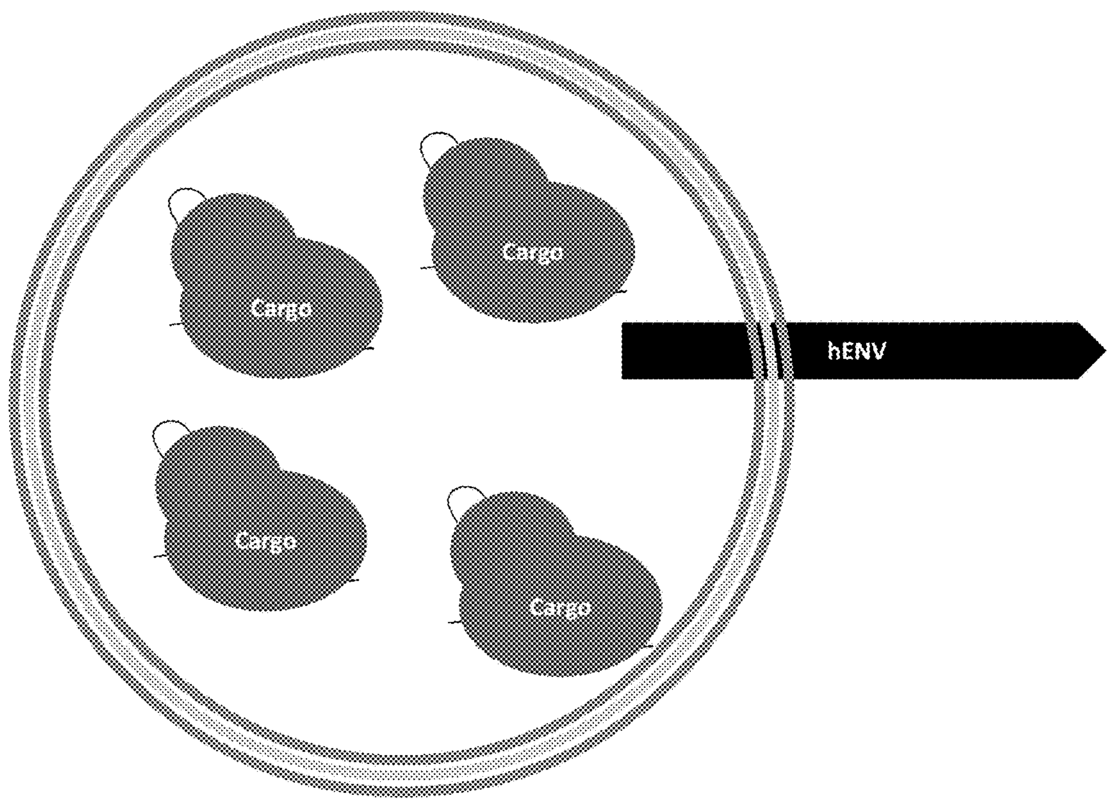
FIG. 5: Depiction of exemplary heVLP and cargo configuration

FIGS. 5-69 provide exemplary heVLP configurations and non-limiting examples of cargo molecules.

Section 2: heVLP Composition, Production, Purification and Applications heVLPs are produced from producer cell lines that are either transiently transfected with at least one plasmid or stably expressing constructs that have been integrated into the producer cell line genomic DNA. In some embodiments, for T1 and T3heVLPs, if a single plasmid is used in the transfection, it should comprise sequences encoding one or more HERV-derived glycoproteins (e.g., as shown in Table 1), one or more HERV-derived GAG proteins, cargo (e.g., a therapeutic protein or a gene editing reagent such as a zinc finger, transcription activator-like effector (TALE), and/or CRISPR-based genome editing/modulating protein and/or RNP such as those found in Tables 2, 3, 4 & 5) with a fusion to a human-endogenous GAG or other plasma membrane recruitment domain (e.g., as shown in Table 6), and a guide RNA, if necessary. Preferably, two to three plasmids are used in the transfection. These two to three plasmids can include the following (any two or more can be combined in a single plasmid):

1. A plasmid comprising sequences encoding a therapeutic protein or a genome editing reagent, with a fusion to a human-endogenous GAG or other plasma membrane recruitment domain.
2. A plasmid comprising one or more HERV-derived glycoproteins (e.g., as listed in Table 1).
3. A plasmid comprising one or more HERV-derived GAG proteins.
4. If the genome editing reagent from plasmid 1 requires one or more guide RNAs, a plasmid comprising one or more guide RNAs apposite for the genome editing reagent in plasmid 1.

If it is desired to deliver a type of DNA molecule other than plasmid(s), the above-mentioned transfection can be performed with double-stranded closed-end linear DNA, episome, mini circle, double-stranded oligonucleotide and/or other specialty DNA molecules. Alternatively, for T2 and T4heVLPs, the producer cell line can be made to stably express the constructs (1 through 3) described in the transfection above.

The plasmids, or other types of specialty DNA molecules described above, will also preferably include other elements to drive expression or translation of the encoded sequences, e.g., a promoter sequence; an enhancer sequence, e.g., 5' untranslated region (UTR) or a 3' UTR; a polyadenylation site; an insulator sequence; or another sequence that increases or controls expression (e.g., an inducible promoter element).

Preferably, appropriate producer cell lines are primary or stable human cell lines refractory to the effects of transfection reagents and fusogenic effects due glycoproteins. Examples of appropriate cell lines include Human Embryonic Kidney (HEK) 293 cells, HEK293 T/17 SF cells kidney-derived Phoenix-AMPHO cells, and placenta-derived BeWo cells. For example, such cells could be selected for their ability to grow as adherent cells, or suspension cells. In some embodiments, the producer cells can be cultured in classical DMEM under serum conditions, serum-free conditions, or exosome-free serum conditions. T1 and T3heVLPs can be produced from cells that have been derived from patients (autologous heVLPs) and other FDA-approved cell lines (allogenic heVLPs) as long as these cells can be transfected with DNA constructs that encode the aforementioned heVLP production components by various techniques known in the art.

In addition, if it is desirable, more than one genome editing reagent can be included in the transfection. The DNA constructs can be designed to overexpress proteins in the producer cell lines. The plasmid backbones, for example, used in the transfection can be familiar to those skilled in the art, such as the pCDNA3 backbone that employs the CMV promoter for RNA polymerase II transcripts or the U6 promoter for RNA polymerase III transcripts. Various techniques known in the art may be employed for introducing nucleic acid molecules into producer cells. Such techniques include chemical-facilitated transfection using compounds such as calcium phosphate, cationic lipids, cationic polymers, liposome-mediated transfection, such as cationic liposome like LIPOFECTAMINE (LIPOFECTAMINE 2000 or 3000 and TransIT-X2), polyethyleneimine, non-chemical methods such as electroporation, particle bombardment, or microinjection.

A human producer cell line that stably expresses the necessary heVLP components in a constitutive and/or inducible fashion can be used for production of T2 and T4heVLPs. T2 and T4heVLPs can be produced from cells that have been derived from patients (autologous heVLPs) and other FDA-approved cell lines (allogenic heVLPs) if these cells have been converted into stable cell lines that express the aforementioned heVLP components.

Also provided herein are the producer cells themselves.

In some embodiments, in order for efficient recruitment of cargo into heVLPs, the cargo comprises a covalent or non-covalent connection to a human-endogenous GAG or other plasma membrane recruitment domain, preferably as shown in Table 6. Covalent connections, for example, can include direct protein-protein fusions generated from a single reading frame, inteins that can form peptide bonds, other proteins that can form covalent connections at R-groups and/or RNA splicing.[52-54] Non-covalent connections, for example, can include DNA/DNA, DNA/RNA, and/or RNA/RNA hybrids (nucleic acids base pairing to other nucleic acids via hydrogen-bonding interactions), protein domains that dimerize or multimerize with or without the need for a chemical compound/molecule to induce the protein-protein binding (such as DmrA/DmrB/DmrC (Takara Bio), FKBP/FRB,[55] dDZFs,[56] and Leucine zippers[57]), single chain variable fragments,[58] nanobodies,[59] affibodies,[60] proteins that bind to DNA and/or RNA, proteins with quaternary structural interactions, optogenetic protein domains that can dimerize or multimerize in the presence of certain light wavelengths,[61] and/or naturally reconstituting split proteins.[62]

In some embodiments, the cargo comprises a fusion to a dimerization domain or protein-protein binding domain that may or may not require a molecule to trigger dimerization or protein-protein binding.

In some embodiments, the producer cells are FDA-approved cells lines, allogenic cells, and/or autologous cells derived from a donor.

In some embodiments, the full or active peptide domains of human CD47 may be incorporated in the heVLP surface to reduce immunogenicity.

Examples of AAV proteins included here are AAV REP 52, REP 78, and VP1-3. The capsid site where proteins can be inserted is T138 starting from the VP1 amino acid counting.[63] Dimerization domains could be inserted at this point in the capsid, for instance.

Examples of dimerization domains included here that may or may not need a small molecule inducer are dDZF1,[56] dDZF2,[56] DmrA (Takara Bio), DmrB (Takara Bio), DmrC (Takara Bio), FKBP,[55] FRB,[55] GCN4 scFv,[58] 10×/24× GCN4,[58] GFP nanobody[59] and GFP.[64]

Examples of split inteins included here are Npu DnaE, Cfa, Vma, and Ssp DnaE.[52]

Examples of other split proteins included here that make a covalent bond together are Spy Tag and Spy Catcher.[53]

Examples of RNA binding proteins included here are MS2, Com, and PP7.[65]

Examples of synthetic DNA-binding zinc fingers included here are ZF6/10, ZF8/7, ZF9, MK10, Zinc Finger 268, and Zinc Finger 268/NRE.[66,67]

Examples of proteins that multimerize as a result of quaternary structure included here are E. coli ferritin, and the other chimeric forms of ferritin.[68,69]

Examples of optogenetic "light-inducible proteins" included here are Cry2, CIBN, and Lov2-Ja.[61]

Examples of peptides the enhance transduction included here are L17E,[70] Vectofusin-1 (Miltenyi Biotec), KALA,[71] and the various forms of nisin.[72]

In another embodiment, T1-T4 heVLPs that are produced and isolated can be loaded with biomolecule or chemical molecule cargo by utilizing nucleofection, lipid, polymer, or $CaCl_2$) transfection, sonication, freeze thaw, incubation at various temperatures, and/or heat shock of purified particles mixed with cargo. These techniques are adapted from techniques employed to load cargo into exosomes for therapeutic or research applications.[73-75] For example, 100 ug of heVLPs can be resuspended in 200-450 ul of 50 mM trehalose in PBS, mixed with cargo at a desired concentration, and electroporated (GenePulser II Electroporation System with capacitance extender, Bio-Rad, Hercules, CA, USA) in a 0.4 cm cuvette at 0.200 kV and 125 uF.

Production of Cargo-Loaded heVLPs and Compositions

Preferably heVLPs are harvested from cell culture medium supernatant 36-48 hours post-transfection, or when heVLPs are at the maximum concentration in the medium of the producer cells (the producer cells are expelling particles into the media and at some point in time, the particle concentration in the media will be optimal for harvesting the particles). Supernatant can be purified by any known methods in the art, such as centrifugation, ultracentrifugation, precipitation, ultrafiltration, and/or chromatography. In some embodiments, the supernatant is first filtered, e.g., to remove particles larger than 1 μm, e.g., through 0.45 pore size polyvinylidene fluoride hydrophilic membrane (Millipore Millex-HV) or 0.8 μm pore size mixed cellulose esters hydrophilic membrane (Millipore Millex-AA). After filtration, the supernatant can be further purified and concentrated, e.g., using ultracentrifugation, e.g., at a speed of 80,000 to 100,000×g at a temperature between 1° C. and 5° C. for 1 to 2 hours, or at a speed of 8,000 to 15,000 g at a temperature between 1° C. and 5° C. for 10 to 16 hours. After this centrifugation step, the heVLPs are concentrated in the form of a centrifugate (pellet), which can be resuspended to a desired concentration, mixed with transduction-enhancing reagents, subjected to a buffer exchange, or used as is. In some embodiments, heVLP-containing supernatant can be filtered, precipitated, centrifuged and resuspended to a concentrated solution. For example, polyethylene glycol (PEG), e.g., PEG 8000, or antibody-bead conjugates that bind to heVLP surface proteins or membrane components can be used to precipitate particles. Purified particles are stable and can be stored at 4° C. for up to a week or −80° C. for years without losing appreciable activity.

Preferably, heVLPs are resuspended or undergo buffer exchange so that particles are suspended in an appropriate carrier. In some embodiments, buffer exchange can be performed by ultrafiltration (Sartorius Vivaspin 500 MWCO 100,000). An exemplary appropriate carrier for heVLPs to be used for in vitro applications would preferably be a cell culture medium that is suitable for the cells that are to be transduced by heVLPs. Transduction-enhancing reagents that can be mixed into the purified and concentrated heVLP solution for in vitro applications include reagents known by those familiar with the art (Miltenyl Biotec Vectofusin-1, Millipore Polybrene, Takara Retronectin, Sigma Protamine Sulfate, and the like). After heVLPs in an appropriate carrier are applied to the cells to be transduced, transduction efficiency can be further increased by centrifugation. Preferably, the plate containing heVLPs applied to cells can be centrifuged at a speed of 1,150 g at room temperature for 30 minutes. After centrifugation, cells are returned into the appropriate cell culture incubator (humidified incubator at 37° C. with 5% $CO_2$).

An appropriate carrier for heVLPs to be administered to a mammal, especially a human, would preferably be a pharmaceutically acceptable composition. A "pharmaceutically acceptable composition" refers to a non-toxic semi-solid, liquid, or aerosolized filler, diluent, encapsulating material, colloidal suspension or formulation auxiliary of any type. Preferably, this composition is suitable for injection. These may be in particular isotonic, sterile, saline solutions (monosodium or disodium phosphate, sodium, potassium, calcium or magnesium chloride and similar solutions or mixtures of such salts), or dry, especially freeze-dried compositions which upon addition, depending on the case, of sterilized water or physiological saline, permit the constitution of injectable solutions. Another appropriate pharmaceutical form would be aerosolized particles for administration by intranasal inhalation or intratracheal intubation.

The pharmaceutical forms suitable for injectable use include sterile aqueous solutions or suspensions. The solution or suspension may comprise additives which are compatible with heVLPs and do not prevent heVLP entry into target cells. In all cases, the form must be sterile and must be fluid to the extent that the form can be administered with a syringe. It must be stable under the conditions of manufacture and storage and must be preserved against the contaminating action of microorganisms, such as bacteria and fungi. An example of an appropriate solution is a buffer, such as phosphate buffered saline.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The compositions comprising cargo-loaded heVLPs can be included in a container, pack, or dispenser together with instructions for administration.

EXAMPLES

The invention is further described in the following examples, which do not limit the scope of the invention described in the claims.

Methods heVLP particles were produced by HEK293T cells using polyethylenimine (PEI) based transfection of plasmids. PEI is Polyethylenimine 25 kD linear (Polysciences #23966-2). To make a stock 'PEI MAX' solution, Ig of PEI was added to 1 L endotoxin-free $dH_2O$ that was previously heated to ~80° C. and cooled to room temperature. This mixture was neutralized to pH 7.1 by addition of TON NaOH and filter sterilized with 0.22 m polyethersulfone (PES). PEI MAX is stored at −20° C.

HEK293T cells were split to reach a confluency of 70%-90% at time of transfection and are cultured in 10% FBS DMEM media. Cargo vectors, such as one encoding a CMV promoter driving expression of a hPLCδ1 PH fusion to codon optimized Cas9 were co-transfected with a U6 promoter-sgRNA encoding plasmid, a $hERVK_{con}GAG$ ($hGAGK_{con}$) encoding plasmid, and a hENVW (Syncytin-1) encoding plasmid. Transfection reactions were assembled in reduced serum media (Opti-MEM; GIBCO #31985-070). For heVLP particle production on 10 cm plates, 5 μg PH-Cas9 expressing plasmid, 5 μg sgRNA-expression plasmid, 5 μg $hERVK_{con}GAG$ expression plasmid, and 5 μg Syncytin-1 expression plasmid were mixed in 1 mL Opti-MEM, followed by addition of 27.5 μl PEI MAX. After 20-30 min incubation at room temperature, the transfection reactions were dispersed dropwise over the HEK293T cells.

heVLPs were harvested at 48-72 hours post-transfection. heVLP supernatants were filtered using 0.8 μm pore size mixed cellulose esters membrane filters and transferred to polypropylene Beckman ultracentrifuge tubes that are used with the SW28 rotor (Beckman Coulter #326823). Each ultracentrifuge tube is filled with heVLP-containing supernatant from 3 10 cm plates to reach an approximate final volume of 35-37.5 ml. heVLP supernatant underwent ultracentrifugation at approximately 100,000×g, or 25,000 rpm, at 4° C. for 2 hours. After ultracentrifugation, supernatants were decanted and heVLP pellets resuspended in DMEM 10% FBS media such that they are now approximately 1,000 times more concentrated than they were before ultracentrifugation. heVLPs were added dropwise to cells that were seeded in a 24-well plate 24 hours prior to transduction. Polybrene (5-10 μg/mL in cell culture medium; Sigma-Aldrich #TR-1003-G) was supplemented to enhance transduction efficiency, if necessary. Vectofusin-1 (10 μg/mL in cell culture medium, Miltenyi Biotec #130-111-163) was supplemented to enhance transduction efficiency, if necessary. Immediately following the addition of heVLPs, the 24-well plate was centrifuged at 1,150×g for 30 min at room temperature to enhance transduction efficiency, if necessary.

Example 1

HEK 293T cells were transduced with T1heVLPs containing PLC PH fused to spCas9, hGAGK$_{con}$ fused to spCas9, or hArc fused to spCas9 targeted to VEGF site #3. T1heVLPs were pseudotyped with either hENVW (left chart) or hENVFRD (right chart). Gene modification was measured by amplicon sequencing. Particle purification and concentration was performed by PVDF filtration and ultracentrifugation at 100,000×g for 2 hours. Results are shown in FIG. 3. Importantly, if HERV-derived GAG (hGAGK$_{con}$) was not overexpressed by itself in producer cells, then efficient delivery was not achieved.

TABLE 1

| # | HERV envelope | Gene name | Accession no. | Position in sequence entry (a) |
|---|---|---|---|---|
| 1. | hENVH1 | envH/p62 | AJ289709.1 | 6313-8067 (+) |
| 2. | hENVH2 | envH/p60 | AJ289710.2 | 5393-7084 (+) |
| 3. | hENVH3 | envH/p59 | AJ289711.1 | 5204-6871 (+) |
| 4. | hENVK1 | envK1 | AC074261.3 | 93508-95604 (+) |
| 5. | hENVK2 | envK2/HML-2.HOM | AC072054.10 | 30365-32464 (−) |
| 6. | hENVK3 | envK3/C19 | Y17833.1 | 5581-7680 (+) |
| 7. | hENVK4 | envK4/K109 | AF164615.1 | 6412-8508 (+) |
| 8. | hENVK5 | envK5/K113 | AY037928.1 | 6451-8550 (+) |
| 9. | hENVK6 | envK6/K115 | AY037929.1 | 6442-8541 (+) |
| 10. | hENVT | envT | AC078899.1 | 154738-156618 (+) |
| 11. | hENVW | Syncytin-1 | AC000064.1 | 35879-37495 (+) |
| 12. | hENVFRD | Syncytin-2 | AL136139.6 | 21355-22972 (−) |
| 13. | hENVR | erv-3 | AC073210.8 | 54963-56978 (−) |
| 14. | hENVR(b) | envRb | AC093488.1 | 78681-80225 (+) |
| 15. | hENVF(c)2 | envFc2 | AC016222.4 | 85216-86963 (+) |
| 16. | hENVF(c)1 | envFc1 | AL354685.2 | 46744-48717 (−) |
| *17. | hENVK$_{con}$ | N/A | N/A | N/A |

(a) '+' and '−' refer to the orientation within the sequence entry

*hENVK$_{con}$ is a consensus sequence derived from ten proviral ENV sequences. The ENV sequences used to derive this consensus ENV sequence are from the following HERVs: HERV-K113, HERV-K101, HERV-K102, HERV-K104, HERV-K107, HERV-K108, HERV-K109, HERV-K115, HERV- K11p22, and HERV-K12q13.

TABLE 2

Exemplary Potential Cas9 and Cas12a orthologs

| DNA-binding Cas ortholog | Enzyme class | Nickase mutation | CI mutations |
|---|---|---|---|
| SpCas9 | Type II-A | D10A | D10A, H840A |
| SaCas9 | Type II-A | D10A | D10A, |
| CjCas9 | Type II-C | D8A | D8A, |
| NmeCas9 | Type II-C | D16A | D16A, H588A |
| asCas12a | Type II-C | | D908A, E993A |
| lbCas12a | Type II-C | | D832A, E925A |

Nickase mutation residues represents a position of the enzyme either known to be required for catalytic activity of the conserved RuvC nuclease domain or predicted to be required for this catalytic activity based on sequence alignment to CjCas9 where structural information is lacking (* indicates which proteins lack sufficient structural information). All positional information refers to the wild-type protein sequences acquired from uniprot.org.

TABLE 3

Exemplary Deaminase domains and their substrate sequence preferences.

| Deaminase | Nucleotide sequence preference |
|---|---|
| hAID | 5'-WRC |
| rAPOBEC1* | 5'-TC ≥ CC ≥ AC > GC |
| mAPOBEC3 | 5'-TYC |
| hAPOBEC3A | 5'-TCG |
| hAPOBEC3B | 5'-TCR > TCT |
| hAPOBEC3C | 5'-WYC |
| hAPOBEC3F | 5'-TTC |
| hAPOBEC3G | 5'-CCC |
| hAPOBEC3H | 5'-TTCA~TTCT~TTCG > ACCCA > TGCA |
| ecTadA | |
| hAdar1 | |
| hAdar2 | |

Nucleotide positions that are poorly specified or are permissive of two or more nucleotides are annotated according to IUPAC codes, where W = A or T, R = A or G, and Y = C or T.

Nucleotide positions that are poorly specified or are permissive of two or more nucleotides are annotated according to IUPAC codes, where W=A or T, R=A or G, and Y=C or T.

TABLE 4

Exemplary Epigenetic modulator domains.

| Epigenetic modulator | Epigenetic modulation |
|---|---|
| VP16 | transcriptional activation |
| VP64 | transcriptional activation |
| P65 | transcriptional activation |
| RTA | transcriptional activation |
| KRAB | transcriptional repression |
| MeCP2 | transcriptional repression |
| Tet1 | Methylation |
| Dnmt3a | Methylation |

TABLE 5

Exemplary CRISPR based RNA-guided RNA binding enzymes

| RNA-binding Cas ortholog | Enzyme class |
|---|---|
| LshCas13a | Type-VI |
| LwaCas13a | Type-VI |
| PspCas13b | Type-VI |
| RfxCas13d | Type-VI |

TABLE 6

Plasma membrane recruitment domains described in this work.

| # | Plasma membrane recruitment domain | Substitution(s) |
|---|---|---|
| 1. | Pleckstrin homology domain of human phospholipase Cδ1 (hPLCδ1) | |
| 2. | Pleckstrin homology domain of human Akt1 | |
| 3. | Mutant Pleckstrin homology domain of human Akt1 | E17K |
| 4. | hArc | |
| *5. | hGAGK$_{con}$ | |
| 6. | Pleckstrin homology domain of human 3-phosphoinositide-dependent protein kinase 1 (hPDPK1) | |
| 7. | Human CD9 | |
| 8. | Human CD47 | |
| 9. | Human CD63 | |
| 10. | Human CD81 | |

*hGAGK$_{con}$ is a consensus sequence derived from ten proviral GAG sequences. The GAG sequences used to derive this consensus GAG sequence are from the following HERVs: HERV-K113, HERV-K101, HERV-K102, HERV-K104, HERV-K107, HERV-K108, HERV-K109, HERV-K115, HERV- K11p22, and HERV-K12q13.

Relevant Protein Sequences:

```
Homo sapiens: Arc
                                          (SEQ ID NO: 1)
MELDHRTSGGLHAYPGPRGGQVAKPNVILQIGKCRAEMLEHVRRT

HRHLLAEVSKQVERELKGLHRSVGKLESNLDGYVPTSDSQRWKKS

IKACLCRCQETIANLERWVKREMHVWREVFYRLERWADRLESTGG

KYPVGSESARHTVSVGVGGPESYCHEADGYDYTVSPYAITPPPAA

GELPGQEPAEAQQYQPWVPGEDGQPSPGVDTQIFEDPREFLSHLE

EYLRQVGGSEEYWLSQIQNHMNGPAKKWWEFKQGSVKNWVEFKKE

FLQYSEGTLSREAIQRELDLPQKQGEPLDQFLWRKRDLYQTLYVD
```

-continued

```
ADEEEIIQYVVGTLQPKLKRFLRHPLPKTLEQLIQRGMEVQDDLE

QAAEPAGPHLPVEDEAETLTPAPNSESVASDRTQPE

>AJ289709.1 Human endogenous retrovirus H
HERV-H/env62
HERV_H/ENV_62-hENVH1:
                                          (SEQ ID NO: 2)
MIFAGKAPSNTSTLMKFYSLLLYSLLFSFPFLCHPLPLPSYLHHT

INLTHSLLAASNPSLVNNCWLCISLSSSAYTAVPAVQTDWATSPI

SLHLRTSFNSPHLYPPEELIYFLDRSSKTSPDISHQQAAALLRTY

LKNLSPYINSTPPIFGPLTTQTTIPVAAPLCISWQRPTGIPLGNL

SPSRCSFTLHLRSPTTNINETIGAFQLHITDKPSINTDKLKNISS

NYCLGRHLPCISLHPWLSSPCSSDSPPRPSSCLLIPSPENNSERL

LVDTRRFLIHHENRTFPSTQLPHQSPLQPLTAAALAGSLGVWVQD

TPFSTPSHLFTLHLQFCLAQGLFFLCGSSTYMCLPANWTGTCTLV

FLTPKIQFANGTEELPVPLMTPTQQKRVIPLIPLMVGLGLSASTV

ALGTGIAGISTSVMTFRSLSNDFSASITDISQTLSVLQAQVDSLA

AVVLQNRRGLDLLTAEKGGLCIFLNEECCFYLNQSGLVYDNIKKL

KDRAQKLANQASNYAEPPWALSNWMSWVLPIVSPLIPIFLLLLFG

PCIFRLVSQFIQNRIQAITNHSIRQMFLLTSPQYHPLPQDLPSA

>AJ289710.2 Human endogenous retrovirus
H HERV-H/env60-
HERV_H_ENV_60-hENVH2:
                                          (SEQ ID NO: 3)
MIFAGRASSNTSTLMKFYSLLLYSLLFSFPILCHPLPLPSYLHHT

INLTHSLLAVSNPSLAKNCWLCISLPSSAYPAVPALQTDWGTSPV

SPHLRTSFNSPHLYPPEKLIYFLDRSSKTSPDISHQQAAALLCTY

LKNLSPYINSTPPTFGPLTTQTTIPVAAPLCISRQRPTGIPLGNL

SPSRCSFTLHLRSPTTHITETNGAFQLHITDKPSINTDKLKNVSS

NYCLGRHLSCISLHPWLFSPCSSDSPPRPSSCLLIPSPKNNSESL

LVDAQRFLIYHENRTSPSTQLPHQSPLQPLTAAPLGGSLRVWVQD

TPFSTPSHLFTLHLQFCLVQSLFFLCGSSTYMCLPANWTGTCTLV

FLTSKIQFANGTEELPVPLMTPTRQKRVIPLIPLMVGLGLSASTV

ALGTGIAGISTSVTTFRILSNDFSASITDISQTLSGLQAQVDSSA

AVVLQNRQGLDLLTAEKGGLCIFLNEESYFYLNQSGLVYDNIKKL

KDKAQNLANQASNYAEPPWPLSNWMSWVLPILSPLIPIFLLLFFR

PCIFHLVSQFIQNHIQAITDHSI

>AJ289711.1 Human endogenous retrovirus H
HERV-H/env59-HERV_H_ENV_59-hENVH3:
                                          (SEQ ID NO: 4)
MILAGRAPSNTSTLMKFYSLLLYSLLFSFPFLYHPLPLPSYLHHT

INLTHSLPAASNPSLANNCWLCISLSSSAYIAVPTLQTDRATSPV

SLHLRTSFNSPHLYPPEELIYFLDRSSKTSPDISHQPAAALLHIY

LKNLSPYINSTPPIFGPLTTQTTIPVAAPLCISRQRPTGIPLGNI

SPSRCSFTLHLQSPTTHVTETIGVFQLHIIDKPSINTDKLKNVSS

NYCLGRHLPYISLHPWLPSPCSSDSPPRPSSCLLTPSPQNNSERL

LVDTQRFLIHHENRTSSSMQLAHQSPLQPLTAAALAGSLGVWVQD
```

-continued

TPFSTPSHPFSLHLQFCLTQGLFFLCGSSTYMCLPANWTGTCTLV
FLTPKIQFANGTKELPVPLMTLTPQKRVIPLIPLMVGLGLSASTI
ALSTGIAGISTSVTTFRSPSNDFSASITDISQTLSVLQAQVDSLA
AVVLQNRRGLGLSILLNEECCFYLNQSGLVYENIKKLKDRAQKLA
NQASNYAESPWALSNWMSWVLPILSPLIPIFLLLLFGPCIFHLVS
QFIQNRIQAITNHSI

>AC074261.3 *Homo sapiens* chromosome 12 clone RP11-55F19 envK1-ENVK1:

(SEQ ID NO: 5)

MHPSEMQRKAPPRRRRHRNRAPLTHKMNKMVTSEQMKLPSTKKAE
PPTWAQLKKLTQLATKYLENTKVTQTPESMLLAALMIVSMVVSLP
MPAGAAAANYTNWAYVPFPPLIRAVTWMDNPIEVYVNDSVWVHGP
IDDRCPAKPEEEGMMINISIGYHYPPICLGRAPGCLMPAVQNWLV
EVPTVSPISRFTYNMVSGMSLRPRVNYLQDFSYQRSLKFRPKGKP
CPKEIPKESKNTEVLVWEECVANSVVILQNNEFGTIIDWAPRGQF
YHNCSGQTQSCPSAQVSPAVDSDLTESLDKHKHKKLQSFYPWEWG
EKGISTPRPKIISPVSGPEHPELWRLTVASHHIRIWSGNQTLETR
DRKPFYTVDLNSSLTVPLQSCVKPPYMLVVGNIVIKPDSQTITCE
NCRLLTCIDSTFNWQHRILLVRAREGVWIPVSMDRPWEASPSIHI
LTEVLKGVLNRSKRFIFTLIAVIMGLIAVTAMAAVAGVALHSFVQ
SVNFVNDWQKNSTRLWNSQSSIDQKLANQINDLRQTVIWMGDRLM
SLEHRFQLQCDWNTSDFCITPQIYNESEHHWDMVRRHLQGREDNL
TLDISKLKEQIFEASKAHLNLVPGTEAIAGVADGLANLNPVTWVK
TIGSTTIINLILILVCLFCLLLVCRFTQQLRRDSYHRERAMMTMV
VLSKRKGGNVGKSKRDQIVTVSV

>AC072054.10 *Homo sapiens* BAC clone RP11-33P21-ENVK2:

(SEQ ID NO: 6)

MNPSEMQRKAPPRRRRHRNRAPLTHKMNKMVTSEEQMKLPSTKKA
EPPTWAQLKKLTQLATKYLENTKVTQTPESMLLAALMIVSMVVSL
PMPAGAAAANYTYWAYVPFPPLIRAVTWMDNPTEVYVNDSVWVPG
PIDDRCPAKPEEEGMMINISIGYHYPPICLGRAPGCLMPAVQNWL
VEVPTVSPICRFTYHMVSGMSLRPRVNYLQDFSYQRSLKFRPKGK
PCPKEIPKESKNTEVLVWEECVANSAVILQNNEFGTIIDWAPRGQ
FYHNCSGQTQSCPSAQVSPAVDSDLTESLDKHKHKKLQSFYPWEW
GEKGISTPRPKIVSPVSGPEHPELWRLTVASHHIRIWSGNQTLET
RDRKPFYTIDLNSSLTVPLQSCVKPPYMLVVGNIVIKPDSQTITC
ENCRLLTCIDSTFNWQHRILLVRAREGVWIPVSMDRPWEASPSVH
ILTEVLKGVLNRSKRFIFTLIAVIMGLIAVTATAAVAGVALHSSV
QSVNFVNDWQKNSTRLWNSQSSIDQKLANQINDLRQTVIWMGDRL
MSLEHRFQLQCDWNTSDFCITPQIYNESEHHWDMVRRHLQGREDN
LTLDISKLKEQIFEASKAHLNLVPGTEAIAGVADGLANLNPVTWV
KTIGSTTIINLILILVCLFCLLLVCRCTQQLRRDSDHRERAMMTM
AVLSKRKGGNVGKSKRDQIVTVSV

>Y17833.1 Human endogenous retrovirus K (HERV-K) envK3-ENVK3:

(SEQ ID NO: 7)

MNPSEMQRKAPPRRRRHRNRAPLTHKMNKMVTSEEQMKLPSTKKA
EPPTWAQLKKLTQLATKYLENTKVTQTPESMLLAALMIVSMVVSL
PMPAGAAAANYTYWAYVPFPPLIRAVTWMDNPIEVYVNDSVWVPG
PTDDHCPAKPEEEGMMINISIGYRYPPICLGRAPGCLMPAVQNWL
VEVPTVSPISRFTYHMVSGMSLRPRVNYLQDFSYQRSFKFRPKGK
PCPKEIPKESKNTEVLVWEECVANSAVILQNNEFGTIIDWAPRGQ
FYHNCSGQTQSCPSAQVSPAVDSDLTESLDKHKHKKLQSFYPWEW
GEKGISTPRPKIISPVSGPEHPELWRLTVASHHIRIWSGNQTLET
RDRKPFYTVDLNSSVTVPLQSCIKPPYMLVVGNIVIKPDSQTITC
ENCRLLTCIDSTFNWQHRILLVRAREGVWIPVSMDRPWETSPSIH
TLTEVLKGVLNRSKRFIFTLIAVIMGLIAVTATAAVAGVALHSSV
QSVNFVNDWQKNSTRLWNSQSSIDQKLANQINDLRQTVIWMGDRL
MSLEHRFQLQCDWNTSDFSITPQIYNESEHHWDMVRRHLQGREDN
LTLDISKLKEQIFEASKAHLNLVPGTEAIAGVADGLANLNPVTWV
KTIGSTTIINLILILVCLFCLLLVCRCTQQLRRDSDHRERAMMTM
AVLSKRKGGNVGKSKRDQIVTVSV

>AF164615.1 *Homo sapiens* endogenous retrovirus HERV-K109 envK4-ENVK4:

(SEQ ID NO: 8)

MNPSEMQRKAPPRRRRHRNRAPLTHKMNKMVTSEEQMKLPSTKKA
EPPTWAQLKKLTQLATKYLENTKVTQTPESMLLAALMIVSMVVSL
PMPAGAAAANYTNWAYVPFPPLIRAVTWMDNPIEVYVNDSVWVPG
PIDDRCPAKPEEEGMMINISIGYRYPICLGRAPGCLMPAVQNWLV
EVPIVSPICRFTYHMVSGMSLRPRVNYLQDFSYQRSLKFRPKGKP
CPKEIPKESKNTEVLVWEECVANSAVILQNNEFGTIIDWTPQGQF
YHNCSGQTQSCPSAQVSPAVDSDLTESLDKHKHKKLQSFYPWEWG
EKGISTPRPKIISPVSGPEHPELWRLTVASHHIRIWSGNQTLETR
DRKPFYTVDLNSSLTLPLQSCVKPPYMLVVGNIVIKPDSQTITCE
NCRLLTCIDSTFNWQHRILLVRAREGVWIPVSMDRPWEASPSIHI
LTEVLKGVLNRSKRFIFTLIAVIMGLIAVTATAAVAGVALHSSVQ
SVNFVNDGQKNSTRLWNSQSSIDQKLANQINDLRQTVIWMGDRLM
SLEHRFQLQCDWNTSDFCITPQIYNESEHHWDMVRRHLQGREDNL
TLDISKLKEQIFEASKAHLNLVPGTEAIAGVADGLANLNPVTWVK
TIGSTTIINLILILVCLFCLLLVCRCTQQLRRDSDHRERAMMTMA
VLSKRKGGNVGKSKRDQIVTVSV

>AY037928.1 Human endogenous retrovirus K113 envK5-ENVK5:

(SEQ ID NO: 9)

MNPSEMQRKAPPRRRRHRNRAPLTHKMNKMVTSEEQMKLPSTKKA
EPPTWAQLKKLTQLATKYLENTKVTQTPESMLLAALMIVSMVVSL

-continued

PMPAGAAAANYTYWAYVPFPPLIRAVTWMDNPIEIYVNDSVWVPG

PTDDCCPAKPEEEGMMINISIGYRYPPICLGRAPGCLMPAVQNWL

VEVPTVSPISRFTYHMVSGMSLRPRVNYLQDFSYQRSLKFRPKGK

PCPKEIPKESKNTEVLVWEECVANSAVILQNNEFGTLIDWAPRGQ

FYHNCSGQTQSCPSAQVSPAVDSDLTESLDKHKHKKLQSFYPWEW

GEKGISTARPKIISPVSGPEHPELWRLTVASHHIRIWSGNQTLET

RDRKPFYTIDLNSSLTVPLQSCVKPPYMLVVGNIVIKPDSQTITC

ENCRLLTCIDSTFNWQHRILLVRAREGVWIPVSMDRPWEASPSVH

ILTEVLKGVLNRSKRFIFTLIAVIMGLIAVTATAAVAGVALHSSV

QSVNFVNDWQNNSTRLWNSQSSIDQKLANQINDLRQTVIWMGDRL

MSLEHRFQLQCDWNTSDFCITPQIYNESEHHWDMVRCHLQGREDN

LTLDISKLKEQIFEASKAHLNLVPGTEAIAGVADGLANLNTVTWV

KTIGSTTIINLILILVCLFCLLLVYRCTQQLRRDSDHRERAMMTM

VVLSKRKGGNVGKSKRDQIVTVSV

>AY037929.1 Human endogenous retrovirus K115 envK6-ENVK6:

(SEQ ID NO: 10)

MNPSEMQRKAPPRRRRHRNRAPLTHKMNKMVTSEEQMKLPSTKKA

EPPTWAQLKKLTQLATKYLENTKVTQTPESMLLAALMIVSMVVSL

PMPAGAAVANYTNWAYVPFPPLIRAVTWMDNPIEVYVNDSVWVPG

PIDDRCPAKPEEEGMMINISIGYRYPPICLGRAPGCLMPAVQNWL

VEVPTVSPISRFTYHMVSGMSLRPRVNYLQDFSYQRSLKFRPKGK

PCPKEIPKESKNTEVLVWEECVANSAVILQNNEFGTIIDWAPRGQ

FYHNCSGQTQSCPSAQVSPAVDSDLTESLDKHKHKKLQSFYPWEW

GEKRISTPRPKIVSPVSGPEHPELWRLTVASHHIRIWSGNQTLET

RDRKPFYTVDLNSSLTLPLQSCVKPPYMLVVGNIVIKPDSQTITC

ENCRLLTCIDSTFNWQHRILLVRAREGVWIPVSMDRPWEASPSVH

ILTEVLKGVLNRSKRFIFTLIAVIMGLIAVTATAAVAGVALHSSV

QSVNFVNDGQKNSTRLWNSQSSIDQKLANQINDLRQTVIWMGDRL

MSLEHRFQLQCDWNTSDFCITPQIYNDSEHHWDMVRRHLQGREDN

LTLDISKLKEQIFEASKAHLNLVPGTEAIAGVADGLANLNPVTWV

KTIGSTTIINLILILVCLFCLLLVCRCTQQLRRDSDHRERAMMTM

AVLSKRKGGNVGKSKRDQIVTVSV

>AC078899.1 *Homo sapiens* chromosome 19, BAC BC371065 envT-ENVT:

(SEQ ID NO: 11)

MGPEAWVRPLKTAPKPGEAIRLILFIYLSCFFLPVMSSEPSYSFL

LTSFTTGRVFANTTWRAGTSKEVSFAVDLCVLFPEPARTHEEQHN

LPVIGAGSVDLAAGFGHSGSQTGCGSSKGAEKGLQNVDFYLCPGN

HPDASCRDTYQFFCPDWTCVTLATYSGGSTRSSTLSISRVPHPKL

CTRKNCNPLTITVHDPNAAQWYYGMSWGLRLYIPGFDVGTMFTIQ

KKILVSWSSPKPIGPLTDLGDPIFQKHPDKVDLTVPLPFLVPRPQ

LQQQHLQPSLMSILGGVHHLLNLTQPKLAQDCWLCLKAKPPYYVG

-continued

LGVEATLKRGPLSCHTRPRALTIGDVSGNASCLISTGYNLSASPF

QATCNQSLLTSISTSVSYQAPNNTWLACTSGLTRCINGTEPGPLL

CVLVHVLPQVYVYSGPEGRQLIAPPELHPRLHQAVPLLVPLLAGL

SIAGSAAIGTAALVQGETGLISLSQQVDADFSNLQSAIDILHSQV

ESLAEVVLQNCRCLDLLFLSQGGLCAALGESCCFYANQSGVIKGT

VKKVRENLDRHQQERENNIPWYQSMFNWNPWLTTLITGLAGPLLI

LLLSLIFGPCILNSFLNFIKQRIASVKLTYLKTQYDTLVNN

>AC000064.1 Human BAC clone RG083M05 from 7q21-7q22 envW (Syncytin-1)-ENVW (Syncytin-1):

(SEQ ID NO: 12)

MALPYHIFLFTVLLPSFTLTAPPPCRCMTSSSPYQEFLWRMQRPG

NIDAPSYRSLSKGTPTFTAHTHMPRNCYHSATLCMHANTHYWTGK

MINPSCPGGLGVTVCWTYFTQTGMSDGGGVQDQAREKHVKEVISQ

LTRVHGTSSPYKGLDLSKLHETLRTHTRLVSLFNTTLTGLHEVSA

QNPTNCWICLPLNFRPYVSIPVPEQWNNFSTEINTTSVLVGPLVS

NLEITHTSNLTCVKFSNTTYTTNSQCIRWVTPPTQIVCLPSGIFF

VCGTSAYRCLNGSSESMCFLSFLVPPMTIYTEQDLYSYVISKPRN

KRVPILPFVIGAGVLGALGTGIGGITTSTQFYYKLSQELNGDMER

VADSLVTLQDQLNSLAAVVLQNRRALDLLTAERGGTCLFLGEECC

YYVNQSGIVTEKVKEIRDRIQRRAEELRNTGPWGLLSQWMPWILP

FLGPLAAIILLLLFGPCIFNLLVNFVSSRIEAVKLQMEPKMQSKT

KIYRRPLDRPASPRSDVNDIKGTPPEEISAAQPLLRPNSAGSS

>AL136139.6 Human DNA sequence from clone RP4-76112 envFRD-ENVFRD (Syncytin-2):

(SEQ ID NO: 13)

MGLLLLVLILTPSLAAYRHPDFPLLEKAQQLLQSTGSPYSTNCWL

CTSSSTETPGTAYPASPREWTSIEAELHISYRWDPNLKGLMRPAN

SLLSTVKQDFPDIRQKPPIFGPIFTNINLMGIAPICVMAKRKNGT

NVGTLPSTVCNVTFTVDSNQQTYQTYTHNQFRHQPRFPKPPNITF

PQGTLLDKSSRFCQGRPSSCSTRNFWFRPADYNQCLQISNLSSTA

EWVLLDQTRNSLFWENKTKGANQSQTPCVQVLAGMTIATSYLGIS

AVSEFFGTSLTPLFHFHISTCLKTQGAFYICGQSIHQCLPSNWTG

TCTIGYVTPDIFIAPGNLSLPIPIYGNSPLPRVRRAIHFIPLLAG

LGILAGTGTGIAGITKASLTYSQLSKEIANNIDTMAKALTTMQEQ

IDSLAAVVLQNRRGLDMLTAAQGGICLALDEKCCFWVNQSGKVQD

NIRQLLNQASSLRERATQGWLNWEGTWKWFSWVLPLTGPLVSLLL

LLLFGPCLLNLITQFVSSRLQAIKLQTNLSAGRHPRNIQESPF

>AC073210.8 *Homo sapiens* BAC clone RP11-460N20 envR-ENVR:

(SEQ ID NO: 14)

MLGMNMLLITLFLLLPLSMLKGEPWEGCLHCTHTTWSGNIMTKTL

LYHTYYECAGTCLGTCTHNQTTYSVCDPGRGQPYVCYDPKSSPGT

WFEIHVGSKEGDLLNQTKVFPSGKDVVSLYFDVCQIVSMGSLFPV

IFSSMEYYSSCHKNRYAHPACSTDSPVTTCWDCTTWSTNQQSLGP

-continued

IMLTKIPLEPDCKTSTCNSVNLTILEPDQPIWTTGLKAPLGARVS

GEEIGPGAYVYLYIIKKTRTRSTQQFRVFESFYEHVNQKLPEPPP

LASNLFAQLAENIASSLHVASCYVCGGMNMGDQWPWEARELMPQD

NFTLTASSLEPAPSSQSIWFLKTSIIGKFCIARWGKAFTDPVGEL

TCLGQQYYNETLGKTLWRGKSNNSESPHPSPFSRFPSLNHSWYQL

EAPNTWQAPSGLYWICGPQAYRQLPAKWSGACVLGTIRPSFFLMP

LKQGEALGYPIYDETKRKSKRGITIGDWKDNEWPPERIIQYYGPA

TWAEDGMWGYRTPVYMLNRIIRLQAVLEIITNETAGALNLLAQQA

TKMRNVIYQNRLALDYLLAQEEGVCGKFNLTNCCLELDDEGKVIK

EITAKIQKLAHIPVQTWKG

>AC093488.1 *Homo sapiens* chromosome 3 clone RP11-1008 envR(b)-ENVR(b):

(SEQ ID NO: 15)

MDPLHTIEKVPARRNIHDRGHQGHRMGDGTPGRPKISVQQMTRFS

LIIFFLSAPFVVNASTSNVFLQWAHSYADGLQQGDPCWVCGSLPV

TNTMELPWWVSPLQGKDWVFFQSFIGDLKQWTGAQMTGVTRKNIS

EWPINKTLNEPGHDKPFSVNETRDKVIAFAIPLLDTKVFVQTSRP

QNTQYRNGFLQIWDGFIWLTATKGHLSQIAPLCWEQRNHSLDNWP

NTTRVMGWIPPGQCRHTILLQQRDLFATDWSQQPGLNWYAPNGTQ

WLCSPNLWPWLPSGWLGCCTLGIPWAQGRWVKTMEVYPYLPHVVN

QGTRAIVHRNDHLPTIFMPSVGLGTVIQHIEALANFTQRALNDSL

QSISLMNAEVYYMHEDILQNRMALDILTAAEGGTCALIKTECCVY

IPNNSRNISLALEDTCRQIQVISSSALSLHDWIASQFSGRPSWWQ

KILIVLATLWSVGIALCCGLYFCRMFSQHIPQTHSIIFQQELPLS

PPSQEHYQSQRDIFHSNAP

>AC016222.4 *Homo sapiens* clone RP11-26J6 envF(c)2-ENVF(c)2:

(SEQ ID NO: 16)

MNSPCDRLQQFIQVLLEESWSFPSFANTLHWPENLLSYIDELVWQ

GSLQNFHQHEVRFDKPPLRLPLTGFSSLTENWSSRQAVSSRLVAT

AASPPAGCQAPIAFLGLKFSSLGPARKNPALCFLYDQSNSKCNTS

WVKENVGCPWHWCNIHEALIRTEKGSDPMFYVNTSTGGRDGFNGF

NLQISDPWDPRWASGVDGGLYEHKTFMYPVAKIRIARTLKTTVTG

LSDLASSIQSAEKELTSQLQPAADQAKSSRFSWLTLISEGAQLLQ

STGVQNLSHCFLCAALRRPPLVAVPLPTPFNYTINSSTPIPPVPK

GQVPLFSDPIRHKFPFCYSTPNASWCNQTRMLTSTPAPPRGYFWC

NSTLTKVLNSTGNHTLCLPISLIPGLTLYSQDELSHLLAWTEPRP

QNKSKWAIFLPLVLGISLASSLVASGLGKGALTHSIQTSQDLSTH

LQLAIEASAESLDSLQRQITTVAQVAAQNRQALDLLMAEKGRTCL

FLQEECCYYLNESGVVENSLQTLKKKKSSKRS

-continued

>AL354685.17 Human DNA sequence from clone RP13-75G22 envF(c)1-ENVF(c)1:

(SEQ ID NO: 17)

MARPSPLCLLLLLTLLTPIVPSNSLLTEPPFRWRFYLHETWTQGN

RLSTVTLATVDCQPHGCQAQVTFNFTSFKSVLRGWSNPTICFVYD

QTHSNCRDYWVDTNGGCPYAYCRMHVTQLHTAKKLQHTYRLTSDG

RTTYFLTIPDPWDSRWVSGVTGRLYRWPTDSYPVGKLRIFLTYIR

VIPQVLSNLKDQADNIKHQEEVINTLVQSHPKADMVTYDDKAEAG

PFSWITLVRHGARLVNMAGLVNLSHCFLCTALSQPPLVAVPLPQA

FNTSGNHTAHPSGVFSEQVPLFRDPLQPQFPFCYTTPNSSWCNQT

YSGSLSNLSAPAGGYFWCNFTLTKHLNISSNNTLSRNLCLPISLV

PRLTLYSEAELSSLVNPPMRQKRAVFPPLVIGVSLTSSLVASGLG

TGAIVHFISSSQDLSIKLQMAIEASAESLASLQRQITSVAKVAMQ

NRRALDLLTADKGGTCMFLGEECCYYINESGLVETSLLTLDKIRD

GLHRPSSTPNYGGGWWQSPLTTWIIPFISPILIICLLLLIAPCVL

KFIKNRISEVSRVTVNQMLLHPYSRLPTSEDHYDDALTQQEAAR

HERV-Kcon ENV-hENVKcon:

(SEQ ID NO: 18)

MNPSEMQRKAPPRRRRHRNRAPLTHKMNKMVTSEEQMKLPSTKKA

EPPTWAQLKKLTQLATKYLENTKVTQTPESMLLAALMIVSMVVSL

PMPAGAAAANYTYWAYVPFPPLIRAVTWMDNPIEVYVNDSVWVPG

PIDDRCPAKPEEEGMMINISIGYRYPPICLGRAPGCLMPAVQNWL

VEVPTVSPISRFTYHMVSGMSLRPRVNYLQDFSYQRSLKFRPKGK

PCPKEIPKESKNTEVLVWEECVANSAVILQNNEFGTIIDWAPRGQ

FYHNCSGQTQSCPSAQVSPAVDSDLTESLDKHKHKKLQSFYPWEW

GEKGISTPRPKIVSPVSGPEHPELWRLTVASHHIRIWSGNQTLET

RDRKPFYTVDLNSSLTVPLQSCVKPPYMLVVGNIVIKPDSQTITC

ENCRLLTCIDSTFNWQHRILLVRAREGVWIPVSMDRPWEASPSVH

ILTEVLKGVLNRSKRFIFTLIAVIMGLIAVTATAAVAGVALHSSV

QSVNFVNDWQKNSTRLWNSQSSIDQKLANQINDLRQTVIWMGDRL

MSLEHRFQLQCDWNTSDFCITPQIYNESEHHWDMVRRHLQGREDN

LTLDISKLKEQIFEASKAHLNLVPGTEAIAGVADGLANLNPVTWV

KTIGSTTIINLILILVCLFCLLLVCRCTQQLRRDSDHRERAMMTM

AVLSKRKGGNVGKSKRDQIVTVSV

HERV-Kcon GAG-hGAGKcon:

(SEQ ID NO: 19)

MGQTKSKIKSKYASYLSFIKILLKRGGVKVSTKNLIKLFQIIEQF

CPWFPEQGTLDLKDWKRIGKELKQAGRKGNIIPLTVWNDWAIIKA

ALEPFQTEEDSVSVSDAPGSCIIDCNENTRKKSQKETEGLHCEYV

AEPVMAQSTQNVDYNQLQEVIYPETLKLEGKGPELVGPSESKPRG

TSPLPAGQVPVTLQPQKQVKENKTQPPVAYQYWPPAELQYRPPPE

SQYGYPGMPPAPQGRAPYPQPPTRRLNPTAPPSRQGSELHEIIDK

SRKEGDTEAWQFPVTLEPMPPGEGAQEGEPPTVEARYKSFSIKML

-continued

KDMKEGVKQYGPNSPYMRTLLDSIAHGHRLIPYDWEILAKSSLSP

SQFLQFKTWWIDGVQEQVRRNRAANPPVNIDADQLLGIGQNWSTI

SQQALMQNEAIEQVRAICLRAWEKIQDPGSTCPSFNTVRQGSKEP

YPDFVARLQDVAQKSIADEKARKVIVELMAYENANPECQSAIKPL

KGKVPAGSDVISEYVKACDGIGGAMHKAMLMAQAITGVVLGGQVR

TFGGKCYNCGQIGHLKKNCPVLNKQNITIQATTTGREPPDLCPRC

KKGKHWASQCRSKFDKNGQPLSGNEQRGQPQAPQQTGAFPIQPFV

PQGFQGQQPPLSQVFQGISQLPQYNNCPPPQAAVQQ

*Rattus norvegicus* & synthetic: APOBEC1-XTEN L8-nspCas9-UGI-SV40 NLS (SEQ ID NO: 20)

MSSETGPVAVDPTLRRRIEPHEFEVFFDPRELRKETCLLYEINWG

GRHSIWRHTSQNTNKHVEVNFIEKFTTERYFCPNTRCSITWFLSW

SPCGECSRAITEFLSRYPHVTLFIYIARLYHHADPRNRQGLRDLI

SSGVTIQIMTEQESGYCWRNFVNYSPSNEAHWPRYPHLWVRLYVL

ELYCIILGLPPCLNILRRKQPQLTFFTIALQSCHYQRLPPHILWA

TGLKSGSETPGTSESATPESDKKYSIGLAIGTNSVGWAVITDEYK

VPSKKFKVLGNTDRHSIKKNLIGALLFDSGETAEATRLKRTARRR

YTRRKNRICYLQEIFSNEMAKVDDSFFHRLEESFLVEEDKKHERH

PIFGNIVDEVAYHEKYPTIYHLRKKLVDSTDKADLRLIYLALAHM

IKFRGHFLIEGDLNPDNSDVDKLFIQLVQTYNQLFEENPINASGV

DAKAILSARLSKSRRLENLIAQLPGEKKNGLFGNLIALSLGLTPN

FKSNFDLAEDAKLQLSKDTYDDDLDNLLAQIGDQYADLFLAAKNL

SDAILLSDILRVNTEITKAPLSASMIKRYDEHHQDLTLLKALVRQ

QLPEKYKEIFFDQSKNGYAGYIDGGASQEEFYKFIKPILEKMDGT

EELLVKLNREDLLRKQRTFDNGSIPHQIHLGELHAILRRQEDFYP

FLKDNREKIEKILTFRIPYYVGPLARGNSRFAWMTRKSEETITPW

NFEEVVDKGASAQSFIERMTNFDKNLPNEKVLPKHSLLYEYFTVY

NELTKVKYVTEGMRKPAFLSGEQKKAIVDLLFKTNRKVTVKQLKE

DYFKKIECFDSVEISGVEDRFNASLGTYHDLLKIIKDKDFLDNEE

NEDILEDIVLTLTLFEDREMIEERLKTYAHLFDDKVMKQLKRRRY

TGWGRLSRKLINGIRDKQSGKTILDFLKSDGFANRNFMQLIHDDS

LTFKEDIQKAQVSGQGDSLHEHIANLAGSPAIKKGILQTVKVVDE

LVKVMGRHKPENIVIEMARENQTTQKGQKNSRERMKRIEEGIKEL

GSQILKEHPVENTQLQNEKLYLYYLQNGRDMYVDQELDINRLSDY

DVDHIVPQSFLKDDSIDNKVLTRSDKNRGKSDNVPSEEVVKKMKN

YWRQLLNAKLITQRKFDNLTKAERGGLSELDKAGFIKRQLVETRQ

ITKHVAQILDSRMNTKYDENDKLIREVKVITLKSKLVSDFRKDFQ

FYKVREINNYHHAHDAYLNAVVGTALIKKYPKLESEFVYGDYKVY

DVRKMIAKSEQEIGKATAKYFFYSNIMNFFKTEITLANGEIRKRP

LIETNGETGEIVWDKGRDFATVRKVLSMPQVNIVKKTEVQTGGFS

KESILPKRNSDKLIARKKDWDPKKYGGFDSPTVAYSVLVVAKVEK

-continued

GKSKKLKSVKELLGITIMERSSFEKNPIDFLEAKGYKEVKKDLII

KLPKYSLFELENGRKRMLASAGELQKGNELALPSKYVNFLYLASH

YEKLKGSPEDNEQKQLFVEQHKHYLDEIIEQISEFSKRVILADAN

LDKVLSAYNKHRDKPIREQAENIIHLFTLTNLGAPAAFKYFDTTI

DRKRYTSTKEVLDATLIHQSITGLYETRIDLSQLGGDSGGSTNLS

DIIEKETGKQLVIQESILMLPEEVEEVIGNKPESDILVHTAYDES

TDENVMLLTSDAPEYKPWALVIQDSNGENKIKMLSGGSPKKKRKV

*Streptococcus pyogenes*: spCas9 Bipartite NLS (SEQ ID NO: 21)

MDKKYSIGLDIGTNSVGWAVITDEYKVPSKKFKVLGNTDRHSIKK

NLIGALLFDSGETAEATRLKRTARRRYTRRKNRICYLQEIFSNEM

AKVDDSFFHRLEESFLVEEDKKHERHPIFGNIVDEVAYHEKYPTI

YHLRKKLVDSTDKADLRLIYLALAHMIKFRGHFLIEGDLNPDNSD

VDKLFIQLVQTYNQLFEENPINASGVDAKAILSARLSKSRRLENL

IAQLPGEKKNGLFGNLIALSLGLTPNFKSNFDLAEDAKLQLSKDT

YDDDLDNLLAQIGDQYADLFLAAKNLSDAILLSDILRVNTEITKA

PLSASMIKRYDEHHQDLTLLKALVRQQLPEKYKEIFFDQSKNGYA

GYIDGGASQEEFYKFIKPILEKMDGTEELLVKLNREDLLRKQRTF

DNGSIPHQIHLGELHAILRRQEDFYPFLKDNREKIEKILTFRIPY

YVGPLARGNSRFAWMTRKSEETITPWNFEEVVDKGASAQSFIERM

TNFDKNLPNEKVLPKHSLLYEYFTVYNELTKVKYVTEGMRKPAFL

SGEQKKAIVDLLFKTNRKVTVKQLKEDYFKKIECFDSVEISGVED

RFNASLGTYHDLLKIIKDKDFLDNEENEDILEDIVLTLTLFEDRE

MIEERLKTYAHLFDDKVMKQLKRRRYTGWGRLSRKLINGIRDKQS

GKTILDFLKSDGFANRNFMQLIHDDSLTFKEDIQKAQVSGQGDSL

HEHIANLAGSPAIKKGILQTVKVVDELVKVMGRHKPENIVIEMAR

ENQTTQKGQKNSRERMKRIEEGIKELGSQILKEHPVENTQLQNEK

LYLYYLQNGRDMYVDQELDINRLSDYDVDHIVPQSFLKDDSIDNK

VLTRSDKNRGKSDNVPSEEVVKKMKNYWRQLLNAKLITQRKFDNL

TKAERGGLSELDKAGFIKRQLVETRQITKHVAQILDSRMNTKYDE

NDKLIREVKVITLKSKLVSDFRKDFQFYKVREINNYHHAHDAYLN

AVVGTALIKKYPKLESEFVYGDYKVYDVRKMIAKSEQEIGKATAK

YFFYSNIMNFFKTEITLANGEIRKRPLIETNGETGEIVWDKGRDF

ATVRKVLSMPQVNIVKKTEVQTGGFSKESILPKRNSDKLIARKKD

WDPKKYGGFDSPTVAYSVLVVAKVEKGKSKKLKSVKELLGITIME

RSSFEKNPIDFLEAKGYKEVKKDLIIKLPKYSLFELENGRKRMLA

SAGELQKGNELALPSKYVNFLYLASHYEKLKGSPEDNEQKQLFVE

QHKHYLDEIIEQISEFSKRVILADANLDKVLSAYNKHRDKPIREQ

AENIIHLFTLTNLGAPAAFKYFDTTIDRKRYTSTKEVLDATLIHQ

SITGLYETRIDLSQLGGDGSGGGGSGKRTADGSEFEPKKKRKVSS

GGDYKDHDGDYKDHDIDYKDDDDK

-continued

*Staphylococcus aureus*: saCas9

(SEQ ID NO: 22)

MKRNYILGLDIGITSVGYGIIDYETRDVIDAGVRLFKEANVENNE

GRRSKRGARRLKRRRRHRIQRVKKLLFDYNLLTDHSELSGINPYE

ARVKGLSQKLSEEEFSAALLHLAKRRGVHNVNEVEEDTGNELSTK

EQISRNSKALEEKYVAELQLERLKKDGEVRGSINRFKTSDYVKEA

KQLLKVQKAYHQLDQSFIDTYIDLLETRRTYYEGPGEGSPFGWKD

IKEWYEMLMGHCTYFPEELRSVKYAYNADLYNALNDLNNLVITRD

ENEKLEYYEKFQIIENVFKQKKKPTLKQIAKEILVNEEDIKGYRV

TSTGKPEFTNLKVYHDIKDITARKEIIENAELLDQIAKILTIYQS

SEDIQEELTNLNSELTQEEIEQISNLKGYTGTHNLSLKAINLILD

ELWHTNDNQIAIFNRLKLVPKKVDLSQQKEIPTTLVDDFILSPVV

KRSFIQSIKVINAIIKKYGLPNDIIIELAREKNSKDAQKMINEMQ

KRNRQTNERIEEIIRTTGKENAKYLIEKIKLHDMQEGKCLYSLEA

IPLEDLLNNPFNYEVDHIIPRSVSFDNSFNNKVLVKQEENSKKGN

RTPFQYLSSSDSKISYETFKKHILNLAKGKGRISKTKKEYLLEER

DINRFSVQKDFINRNLVDTRYATRGLMNLLRSYFRVNNLDVKVKS

INGGFTSFLRRKWKFKKERNKGYKHHAEDALIIANADFIFKEWKK

LDKAKKVMENQMFEEKQAESMPEIETEQEYKEIFITPHQIKHIKD

FKDYKYSHRVDKKPNRELINDTLYSTRKDDKGNTLIVNNLNGLYD

KDNDKLKKLINKSPEKLLMYHHDPQTYQKLKLIMEQYGDEKNPLY

KYYEETGNYLTKYSKKDNGPVIKKIKYYGNKLNAHLDITDDYPNS

RNKWVKLSLKPYRFDVYLDNGVYKFVTVKNLDVIKKENYYEVNSK

CYEEAKKLKKISNQAEFIASFYNNDLIKINGELYRVIGVNNDLLN

RIEVNMIDITYREYLENMNDKRPPRIIKTIASKTQSIKKYSTDIL

GNLYEVKSKKHPQIIKKG

Acidaminococcus sp.: asCas12a (SEQ ID NO: 23)

MTQFEGFTNLYQVSKTLRFELIPQGKTLKHIQEQGFIEEDKARND

HYKELKPIIDRIYKTYADQCLQLVQLDWENLSAAIDSYRKEKTEE

TRNALIEEQATYRNAIHDYFIGRTDNLTDAINKRHAEIYKGLFKA

ELFNGKVLKQLGTVTTTEHENALLRSFDKFTTYFSGFYENRKNVF

SAEDISTAIPHRIVQDNFPKFKENCHIFTRLITAVPSLREHFENV

KKAIGIFVSTSIEEVFSFPFYNQLLTQTQIDLYNQLLGGISREAG

TEKIKGLNEVLNLAIQKNDETAHIIASLPHRFIPLFKQILSDRNT

LSFILEEFKSDEEVIQSFCKYKTLLRNENVLETAEALFNELNSID

LTHIFISHKKLETISSALCDHWDTLRNALYERRISELTGKITKSA

KEKVQRSLKHEDINLQEIISAAGKELSEAFKQKTSEILSHAHAAL

DQPLPTTLKKQEEKEILKSQLDSLLGLYHLLDWFAVDESNEVDPE

FSARLTGIKLEMEPSLSFYNKARNYATKKPYSVEKFKLNFQMPTL

ASGWDVNKEKNNGAILFVKNGLYYLGIMPKQKGRYKALSFEPTEK

TSEGFDKMYYDYFPDAAKMIPKCSTQLKAVTAHFQTHTTPILLSN

NFIEPLEITKEIYDLNNPEKEPKKFQTAYAKKTGDQKGYREALCK

-continued

WIDFTRDFLSKYTKTTSIDLSSLRPSSQYKDLGEYYAELNPLLYH

ISFQRIAEKEIMDAVETGKLYLFQIYNKDFAKGHHGKPNLHTLYW

TGLFSPENLAKTSIKLNGQAELFYRPKSRMKRMAHRLGEKMLNKK

LKDQKTPIPDTLYQELYDYVNHRLSHDLSDEARALLPNVITKEVS

HEIIKDRRFTSDKFFFHVPITLNYQAANSPSKFNQRVNAYLKEHP

ETPIIGIDRGERNLIYITVIDSTGKILEQRSLNTIQQFDYQKKLD

NREKERVAARQAWSVVGTIKDLKQGYLSQVIHEIVDLMIHYQAVV

VLENLNFGFKSKRTGIAEKAVYQQFEKMLIDKLNCLVLKDYPAEK

VGGVLNPYQLTDQFTSFAKMGTQSGFLFYVPAPYTSKIDPLTGFV

DPFVWKTIKNHESRKHFLEGFDFLHYDVKTGDFILHFKMNRNLSF

QRGLPGFMPAWDIVFEKNETQFDAKGTPFIAGKRIVPVIENHRFT

GRYRDLYPANELIALLEEKGIVFRDGSNILPKLLENDDSHAIDTM

VALIRSVLQMRNSNAATGEDYINSPVRDLNGVCFDSRFQNPEWPM

DADANGAYHIALKGQLLLNHLKESKDLKLQNGISNQDWLAYIQEL

RN

Pleckstrin homology domain of *Homo sapiens* phospholipase C81 (hPLC81)

(SEQ ID NO: 24)

MDSGRDFLTLHGLQDDEDLQALLKGSQLLKVKSSSWRRERFYKLQ

EDCKTIWQESRKVMRTPESQLFSIEDIQEVRMGHRTEGLEKFARD

VPEDRCFSIVFKDQRNTLDLIAPSPADAQHWVLGLHKIIHHSGSM

DQRQKLQHWIHSCLRKADKNKDNKMSFKELQNFLKELNIQ

Pleckstrin homology domain of *Homo sapiens* Akt1 (hAkt)

(SEQ ID NO: 25)

MSDVAIVKEGWLHKRGEYIKTWRPRYFLLKNDGTFIGYKERPQDV

DQREAPLNNFSVAQCQLMKTERPRPNTFIIRCLQWTTVIERTFHV

ETPEEREEWTTAIQTVADGLKKQEEEEMDFRSGSPSDNSGAEEME

VSLAKPKHRVTMNEFEYLKLLGKGTFGKVDPPV

Pleckstrin homology domain of *Homo sapiens* PDPK1 (hPDPK1)

(SEQ ID NO: 26)

KMGPVDKRKGLFARRRQLLLTEGPHLYYVDPVNKVLKGEIPWSQE

LRPEAKNFKTFFVHTPNRTYYLMDPSGNAHKWCRKIQEVWRQRYQ

SH

*Homo sapiens*: CD9 Complete Protein (SEQ ID ID NO: 27)

MSPVKGGTKCIKYLLFGFNFIFWLAGIAVLAIGLWLRFDSQTKSI

FEQETNNNNSSFYTGVYILIGAGALMMLVGFLGCCGAVQESQCML

GLFFGFLLVIFAIEIAAAIWGYSHKDEVIKEVQEFYKDTYNKLKT

KDEPQRETLKAIHYALNCCGLAGGVEQFISDICPKKDVLETFTVK

SCPDAIKEVFDNKFHIIGAVGIGIAVVMIFGMIFSMILCCAIRRN

REMV

*Homo sapiens*: CD63 Complete Protein (SEQ ID NO: 28)

MAVEGGMKCVKFLLYVLLLAFCACAVGLIAVGVGAQLVLSQTIIQ

GATPGSLLPVVIIAVGVFLFLVAFVGCCGACKENYCLMITFAIFL

-continued

SLIMLVEVAAAIAGYVFRDKVMSEFNNNFRQQMENYPKNNHTASI

LDRMQADFKCCGAANYTDWEKIPSMSKNRVPDSCCINVTVGCGIN

FNEKAIHKEGCVEKIGGWLRKNVLVVAAAALGIAFVEVLGIVFAC

CLVKSIRSGYEVM

*Homo sapiens*: CD81 Complete Protein (SEQ ID NO: 29)

MGVEGCTKCIKYLLFVFNFVFWLAGGVILGVALWLRHDPQTTNLL

YLELGDKPAPNTFYVGIYILIAVGAVMMFVGFLGCYGAIQESQCL

LGTFFTCLVILFACEVAAGIWGFVNKDQIAKDVKQFYDQALQQAV

VDDDANNAKAVVKTFHETLDCCGSSTLTALTTSVLKNNLCPSGSN

IISNLFKEDCHQKIDDLFSGKLYLIGIAAIVVAVIMIFEMILSMV

LCCGIRNSSVY

*Homo sapiens*: CD47 "Self Hairpin" 10 Amino Acids (SEQ ID NO: 30)

EVTELTREGE

*Homo sapiens*: CD47 "Self Hairpin" 21 Amino Acids (SEQ ID NO: 31)

GNYTCEVTELTREGETIIELK

*Homo sapiens*: CD47 Complete Protein (SEQ ID NO: 32)

MWPLVAALLLGSACCGSAQLLFNKTKSVEFTFCNDTVVIPCFVTN

MEAQNTTEVYVKWKFKGRDIYTFDGALNKSTVPTDFSSAKIEVSQ

LLKGDASLKMDKSDAVSHTGNYTCEVTELTREGETIIELKYRVVS

WFSPNENILIVIFPIFAILLFWGQFGIKTLKYRSGGMDEKTIALL

VAGLVITVIVIVGAILFVPGEYSLKNATGLGLIVTSTGILILLHY

YVFSTAIGLTSFVIAILVIQVIAYILAVVGLSLCIAACIPMHGPL

LISGLSILALAQLLGLVYMKFVE

Synthetic: dDZF1

(SEQ ID NO: 33)

FKCEHCRILFLDHVMFTIHMGCHGFRDPFKCNMCGEKCDGPVGLF

VHMARNAHGEKPFYCEHCEITFRDVVMYSLHKGYHGFRDPFECNI

CGYHSQDRYEFSSHIVRGEH

Synthetic: dDZF2

(SEQ ID NO: 34)

HHCQHCDMYFADNILYTIHMGCHSCDDVFKCNMCGEKCDGPVGLF

VHMARNAHGEKPTKCVHCGIVFLDEVMYALHMSCHGFRDPFECNI

CGYHSQDRYEFSSHIVRGEH

Synthetic: DmrA (SEQ ID NO: 35)

MGRGVQVETISPGDGRTFPKRGQTCVVHYTGMLEDGKKFDSSRDR

NKPFKFMLGKQEVIRGWEEGVAQMSVGQRAKLTISPDYAYGATGH

PGIIPPHATLVFDVELLKLE

Synthetic: DmrB (SEQ ID NO: 36)

MASRGVQVETISPGDGRTFPKRGQTCVVHYTGMLEDGKKVDSSRD

RNKPFKFMLGKQEVIRGWEEGVAQMSVGQRAKLTISPDYAYGATG

HPGIIPPHATLVFDVELLKLE

-continued

Synthetic: DmrC (SEQ ID NO: 37)

MGSRILWHEMWHEGLEEASRLYFGERNVKGMFEVLEPLHAMMERG

PQTLKETSFNQAYGRDLMEAQEWCRKYMKSGNVKDLLQAWDLYYH

VFRRISK

*Homo sapiens*/Synthetic: FKBP (SEQ ID NO: 38)

MGVQVETISPGDGRTFPKRGQTCVVHYTGMLEDGKKFDSSRDRNK

PFKFMLGKQEVIRGWEEGVAQMSVGQRAKLTISPDYAYGATGHPG

IIPPHATLVFDVELLKLE

*Homo sapiens*/Synthetic: FRB (SEQ ID NO: 39)

QGMLEMWHEGLEEASRLYFGERNVKGMFEVLEPLHAMMERGPQTL

KETSFNQAYGRDLMEAQEWCRKYMKSGNVKDLLQAWDLYYHVFRR

ISK

Synthetic: Anti-GCN4 scFv (SEQ ID NO: 40)

MGPDIVMTQSPSSLSASVGDRVTITCRSSTGAVTTSNYASWVQEK

PGKLFKGLIGGTNNRAPGVPSRFSGSLIGDKATLTISSLQPEDFA

TYFCALWYSNHWVFGQGTKVELKRGGGGSGGGGSGGGGSSGGGSE

VKLLESGGGLVQPGGSLKLSCAVSGFSLTDYGVNWVRQAPGRGLE

WIGVIWGDGITDYNSALKDRFIISKDNGKNTVYLQMSKVRSDDTA

LYYCVTGLFDYWGQGTLVTVSSYPYDVPDYAGGGGGSGGGGSGGG

GSGGGGS

Synthetic: 10x-GCN4 Repeats (SEQ ID NO: 41)

EELLSKNYHLENEVARLKKGSGSGEELLSKNYHLENEVARLKKGS

GSGEELLSKNYHLENEVARLKKGSGSGEELLSKNYHLENEVARLK

KGSGSGEELLSKNYHLENEVARLKKGSGSGEELLSKNYHLENEVA

RLKKGSGSGEELLSKNYHLENEVARLKKGSGSGEELLSKNYHLEN

EVARLKKGSGSGEELLSKNYHLENEVARLKKGSGSGEELLSKNYH

LENEVARLKKGS

Synthetic: 24x-GCN4 Repeats (SEQ ID NO: 42)

EELLSKNYHLENEVARLKKGSGSGEELLSKNYHLENEVARLKKGS

GSGEELLSKNYHLENEVARLKKGSGSGEELLSKNYHLENEVARLK

KGSGSGEELLSKNYHLENEVARLKKGSGSGEELLSKNYHLENEVA

RLKKGSGSGEELLSKNYHLENEVARLKKGSGSGEELLSKNYHLEN

EVARLKKGSGSGEELLSKNYHLENEVARLKKGSGSGEELLSKNYH

LENEVARLKKGSGSGEELLSKNYHLENEVARLKKGSGSGEELLSK

NYHLENEVARLKKGSGSGEELLSKNYHLENEVARLKKGSGSGEEL

LSKNYHLENEVARLKKGSGSGEELLSKNYHLENEVARLKKGSGSG

EELLSKNYHLENEVARLKKGSGSGEELLSKNYHLENEVARLKKGS

GSGEELLSKNYHLENEVARLKKGSGSGEELLSKNYHLENEVARLK

KGSGSGEELLSKNYHLENEVARLKKGSGSGEELLSKNYHLENEVA

RLKKGSGSGEELLSKNYHLENEVARLKKGSGSGEELLSKDYHLEN

EVARLKKGSGSGEELLSKNYHLENEVARLKKGS

-continued

Synthetic: GFP-targeting Nanobody
(SEQ ID NO: 43)
VQLVESGGALVQPGGSLRLSCAASGFPVNRYSMRWYRQAPGKERE WVAGMSSAGDRSSYEDSVKGRFTISRDDARNTVYLQMNSLKPEDT AVYYSNVNVGFEYWGQGTQVTVSS

*Nostoc punctiforme*:
Npu DnaE N-terminal Split Intein
(SEQ ID NO: 44)
CLSYETEILTVEYGLLPIGKIVEKRIECTVYSVDNNGNIYTQPVA QWHDRGEQEVFEYCLEDGSLIRATKDHKFMTVDGQMLPIDEIFER ELDLMRVDNLPN

*Nostoc punctiforme*:
Npu DnaE C-terminal Split Intein
(SEQ ID NO: 45)
MIKIATRKYLGKQNVYDIGVERDHNFALKNGFIASNCFN Synthetic: Cfa N-Terminal Split Intein
(SEQ ID NO: 46)
CLSYDTEILTVEYGFLPIGKIVEERIECTVYTVDKNGFVYTQPIA QWHNRGEQEVFEYCLEDGSIIRATKDHKFMTTDGQMLPIDEIFER GLDLKQVDGLP Synthetic: Cfa C-Terminal Split Intein
(SEQ ID NO: 47)
MVKIISRKSLGTQNVYDIGVEKDHNFLLKNGLVASN

*Saccharomyces cerevisiae*:
Vma N-terminal Split Intein
(SEQ ID NO: 48)
CFAKGTNVLMADGSIECIENIEVGNKVMGKDGRPREVIKLPRGRE TMYSVVQKSQHRAHKSDSSREVPELLKFTCNATHELWRTPRSVRR LSRTIKGVEYFEVITFEMGQKKAPDGRIVELVKEVSKSYPISEGP ERANELVESYRKASNKAYFEWTIEARDLSLLGSHVRKATYQTYAP ILY

*Saccharomyces cerevisiae*:
Vma C-terminal Split Intein
(SEQ ID NO: 49)
VLLNVLSKCAGSKKFRPAPAAAFARECRGFYFELQELKEDDYYGI TLSDDSDHQFLLANQVVVHN

*Synechocystis* sp. PCC 6803:
Ssp DnaE N-terminal Split Intein
(SEQ ID NO: 50)
CLSFGTEILTVEYGPLPIGKIVSEEINCSVYSVDPEGRVYTQAIA QWHDRGEQEVLEYELEDGSVIRATSDHRFLTTDYQLLAIEEIFAR QLDLLTLENIKQTEEALDNHRLPFPLLDAGTIK

*Synechocystis* sp. PCC 6803: Ssp DnaE
C-terminal Split Intein
(SEQ ID NO: 51)
MVKVIGRRSLGVQRIFDIGLPQDHNFLLANGAIAAN Synthetic: Spy Tag
(SEQ ID NO: 52)
VPTIVMVDAYKRYK Synthetic: Spy Catcher
(SEQ ID NO: 53)
MVTTLSGLSGEQGPSGDMTTEEDSATHIKFSKRDEDGRELAGATM ELRDSSGKTISTWISDGHVKDFYLYPGKYTFVETAAPDGYEVATA ITFTVNEQGQVTVNGEATKGDAHTGSSGS -continued Bacteriophage MS2: MS2 RNA Binding Protein
(SEQ ID NO: 54)
MASNFTQFVLVDNGGTGDVTVAPSNFANGVAEWISSNSRSQAYKV TCSVRQSSAQNRKYTIKVEVPKVATQTVGGVELPVAAWRSYLNME LTIPIFATNSDCELIVKAMQGLLKDGNPIPSAIAANSGIY Bacteriophage MS2:
MS2 (N55K) RNA Binding Protein
(SEQ ID NO: 55)
MASNFTQFVLVDNGGTGDVTVAPSNFANGVAEWISSNSRSQAYKV TCSVRQSSAQKRKYTIKVEVPKVATQTVGGVELPVAAWRSYLNME LTIPIFATNSDCELIVKAMQGLLKDGNPIPSAIAANSGIY Bacteriophage MS2: MS2 (N55K)(V291)
RNA Binding Protein
(SEQ ID NO: 56)
MASNFTQFVLVDNGGTGDVTVAPSNFANGIAEWISSNSRSQAYKV TCSVRQSSAQKRKYTIKVEVPKVATQTVGGVELPVAAWRSYLNME LTIPIFATNSDCELIVKAMQGLLKDGNPIPSAIAANSGIY Bacteriophage PP7: PP7 RNA Binding Protein
(SEQ ID NO: 57)
KTIVLSVGEATRTLTEIQSTADRQIFEEKVGPLVGRLRLTASLRQ NGAKTAYRVNLKLDQADWVDSGLPKVRYTQVWSHDVTIVANSTEA SRKSLYDLTKSLVATSQVEDLVVNLVPLGRS Bacteriophage Mu: COM RNA Binding Protein
(SEQ ID NO: 58)
MKSIRCKNCNKLLFKADSFDHIEIRCPRCKRHIIMLNACEHPTEK HCGKREKITHSDETVRY Synthetic: Zinc Finger ZF6/10
(SEQ ID NO: 59)
STRPGERPFQCRICMRNFSIPNHLARHTRTHTGEKPFQCRICMRN FSQSAHLKRHLRTHTGEKPFQCRICMRNFSQDVSLVRHLKTHLRQ KDGERPFQCRICMRNFSSAQALARHTRTHTGEKPFQCRICMRNFS QGGNLTRHLRTHTGEKPFQCRICMRNFSQHPNLTRHLKTHLRGS Synthetic: Zinc Finger ZF8/7
(SEQ ID NO: 60)
SRPGERPFQCRICMRNFSTMAVLRRHTRTHTGEKPFQCRICMRNF SRREVLENHLRTHTGEKPFQCRICMRNFSQTVNLDRHLKTHLRQK DGERPFQCRICMRNFSKKDHLHRHTRTHTGEKPFQCRICMRNFSQ RPHLTNHLRTHTGEKPFQCRICMRNFSVGASLKRHLKTHLRGS Synthetic: Zinc Finger ZF9
(SEQ ID NO: 61)
SRPGERPFQCRICMRNFSDKTKLRVHTRTHTGEKPFQCRICMRNF SVRHNLTRHLRTHTGEKPFQCRICMRNFSQSTSLQRHLKTHLRGF Synthetic: Zinc Finger MK10
(SEQ ID NO: 62)
SRPGERPFQCRICMRNFSRRHGLDRHTRTHTGEKPFQCRICMRNF SDHSSLKRHLRTHTGSQKPFQCRICMRNFSVRHNLTRHLRTHTGE KPFQCRICMRNFSDHSNLSRHLKTHTGSQKPFQCRICMRNFSQRS SLVRHLRTHTGEKPFQCRICMRNFSESGHLKRHLRTHLRGS -continued Synthetic: FokI Zinc Finger Nuclease 17-2 Targeting GFP (SEQ ID NO: 63)

SRPGERPFQCRICMRNFSTRQNLDTHTRTHTGEKPFQCRICMRNF

SRRDTLERHLRTHTGEKPFQCRICMRNFSRPDALPRHLKTHLRGS

QLVKSELEEKKSELRHKLKYVPHEYIELIEIARNSTQDRILEMKV

MEFFMKVYGYRGKHLGGSRKPDGAIYTVGSPIDYGVIVDTKAYSG

GYNLPIGQADEMQRYVEENQTRNKHINPNEWWKVYPSSVTEFKFL

FVSGHFKGNYKAQLTRLNHITNCNGAVLSVEELLIGGEMIKAGTL

TLEEVRRKFNNGEINF

Synthetic: FokI Zinc Finger Nuclease 18-2 Targeting GFP (SEQ ID NO: 64)

SRPGERPFQCRICMRNFSSPSKLIRHTRTHTGEKPFQCRICMRNF

SDGSNLARHLRTHTGEKPFQCRICMRNFSRVDNLPRHLKTHLRGS

QLVKSELEEKKSELRHKLKYVPHEYIELIEIARNSTQDRILEMKV

MEFFMKVYGYRGKHLGGSRKPDGAIYTVGSPIDYGVIVDTKAYSG

GYNLPIGQADEMQRYVEENQTRNKHINPNEWWKVYPSSVTEFKFL

FVSGHFKGNYKAQLTRLNHITNCNGAVLSVEELLIGGEMIKAGTL

TLEEVRRKFNNGEINF

Synthetic: FokI Nuclease Domain (SEQ ID NO: 65)

QLVKSELEEKKSELRHKLKYVPHEYIELIEIARNSTQDRILEMKV

MEFFMKVYGYRGKHLGGSRKPDGAIYTVGSPIDYGVIVDTKAYSG

GYNLPIGQADEMQRYVEENQTRNKHINPNEWWKVYPSSVTEFKFL

FVSGHFKGNYKAQLTRLNHITNCNGAVLSVEELLIGGEMIKAGTL

TLEEVRRKFNNGEINF

Synthetic: AcuI Nuclease Domain (SEQ ID NO: 66)

VHDHKLELAKLIRNYETNRKECLNSRYNETLLRSDYLDPFFELLG

WDIKNKAGKPTNEREVVLEEALKASASEHSKKPDYTFRLFSERKF

FLEAKKPSVHIESDNETAKQVRRYGFTAKLKISVLSNFEYLVIYD

TSVKVDGDDTFNKARIKKYHYTEYETHFDEICDLLGRESVYSGNF

DKEWLSIENKINHFSVDTL

Synthetic: Truncated AcuI Nuclease Domain (SEQ ID NO: 67)

YNETLLRSDYLDPFFELLGWDIKNKAGKPTNEREVVLEEALKASA

SEHSKKPDYTFRLFSERKFFLEAKKPSVHIESDNETAKQVRRYGF

TAKLKISVLSNFEYLVIYDTSVKVDGDDT

*Ruminococcus flavefaciens*: RfxCas13d (CasRx)

(SEQ ID NO: 68)

EASIEKKKSFAKGMGVKSTLVSGSKVYMTTFAEGSDARLEKIVEG

DSIRSVNEGEAFSAEMADKNAGYKIGNAKFSHPKGYAWVANNPLY

TGPVQQDMLGLKETLEKRYFGESADGNDNICIQVIHNILDIEKIL

AEYITNAAYAVNNISGLDKDIIGFGKFSTVYTYDEFKDPEHHRAA

FNNNDKLINAIKAQYDEFDNFLDNPRLGYFGQAFFSKEGRNYIIN

YGNECYDILALLSGLRHWVVHNNEEESRISRTWLYNLDKNLDNEY

-continued

ISTLNYLYDRITNELTNSFSKNSAANVNYIAETLGINPAEFAEQY

FRFSIMKEQKNLGFNITKLREVMLDRKDMSEIRKNHKVFDSIRTK

VYTMMDFVIYRYYIEEDAKVAAANKSLPDNEKSLSEKDIFVINLR

GSFNDDQKDALYYDEANRIWRKLENIMHNIKEFRGNKTREYKKKD

APRLPRILPAGRDVSAFSKLMYALTMFLDGKEINDLLTTLINKFD

NIQSFLKVMPLIGVNAKFVEEYAFFKDSAKIADELRLIKSFARMG

EPIADARRAMYIDAIRILGTNLSYDELKALADTFSLDENGNKLKK

GKHGMRNFIINNVISNKRFHYLIRYGDPAHLHEIAKNEAVVKFVL

GRIADIQKKQGQNGKNQIDRYYETCIGKDKGKSVSEKVDALTKII

TGMNYDQFDKKRSVIEDTGRENAEREKFKKIISLYLTVIYHILKN

IVNINARYVIGFHCVERDAQLYKEKGYDINLKKLEEKGFSSVTKL

CAGIDETAPDKRKDVEKEMAERAKESIDSLESANPKLYANYIKYS

DEKKAEEFTRQINREKAKTALNAYLRNTKWNVIIREDLLRIDNKT

CTLFRNKAVHLEVARYVHAYINDIAEVNSYFQLYHYIMQRIIMNE

RYEKSSGKVSEYFDAVNDEKKYNDRLLKLLCVPFGYCIPRFKNLS

IEALFDRNEAAKFDKEKKKVSGNSGSG

*Ruminococcus flavefaciens* & Synthetic: dead RfxCas13d (dCasRx)

(SEQ ID NO: 69)

EASIEKKKSFAKGMGVKSTLVSGSKVYMTTFAEGSDARLEKIVEG

DSIRSVNEGEAFSAEMADKNAGYKIGNAKFSHPKGYAWVANNPLY

TGPVQQDMLGLKETLEKRYFGESADGNDNICIQVIHNILDIEKIL

AEYITNAAYAVNNISGLDKDIIGFGKFSTVYTYDEFKDPEHHRAA

FNNNDKLINAIKAQYDEFDNFLDNPRLGYFGQAFFSKEGRNYIIN

YGNECYDILALLSGLAHWVVANNEEESRISRTWLYNLDKNLDNEY

ISTLNYLYDRITNELTNSFSKNSAANVNYIAETLGINPAEFAEQY

FRFSIMKEQKNLGFNITKLREVMLDRKDMSEIRKNHKVFDSIRTK

VYTMMDFVIYRYYIEEDAKVAAANKSLPDNEKSLSEKDIFVINLR

GSFNDDQKDALYYDEANRIWRKLENIMHNIKEFRGNKTREYKKKD

APRLPRILPAGRDVSAFSKLMYALTMFLDGKEINDLLTTLINKFD

NIQSFLKVMPLIGVNAKFVEEYAFFKDSAKIADELRLIKSFARMG

EPIADARRAMYIDAIRILGTNLSYDELKALADTFSLDENGNKLKK

GKHGMRNFIINNVISNKRFHYLIRYGDPAHLHEIAKNEAVVKFVL

GRIADIQKKQGQNGKNQIDRYYETCIGKDKGKSVSEKVDALTKII

TGMNYDQFDKKRSVIEDTGRENAEREKFKKIISLYLTVIYHILKN

IVNINARYVIGFHCVERDAQLYKEKGYDINLKKLEEKGFSSVTKL

CAGIDETAPDKRKDVEKEMAERAKESIDSLESANPKLYANYIKYS

DEKKAEEFTRQINREKAKTALNAYLRNTKWNVIIREDLLRIDNKT

CTLFANKAVALEVARYVHAYINDIAEVNSYFQLYHYIMQRIIMNE

RYEKSSGKVSEYFDAVNDEKKYNDRLLKLLCVPFGYCIPRFKNLS

IEALFDRNEAAKFDKEKKKVSGNSGSGPKKKRKVAAAYPYDVPDY

A

-continued

Synthetic: L17E
(SEQ ID NO: 70)
IWLTALKFLGKHAAKHEAKQQLSKL

Synthetic: L17E-Transmembrane
(SEQ ID NO: 71)
IWLTALKFLGKHAAKHEAKQQLSKLNAVGQDTQEVIVVPHSLPFK
VVVISAILALVVLTIISLIILIMLWQKKPR Synthetic: KALA
(SEQ ID NO: 72)
WEAKLAKALAKALAKHLAKALAKALKACEA Synthetic: KALA-Transmembrane
(SEQ ID NO: 73)
WEAKLAKALAKALAKHLAKALAKALKACEANAVGQDTQEVIVVPH
SLPFKVVVISAILALWVLTIISLIILIMLWQKKPR Synthetic: Vectofusin
(SEQ ID NO: 74)
KKALLHAALAHLLALAHHLLALLKKA Synthetic: Vectofusin-Transmembrane
(SEQ ID NO: 75)
KKALLHAALAHLLALAHHLLALLKKANAVGQDTQEVIVVPHSLPF
KVVVISAILALVVLTIISLIILIMLWQKKPR Synthetic: Transmembrane Domain
(SEQ ID NO: 76)
NAVGQDTQEVIVVPHSLPFKVVVISAILALVVLTIISLIILIMLW
QKKPR

*Lactococcus lactis*: Nisin A
(SEQ ID NO: 77)
ITSISLCTPGCKTGALMGCNMKTATCHCSIHVSK

*Lactococcus lactis* NIZO 22186: Nisin Z
(SEQ ID NO: 78)
ITSISLCTPGCKTGALMGCNMKTATCNCSIHVSK

*Lactococcus lactis* subsp. lactis F10: Nisin F
(SEQ ID NO: 79)
ITSISLCTPGCKTGALMGCNMKTATCNCSVHVSK

*Lactococcus lactis* 61-14: Nisin Q
(SEQ ID NO: 80)
ITSISLCTPGCKTGVLMGCNLKTATCNCSVHVSK

*Streptococcus hyointestinalis*: Nisin H
(SEQ ID NO: 81)
FTSISMCTPGCKTGALMTCNYKTATCHCSIKVSK

*Streptococcus uberis*: Nisin U
(SEQ ID NO: 82)
ITSKSLCTPGCKTGILMTCPLKTATCGCHFG

*Streptococcus uberis*: Nisin U2
(SEQ ID NO: 83)
VTSKSLCTPGCKTGILMTCPLKTATCGCHFG

*Streptococcus galloyticus* subsp. *pasteurianus*: Nisin P
(SEQ ID NO: 84)
VTSKSLCTPGCKTGILMTCAIKTATCGCHFG

*L. lactis* NZ9800: Nisin A S29A
(SEQ ID NO: 85)
ITSISLCTPGCKTGALMGCNMKTATCHCAIHVSK

*L. lactis* NZ9800: Nisin A S29D
(SEQ ID NO: 86)
ITSISLCTPGCKTGALMGCNMKTATCHCDIHVSK

*L. lactis* NZ9800: Nisin A S29E
(SEQ ID NO: 87)
ITSISLCTPGCKTGALMGCNMKTATCHCEIHVSK

*L. lactis* NZ9800: Nisin A S29G
(SEQ ID NO: 88)
ITSISLCTPGCKTGALMGCNMKTATCHCGIHVSK

*L. lactis* NZ9800: Nisin A K22T
(SEQ ID NO: 89)
ITSISLCTPGCKTGALMGCNMTTATCHCSIHVSK

*L. lactis* NZ9800: Nisin A N20P
(SEQ ID NO: 90)
ITSISLCTPGCKTGALMGCPMKTATCHCSIHVSK

*L. lactis* NZ9800: Nisin A M21V
(SEQ ID NO: 91)
ITSISLCTPGCKTGALMGCNVKTATCHCSIHVSK

*L. lactis* NZ9800: Nisin A K22S
(SEQ ID NO: 92)
ITSISLCTPGCKTGALMGCNMSTATCHCSIHVSK

*L. lactis* NZ9800: Nisin Z N20K
(SEQ ID NO: 93)
ITSISLCTPGCKTGALMGCKMKTATCNCSIHVSK

*L. lactis* NZ9800: Nisin Z M21K
(SEQ ID NO: 94)
ITSISLCTPGCKTGALMGCNKKTATCNCSIHVSK AAV2: REP52
(SEQ ID NO: 95)
MELVGWLVDKGITSEKQWIQEDQASYISFNAASNSRSQIKAALDN
AGKIMSLTKTAPDYLVGQQPVEDISSNRIYKILELNGYDPQYAAS
VFLGWATKKFGKRNTIWLFGPATTGKTNIAEAIAHTVPFYGCVNW
TNENFPFNDCVDKMVIWWEEGKMTAKVVESAKAILGGSKVRVDQK
CKSSAQIDPTPVIVTSNTNMCAVIDGNSTTFEHQQPLQDRMFKFE
LTRRLDHDFGKVTKQEVKDFFRWAKDHVVEVEHEFYVKKGGAKKR
PAPSDADISEPKRVRESVAQPSTSDAEASINYADRYQNKCSRHVG
MNLMLFPCRQCERMNQNSNICFTHGQKDCLECFPVSESQPVSVVK
KAYQKLCYIHHIMGKVPDACTACDLVNVDLDDCIFEQ AAV2: REP78
(SEQ ID NO: 96)
MPGFYEIVIKVPSDLDEHLPGISDSFVNWVAEKEWELPPDSDMDL
NLIEQAPLTVAEKLQRDFLTEWRRVSKAPEALFFVQFEKGESYFH
MHVLVETTGVKSMVLGRFLSQIREKLIQRIYRGIEPTLPNWFAVT
KTRNGAGGGNKVVDECYIPNYLLPKTQPELQWAWTNMEQYLSACL
NLTERKRLVAQHLTHVSQTQEQNKENQNPNSDAPVIRSKTSARYM
ELVGWLVDKGITSEKQWIQEDQASYISFNAASNSRSQIKAALDNA
GKIMSLTKTAPDYLVGQQPVEDISSNRIYKILELNGYDPQYAASV
FLGWATKKFGKRNTIWLFGPATTGKTNIAEAIAHTVPFYGCVNWT
NENFPFNDCVDKMVIWWEEGKMTAKVVESAKAILGGSKVRVDQKC
KSSAQIDPTPVIVTSNTNMCAVIDGNSTTFEHQQPLQDRMFKFEL
TRRLDHDFGKVTKQEVKDFFRWAKDHVVEVEHEFYVKKGGAKKRP
APSDADISEPKRVRESVAQPSTSDAEASINYADRYQNKCSRHVGM
NLMLFPCRQCERMNQNSNICFTHGQKDCLECFPVSESQPVSVVKK
AYQKLCYIHHIMGKVPDACTACDLVNVDLDDCIFEQ -continued

AAV2: VP1

(SEQ ID NO: 97)

MAADGYLPDWLEDTLSEGIRQWWKLKPGPPPPKPAERHKDDSRGL

VLPGYKYLGPFNGLDKGEPVNEADAAALEHDKAYDRQLDSGDNPY

LKYNHADAEFQERLKEDTSFGGNLGRAVFQAKKRVLEPLGLVEEP

VKTAPGKKRPVEHSPVEPDSSSGTGKAGQQPARKRLNFGQTGDAD

SVPDPQPLGQPPAAPSGLGTNTMATGSGAPMADNNEGADGVGNSS

GNWHCDSTWMGDRVITTSTRTWALPTYNNHLYKQISSQSGASNDN

HYFGYSTPWGYFDFNRFHCHFSPRDWQRLINNNWGFRPKRLNFKL

FNIQVKEVTQNDGTTTIANNLTSTVQVFTDSEYQLPYVLGSAHQG

CLPPFPADVFMVPQYGYLTLNNGSQAVGRSSFYCLEYFPSQMLRT

GNNFTFSYTFEDVPFHSSYAHSQSLDRLMNPLIDQYLYYLSRTNT

PSGTTTQSRLQFSQAGASDIRDQSRNWLPGPCYRQQRVSKTSADN

NNSEYSWTGATKYHLNGRDSLVNPGPAMASHKDDEEKFFPQSGVL

IFGKQGSEKTNVDIEKVMITDEEEIRTTNPVATEQYGSVSTNLQR

GNRQAATADVNTQGVLPGMVWQDRDVYLQGPIWAKIPHTDGHFHP

SPLMGGFGLKHPPPQILIKNTPVPANPSTTFSAAKFASFITQYST

GQVSVEIEWELQKENSKRWNPEIQYTSNYNKSVNVDFTVDTNGVY

SEPRPIGTRYLTRNL

AAV2: VP2

(SEQ ID NO: 98)

APGKKRPVEHSPVEPDSSSGTGKAGQQPARKRLNFGQTGDADSVP

DPQPLGQPPAAPSGLGTNTMATGSGAPMADNNEGADGVGNSSGNW

HCDSTWMGDRVITTSTRTWALPTYNNHLYKQISSQSGASNDNHYF

GYSTPWGYFDFNRFHCHFSPRDWQRLINNNWGFRPKRLNFKLFNI

QVKEVTQNDGTTTIANNLTSTVQVFTDSEYQLPYVLGSAHQGCLP

PFPADVFMVPQYGYLTLNNGSQAVGRSSFYCLEYFPSQMLRTGNN

FTFSYTFEDVPFHSSYAHSQSLDRLMNPLIDQYLYYLSRTNTPSG

TTTQSRLQFSQAGASDIRDQSRNWLPGPCYRQQRVSKTSADNNNS

EYSWTGATKYHLNGRDSLVNPGPAMASHKDDEEKFFPQSGVLIFG

KQGSEKTNVDIEKVMITDEEEIRTTNPVATEQYGSVSTNLQRGNR

QAATADVNTQGVLPGMVWQDRDVYLQGPIWAKIPHTDGHFHPSPL

MGGFGLKHPPPQILIKNTPVPANPSTTFSAAKFASFITQYSTGQV

SVEIEWELQKENSKRWNPEIQYTSNYNKSVNVDFTVDTNGVYSEP

RPIGTRYLTRNL

AAV2: VP3

(SEQ ID NO: 99)

MATGSGAPMADNNEGADGVGNSSGNWHCDSTWMGDRVITTSTRTW

ALPTYNNHLYKQISSQSGASNDNHYFGYSTPWGYFDFNRFHCHFS

PRDWQRLINNNWGFRPKRLNFKLFNIQVKEVTQNDGTTTIANNLT

STVQVFTDSEYQLPYVLGSAHQGCLPPFPADVFMVPQYGYLTLNN

GSQAVGRSSFYCLEYFPSQMLRTGNNFTFSYTFEDVPFHSSYAHS

QSLDRLMNPLIDQYLYYLSRTNTPSGTTTQSRLQFSQAGASDIRD

-continued

QSRNWLPGPCYRQQRVSKTSADNNNSEYSWTGATKYHLNGRDSLV

NPGPAMASHKDDEEKFFPQSGVLIFGKQGSEKTNVDIEKVMITDE

EEIRTTNPVATEQYGSVSTNLQRGNRQAATADVNTQGVLPGMVWQ

DRDVYLQGPIWAKIPHTDGHFHPSPLMGGFGLKHPPPQILIKNTP

VPANPSTTFSAAKFASFITQYSTGQVSVEIEWELQKENSKRWNPE

IQYTSNYNKSVNVDFTVDTNGVYSEPRPIGTRYLTRNL

Relevant RNA Sequences (5'-3')

Synthetic: MS2 Stem Loop spCas9 Scaffold RNA for sgRNA with Terminator Example 1

(SEQ ID NO: 100)

GUUUUAGAGCUAGGCCAACAUGAGGAUCACCCAUGUCUGCAGGGC

CUAGCAAGUUAAAAUAAGGCUAGUCCGUUAUCAACUUGGCCAACA

UGAGGAUCACCCAUGUCUGCAGGGCCAAGUGGCACCGAGUCGGUG

CUUUUUUU

Synthetic: MS2 Stem Loop spCas9 Scaffold RNA for sgRNA with Terminator Example 2

(SEQ ID NO: 101)

GUUUUAGAGCUAGGCCAACAUGAGGAUCACCCAUGUCUGCAGGGC

CUAGCAAGUUAAAAUAAGGCUAGUCCGUUAUCAACUUGGCCAACA

UGAGGAUCACCCAUGUCUGCAGGGCCAAGUGGCACCGAGUCGGUG

CGGGAGCACAUGAGGAUCACCCAUGUGCGACUCCCACAGUCACUG

GGGAGUCUUCCCUUUUUUU

Synthetic: MS2 Stem Loop spCas9 Scaffold RNA for sgRNA with Terminator Example 3

(SEQ ID NO: 102)

GUUUAAGAGCUAUGCUGGAAACAGCAUAGCAAGUUUAAAUAAGGC

UAGUCCGUUAUCAACUUGAAAAAGUGGCACCGAGUCGGUGCGGGA

GCACAUGAGGAUCACCCAUGUGCGACUCCCACAGUCACUGGGGAG

UCUUCCCUUUUUUU

Synthetic: 4xMS2 Stem Loop RNA Scaffold Example (SEQ ID NO: 103)

UUCUAGAUCAUCGAAACAUGAGGAUCACCCAUAUCUGCAGUCGAC

AUCGAAACAUGAGGAUCACCCAUGUCUGCAGUCGACAUCGAAACA

UGAGGAUCACCCAUGUCUGCAGUCGACAUCGAAACAUGAGGAUCA

CCCAUGUCUGCAGUCGACAUCGAAAUCGAUAAGCUUCAGAUCAGA

UCCUAG

Synthetic: MS2 Stem Loop Example 1

(SEQ ID NO: 104)

ACAUGAGGAUCACCCAUGU

Synthetic: MS2 Stem Loop Example 2

(SEQ ID NO: 105)

ACAUGAGGAUCACCCAUAU

Synthetic: MS2 Stem Loop Example 3

(SEQ ID NO: 106)

CCACAGUCACUGGG

Synthetic: 2xMS2 Stem Loop Example (SEQ ID NO: 107)

ACAUGAGGAUCACCCAUGUCUGCAGGGCCUAGCAAGUUAAAAUAA

GGCUAGUCCGUUAUCAACUUGGCCAACAUGAGGAUCACCCAUGU

-continued

Synthetic: 2xPP7 Stem Loop spCas9 Scaffold RNA for sgRNA with Terminator Example (SEQ ID NO: 108)

GUUUUAGAGCUAGGCCGGAGCAGACGAUAUGGCGUCGCUCCGGCC

UAGCAAGUUAAAAUAAGGCUAGUCCGUUAUCAACUUGGCCGGAGC

AGACGAUAUGGCGUCGCUCCGGCCAAGUGGCACCGAGUCGGUGCU

UUUUUU

Synthetic: PP7 Stem Loop Example (SEQ ID NO: 109)

GCCGGAGCAGACGAUAUGGCGUCGCUCCGGCC

Synthetic: COM Stem Loop spCas9 Scaffold RNA for sgRNA with Terminator Example (SEQ ID NO: 110)

GUUUAAGAGCUAUGCUGGAAACAGCAUAGCAAGUUUAAAUAAGGC

UAGUCCGUUAUCAACUUGAAAAAGUGGCACCGAGUCGGUGCCUGA

AUGCCUGCGAGCAUCUUUUUUU

Synthetic: COM Stem Loop Example (SEQ ID NO: 111)

CUGAAUGCCUGCGAGCAUC

Relevant DNA Sequences (5'-3')

Synthetic: Zinc Finger ZF6/10 Binding Site (SEQ ID NO: 112)

GAAGAAGCTGCAGGAGGT

Synthetic: Zinc Finger ZF8/7 Binding Site (SEQ ID NO: 113)

GCTGGAGGGGAAGTGGTC

Synthetic: Zinc Finger ZF6/10 & ZF8/7 Binding Site (SEQ ID NO: 114)

GAAGAAGCTGCAGGAGGTGCTGGAGGGGAAGTGGTC

Synthetic: Zinc Finger ZF6/10 & ZF8/7 Binding Site 8x Repeat Example (SEQ ID NO: 115)

TGAAGAAGCTGCAGGAGGTGCTGGAGGGGAAGTGGTCCGGATCTT

GAAGAAGCTGCAGGAGGTGCTGGAGGGGAAGTGGTCCGGATCTTG

AAGAAGCTGCAGGAGGTGCTGGAGGGGAAGTGGTCCGGATCTTGA

AGAAGCTGCAGGAGGTGCTGGAGGGGAAGTGGTCCGGATCTTGAA

GAAGCTGCAGGAGGTGCTGGAGGGGAAGTGGTCCGGATCTTGAAG

AAGCTGCAGGAGGTGCTGGAGGGGAAGTGGTCCGGATCTTGAAGA

AGCTGCAGGAGGTGCTGGAGGGGAAGTGGTCCGGATCTTGAAGAA

GCTGCAGGAGGTGCTGGAGGGGAAGTGGTCC

Synthetic: Zinc Finger ZF9 Binding Site (SEQ ID NO: 116)

GTAGATGGA

Synthetic: Zinc Finger MK10 Binding Site (SEQ ID NO: 117)

CGGCGTAGCCGATGTCGCGC

Synthetic: Zinc Finger 268 Binding Site (SEQ ID NO: 118)

AAGGGTTCA

Synthetic: Zinc Finger NRE Binding Site (SEQ ID NO: 119)

GCGTGGGCG

-continued

Synthetic: Zinc Finger 268/NRE or 268//NRE Binding Site Example 1

(SEQ ID NO: 120)

AAGGGTTCAGCGTGGGCG

Synthetic: Zinc Finger 268/NRE or 268//NRE Binding Site Example 2

(SEQ ID NO: 121)

AAGGGTTCAGGCGTGGGCG

Synthetic: Zinc Finger 268/NRE or 268//NRE Binding Site Example 3

(SEQ ID NO: 122)

AAGGGTTCAGTGCGTGGGCG

Synthetic: FokI Zinc Finger Nuclease 17-2 & 18-2 Binding Site in GFP (SEQ ID NO: 123)

GATCCGCCACAACATCGAGGACGGCA

LITERATURE CITED

1. Parseval, N. et al. Survey of human genes of retroviral origin: identification and transcriptome of the genes with coding capacity for complete envelope proteins. Journal of Virology 77, 10414-10422, (2003).
2. Okimoto, T. et al. VSV-G envelope glycoprotein forms complexes with plasmid DNA and MLV retrovirus-like particles in cell-free conditions and enhances DNA transfection. Molecular Therapy 4, 232-238, (2001).
3. Mangeot, P. et al. Protein transfer into human cells by VSV-G-induced nanovesicles. Molecular Therapy 19, 1656-1666, (2011).
4. Wagner, D. et al. High prevalence of *Streptococcus pyogenes* Cas9-reactive T cells within the adult human population. Nature Medicine 25, 242-248 (2019)
5. Kim, S. et al. CRISPR RNAs trigger innate immune responses in human cells. Genome Research 28, 1-7 (2018).
6. Charlesworth, C. et al. Identification of preexisting adaptive immunity to Cas9 proteins in humans. Nature Medicine 25, 249-254 (2019)
7. Ferdosi, S. et al. Multifunctional CRISPR-Cas9 with engineered immunosilenced human T cell epitopes. Nature Communications 10, Article number: 1842 (2019).
8. Wang, D. et al. Adenovirus-mediated somatic genome editing of Pten by CRISPR/Cas9 in mouse liver in spite of Cas9-specific immune responses. Human Gene Therapy 26, 432-442 (2015).
9. Devanabanda, M. et al. Immunotoxic effects of gold and silver nanoparticles: Inhibition of mitogen-induced proliferative responses and viability of human and murine lymphocytes in vitro. Journal of Immunotoxicology 13, 1547-6901 (2016).
10. Mout, R. et al. Direct cytosolic delivery of CRISPR/Cas9-ribonucleoprotein for efficient gene editing. ACS Nano 11, 2452-2458 (2017).
11. Yin, H. et al. structure-guided chemical modification of guide RNA enables potent non-viral in vivo genome editing. Nature Biotechnology 35, 1179-1187 (2017).
12. Qiao, J. et al. Cytosolic delivery of CRISPR/Cas9 ribonucleoproteins for genome editing using chitosan-coated red fluorescent protein. Chemical Communications 55, 4707-4710 (2019).
13. Li, L. et al. A rationally designed semiconducting polymer brush for NIR-II imaging guided light-triggered remote control of CRISPR/Cas9 genome editing.
Advanced Materials 1901187, 1-9 (2019).
14. Gao, X. et al. Treatment of autosomal dominant hearing loss by in vivo delivery of genome editing agents. Nature 553, 217-221 (2018)

15. Lee, K. et al. Nanoparticle delivery of Cas9 ribonucleoprotein and donor DNA in vivo induces homology-directed DNA repair. Nature Biomedical Engineering 1, 889-901 (2017).

16. Staahl, B. et al. Efficient genome editing in the mouse brain by local delivery of engineered Cas9 ribonucleoprotein complexes. Nature Biotechnology 35, 431-433 (2017).

17. Zuris, J. et al. Cationic lipid-mediated delivery of proteins enables efficient protein-based genome editing in vitro and in vivo. Nature Biotechnology 33, 73-79 (2015).

18. Finn, J. et al. A single administration of CRISPR/Cas9 lipid nanoparticles achieves robust and persistent in vivo genome editing. Cell Reports 22, 2227-2235 (2018).

19. Wang, H. et al. Nonviral gene editing via CRISPR/Cas9 delivery by membrane-disruptive and endosomolytic helical polypeptide. PNAS 115, 4903-4908 (2018).

20. Del'Guidice, T. et al. Membrane permeabilizing amphiphilic peptide delivers recombinant transcription factor and CRISPR-Cas9/Cpf1 ribonucleoproteins in hard-to-modify cells. PLOS ONE 13, e0195558 (2018).

21. Colella, P. et al. Emerging Issues in AAV-Mediated In Vivo Gene Therapy. Molecular Therapy: Methods & Clinical Development 8, 87-104 (2018).

22. Naso, F. et al. Adeno-Associated Virus (AAV) as a Vector for Gene Therapy. BioDrugs 31, 317-334 (2017).

23. Handel, E. et al. Versatile and efficient genome editing in human cells by combining zinc-finger nucleases with adeno-associated viral vectors. Human Gene Therapy 23, 321-329 (2012).

24. Chadwick, A. et al. Reduced Blood Lipid Levels With In Vivo CRISPR-Cas9 Base Editing of ANGPTL3. Circulation 137, 975-977 (2018).

25. Schenkwein, D. et al. Production of HIV-1 Integrase Fusion Protein-Carrying Lentiviral Vectors for Gene Therapy and Protein Transduction. Human Gene Therapy 21, 589-602 (2010).

26. Cai, Y. et al. Targeted genome editing by lentiviral protein transduction of zinc-finger and TAL-effector nucleases. eLife 3, e01911 (2014).

27. Choi, J. et al. Lentivirus pre-packed with Cas9 protein for safer gene editing. Gene Therapy 23, 627-633 (2016).

28. Meyer, C. et al. Pseudotyping exosomes for enhanced protein delivery in mammalian cells. International Journal of Nanomedicine 12, 3153-3170 (2017).

29. Mangeot, P. et al. Genome editing in primary cells and in vivo using viral-derived Nanoblades loaded with Cas9-sgRNA ribonucleoproteins. Nature Communications 10, Article number: 45 (2019).

30. Lu, B. et al. Delivering SaCas9 mRNA by lentivirus-like bionanoparticles for transient expression and efficient genome editing. Nucleic Acids Research 47, e44 (2019).

31. Wang, Q. et al. ARMMs as a versatile platform for intracellular delivery of macromolecules. Nature Communications 9, 1-7 (2018).

32. Lainscek, D. et al. Delivery of an Artificial Transcription Regulator dCas9-VPR by Extracellular Vesicles for Therapeutic Gene Activation. ACS Synthetic Biology 7, 2715-2725 (2018).

33. Fuchs, J. et al. First-in-Human Evaluation of the Safety and Immunogenicity of a Recombinant Vesicular Stomatitis Virus Human Immunodeficiency Virus-1 gag Vaccine (HVTN 090). Open Forum Infectious Diseases 2, 1-9, (2015).

34. Cong, L. et al. Multiplex Genome Engineering Using CRISPR/Cas Systems. Science 339, 819-823, (2013).

35. Ran, F. et al. In vivo genome editing using *Staphylococcus aureus* Cas9. Nature 520, 186-191, (2015).

36. Zetsche, B. et al. Cpf1 Is a Single RNA-Guided Endonuclease of a Class 2 CRISPR-Cas System. Cell 163, 759-771, (2015).

37. Komor, A. et al. Programmable editing of a target base in genomic DNA without double-stranded DNA cleavage. Nature 533, 420-424, (2016).

38. Gaudelli, N. et al. Programmable base editing of A•T to G•C in genomic DNA without DNA cleavage. Nature 551, 464-471, (2017).

39. Voelkel, C. et al. Protein transduction from retroviral Gag precursors. Proc Natl Acad Sci USA 107, 7805-7810, (2010).

40. Kaczmarczyk, S. et al. Protein delivery using engineered virus-like particles. Proc Natl Acad Sci USA 108, 16998-17003, (2011).

41. Ebner, M. et al. PI(3,4,5)$P_3$ Engagement Restricts Akt Activity to Cellular Membranes. Mol Cell 65, 416-431, (2017).

42. Urano, E. et al. Substitution of the myristoylation signal of human immunodeficiency virus type 1 Pr55Gag with the phospholipase C-d1 pleckstrin homology domain results in infectious pseudovirion production. J. Gen Virology 89, 3144-3149, (2008).

43. Pastuzyn, E. et al. The Neuronal Gene Arc Encodes a Repurposed Retrotransposon Gag Protein that Mediates Intercellular RNA Transfer. Cell 172, 275-288, (2018).

44. Lukacs, G. et al. Size-dependent DNA Mobility in Cytoplasm and Nucleus. Journal of Biological Chemistry 275, 1625-1629, (1999).

45. Kreiss, P. et al. Plasmid DNA size does not affect the physicochemical properties of lipoplexes but modulates gene transfer efficiency. Nucleic Acids Research 27, 3792-3798 (1999).

46. Nafissi, N. et al. DNA Ministrings: Highly Safe and Effective Gene Delivery Vectors. Molecular Therapy-Nucleic Acids 3, e165, (2014).

47. Fujimoto, T. et al. Selective EGLN Inhibition Enables Ablative Radiotherapy and Improves Survival in Unresectable Pancreatic Cancer. Cancer Research 79, 2327-2338 (2019).

48. Tai, S. et al. Differential Expression of Metallothionein 1 and 2 Isoforms in Breast Cancer Lines with Different Invasive Potential: Identification of a Novel Nonsilent Metallothionein-1H Mutant Variant. American Journal of Pathology 163, 2009-2019 (2003).

49. Caussinus, E. et al. Fluorescent fusion protein knockout mediated by anti-GFP nanobody. Nature Structural & Molecular Biology 19, 117-121, (2012).

50. Zhao, W. et al. Quantitatively Predictable Control of Cellular Protein Levels through Proteasomal Degradation. ACS Synthetic Biology 7, 540-552, (2018).

51. Clift, D. et al. A Method for the Acute and Rapid Degradation of Endogenous Proteins. Cell 171, 1692-1706, (2017).

52. Selgrade, D. et al. Protein Scaffold-Activated Protein Trans-Splicing in Mammalian Cells. J. Am. Chem. Soc. 135, 7713-7719, (2013).

53. Zhao, Y. et al. SpyCLIP: an easy-to-use and high-throughput compatible CLIP platform for the characterization of protein-RNA interactions with high accuracy. Nucleic Acids Research 47, 1-12, (2019).

54. Kramer, M. et al. Combinatorial Control of *Drosophila* Circular RNA Expression by Intronic Repeats, hnRNPs, and SR Proteins. Genes Dev. 29, 2168-2182, (2015).

55. Inobe, T. & Nukina, N. Rapamycin-induced oligomer formation system of FRB-FKBP fusion proteins. Journal of Bioscience and Bioengineering 122, 40-46, (2016).
56. Giesecke, A. et al. Synthetic protein-protein interaction domains created by shuffling Cys2His2 zinc-fingers. Molecular Systems Biology 2, 1-15, (2006).
57. Azuma, Y. et al. Controlling leucine-zipper partner recognition in cells through modification of a-g interactions. Chemical Communications 50, 6364-6367, (2014).
58. Chavez, A. et al. Comparison of Cas9 Activators in Multiple Species. Nature Methods 13, 563-567, (2016).
59. Kubala, M. et al. Structural and Thermodynamic Analysis of the GFP:GFP-nanobody Complex. Protein Sci. 19, 2389-2401, (2010).
60. Frejd, F. et al. Affibody molecules as engineered protein drugs. Experimental & Molecular Medicine 49, 1-8, (2017).
61. Kennedy, M. et al. Rapid blue-light-mediated induction of protein interactions in living cells. Nature Methods 7, 973-975, (2010).
62. Feng, S. et al. Improved split fluorescent proteins for endogenous protein labeling. Nature Communications 8, 1-11, (2017).
63. Warrington, Jr., K. et al. Adeno-Associated Virus Type 2 VP2 Capsid Protein Is Nonessential and Can Tolerate Large Peptide Insertions at Its N Terminus. J. Virol. 78, 6595-6609, (2004).
64. Hiem, R. & Tsien, R. Engineering green fluorescent protein for improved brightness, longer wavelengths and fluorescence resonance energy transfer. Current Biology 6, 178-182, (1996).
65. Wroblewska, L. Mammalian synthetic circuits with RNA binding proteins for RNA-only Delivery. Nature Biotechnology 33, 839-841, (2015).
66. Slomovic, S. & Collins, J. DNA sense-and-respond protein modules for mammalian cells. Nature Methods 12, 1085-1089, (2015).
67. Kim, J. S. & Pabo, C. Getting a handhold on DNA: Design of poly-zinc finger proteins with femtomolar dissociation constants. PNAS 95, 2812-2817, (1998).
68. Liu, X. et al. Engineering Genetically-Encoded Mineralization and Magnetism via Directed Evolution. Scientific Reports 6, 1-10, (2016).
69. Iordanova, B. et al. Design and characterization of a chimeric ferritin with enhanced iron loading and transverse NMR relaxation rate. J. Biol. Inorg. Chem. 15, 957-965, (2010).
70. Akishiba, M. el al. Cytosolic antibody delivery by lipid-sensitive endosomolytic peptide. Nature Chemistry 9, 751-761, (2017).
71. Rittner, K. et al. New Basic Membrane-Destabilizing Peptides for Plasmid-Based Gene Delivery in Vitro and in Vivo. Molecular Therapy 5, 104-114, (2002).
72. Shin, J. M. Biomedical applications of nisin. J. Applied Microbiol. 120, 1449-1465, (2015).
73. Momen-Heravi, F. et al. Exosome-mediated delivery of functionally active miRNA-155 inhibitor to macrophages. Nanomedicine: Nanotechnology, Biology, and Medicine 10, 1517-1527, (2014).
74. Bendix Johnsen, K. et al. Evaluation of electroporation-induced adverse effects on adipose-derived stem cell exosomes. Cytotechnology 68, 2125-2138 (2016).
75. Luan, X. et al. Engineering exosomes as refined biological nanoplatforms for drug delivery. Acta Pharmacologica Sinica 38, 754-763, (2017).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A cell comprising:

(a) an exogenous nucleic acid molecule that encodes a human endogenous retrovirus (HERV) glycoprotein, and (b) an exogenous nucleic acid molecule that encodes a protein comprising a therapeutic cargo fused to a plasma membrane recruitment domain, wherein the plasma membrane recruitment domain is not a viral GAG protein or a CD63 protein.

2. The cell of claim 1, wherein the therapeutic cargo comprises a DNA binding protein or an RNA binding protein.

3. The cell of claim 1, wherein the therapeutic cargo comprises a gene editing reagent.

4. The cell of claim 3, wherein the gene editing reagent comprises a zinc finger (ZF), a transcription activator-like effector (TALE), a CRISPR-based genome editing or modulating protein; or a ribonucleoprotein complex (RNP) comprising the CRISPR-based genome editing or modulating protein.

5. The cell of claim 3, wherein the gene editing reagent comprises an RNA guided protein.

6. The cell of claim 3, wherein the gene editing reagent is configured to bind a guide RNA.

7. The cell of claim 1, wherein the plasma membrane recruitment domain is a human endogenous gag protein.

8. The cell of claim 7, wherein the human endogenous gag protein comprises a HERV GAG protein.

9. The cell of claim 7, wherein the human endogenous gag protein comprises a HERV GAG consensus sequence.

10. The cell of claim 1, wherein the plasma membrane recruitment domain is a human plasma membrane recruitment domain.

11. The cell of claim 1, wherein the plasma membrane recruitment domain comprises a pleckstrin homology (PH) domain.

12. The cell of claim 11, wherein the PH domain is selected from the group consisting of a pleckstrin homology domain of phospholipase Cδ1 (PLCδ1), Pleckstrin homology domain of Akt1 or a mutant thereof, and Pleckstrin homology domain of PDK1.

13. The cell of claim 11, wherein the PH domain is a mutant pleckstrin homology domain of Akt1 that comprises an amino acid substitution relative to a corresponding wild type Pleckstrin homology domain of Akt1.

14. The cell of claim 13, wherein the amino acid substitution comprises an amino acid substitution of amino acid residue E17 relative to the corresponding wild type pleckstrin homology domain of Akt1.

15. The cell of claim 14, wherein the amino acid substitution is E17K.

16. The cell of claim 1, wherein the plasma membrane recruitment domain comprises the amino acid sequence selected from the group consisting of the amino acid sequence of any one of SEQ ID NO: 19, 24-27, and 29-32.

17. The cell of claim 1, wherein the HERV glycoprotein is selected from the group consisting of: hENVH1, hENVH2, hENVH3, hENVK1, hENVK2, hENVK3, hENVK4, hENVK5, hENVK6, hENVT, hENVW, hENVFRD, hENVR, hENVR(b), hENVF(c)2, hENVF(c)1, and hENVKcon.

18. The cell of claim 1, wherein the HERV glycoprotein comprises the amino acid sequence of any one of SEQ ID NOs: 2-18.

19. The cell of claim 1, wherein the HERV glycoprotein is fused to a targeting polypeptide.

20. The cell of claim 19, wherein the targeting polypeptide comprises a single-chain variable fragment (ScFv).

21. The cell of claim 1, wherein the cell further comprises an exogenous nucleic acid molecule encoding HERV GAG protein.

22. The cell of claim 21, wherein the HERV GAG protein comprises a gag protein sequence of HERV-K113, HERV-K101, HERV-K102, HERV-K104, HERV-K107, HERV-K108, HERV-K109, HERV-K115, HERV-K11p22, or HERV-K12q13.

23. The cell of claim 22, wherein the HERV GAG protein comprises a HERV GAG consensus sequence.

24. The cell of claim 23, wherein the HERV GAG consensus sequence comprises the amino acid sequence of SEQ ID NO: 19.

25. A population of cells comprising the cell of claim 1.

26. A composition comprising:

a nucleic acid molecule that encodes a HERV glycoprotein, and a nucleic acid molecule that encodes a protein comprising a therapeutic cargo fused to a plasma membrane recruitment domain, wherein the plasma membrane recruitment domain is not a viral GAG protein or a CD63 protein.

27. A method of producing a particle that comprises a therapeutic cargo, the method comprising:

providing a cell comprising:

(a) an exogenous nucleic acid molecule that encodes a HERV glycoprotein, and (b) an exogenous nucleic acid molecule that encodes a protein comprising a therapeutic cargo fused to a plasma membrane recruitment domain, wherein the plasma membrane recruitment domain is not a viral gag protein or a CD63 protein, and maintaining the cell under conditions such that the cell produces the particle.

28. The method of claim 27, wherein the method further comprises purifying the particle from the cell.

* * * * *

SEQUENCE LISTING

```
Sequence total quantity: 123
SEQ ID NO: 1           moltype = AA  length = 396
FEATURE                Location/Qualifiers
source                 1..396
                       mol_type = protein
                       organism = Homo sapiens
SEQUENCE: 1
MELDHRTSGG LHAYPGPRGG QVAKPNVILQ IGKCRAEMLE HVRRTHRHLL AEVSKQVERE  60
LKGLHRSVGK LESNLDGYVP TSDSQRWKKS IKACLCRCQE TIANLERWVK REMHVWREVF  120
YRLERWADRL ESTGGKYPVG SESARHTVSV GVGGPESYCH EADGYDYTVS PYAITPPPAA  180
GELPGQEPAE AQQYQPWVPG EDGQPSPGVD TQIFEDPREF LSHLEEYLRQ VGGSEEYWLS  240
QIQNHMNGPA KKWWEFKQGS VKNWVEFKKE FLQYSEGTLS REAIQRELDL PQKQGEPLDQ  300
FLWRKRDLYQ TLYVDADEEE IIQYVVGTLQ PKLKRFLRHP LPKTLEQLIQ RGMEVQDDLE  360
QAAEPAGPHL PVEDEAETLT PAPNSESVAS DRTQPE                           396

SEQ ID NO: 2           moltype = AA  length = 584
FEATURE                Location/Qualifiers
source                 1..584
                       mol_type = protein
                       organism = Homo sapiens
SEQUENCE: 2
MIFAGKAPSN TSTLMKFYSL LLYSLLFSFP FLCHPLPLPS YLHHTINLTH SLLAASNPSL  60
VNNCWLCISL SSSAYTAVPA VQTDWATSPI SLHLRTSFNS PHLYPPEELI YFLDRSSKTS  120
PDISHQQAAA LLRTYLKNLS PYINSTPPIF GPLTTQTTIP VAAPLCISWQ RPTGIPLGNL  180
SPSRCSFTLH LRSPTTNINE TIGAFQLHIT DKPSINTDKL KNISSNYCLG RHLPCISLHP  240
WLSSPCSSDS PPRPSSCLLI PSPENNSERL LVDTRRFLIH HENRTFPSTQ LPHQSPLQPL  300
TAAALAGSLG VWVQDTPFST PSHLFTLHLQ FCLAQGLFFL CGSSTYMCLP ANWTGTCTLV  360
FLTPKIQFAN GTEELPVPLM TPTQQKRVIP LIPLMVGLGL SASTVALGTG IAGISTSVMT  420
FRSLSNDFSA SITDISQTLS VLQAQVDSLA AVVLQNRRGL DLLTAEKGGL CIFLNEECCF  480
YLNQSGLVYD NIKKLKDRAQ KLANQASNYA EPPWALSNWM SWVLPIVSPL IPIFLLLLFG  540
PCIFRLVSQF IQNRIQAITN HSIRQMFLLT SPQYHPLPQD LPSA                 584
```

-continued

```
SEQ ID NO: 3           moltype = AA  length = 563
FEATURE                Location/Qualifiers
source                 1..563
                       mol_type = protein
                       organism = Homo sapiens
SEQUENCE: 3
MIFAGRASSN TSTLMKFYSL LLYSLLFSFP ILCHPLPLPS YLHHTINLTH SLLAVSNPSL  60
AKNCWLCISL PSSAYPAVPA LQTDWGTSPV SPHLRTSFNS PHLYPPEKLI YFLDRSSKTS  120
PDISHQQAAA LLCTYLKNLS PYINSTPPTF GPLTTQTTIP VAAPLCISRQ RPTGIPLGNL  180
SPSRCSFTLH LRSPTTHITE TNGAFQLHIT DKPSINTDKL KNVSSNYCLG RHLSCISLHP  240
WLFSPCSSDS PPRPSSCLLI PSPKNNSESL LVDAQRFLIY HENRTSPSTQ LPHQSPLQPL  300
TAAPLGGSLR VWVQDTPFST PSHLFTLHLQ FCLVQSLFFL CGSSTYMCLP ANWTGTCTLV  360
FLTSKIQFAN GTEELPVPLM TPTRQKRVIP LIPLMVGLGL SASTVALGTG IAGISTSVTT  420
FRILSNDFSA SITDISQTLS GLQAQVDSSA AVVLQNRQGL DLLTAEKGGL CIFLNEESYF  480
YLNQSGLVYD NIKKLKDKAQ NLANQASNYA EPPWPLSNWM SWVLPILSPL IPIFLLLFFR  540
PCIFHLVSQF IQNHIQAITD HSI                                         563

SEQ ID NO: 4           moltype = AA  length = 555
FEATURE                Location/Qualifiers
source                 1..555
                       mol_type = protein
                       organism = Homo sapiens
SEQUENCE: 4
MILAGRAPSN TSTLMKFYSL LLYSLLFSFP FLYHPLPLPS YLHHTINLTH SLPAASNPSL  60
ANNCWLCISL SSSAYIAVPT LQTDRATSPV SLHLRTSFNS PHLYPPEELI YFLDRSSKTS  120
PDISHQPAAA LLHIYLKNLS PYINSTPPIF GPLTTQTTIP VAAPLCISRQ RPTGIPLGNI  180
SPSRCSFTLH LQSPTTHVTE TIGVFQLHII DKPSINTDKL KNVSSNYCLG RHLPYISLHP  240
WLPSPCSSDS PPRPSSCLLT PSPQNNSERL LVDTQRFLIH HENRTSSSMQ LAHQSPLQPL  300
TAAALAGSLG VWVQDTPFST PSHPFSLHLQ FCLTQGLFFL CGSSTYMCLP ANWTGTCTLV  360
FLTPKIQFAN GTKELPVPLM TLTPQKRVIP LIPLMVGLGL SASTIALSTG IAGISTSVTT  420
FRSPSNDFSA SITDISQTLS VLQAQVDSLA AVVLQNRRGL GLSILLNEEC CFYLNQSGLV  480
YENIKKLKDR AQKLANQASN YAESPWALSN WMSWVLPILS PLIPIFLLLL FGPCIFHLVS  540
QFIQNRIQAI TNHSI                                                  555

SEQ ID NO: 5           moltype = AA  length = 698
FEATURE                Location/Qualifiers
source                 1..698
                       mol_type = protein
                       organism = Homo sapiens
SEQUENCE: 5
MHPSEMQRKA PPRRRRHRNR APLTHKMNKM VTSEQMKLPS TKKAEPPTWA QLKKLTQLAT  60
KYLENTKVTQ TPESMLLAAL MIVSMVVSLP MPAGAAAANY TNWAYVPFPP LIRAVTWMDN  120
PIEVYVNDSV WVHGPIDDRC PAKPEEEGMM INISIGYHYP PICLGRAPGC LMPAVQNWLV  180
EVPTVSPISR FTYNMVSGMS LRPRVNYLQD FSYQRSLKFR PKGKPCPKEI PKESKNTEVL  240
VWEECVANSV VILQNNEFGT IIDWAPRGQF YHNCSGQTQS CPSAQVSPAV DSDLTESLDK  300
HKHKKLQSFY PWEWGEKGIS TPRPKIISPV SGPEHPELWR LTVASHHIRI WSGNQTLETR  360
DRKPFYTVDL NSSLTVPLQS CVKPPYMLVV GNIVIKPDSQ TITCENCRLL TCIDSTFNWQ  420
HRILLVRARE GVWIPVSMDR PWEASPSIHI LTEVLKGVLN RSKRFIFTLI AVIMGLIAVT  480
AMAAVAGVAL HSFVQSVNFV NDWQKNSTRL WNSQSSIDQK LANQINDLRQ TVIWMGDRLM  540
SLEHRFQLQC DWNTSDFCIT PQIYNESEHH WDMVRRHLQG REDNLTLDIS KLKEQIFEAS  600
KAHLNLVPGT EAIAGVADGL ANLNPVTWVK TIGSTTIINL ILILVCLFCL LLVCRFTQQL  660
RRDSYHRERA MMTMVVLSKR KGGNVGKSKR DQIVTVSV                         698

SEQ ID NO: 6           moltype = AA  length = 699
FEATURE                Location/Qualifiers
source                 1..699
                       mol_type = protein
                       organism = Homo sapiens
SEQUENCE: 6
MNPSEMQRKA PPRRRRHRNR APLTHKMNKM VTSEEQMKLP STKKAEPPTW AQLKKLTQLA  60
TKYLENTKVT QTPESMLLAA LMIVSMVVSL PMPAGAAAAN YTYWAYVPFP PLIRAVTWMD  120
NPTEVYVNDS VWVPGPIDDR CPAKPEEEGM MINISIGYHY PPICLGRAPG CLMPAVQNWL  180
VEVPTVSPIC RFTYHMVSGM SLRPRVNYLQ DFSYQRSLKF RPKGKPCPKE IPKESKNTEV  240
LVWEECVANS AVILQNNEFG TIIDWAPRGQ FYHNCSGQTQ SCPSAQVSPA VDSDLTESLD  300
KHKHKKLQSF YPWEWGEKGI STPRPKIVSP VSGPEHPELW RLTVASHHIR IWSGNQTLET  360
RDRKPFYTID LNSSLTVPLQ SCVKPPYMLV VGNIVIKPDS QTITCENCRL LTCIDSTFNW  420
QHRILLVRAR EGVWIPVSMD RPWEASPSVH ILTEVLKGVL NRSKRFIFTL IAVIMGLIAV  480
TATAAVAGVA LHSSVQSVNF VNDWQKNSTR LWNSQSSIDQ KLANQINDLR QTVIWMGDRL  540
MSLEHRFQLQ CDWNTSDFCI TPQIYNESEH HWDMVRRHLQ GREDNLTLDI SKLKEQIFEA  600
SKAHLNLVPG TEAIAGVADG LANLNPVTWV KTIGSTTIIN LILILVCLFC LLLVCRCTQQ  660
LRRDSDHRER AMMTMAVLSK RKGGNVGKSK RDQIVTVSV                        699

SEQ ID NO: 7           moltype = AA  length = 699
FEATURE                Location/Qualifiers
source                 1..699
                       mol_type = protein
                       organism = Homo sapiens
SEQUENCE: 7
MNPSEMQRKA PPRRRRHRNR APLTHKMNKM VTSEEQMKLP STKKAEPPTW AQLKKLTQLA  60
```

```
TKYLENTKVT QTPESMLLAA LMIVSMVVSL PMPAGAAAAN YTYWAYVPFP PLIRAVTWMD  120
NPIEVYVNDS VWVPGPTDDH CPAKPEEEGM MINISIGYRY PPICLGRAPG CLMPAVQNWL  180
VEVPTVSPIS RFTYHMVSGM SLRPRVNYLQ DFSYQRSFKF RPKGKPCPKE IPKESKNTEV  240
LVWEECVANS AVILQNNEFG TIIDWAPRGQ FYHNCSGQTQ SCPSAQVSPA VDSDLTESLD  300
KHKHKKLQSF YPWEWGEKGI STPRPKIISP VSGPEHPELW RLTVASHHIR IWSGNQTLET  360
RDRKPFYTVD LNSSVTVPLQ SCIKPPYMLV VGNIVIKPDS QTITCENCRL LTCIDSTFNW  420
QHRILLVRAR EGVWIPVSMD RPWETSPSIH TLTEVLKGVL NRSKRFIFTL IAVIMGLIAV  480
TATAAVAGVA LHSSVQSVNF VNDWQKNSTR LWNSQSSIDQ KLANQINDLR QTVIWMGDRL  540
MSLEHRFQLQ CDWNTSDFSI TPQIYNESEH HWDMVRRHLQ GREDNLTLDI SKLKEQIFEA  600
SKAHLNLVPG TEAIAGVADG LANLNPVTWV KTIGSTTIIN LILILVCLFC LLLVCRCTQQ  660
LRRDSDHRER AMMTMAVLSK RKGGNVGKSK RDQIVTVSV                         699

SEQ ID NO: 8            moltype = AA  length = 698
FEATURE                 Location/Qualifiers
source                  1..698
                        mol_type = protein
                        organism = Homo sapiens
SEQUENCE: 8
MNPSEMQRKA PPRRRRHRNR APLTHKMNKM VTSEEQMKLP STKKAEPPTW AQLKKLTQLA  60
TKYLENTKVT QTPESMLLAA LMIVSMVVSL PMPAGAAAAN YTNWAYVPFP PLIRAVTWMD  120
NPIEVYVNDS VWVPGPIDDR CPAKPEEEGM MINISIGYRY PICLGRAPGC LMPAVQNWLV  180
EVPIVSPICR FTYHMVSGMS LRPRVNYLQD FSYQRSLKFR PKGKPCPKEI PKESKNTEVL  240
VWEECVANSA VILQNNEFGT IIDWTPQGQF YHNCSGQTQS CPSAQVSPAV DSDLTESLDK  300
HKHKKLQSFY PWEWGEKGIS TPRPKIISPV SGPEHPELWR LTVASHHIRI WSGNQTLETR  360
DRKPFYTVDL NSSLTLPLQS CVKPPYMLVV GNIVIKPDSQ TITCENCRLL TCIDSTFNWQ  420
HRILLVRARE GVWIPVSMDR PWEASPSIHI LTEVLKGVLN RSKRFIFTLI AVIMGLIAVT  480
ATAAVAGVAL HSSVQSVNFV NDGQKNSTRL WNSQSSIDQK LANQINDLRQ TVIWMGDRLM  540
SLEHRFQLQC DWNTSDFCIT PQIYNESEHH WDMVRRHLQG REDNLTLDIS KLKEQIFEAS  600
KAHLNLVPGT EAIAGVADGL ANLNPVTWVK TIGSTTIINL ILILVCLFCL LLVCRCTQQL  660
RRDSDHRERA MMTMAVLSKR KGGNVGKSKR DQIVTVSV                          698

SEQ ID NO: 9            moltype = AA  length = 699
FEATURE                 Location/Qualifiers
source                  1..699
                        mol_type = protein
                        organism = Homo sapiens
SEQUENCE: 9
MNPSEMQRKA PPRRRRHRNR APLTHKMNKM VTSEEQMKLP STKKAEPPTW AQLKKLTQLA  60
TKYLENTKVT QTPESMLLAA LMIVSMVVSL PMPAGAAAAN YTYWAYVPFP PLIRAVTWMD  120
NPIEIYVNDS VWVPGPTDDC CPAKPEEEGM MINISIGYRY PPICLGRAPG CLMPAVQNWL  180
VEVPTVSPIS RFTYHMVSGM SLRPRVNYLQ DFSYQRSLKF RPKGKPCPKE IPKESKNTEV  240
LVWEECVANS AVILQNNEFG TLIDWAPRGQ FYHNCSGQTQ SCPSAQVSPA VDSDLTESLD  300
KHKHKKLQSF YPWEWGEKGI STARPKIISP VSGPEHPELW RLTVASHHIR IWSGNQTLET  360
RDRKPFYTID LNSSLTVPLQ SCVKPPYMLV VGNIVIKPDS QTITCENCRL LTCIDSTFNW  420
QHRILLVRAR EGVWIPVSMD RPWEASPSVH ILTEVLKGVL NRSKRFIFTL IAVIMGLIAV  480
TATAAVAGVA LHSSVQSVNF VNDWQNNSTR LWNSQSSIDQ KLANQINDLR QTVIWMGDRL  540
MSLEHRFQLQ CDWNTSDFCI TPQIYNESEH HWDMVRCHLQ GREDNLTLDI SKLKEQIFEA  600
SKAHLNLVPG TEAIAGVADG LANLNTVTWV KTIGSTTIIN LILILVCLFC LLLVYRCTQQ  660
LRRDSDHRER AMMTMVVLSK RKGGNVGKSK RDQIVTVSV                         699

SEQ ID NO: 10           moltype = AA  length = 699
FEATURE                 Location/Qualifiers
source                  1..699
                        mol_type = protein
                        organism = Homo sapiens
SEQUENCE: 10
MNPSEMQRKA PPRRRRHRNR APLTHKMNKM VTSEEQMKLP STKKAEPPTW AQLKKLTQLA  60
TKYLENTKVT QTPESMLLAA LMIVSMVVSL PMPAGAAVAN YTNWAYVPFP PLIRAVTWMD  120
NPIEVYVNDS VWVPGPIDDR CPAKPEEEGM MINISIGYRY PPICLGRAPG CLMPAVQNWL  180
VEVPTVSPIS RFTYHMVSGM SLRPRVNYLQ DFSYQRSLKF RPKGKPCPKE IPKESKNTEV  240
LVWEECVANS AVILQNNEFG TIIDWAPRGQ FYHNCSGQTQ SCPSAQVSPA VDSDLTESLD  300
KHKHKKLQSF YPWEWGEKRI STPRPKIVSP VSGPEHPELW RLTVASHHIR IWSGNQTLET  360
RDRKPFYTVD LNSSLTLPLQ SCVKPPYMLV VGNIVIKPDS QTITCENCRL LTCIDSTFNW  420
QHRILLVRAR EGVWIPVSMD RPWEASPSVH ILTEVLKGVL NRSKRFIFTL IAVIMGLIAV  480
TATAAVAGVA LHSSVQSVNF VNDGQKNSTR LWNSQSSIDQ KLANQINDLR QTVIWMGDRL  540
MSLEHRFQLQ CDWNTSDFCI TPQIYNDSEH HWDMVRRHLQ GREDNLTLDI SKLKEQIFEA  600
SKAHLNLVPG TEAIAGVADG LANLNPVTWV KTIGSTTIIN LILILVCLFC LLLVCRCTQQ  660
LRRDSDHRER AMMTMAVLSK RKGGNVGKSK RDQIVTVSV                         699

SEQ ID NO: 11           moltype = AA  length = 626
FEATURE                 Location/Qualifiers
source                  1..626
                        mol_type = protein
                        organism = Homo sapiens
SEQUENCE: 11
MGPEAWVRPL KTAPKPGEAI RLILFIYLSC FFLPVMSSEP SYSFLLTSFT TGRVFANTTW  60
RAGTSKEVSF AVDLCVLFPE PARTHEEQHN LPVIGAGSVD LAAGFGHSGS QTGCGSSKGA  120
EKGLQNVDFY LCPGNHPDAS CRDTYQFFCP DWTCVTLATY SGGSTRSSTL SISRVPHPKL  180
CTRKNCNPLT ITVHDPNAAQ WYYGMSWGLR LYIPGFDVGT MFTIQKKILV SWSSPKPIGP  240
```

```
LTDLGDPIFQ KHPDKVDLTV PLPFLVPRPQ LQQQHLQPSL MSILGGVHHL LNLTQPKLAQ  300
DCWLCLKAKP PYYVGLGVEA TLKRGPLSCH TRPRALTIGD VSGNASCLIS TGYNLSASPF  360
QATCNQSLLT SISTSVSYQA PNNTWLACTS GLTRCINGTE PGPLLCVLVH VLPQVYVYSG  420
PEGRQLIAPP ELHPRLHQAV PLLVPLLAGL SIAGSAAIGT AALVQGETGL ISLSQQVDAD  480
FSNLQSAIDI LHSQVESLAE VVLQNCRCLD LLFLSQGGLC AALGESCCFY ANQSGVIKGT  540
VKKVRENLDR HQQERENNIP WYQSMFNWNP WLTTLITGLA GPLLILLLSL IFGPCILNSF  600
LNFIKQRIAS VKLTYLKTQY DTLVNN                                        626

SEQ ID NO: 12          moltype = AA  length = 538
FEATURE                Location/Qualifiers
source                 1..538
                       mol_type = protein
                       organism = Homo sapiens
SEQUENCE: 12
MALPYHIFLF TVLLPSFTLT APPPCRCMTS SSPYQEFLWR MQRPGNIDAP SYRSLSKGTP  60
TFTAHTHMPR NCYHSATLCM HANTHYWTGK MINPSCPGGL GVTVCWTYFT QTGMSDGGGV  120
QDQAREKHVK EVISQLTRVH GTSSPYKGLD LSKLHETLRT HTRLVSLFNT TLTGLHEVSA  180
QNPTNCWICL PLNFRPYVSI PVPEQWNNFS TEINTTSVLV GPLVSNLEIT HTSNLTCVKF  240
SNTTYTTNSQ CIRWVTPPTQ IVCLPSGIFF VCGTSAYRCL NGSSESMCFL SFLVPPMTIY  300
TEQDLYSYVI SKPRNKRVPI LPFVIGAGVL GALGTGIGGI TTSTQFYYKL SQELNGDMER  360
VADSLVTLQD QLNSLAAVVL QNRRALDLLT AERGGTCLFL GEECCYYVNQ SGIVTEKVKE  420
IRDRIQRRAE ELRNTGPWGL LSQWMPWILP FLGPLAAIIL LLLFGPCIFN LLVNFVSSRI  480
EAVKLQMEPK MQSKTKIYRR PLDRPASPRS DVNDIKGTPP EEISAAQPLL RPNSAGSS    538

SEQ ID NO: 13          moltype = AA  length = 538
FEATURE                Location/Qualifiers
source                 1..538
                       mol_type = protein
                       organism = Homo sapiens
SEQUENCE: 13
MGLLLLVLIL TPSLAAYRHP DFPLLEKAQQ LLQSTGSPYS TNCWLCTSSS TETPGTAYPA  60
SPREWTSIEA ELHISYRWDP NLKGLMRPAN SLLSTVKQDF PDIRQKPPIF GPIFTNINLM  120
GIAPICVMAK RKNGTNVGTL PSTVCNVTFT VDSNQQTYQT YTHNQFRHQP RFPKPPNITF  180
PQGTLLDKSS RFCQGRPSSC STRNFWFRPA DYNQCLQISN LSSTAEWVLL DQTRNSLFWE  240
NKTKGANQSQ TPCVQVLAGM TIATSYLGIS AVSEFFGTSL TPLFHFHIST CLKTQGAFYI  300
CGQSIHQCLP SNWTGTCTIG YVTPDIFIAP GNLSLPIPIY GNSPLPRVRR AIHFIPLLAG  360
LGILAGTGTG IAGITKASLT YSQLSKEIAN NIDTMAKALT TMQEQIDSLA AVVLQNRRGL  420
DMLTAAQGGI CLALDEKCCF WVNQSGKVQD NIRQLLNQAS SLRERATQGW LNWEGTWKWF  480
SWVLPLTGPL VSLLLLLLFG PCLLNLITQF VSSRLQAIKL QTNLSAGRHP RNIQESPF    538

SEQ ID NO: 14          moltype = AA  length = 604
FEATURE                Location/Qualifiers
source                 1..604
                       mol_type = protein
                       organism = Homo sapiens
SEQUENCE: 14
MLGMNMLLIT LFLLLPLSML KGEPWEGCLH CTHTTWSGNI MTKTLLYHTY YECAGTCLGT  60
CTHNQTTYSV CDPGRGQPYV CYDPKSSPGT WFEIHVGSKE GDLLNQTKVF PSGKDVVSLY  120
FDVCQIVSMG SLFPVIFSSM EYSSCHKNR YAHPACSTDS PVTTCWDCTT WSTNQQSLGP  180
IMLTKIPLEP DCKTSTCNSV NLTILEPDQP IWTTGLKAPL GARVSGEEIG PGAYVVLYII  240
KKTRTRSTQQ FRVFESFYEH VNQKLPEPPP LASNLFAQLA ENIASSLHVA SCYVCGGMNM  300
GDQWPWEARE LMPQDNFTLT ASSLEPAPSS QSIWFLKTSI IGKFCIARWG KAFTDPVGEL  360
TCLGQQYYNE TLGKTLWRGK SNNSESPHPS PFSRFPSLNH SWYQLEAPNT WQAPSGLYWI  420
CGPQAYRQLP AKWSGACVLG TIRPSFFLMP LKQGEALGYP IYDETKRKSK RGITIGDWKD  480
NEWPPERIIQ YYGPATWAED GMWGYRTPVY MLNRIIRLQA VLEIITNETA GALNLLAQQA  540
TKMRNVIYQN RLALDYLLAQ EEGVCGKFNL TNCCLELDDE GKVIKEITAK IQKLAHIPVQ  600
TWKG                                                                604

SEQ ID NO: 15          moltype = AA  length = 514
FEATURE                Location/Qualifiers
source                 1..514
                       mol_type = protein
                       organism = Homo sapiens
SEQUENCE: 15
MDPLHTIEKV PARRNIHDRG HQGHRMGDGT PGRPKISVQQ MTRFSLIIFF LSAPFVVNAS  60
TSNVFLQWAH SYADGLQQGD PCWVCGSLPV TNTMELPWWV SPLQGKDWVF FQSFIGDLKQ  120
WTGAQMTGVT RKNISEWPIN KTLNEPGHDK PFSVNETRDK VIAFAIPLLD TKVFVQTSRP  180
QNTQYRNGFL QIWDGFIWLT ATKGHLSQIA PLCWEQRNHS LDNWPNTTRV MGWIPPGQCR  240
HTILLQQRDL FATDWSQQPG LNWYAPNGTQ WLCSPNLWPW LPSGWLGCCT LGIPWAQGRW  300
VKTMEVYPYL PHVVNQGTRA IVHRNDHLPT IFMPSVGLGT VIQHIEALAN FTQRALNDSL  360
QSISLMNAEV YYMHEDILQN RMALDILTAA EGGTCALIKT ECCVYIPNNS RNISLALEDT  420
CRQIQVISSS ALSLHDWIAS QFSGRPSWWQ KILIVLATLW SVGIALCCGL YFCRMFSQHI  480
PQTHSIIFQQ ELPLSPPSQE HYQSQRDIFH SNAP                               514

SEQ ID NO: 16          moltype = AA  length = 527
FEATURE                Location/Qualifiers
source                 1..527
                       mol_type = protein
                       organism = Homo sapiens
```

```
SEQUENCE: 16
MNSPCDRLQQ FIQVLLEESW SFPSFANTLH WPENLLSYID ELVWQGSLQN FHQHEVRFDK  60
PPLRLPLTGF SSLTENWSSR QAVSSRLVAT AASPPAGCQA PIAFLGLKFS SLGPARKNPA  120
LCFLYDQSNS KCNTSWVKEN VGCPWHWCNI HEALIRTEKG SDPMFYVNTS TGGRDGFNGF  180
NLQISDPWDP RWASGVDGGL YEHKTFMYPV AKIRIARTLK TTVTGLSDLA SSIQSAEKEL  240
TSQLQPAADQ AKSSRFSWLT LISEGAQLLQ STGVQNLSHC FLCAALRRPP LVAVPLPTPF  300
NYTINSSTPI PPVPKGQVPL FSDPIRHKFP FCYSTPNASW CNQTRMLTST PAPPRGYFWC  360
NSTLTKVLNS TGNHTLCLPI SLIPGLTLYS QDELSHLLAW TEPRPQNKSK WAIFLPLVLG  420
ISLASSLVAS GLGKGALTHS IQTSQDLSTH LQLAIEASAE SLDSLQRQIT TVAQVAAQNR  480
QALDLLMAEK GRTCLFLQEE CCYYLNESGV VENSLQTLKK KKSSKRS                527

SEQ ID NO: 17          moltype = AA  length = 584
FEATURE                Location/Qualifiers
source                 1..584
                       mol_type = protein
                       organism = Homo sapiens
SEQUENCE: 17
MARPSPLCLL LLLTLLTPIV PSNSLLTEPP FRWRFYLHET WTQGNRLSTV TLATVDCQPH  60
GCQAQVTFNF TSFKSVLRGW SNPTICFVYD QTHSNCRDYW VDTNGGCPYA YCRMHVTQLH  120
TAKKLQHTYR LTSDGRTTYF LTIPDPWDSR WVSGVTGRLY RWPTDSYPVG KLRIFLTYIR  180
VIPQVLSNLK DQADNIKHQE EVINTLVQSH PKADMVTYDD KAEAGPFSWI TLVRHGARLV  240
NMAGLVNLSH CFLCTALSQP PLVAVPLPQA FNTSGNHTAH PSGVFSEQVP LFRDPLQPQF  300
PFCYTTPNSS WCNQTYSGSL SNLSAPAGGY FWCNFTLTKH LNISSNNTLS RNLCLPISLV  360
PRLTLYSEAE LSSLVNPPMR QKRAVFPPLV IGVSLTSSLV ASGLGTGAIV HFISSSQDLS  420
IKLQMAIEAS AESLASLQRQ ITSVAKVAMQ NRRALDLLTA DKGGTCMFLG EECCYYINES  480
GLVETSLLTL DKIRDGLHRP SSTPNYGGGW WQSPLTTWII PFISPILIIC LLLLIAPCVL  540
KFIKNRISEV SRVTVNQMLL HPYSRLPTSE DHYDDALTQQ EAAR                   584

SEQ ID NO: 18          moltype = AA  length = 699
FEATURE                Location/Qualifiers
source                 1..699
                       mol_type = protein
                       organism = synthetic construct
SEQUENCE: 18
MNPSEMQRKA PPRRRRHRNR APLTHKMNKM VTSEEQMKLP STKKAEPPTW AQLKKLTQLA  60
TKYLENTKVT QTPESMLLAA LMIVSMVVSL PMPAGAAAAN YTYWAYVPFP PLIRAVTWMD  120
NPIEVYVNDS VWVPGPIDDR CPAKPEEEGM MINISIGYRY PPICLGRAPG CLMPAVQNWL  180
VEVPTVSPIS RFTYHMVSGM SLRPRVNYLQ DFSYQRSLKF RPKGKPCPKE IPKESKNTEV  240
LVWEECVANS AVILQNNEFG TIIDWAPRGQ FYHNCSGQTQ SCPSAQVSPA VDSDLTESLD  300
KHKHKKLQSF YPWEWGEKGI STPRPKIVSP VSGPEHPELW RLTVASHHIR IWSGNQTLET  360
RDRKPFYTVD LNSSLTVPLQ SCVKPPYMLV VGNIVIKPDS QTITCENCRL LTCIDSTFNW  420
QHRILLVRAR EGVWIPVSMD RPWEASPSVH ILTEVLKGVL NRSKRFIFTL IAVIMGLIAV  480
TATAAVAGVA LHSSVQSVNF VNDWQKNSTR LWNSQSSIDQ KLANQINDLR QTVIWMGDRL  540
MSLEHRFQLQ CDWNTSDFCI TPQIYNESEH HWDMVRRHLQ GREDNLTLDI SKLKEQIFEA  600
SKAHLNLVPG TEAIAGVADG LANLNPVTWV KTIGSTTIIN LILILVCLFC LLLVCRCTQQ  660
LRRDSDHRER AMMTMAVLSK RKGGNVGKSK RDQIVTVSV                         699

SEQ ID NO: 19          moltype = AA  length = 666
FEATURE                Location/Qualifiers
source                 1..666
                       mol_type = protein
                       organism = synthetic construct
SEQUENCE: 19
MGQTKSKIKS KYASYLSFIK ILLKRGGVKV STKNLIKLFQ IIEQFCPWFP EQGTLDLKDW  60
KRIGKELKQA GRKGNIIPLT VWNDWAIIKA ALEPFQTEED SVSVSDAPGS CIIDCNENTR  120
KKSQKETEGL HCEYVAEPVM AQSTQNVDYN QLQEVIYPET LKLEGKGPEL VGPSESKPRG  180
TSPLPAGQVP VTLQPQKQVK ENKTQPPVAY QYWPPAELQY RPPPESQYGY PGMPPAPQGR  240
APYPQPPTRR LNPTAPPSRQ GSELHEIIDK SRKEGDTEAW QFPVTLEPMP PGEGAQEGEP  300
PTVEARYKSF SIKMLKDMKE GVKQYGPNSP YMRTLLDSIA HGHRLIPYDW EILAKSSLSP  360
SQFLQFKTWW IDGVQEQVRR NRAANPPVNI DADQLLGIGQ NWSTISQQAL MQNEAIEQVR  420
AICLRAWEKI QDPGSTCPSF NTVRQGSKEP YPDFVARLQD VAQKSIADEK ARKVIVELMA  480
YENANPECQS AIKPLKGKVP AGSDVISEYV KACDGIGGAM HKAMLMAQAI TGVVLGGQVR  540
TFGGKCYNCG QIGHLKKNCP VLNKQNITIQ ATTGREPPD LCPRCKKGKH WASQCRSKFD  600
KNGQPLSGNE QRGQPQAPQQ TGAFPIQPFV PQGFQGQQPP LSQVFQGISQ LPQYNNCPPP  660
QAAVQQ                                                             666

SEQ ID NO: 20          moltype = AA  length = 1710
FEATURE                Location/Qualifiers
source                 1..1710
                       mol_type = protein
                       organism = synthetic construct
SEQUENCE: 20
MSSETGPVAV DPTLRRRIEP HEFEVFFDPR ELRKETCLLY EINWGGRHSI WRHTSQNTNK  60
HVEVNFIEKF TTERYFCPNT RCSITWFLSW SPCGECSRAI TEFLSRYPHV TLFIYIARLY  120
HHADPRNRQG LRDLISSGVT IQIMTEQESG YCWRNFVNYS PSNEAHWPRY PHLWVRLYVL  180
ELYCIILGLP PCLNILRRKQ PQLTFFTIAL QSCHYQRLPP HILWATGLKS GSETPGTSES  240
ATPESDKKYS IGLAIGTNSV GWAVITDEYK VPSKKFKVLG NTDRHSIKKN LIGALLFDSG  300
ETAEATRLKR TARRRYTRRK NRICYLQEIF SNEMAKVDDS FFHRLEESFL VEEDKKHERH  360
PIFGNIVDEV AYHEKYPTIY HLRKKLVDST DKADLRLIYL ALAHMIKFRG HFLIEGDLNP  420
```

```
DNSDVDKLFI QLVQTYNQLF EENPINASGV DAKAILSARL SKSRRLENLI AQLPGEKKNG  480
LFGNLIALSL GLTPNFKSNF DLAEDAKLQL SKDTYDDDLD NLLAQIGDQY ADLFLAAKNL  540
SDAILLSDIL RVNTEITKAP LSASMIKRYD EHHQDLTLLK ALVRQQLPEK YKEIFFDQSK  600
NGYAGYIDGG ASQEEFYKFI KPILEKMDGT EELLVKLNRE DLLRKQRTFD NGSIPHQIHL  660
GELHAILRRQ EDFYPFLKDN REKIEKILTF RIPYYVGPLA RGNSRFAWMT RKSEETITPW  720
NFEEVVDKGA SAQSFIERMT NFDKNLPNEK VLPKHSLLYE YFTVYNELTK VKYVTEGMRK  780
PAFLSGEQKK AIVDLLFKTN RKVTVKQLKE DYFKKIECFD SVEISGVEDR FNASLGTYHD  840
LLKIIKDKDF LDNEENEDIL EDIVLTLTLF EDREMIEERL KTYAHLFDDK VMKQLKRRRY  900
TGWGRLSRKL INGIRDKQSG KTILDFLKSD GFANRNFMQL IHDDSLTFKE DIQKAQVSGQ  960
GDSLHEHIAN LAGSPAIKKG ILQTVKVVDE LVKVMGRHKP ENIVIEMARE NQTTQKGQKN  1020
SRERMKRIEE GIKELGSQIL KEHPVENTQL QNEKLYLYYL QNGRDMYVDQ ELDINRLSDY  1080
DVDHIVPQSF LKDDSIDNKV LTRSDKNRGK SDNVPSEEVV KKMKNYWRQL LNAKLITQRK  1140
FDNLTKAERG GLSELDKAGF IKRQLVETRQ ITKHVAQILD SRMNTKYDEN DKLIREVKVI  1200
TLKSKLVSDF RKDFQFYKVR EINNYHHAHD AYLNAVVGTA LIKKYPKLES EFVYGDYKVY  1260
DVRKMIAKSE QEIGKATAKY FFYSNIMNFF KTEITLANGE IRKRPLIETN GETGEIVWDK  1320
GRDFATVRKV LSMPQVNIVK KTEVQTGGFS KESILPKRNS DKLIARKKDW DPKKYGGFDS  1380
PTVAYSVLVV AKVEKGKSKK LKSVKELLGI TIMERSSFEK NPIDFLEAKG YKEVKKDLII  1440
KLPKYSLFEL ENGRKRMLAS AGELQKGNEL ALPSKYVNFL YLASHYEKLK GSPEDNEQKQ  1500
LFVEQHKHYL DEIIEQISEF SKRVILADAN LDKVLSAYNK HRDKPIREQA ENIIHLFTLT  1560
NLGAPAAFKY FDTTIDRKRY TSTKEVLDAT LIHQSITGLY ETRIDLSQLG GDSGGSTNLS  1620
DIIEKETGKQ LVIQESILML PEEVEEVIGN KPESDILVHT AYDESTDENV MLLTSDAPEY  1680
KPWALVIQDS NGENKIKMLS GGSPKKKRKV                                   1710

SEQ ID NO: 21           moltype = AA  length = 1419
FEATURE                 Location/Qualifiers
source                  1..1419
                        mol_type = protein
                        organism = Streptococcus pyogenes
SEQUENCE: 21
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGS GGGGSGKRTA  1380
DGSEFEPKKK RKVSSGGDYK DHDGDYKDHD IDYKDDDDK                         1419

SEQ ID NO: 22           moltype = AA  length = 1053
FEATURE                 Location/Qualifiers
source                  1..1053
                        mol_type = protein
                        organism = Staphylococcus aureus
SEQUENCE: 22
MKRNYILGLD IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                               1053
```

```
SEQ ID NO: 23          moltype = AA  length = 1307
FEATURE                Location/Qualifiers
source                 1..1307
                       mol_type = protein
                       organism = Acidaminococcus sp.
SEQUENCE: 23
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN  1307

SEQ ID NO: 24          moltype = AA  length = 175
FEATURE                Location/Qualifiers
source                 1..175
                       mol_type = protein
                       organism = Homo sapiens
SEQUENCE: 24
MDSGRDFLTL HGLQDDEDLQ ALLKGSQLLK VKSSSWRRER FYKLQEDCKT IWQESRKVMR  60
TPESQLFSIE DIQEVRMGHR TEGLEKFARD VPEDRCFSIV FKDQRNTLDL IAPSPADAQH  120
WVLGLHKIIH HSGSMDQRQK LQHWIHSCLR KADKNKDNKM SFKELQNFLK ELNIQ  175

SEQ ID NO: 25          moltype = AA  length = 168
FEATURE                Location/Qualifiers
source                 1..168
                       mol_type = protein
                       organism = Homo sapiens
SEQUENCE: 25
MSDVAIVKEG WLHKRGEYIK TWRPRYFLLK NDGTFIGYKE RPQDVDQREA PLNNFSVAQC  60
QLMKTERPRP NTFIIRCLQW TTVIERTFHV ETPEEREEWT TAIQTVADGL KKQEEEEMDF  120
RSGSPSDNSG AEEMEVSLAK PKHRVTMNEF EYLKLLGKGT FGKVDPPV  168

SEQ ID NO: 26          moltype = AA  length = 92
FEATURE                Location/Qualifiers
source                 1..92
                       mol_type = protein
                       organism = Homo sapiens
SEQUENCE: 26
KMGPVDKRKG LFARRRQLLL TEGPHLYYVD PVNKVLKGEI PWSQELRPEA KNFKTFFVHT  60
PNRTYYLMDP SGNAHKWCRK IQEVWRQRYQ SH  92

SEQ ID NO: 27          moltype = AA  length = 229
FEATURE                Location/Qualifiers
source                 1..229
                       mol_type = protein
                       organism = Homo sapiens
SEQUENCE: 27
MSPVKGGTKC IKYLLFGFNF IFWLAGIAVL AIGLWLRFDS QTKSIFEQET NNNNSSFYTG  60
VYILIGAGAL MMLVGFLGCC GAVQESQCML GLFFGFLLVI FAIEIAAAIW GYSHKDEVIK  120
EVQEFYKDTY NKLKTKDEPQ RETLKAIHYA LNCCGLAGGV EQFISDICPK KDVLETFTVK  180
SCPDAIKEVF DNKFHIIGAV GIGIAVVMIF GMIFSMILCC AIRRNREMV  229

SEQ ID NO: 28          moltype = AA  length = 238
FEATURE                Location/Qualifiers
source                 1..238
                       mol_type = protein
                       organism = Homo sapiens
SEQUENCE: 28
MAVEGGMKCV KFLLYVLLLA FCACAVGLIA VGVGAQLVLS QTIIQGATPG SLLPVVIIAV  60
GVFLFLVAFV GCCGACKENY CLMITFAIFL SLIMLVEVAA AIAGYVFRDK VMSEFNNNFR  120
QQMENYPKNN HTASILDRMQ ADFKCCGAAN YTDWEKIPSM SKNRVPDSCC INVTVGCGIN  180
FNEKAIHKEG CVEKIGGWLR KNVLVVAAAA LGIAFVEVLG IVFACCLVKS IRSGYEVM  238
```

```
SEQ ID NO: 29           moltype = AA  length = 236
FEATURE                 Location/Qualifiers
source                  1..236
                        mol_type = protein
                        organism = Homo sapiens
SEQUENCE: 29
MGVEGCTKCI KYLLFVFNFV FWLAGGVILG VALWLRHDPQ TTNLLYLELG DKPAPNTFYV  60
GIYILIAVGA VMMFVGFLGC YGAIQESQCL LGTFFTCLVI LFACEVAAGI WGFVNKDQIA  120
KDVKQFYDQA LQQAVVDDDA NNAKAVVKTF HETLDCCGSS TLTALTTSVL KNNLCPSGSN  180
IISNLFKEDC HQKIDDLFSG KLYLIGIAAI VVAVIMIFEM ILSMVLCCGI RNSSVY      236

SEQ ID NO: 30           moltype = AA  length = 10
FEATURE                 Location/Qualifiers
source                  1..10
                        mol_type = protein
                        organism = Homo sapiens
SEQUENCE: 30
EVTELTREGE                                                        10

SEQ ID NO: 31           moltype = AA  length = 21
FEATURE                 Location/Qualifiers
source                  1..21
                        mol_type = protein
                        organism = Homo sapiens
SEQUENCE: 31
GNYTCEVTEL TREGETIIEL K                                           21

SEQ ID NO: 32           moltype = AA  length = 293
FEATURE                 Location/Qualifiers
source                  1..293
                        mol_type = protein
                        organism = Homo sapiens
SEQUENCE: 32
MWPLVAALLL GSACCGSAQL LFNKTKSVEF TFCNDTVVIP CFVTNMEAQN TTEVYVKWKF  60
KGRDIYTFDG ALNKSTVPTD FSSAKIEVSQ LLKGDASLKM DKSDAVSHTG NYTCEVTELT  120
REGETIIELK YRVVSWFSPN ENILIVIFPI FAILLFWGQF GIKTLKYRSG GMDEKTIALL  180
VAGLVITVIV IVGAILFVPG EYSLKNATGL GLIVTSTGIL ILLHYYVFST AIGLTSFVIA  240
ILVIQVIAYI LAVVGLSLCI AACIPMHGPL LISGLSILAL AQLLGLVYMK FVE        293

SEQ ID NO: 33           moltype = AA  length = 110
FEATURE                 Location/Qualifiers
source                  1..110
                        mol_type = protein
                        organism = synthetic construct
SEQUENCE: 33
FKCEHCRILF LDHVMFTIHM GCHGFRDPFK CNMCGEKCDG PVGLFVHMAR NAHGEKPFYC  60
EHCEITFRDV VMYSLHKGYH GFRDPPFECNI CGYHSQDRYE FSSHIVRGEH           110

SEQ ID NO: 34           moltype = AA  length = 110
FEATURE                 Location/Qualifiers
source                  1..110
                        mol_type = protein
                        organism = synthetic construct
SEQUENCE: 34
HHCQHCDMYF ADNILYTIHM GCHSCDDVFK CNMCGEKCDG PVGLFVHMAR NAHGEKPTKC  60
VHCGIVFLDE VMYALHMSCH GFRDPFECNI CGYHSQDRYE FSSHIVRGEH            110

SEQ ID NO: 35           moltype = AA  length = 110
FEATURE                 Location/Qualifiers
source                  1..110
                        mol_type = protein
                        organism = synthetic construct
SEQUENCE: 35
MGRGVQVETI SPGDGRTFPK RGQTCVVHYT GMLEDGKKFD SSRDRNKPFK FMLGKQEVIR  60
GWEEGVAQMS VGQRAKLTIS PDYAYGATGH PGIIPPHATL VFDVELLKLE            110

SEQ ID NO: 36           moltype = AA  length = 111
FEATURE                 Location/Qualifiers
source                  1..111
                        mol_type = protein
                        organism = synthetic construct
SEQUENCE: 36
MASRGVQVET ISPGDGRTFP KRGQTCVVHY TGMLEDGKKV DSSRDRNKPF KFMLGKQEVI  60
RGWEEGVAQM SVGQRAKLTI SPDYAYGATG HPGIIPPHAT LVFDVELLKL E          111

SEQ ID NO: 37           moltype = AA  length = 97
FEATURE                 Location/Qualifiers
source                  1..97
```

```
                        mol_type = protein
                        organism = synthetic construct
SEQUENCE: 37
MGSRILWHEM WHEGLEEASR LYFGERNVKG MFEVLEPLHA MMERGPQTLK ETSFNQAYGR  60
DLMEAQEWCR KYMKSGNVKD LLQAWDLYYH VFRRISK                           97

SEQ ID NO: 38           moltype = AA  length = 108
FEATURE                 Location/Qualifiers
source                  1..108
                        mol_type = protein
                        organism = synthetic construct
SEQUENCE: 38
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLE               108

SEQ ID NO: 39           moltype = AA  length = 93
FEATURE                 Location/Qualifiers
source                  1..93
                        mol_type = protein
                        organism = synthetic construct
SEQUENCE: 39
QGMLEMWHEG LEEASRLYFG ERNVKGMFEV LEPLHAMMER GPQTLKETSF NQAYGRDLME  60
AQEWCRKYMK SGNVKDLLQA WDLYYHVFRR ISK                               93

SEQ ID NO: 40           moltype = AA  length = 277
FEATURE                 Location/Qualifiers
source                  1..277
                        mol_type = protein
                        organism = synthetic construct
SEQUENCE: 40
MGPDIVMTQS PSSLSASVGD RVTITCRSST GAVTTSNYAS WVQEKPGKLF KGLIGGTNNR  60
APGVPSRFSG SLIGDKATLT ISSLQPEDFA TYFCALWYSN HWVFGQGTKV ELKRGGGGSG  120
GGGSGGGGSS GGGSEVKLLE SGGGLVQPGG SLKLSCAVSG FSLTDYGVNW VRQAPGRGLE  180
WIGVIWGDGI TDYNSALKDR FIISKDNGKN TVYLQMSKVR SDDTALYYCV TGLFDYWGQG  240
TLVTVSSYPY DVPDYAGGGG GSGGGGSGGG GSGGGGS                           277

SEQ ID NO: 41           moltype = AA  length = 237
FEATURE                 Location/Qualifiers
source                  1..237
                        mol_type = protein
                        organism = synthetic construct
SEQUENCE: 41
EELLSKNYHL ENEVARLKKG SGSGEELLSK NYHLENEVAR LKKGSGSGEE LLSKNYHLEN  60
EVARLKKGSG SGEELLSKNY HLENEVARLK KGSGSGEELL SKNYHLENEV ARLKKGSGSG  120
EELLSKNYHL ENEVARLKKG SGSGEELLSK NYHLENEVAR LKKGSGSGEE LLSKNYHLEN  180
EVARLKKGSG SGEELLSKNY HLENEVARLK KGSGSGEELL SKNYHLENEV ARLKKGS     237

SEQ ID NO: 42           moltype = AA  length = 573
FEATURE                 Location/Qualifiers
source                  1..573
                        mol_type = protein
                        organism = synthetic construct
SEQUENCE: 42
EELLSKNYHL ENEVARLKKG SGSGEELLSK NYHLENEVAR LKKGSGSGEE LLSKNYHLEN  60
EVARLKKGSG SGEELLSKNY HLENEVARLK KGSGSGEELL SKNYHLENEV ARLKKGSGSG  120
EELLSKNYHL ENEVARLKKG SGSGEELLSK NYHLENEVAR LKKGSGSGEE LLSKNYHLEN  180
EVARLKKGSG SGEELLSKNY HLENEVARLK KGSGSGEELL SKNYHLENEV ARLKKGSGSG  240
EELLSKNYHL ENEVARLKKG SGSGEELLSK NYHLENEVAR LKKGSGSGEE LLSKNYHLEN  300
EVARLKKGSG SGEELLSKNY HLENEVARLK KGSGSGEELL SKNYHLENEV ARLKKGSGSG  360
EELLSKNYHL ENEVARLKKG SGSGEELLSK NYHLENEVAR LKKGSGSGEE LLSKNYHLEN  420
EVARLKKGSG SGEELLSKNY HLENEVARLK KGSGSGEELL SKNYHLENEV ARLKKGSGSG  480
EELLSKNYHL ENEVARLKKG SGSGEELLSK NYHLENEVAR LKKGSGSGEE LLSKDYHLEN  540
EVARLKKGSG SGEELLSKNY HLENEVARLK KGS                               573

SEQ ID NO: 43           moltype = AA  length = 114
FEATURE                 Location/Qualifiers
source                  1..114
                        mol_type = protein
                        organism = synthetic construct
SEQUENCE: 43
VQLVESGGAL VQPGGSLRLS CAASGFPVNR YSMRWYRQAP GKEREWVAGM SSAGDRSSYE  60
DSVKGRFTIS RDDARNTVYL QMNSLKPEDT AVYYSNVNVG FEYWGQGTQV TVSS        114

SEQ ID NO: 44           moltype = AA  length = 102
FEATURE                 Location/Qualifiers
source                  1..102
                        mol_type = protein
                        organism = Nostoc punctiforme
SEQUENCE: 44
```

-continued

```
CLSYETEILT VEYGLLPIGK IVEKRIECTV YSVDNNGNIY TQPVAQWHDR GEQEVFEYCL  60
EDGSLIRATK DHKFMTVDGQ MLPIDEIFER ELDLMRVDNL PN                    102

SEQ ID NO: 45           moltype = AA  length = 39
FEATURE                 Location/Qualifiers
source                  1..39
                        mol_type = protein
                        organism = Nostoc punctiforme
SEQUENCE: 45
MIKIATRKYL GKQNVYDIGV ERDHNFALKN GFIASNCFN                        39

SEQ ID NO: 46           moltype = AA  length = 101
FEATURE                 Location/Qualifiers
source                  1..101
                        mol_type = protein
                        organism = synthetic construct
SEQUENCE: 46
CLSYDTEILT VEYGFLPIGK IVEERIECTV YTVDKNGFVY TQPIAQWHNR GEQEVFEYCL  60
EDGSIIRATK DHKFMTTDGQ MLPIDEIFER GLDLKQVDGL P                     101

SEQ ID NO: 47           moltype = AA  length = 36
FEATURE                 Location/Qualifiers
source                  1..36
                        mol_type = protein
                        organism = synthetic construct
SEQUENCE: 47
MVKIISRKSL GTQNVYDIGV EKDHNFLLKN GLVASN                           36

SEQ ID NO: 48           moltype = AA  length = 184
FEATURE                 Location/Qualifiers
source                  1..184
                        mol_type = protein
                        organism = Saccharomyces cerevisiae
SEQUENCE: 48
CFAKGTNVLM ADGSIECIEN IEVGNKVMGK DGRPREVIKL PRGRETMYSV VQKSQHRAHK  60
SDSSREVPEL LKFTCNATHE LVVRTPRSVR RLSRTIKGVE YFEVITFEMG QKKAPDGRIV  120
ELVKEVSKSY PISEGPERAN ELVESYRKAS NKAYFEWTIE ARDLSLLGSH VRKATYQTYA  180
PILY                                                              184

SEQ ID NO: 49           moltype = AA  length = 65
FEATURE                 Location/Qualifiers
source                  1..65
                        mol_type = protein
                        organism = Saccharomyces cerevisiae
SEQUENCE: 49
VLLNVLSKCA GSKKFRPAPA AAFARECRGF YFELQELKED DYYGITLSDD SDHQFLLANQ  60
VVVHN                                                             65

SEQ ID NO: 50           moltype = AA  length = 123
FEATURE                 Location/Qualifiers
source                  1..123
                        mol_type = protein
                        organism = Synechocystis sp.
SEQUENCE: 50
CLSFGTEILT VEYGPLPIGK IVSEEINCSV YSVDPEGRVY TQAIAQWHDR GEQEVLEYEL  60
EDGSVIRATS DHRFLTTDYQ LLAIEEIFAR QLDLLTLENI KQTEEALDNH RLPFPLLDAG  120
TIK                                                               123

SEQ ID NO: 51           moltype = AA  length = 36
FEATURE                 Location/Qualifiers
source                  1..36
                        mol_type = protein
                        organism = Synechocystis sp.
SEQUENCE: 51
MVKVIGRRSL GVQRIFDIGL PQDHNFLLAN GAIAAN                           36

SEQ ID NO: 52           moltype = AA  length = 14
FEATURE                 Location/Qualifiers
source                  1..14
                        mol_type = protein
                        organism = synthetic construct
SEQUENCE: 52
VPTIVMVDAY KRYK                                                   14

SEQ ID NO: 53           moltype = AA  length = 119
FEATURE                 Location/Qualifiers
source                  1..119
                        mol_type = protein
                        organism = synthetic construct
```

```
SEQUENCE: 53
MVTTLSGLSG EQGPSGDMTT EEDSATHIKF SKRDEDGREL AGATMELRDS SGKTISTWIS  60
DGHVKDFYLY PGKYTFVETA APDGYEVATA ITFTVNEQGQ VTVNGEATKG DAHTGSSGS   119

SEQ ID NO: 54          moltype = AA  length = 130
FEATURE                Location/Qualifiers
source                 1..130
                       mol_type = protein
                       organism = Enterobacteria phage MS2
SEQUENCE: 54
MASNFTQFVL VDNGGTGDVT VAPSNFANGV AEWISSNSRS QAYKVTCSVR QSSAQNRKYT  60
IKVEVPKVAT QTVGGVELPV AAWRSYLNME LTIPIFATNS DCELIVKAMQ GLLKDGNPIP  120
SAIAANSGIY                                                        130

SEQ ID NO: 55          moltype = AA  length = 130
FEATURE                Location/Qualifiers
source                 1..130
                       mol_type = protein
                       organism = Enterobacteria phage MS2
SEQUENCE: 55
MASNFTQFVL VDNGGTGDVT VAPSNFANGV AEWISSNSRS QAYKVTCSVR QSSAQKRKYT  60
IKVEVPKVAT QTVGGVELPV AAWRSYLNME LTIPIFATNS DCELIVKAMQ GLLKDGNPIP  120
SAIAANSGIY                                                        130

SEQ ID NO: 56          moltype = AA  length = 130
FEATURE                Location/Qualifiers
source                 1..130
                       mol_type = protein
                       organism = Enterobacteria phage MS2
SEQUENCE: 56
MASNFTQFVL VDNGGTGDVT VAPSNFANGI AEWISSNSRS QAYKVTCSVR QSSAQKRKYT  60
IKVEVPKVAT QTVGGVELPV AAWRSYLNME LTIPIFATNS DCELIVKAMQ GLLKDGNPIP  120
SAIAANSGIY                                                        130

SEQ ID NO: 57          moltype = AA  length = 121
FEATURE                Location/Qualifiers
source                 1..121
                       mol_type = protein
                       organism = Pseudomonas phage PP7
SEQUENCE: 57
KTIVLSVGEA TRTLTEIQST ADRQIFEEKV GPLVGRLRLT ASLRQNGAKT AYRVNLKLDQ  60
ADVVDSGLPK VRYTQVWSHD VTIVANSTEA SRKSLYDLTK SLVATSQVED LVVNLVPLGR  120
S                                                                 121

SEQ ID NO: 58          moltype = AA  length = 62
FEATURE                Location/Qualifiers
source                 1..62
                       mol_type = protein
                       organism = Escherichia virus Mu
SEQUENCE: 58
MKSIRCKNCN KLLFKADSFD HIEIRCPRCK RHIIMLNACE HPTEKHCGKR EKITHSDETV  60
RY                                                                62

SEQ ID NO: 59          moltype = AA  length = 179
FEATURE                Location/Qualifiers
source                 1..179
                       mol_type = protein
                       organism = synthetic construct
SEQUENCE: 59
STRPGERPFQ CRICMRNFSI PNHLARHTRT HTGEKPFQCR ICMRNFSQSA HLKRHLRTHT  60
GEKPFQCRIC MRNFSQDVSL VRHLKTHLRQ KDGERPFQCR ICMRNFSSAQ ALARHTRTHT  120
GEKPFQCRIC MRNFSQGGNL TRHLRTHTGE KPFQCRICMR NFSQHPNLTR HLKTHLRGS   179

SEQ ID NO: 60          moltype = AA  length = 178
FEATURE                Location/Qualifiers
source                 1..178
                       mol_type = protein
                       organism = synthetic construct
SEQUENCE: 60
SRPGERPFQC RICMRNFSTM AVLRRHTRTH TGEKPFQCRI CMRNFSRREV LENHLRTHTG  60
EKPFQCRICM RNFSQTVNLD RHLKTHLRQK DGERPFQCRI CMRNFSKKDH LHRHTRTHTG  120
EKPFQCRICM RNFSQRPHLT NHLRTHTGEK PFQCRICMRN FSVGASLKRH LKTHLRGS    178

SEQ ID NO: 61          moltype = AA  length = 90
FEATURE                Location/Qualifiers
source                 1..90
                       mol_type = protein
                       organism = synthetic construct
SEQUENCE: 61
```

```
SRPGERPFQC RICMRNFSDK TKLRVHTRTH TGEKPFQCRI CMRNFSVRHN LTRHLRTHTG  60
EKPFQCRICM RNFSQSTSLQ RHLKTHLRGF                                   90

SEQ ID NO: 62          moltype = AA  length = 176
FEATURE                Location/Qualifiers
source                 1..176
                       mol_type = protein
                       organism = synthetic construct
SEQUENCE: 62
SRPGERPFQC RICMRNFSRR HGLDRHTRTH TGEKPFQCRI CMRNFSDHSS LKRHLRTHTG  60
SQKPFQCRIC MRNFSVRHNL TRHLRTHTGE KPFQCRICMR NFSDHSNLSR HLKTHTGSQK  120
PFQCRICMRN FSQRSSLVRH LRTHTGEKPF QCRICMRNFS ESGHLKRHLR THLRGS      176

SEQ ID NO: 63          moltype = AA  length = 286
FEATURE                Location/Qualifiers
source                 1..286
                       mol_type = protein
                       organism = synthetic construct
SEQUENCE: 63
SRPGERPFQC RICMRNFSTR QNLDTHTRTH TGEKPFQCRI CMRNFSRRDT LERHLRTHTG  60
EKPFQCRICM RNFSRPDALP RHLKTHLRGS QLVKSELEEK KSELRHKLKY VPHEYIELIE  120
IARNSTQDRI LEMKVMEFFM KVYGYRGKHL GGSRKPDGAI YTVGSPIDYG VIVDTKAYSG  180
GYNLPIGQAD EMQRYVEENQ TRNKHINPNE WWKVYPSSVT EFKFLFVSGH FKGNYKAQLT  240
RLNHITNCNG AVLSVEELLI GGEMIKAGTL TLEEVRRKFN NGEINF                 286

SEQ ID NO: 64          moltype = AA  length = 286
FEATURE                Location/Qualifiers
source                 1..286
                       mol_type = protein
                       organism = synthetic construct
SEQUENCE: 64
SRPGERPFQC RICMRNFSSP SKLIRHTRTH TGEKPFQCRI CMRNFSDGSN LARHLRTHTG  60
EKPFQCRICM RNFSRVDNLP RHLKTHLRGS QLVKSELEEK KSELRHKLKY VPHEYIELIE  120
IARNSTQDRI LEMKVMEFFM KVYGYRGKHL GGSRKPDGAI YTVGSPIDYG VIVDTKAYSG  180
GYNLPIGQAD EMQRYVEENQ TRNKHINPNE WWKVYPSSVT EFKFLFVSGH FKGNYKAQLT  240
RLNHITNCNG AVLSVEELLI GGEMIKAGTL TLEEVRRKFN NGEINF                 286

SEQ ID NO: 65          moltype = AA  length = 196
FEATURE                Location/Qualifiers
source                 1..196
                       mol_type = protein
                       organism = synthetic construct
SEQUENCE: 65
QLVKSELEEK KSELRHKLKY VPHEYIELIE IARNSTQDRI LEMKVMEFFM KVYGYRGKHL  60
GGSRKPDGAI YTVGSPIDYG VIVDTKAYSG GYNLPIGQAD EMQRYVEENQ TRNKHINPNE  120
WWKVYPSSVT EFKFLFVSGH FKGNYKAQLT RLNHITNCNG AVLSVEELLI GGEMIKAGTL  180
TLEEVRRKFN NGEINF                                                  196

SEQ ID NO: 66          moltype = AA  length = 199
FEATURE                Location/Qualifiers
source                 1..199
                       mol_type = protein
                       organism = synthetic construct
SEQUENCE: 66
VHDHKLELAK LIRNYETNRK ECLNSRYNET LLRSDYLDPF FELLGWDIKN KAGKPTNERE  60
VVLEEALKAS ASEHSKKPDY TFRLFSERKF FLEAKKPSVH IESDNETAKQ VRRYGFTAKL  120
KISVLSNFEY LVIYDTSVKV DGDDTFNKAR IKKYHYTEYE THFDEICDLL GRESVYSGNF  180
DKEWLSIENK INHFSVDTL                                               199

SEQ ID NO: 67          moltype = AA  length = 119
FEATURE                Location/Qualifiers
source                 1..119
                       mol_type = protein
                       organism = synthetic construct
SEQUENCE: 67
YNETLLRSDY LDPFFELLGW DIKNKAGKPT NEREVVLEEA LKASASEHSK KPDYTFRLFS  60
ERKFFLEAKK PSVHIESDNE TAKQVRRYGF TAKLKISVLS NFEYLVIYDT SVKVDGDDT   119

SEQ ID NO: 68          moltype = AA  length = 972
FEATURE                Location/Qualifiers
source                 1..972
                       mol_type = protein
                       organism = Ruminococcus flavefaciens
SEQUENCE: 68
EASIEKKKSF AKGMGVKSTL VSGSKVYMTT FAEGSDARLE KIVEGDSIRS VNEGEAFSAE  60
MADKNAGYKI GNAKFSHPKG YAVVANNPLY TGPVQQDMLG LKETLEKRYF GESADGNDNI  120
CIQVIHNILD IEKILAEYIT NAAYAVNNIS GLDKDIIGFG KFSTVYTYDE FKDPEHHRAA  180
FNNNDKLINA IKAQYDEFDN FLDNPRLGYF GQAFFSKEGR NYIINYGNEC YDILALLSGL  240
RHWVVHNNEE ESRISRTWLY NLDKNLDNEY ISTLNYLYDR ITNELTNSFS KNSAANVNYI  300
```

-continued

```
AETLGINPAE FAEQYFRFSI MKEQKNLGFN ITKLREVMLD RKDMSEIRKN HKVFDSIRTK  360
VYTMMDFVIY RYYIEEDAKV AAANKSLPDN EKSLSEKDIF VINLRGSFND DQKDALYYDE  420
ANRIWRKLEN IMHNIKEFRG NKTREYKKKD APRLPRILPA GRDVSAFSKL MYALTMFLDG  480
KEINDLLTTL INKFDNIQSF LKVMPLIGVN AKFVEEYAFF KDSAKIADEL RLIKSFARMG  540
EPIADARRAM YIDAIRILGT NLSYDELKAL ADTFSLDENG NKLKKGKHGM RNFIINNVIS  600
NKRFHYLIRY GDPAHLHEIA KNEAVVKFVL GRIADIQKKQ GQNGKNQIDR YYETCIGKDK  660
GKSVSEKVDA LTKIITGMNY DQFDKKRSVI EDTGRENAER EKFKKIISLY LTVIYHILKN  720
IVNINARYVI GFHCVERDAQ LYKEKGYDIN LKKLEEKGFS SVTKLCAGID ETAPDKRKDV  780
EKEMAERAKE SIDSLESANP KLYANYIKYS DEKKAEEFTR QINREKAKTA LNAYLRNTKW  840
NVIIREDLLR IDNKTCTLFR NKAVHLEVAR YVHAYINDIA EVNSYFQLYH YIMQRIIMNE  900
RYEKSSGKVS EYFDAVNDEK KYNDRLLKLL CVPFGYCIPR FKNLSIEALF DRNEAAKFDK  960
EKKKVSGNSG SG                                                     972

SEQ ID NO: 69          moltype = AA  length = 991
FEATURE                Location/Qualifiers
source                 1..991
                       mol_type = protein
                       organism = synthetic construct
SEQUENCE: 69
EASIEKKKSF AKGMGVKSTL VSGSKVYMTT FAEGSDARLE KIVEGDSIRS VNEGEAFSAE  60
MADKNAGYKI GNAKFSHPKG YAVVANNPLY TGPVQQDMLG LKETLEKRYF GESADGNDNI  120
CIQVIHNILD IEKILAEYIT NAAYAVNNIS GLDKDIIGFG KFSTVYTYDE FKDPEHHRAA  180
FNNNDKLINA IKAQYDEFDN FLDNPRLGYF GQAFFSKEGR NYIINYGNEC YDILALLSGL  240
AHWVVANNEE ESRISRTWLY NLDKNLDNEY ISTLNYLYDR ITNELTNSFS KNSAANVNYI  300
AETLGINPAE FAEQYFRFSI MKEQKNLGFN ITKLREVMLD RKDMSEIRKN HKVFDSIRTK  360
VYTMMDFVIY RYYIEEDAKV AAANKSLPDN EKSLSEKDIF VINLRGSFND DQKDALYYDE  420
ANRIWRKLEN IMHNIKEFRG NKTREYKKKD APRLPRILPA GRDVSAFSKL MYALTMFLDG  480
KEINDLLTTL INKFDNIQSF LKVMPLIGVN AKFVEEYAFF KDSAKIADEL RLIKSFARMG  540
EPIADARRAM YIDAIRILGT NLSYDELKAL ADTFSLDENG NKLKKGKHGM RNFIINNVIS  600
NKRFHYLIRY GDPAHLHEIA KNEAVVKFVL GRIADIQKKQ GQNGKNQIDR YYETCIGKDK  660
GKSVSEKVDA LTKIITGMNY DQFDKKRSVI EDTGRENAER EKFKKIISLY LTVIYHILKN  720
IVNINARYVI GFHCVERDAQ LYKEKGYDIN LKKLEEKGFS SVTKLCAGID ETAPDKRKDV  780
EKEMAERAKE SIDSLESANP KLYANYIKYS DEKKAEEFTR QINREKAKTA LNAYLRNTKW  840
NVIIREDLLR IDNKTCTLFA NKAVALEVAR YVHAYINDIA EVNSYFQLYH YIMQRIIMNE  900
RYEKSSGKVS EYFDAVNDEK KYNDRLLKLL CVPFGYCIPR FKNLSIEALF DRNEAAKFDK  960
EKKKVSGNSG SGPKKKRKVA AAYPYDVPDY A                                991

SEQ ID NO: 70          moltype = AA  length = 25
FEATURE                Location/Qualifiers
source                 1..25
                       mol_type = protein
                       organism = synthetic construct
SEQUENCE: 70
IWLTALKFLG KHAAKHEAKQ QLSKL                                       25

SEQ ID NO: 71          moltype = AA  length = 75
FEATURE                Location/Qualifiers
source                 1..75
                       mol_type = protein
                       organism = synthetic construct
SEQUENCE: 71
IWLTALKFLG KHAAKHEAKQ QLSKLNAVGQ DTQEVIVVPH SLPFKVVVIS AILALVVLTI  60
ISLIILIMLW QKKPR                                                  75

SEQ ID NO: 72          moltype = AA  length = 30
FEATURE                Location/Qualifiers
source                 1..30
                       mol_type = protein
                       organism = synthetic construct
SEQUENCE: 72
WEAKLAKALA KALAKHLAKA LAKALKACEA                                  30

SEQ ID NO: 73          moltype = AA  length = 80
FEATURE                Location/Qualifiers
source                 1..80
                       mol_type = protein
                       organism = synthetic construct
SEQUENCE: 73
WEAKLAKALA KALAKHLAKA LAKALKACEA NAVGQDTQEV IVVPHSLPFK VVVISAILAL  60
VVLTIISLII LIMLWQKKPR                                             80

SEQ ID NO: 74          moltype = AA  length = 26
FEATURE                Location/Qualifiers
source                 1..26
                       mol_type = protein
                       organism = synthetic construct
SEQUENCE: 74
KKALLHAALA HLLALAHHLL ALLKKA                                      26
```

```
SEQ ID NO: 75          moltype = AA  length = 76
FEATURE                Location/Qualifiers
source                 1..76
                       mol_type = protein
                       organism = synthetic construct
SEQUENCE: 75
KKALLHAALA HLLALAHHLL ALLKKANAVG QDTQEVIVVP HSLPFKVVVI SAILALVVLT  60
IISLIILIML WQKKPR                                                   76

SEQ ID NO: 76          moltype = AA  length = 50
FEATURE                Location/Qualifiers
source                 1..50
                       mol_type = protein
                       organism = synthetic construct
SEQUENCE: 76
NAVGQDTQEV IVVPHSLPFK VVVISAILAL VVLTIISLII LIMLWQKKPR             50

SEQ ID NO: 77          moltype = AA  length = 34
FEATURE                Location/Qualifiers
source                 1..34
                       mol_type = protein
                       organism = Lactococcus lactis
SEQUENCE: 77
ITSISLCTPG CKTGALMGCN MKTATCHCSI HVSK                               34

SEQ ID NO: 78          moltype = AA  length = 34
FEATURE                Location/Qualifiers
source                 1..34
                       mol_type = protein
                       organism = Lactococcus lactis
SEQUENCE: 78
ITSISLCTPG CKTGALMGCN MKTATCNCSI HVSK                               34

SEQ ID NO: 79          moltype = AA  length = 34
FEATURE                Location/Qualifiers
source                 1..34
                       mol_type = protein
                       organism = Lactococcus lactis
SEQUENCE: 79
ITSISLCTPG CKTGALMGCN MKTATCNCSV HVSK                               34

SEQ ID NO: 80          moltype = AA  length = 34
FEATURE                Location/Qualifiers
source                 1..34
                       mol_type = protein
                       organism = Lactococcus lactis
SEQUENCE: 80
ITSISLCTPG CKTGVLMGCN LKTATCNCSV HVSK                               34

SEQ ID NO: 81          moltype = AA  length = 34
FEATURE                Location/Qualifiers
source                 1..34
                       mol_type = protein
                       organism = Streptococcus hyointestinalis
SEQUENCE: 81
FTSISMCTPG CKTGALMTCN YKTATCHCSI KVSK                               34

SEQ ID NO: 82          moltype = AA  length = 31
FEATURE                Location/Qualifiers
source                 1..31
                       mol_type = protein
                       organism = Streptococcus uberis
SEQUENCE: 82
ITSKSLCTPG CKTGILMTCP LKTATCGCHF G                                  31

SEQ ID NO: 83          moltype = AA  length = 31
FEATURE                Location/Qualifiers
source                 1..31
                       mol_type = protein
                       organism = Streptococcus uberis
SEQUENCE: 83
VTSKSLCTPG CKTGILMTCP LKTATCGCHF G                                  31

SEQ ID NO: 84          moltype = AA  length = 31
FEATURE                Location/Qualifiers
source                 1..31
                       mol_type = protein
                       organism = Streptococcus galloyticus
SEQUENCE: 84
```

```
VTSKSLCTPG CKTGILMTCA IKTATCGCHF G                               31

SEQ ID NO: 85          moltype = AA  length = 34
FEATURE                Location/Qualifiers
source                 1..34
                       mol_type = protein
                       organism = Lactococcus lactis
SEQUENCE: 85
ITSISLCTPG CKTGALMGCN MKTATCHCAI HVSK                            34

SEQ ID NO: 86          moltype = AA  length = 34
FEATURE                Location/Qualifiers
source                 1..34
                       mol_type = protein
                       organism = Lactococcus lactis
SEQUENCE: 86
ITSISLCTPG CKTGALMGCN MKTATCHCDI HVSK                            34

SEQ ID NO: 87          moltype = AA  length = 34
FEATURE                Location/Qualifiers
source                 1..34
                       mol_type = protein
                       organism = Lactococcus lactis
SEQUENCE: 87
ITSISLCTPG CKTGALMGCN MKTATCHCEI HVSK                            34

SEQ ID NO: 88          moltype = AA  length = 34
FEATURE                Location/Qualifiers
source                 1..34
                       mol_type = protein
                       organism = Lactococcus lactis
SEQUENCE: 88
ITSISLCTPG CKTGALMGCN MKTATCHCGI HVSK                            34

SEQ ID NO: 89          moltype = AA  length = 34
FEATURE                Location/Qualifiers
source                 1..34
                       mol_type = protein
                       organism = Lactococcus lactis
SEQUENCE: 89
ITSISLCTPG CKTGALMGCN MTTATCHCSI HVSK                            34

SEQ ID NO: 90          moltype = AA  length = 34
FEATURE                Location/Qualifiers
source                 1..34
                       mol_type = protein
                       organism = Lactococcus lactis
SEQUENCE: 90
ITSISLCTPG CKTGALMGCP MKTATCHCSI HVSK                            34

SEQ ID NO: 91          moltype = AA  length = 34
FEATURE                Location/Qualifiers
source                 1..34
                       mol_type = protein
                       organism = Lactococcus lactis
SEQUENCE: 91
ITSISLCTPG CKTGALMGCN VKTATCHCSI HVSK                            34

SEQ ID NO: 92          moltype = AA  length = 34
FEATURE                Location/Qualifiers
source                 1..34
                       mol_type = protein
                       organism = Lactococcus lactis
SEQUENCE: 92
ITSISLCTPG CKTGALMGCN MSTATCHCSI HVSK                            34

SEQ ID NO: 93          moltype = AA  length = 34
FEATURE                Location/Qualifiers
source                 1..34
                       mol_type = protein
                       organism = Lactococcus lactis
SEQUENCE: 93
ITSISLCTPG CKTGALMGCK MKTATCNCSI HVSK                            34

SEQ ID NO: 94          moltype = AA  length = 34
FEATURE                Location/Qualifiers
source                 1..34
                       mol_type = protein
                       organism = Lactococcus lactis
```

```
SEQUENCE: 94
ITSISLCTPG CKTGALMGCN KKTATCNCSI HVSK                          34

SEQ ID NO: 95          moltype = AA  length = 397
FEATURE                Location/Qualifiers
source                 1..397
                       mol_type = protein
                       note = Adeno-associated virus - 2
                       organism = Adeno-associated virus
SEQUENCE: 95
MELVGWLVDK GITSEKQWIQ EDQASYISFN AASNSRSQIK AALDNAGKIM SLTKTAPDYL  60
VGQQPVEDIS SNRIYKILEL NGYDPQYAAS VFLGWATKKF GKRNTIWLFG PATTGKTNIA  120
EAIAHTVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL DHDFGKVTKQ  240
EVKDFFRWAK DHVVEVEHEF YVKKGGAKKR PAPSDADISE PKRVRESVAQ PSTSDAEASI  300
NYADRYQNKC SRHVGMNLML FPCRQCERMN QNSNICFTHG QKDCLECFPV SESQPVSVVK  360
KAYQKLCYIH HIMGKVPDAC TACDLVNVDL DDCIFEQ                           397

SEQ ID NO: 96          moltype = AA  length = 621
FEATURE                Location/Qualifiers
source                 1..621
                       mol_type = protein
                       note = Adeno-associated virus - 2
                       organism = Adeno-associated virus
SEQUENCE: 96
MPGFYEIVIK VPSDLDEHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEQYLSACL  180
NLTERKRLVA QHLTHVSQTQ EQNKENQNPN SDAPVIRSKT SARYMELVGW LVDKGITSEK  240
QWIQEDQASY ISFNAASNSR SQIKAALDNA GKIMSLTKTA PDYLVGQQPV EDISSNRIYK  300
ILELNGYDPQ YAASVFLGWA TKKFGKRNTI WLFGPATTGK TNIAEAIAHT VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLDHDFGK VTKQEVKDFF RWAKDHVVEV  480
EHEFYVKKGG AKKRPAPSDA DISEPKRVRE SVAQPSTSDA EASINYADRY QNKCSRHVGM  540
NLMLFPCRQC ERMNQNSNIC FTHGQKDCLE CFPVSESQPV SVVKKAYQKL CYIHHIMGKV  600
PDACTACDLV NVDLDDCIFE Q                                            621

SEQ ID NO: 97          moltype = AA  length = 735
FEATURE                Location/Qualifiers
source                 1..735
                       mol_type = protein
                       note = Adeno-associated virus - 2
                       organism = Adeno-associated virus
SEQUENCE: 97
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                   735

SEQ ID NO: 98          moltype = AA  length = 597
FEATURE                Location/Qualifiers
source                 1..597
                       mol_type = protein
                       note = Adeno-associated virus - 2
                       organism = Adeno-associated virus
SEQUENCE: 98
APGKKRPVEH SPVEPDSSSG TGKAGQQPAR KRLNFGQTGD ADSVPDPQPL GQPPAAPSGL  60
GTNTMATGSG APMADNNEGA DGVGNSSGNW HCDSTWMGDR VITTSTRTWA LPTYNNHLYK  120
QISSQSGASN DNHYFGYSTP WGYFDFNRFH CHFSPRDWQR LINNNWGFRP KRLNFKLFNI  180
QVKEVTQNDG TTTIANNLTS TVQVFTDSEY QLPYVLGSAH QGCLPPFPAD VFMVPQYGYL  240
TLNNGSQAVG RSSFYCLEYF PSQMLRTGNN FTFSYTFEDV PFHSSYAHSQ SLDRLMNPLI  300
DQYLYYLSRT NTPSGTTTQS RLQFSQAGAS DIRDQSRNWL PGPCYRQQRV SKTSADNNNS  360
EYSWTGATKY HLNGRDSLVN PGPAMASHKD DEEKFFPQSG VLIFGKQGSE KTNVDIEKVM  420
ITDEEEIRTT NPVATEQYGS VSTNLQRGNR QAATADVNTQ GVLPGMVWQD RDVYLQGPIW  480
AKIPHTDGHF HPSPLMGGFG LKHPPPQILI KNTPVPANPS TTFSAAKFAS FITQYSTGQV  540
SVEIEWELQK ENSKRWNPEI QYTSNYNKSV NVDFTVDTNG VYSEPRPIGT RYLTRNL     597

SEQ ID NO: 99          moltype = AA  length = 533
FEATURE                Location/Qualifiers
source                 1..533
```

```
                        mol_type = protein
                        note = Adeno-associated virus - 2
                        organism = Adeno-associated virus
SEQUENCE: 99
MATGSGAPMA DNNEGADGVG NSSGNWHCDS TWMGDRVITT STRTWALPTY NNHLYKQISS  60
QSGASNDNHY FGYSTPWGYF DFNRFHCHFS PRDWQRLINN NWGFRPKRLN FKLFNIQVKE  120
VTQNDGTTTI ANNLTSTVQV FTDSEYQLPY VLGSAHQGCL PPFPADVFMV PQYGYLTLNN  180
GSQAVGRSSF YCLEYFPSQM LRTGNNFTFS YTFEDVPFHS SYAHSQSLDR LMNPLIDQYL  240
YYLSRTNTPS GTTTQSRLQF SQAGASDIRD QSRNWLPGPC YRQQRVSKTS ADNNNSEYSW  300
TGATKYHLNG RDSLVNPGPA MASHKDDEEK FFPQSGVLIF GKQGSEKTNV DIEKVMITDE  360
EEIRTTNPVA TEQYGSVSTN LQRGNRQAAT ADVNTQGVLP GMVWQDRDVY LQGPIWAKIP  420
HTDGHFHPSP LMGGFGLKHP PPQILIKNTP VPANPSTTFS AAKFASFITQ YSTGQVSVEI  480
EWELQKENSK RWNPEIQYTS NYNKSVNVDF TVDTNGVYSE PRPIGTRYLT RNL         533

SEQ ID NO: 100          moltype = RNA  length = 143
FEATURE                 Location/Qualifiers
source                  1..143
                        mol_type = other RNA
                        organism = synthetic construct
SEQUENCE: 100
gttttagagc taggccaaca tgaggatcac ccatgtctgc agggcctagc aagttaaaat  60
aaggctagtc cgttatcaac ttggccaaca tgaggatcac ccatgtctgc agggccaagt  120
ggcaccgagt cggtgctttt ttt                                          143

SEQ ID NO: 101          moltype = RNA  length = 199
FEATURE                 Location/Qualifiers
source                  1..199
                        mol_type = other RNA
                        organism = synthetic construct
SEQUENCE: 101
gttttagagc taggccaaca tgaggatcac ccatgtctgc agggcctagc aagttaaaat  60
aaggctagtc cgttatcaac ttggccaaca tgaggatcac ccatgtctgc agggccaagt  120
ggcaccgagt cggtgcggga gcacatgagg atcacccatg tgcgactccc acagtcactg  180
gggagtcttc cctttttt                                                199

SEQ ID NO: 102          moltype = RNA  length = 149
FEATURE                 Location/Qualifiers
source                  1..149
                        mol_type = other RNA
                        organism = synthetic construct
SEQUENCE: 102
gtttaagagc tatgctggaa acagcatagc aagtttaaat aaggctagtc cgttatcaac  60
ttgaaaaagt ggcaccgagt cggtgcggga gcacatgagg atcacccatg tgcgactccc  120
acagtcactg gggagtcttc cctttttt                                     149

SEQ ID NO: 103          moltype = RNA  length = 186
FEATURE                 Location/Qualifiers
source                  1..186
                        mol_type = other RNA
                        organism = synthetic construct
SEQUENCE: 103
ttctagatca tcgaaacatg aggatcaccc atatctgcag tcgacatcga aacatgagga  60
tcacccatgt ctgcagtcga catcgaaaca tgaggatcac ccatgtctgc agtcgacatc  120
gaaacatgag gatcacccat gtctgcagtc gacatcgaaa tcgataagct tcagatcaga  180
tcctag                                                             186

SEQ ID NO: 104          moltype = RNA  length = 19
FEATURE                 Location/Qualifiers
source                  1..19
                        mol_type = other RNA
                        organism = synthetic construct
SEQUENCE: 104
acatgaggat cacccatgt                                               19

SEQ ID NO: 105          moltype = RNA  length = 19
FEATURE                 Location/Qualifiers
source                  1..19
                        mol_type = other RNA
                        organism = synthetic construct
SEQUENCE: 105
acatgaggat cacccatat                                               19

SEQ ID NO: 106          moltype = RNA  length = 14
FEATURE                 Location/Qualifiers
source                  1..14
                        mol_type = other RNA
                        organism = synthetic construct
SEQUENCE: 106
ccacagtcac tggg                                                    14
```

```
SEQ ID NO: 107          moltype = RNA  length = 89
FEATURE                 Location/Qualifiers
source                  1..89
                        mol_type = other RNA
                        organism = synthetic construct
SEQUENCE: 107
acatgaggat cacccatgtc tgcagggcct agcaagttaa aataaggcta gtccgttatc  60
aacttggcca acatgaggat cacccatgt                                    89

SEQ ID NO: 108          moltype = RNA  length = 141
FEATURE                 Location/Qualifiers
source                  1..141
                        mol_type = other RNA
                        organism = synthetic construct
SEQUENCE: 108
gttttagagc taggccggag cagacgatat ggcgtcgctc cggcctagca agttaaaata  60
aggctagtcc gttatcaact tggccggagc agacgatatg gcgtcgctcc ggccaagtgg  120
caccgagtcg gtgctttttt t                                            141

SEQ ID NO: 109          moltype = RNA  length = 32
FEATURE                 Location/Qualifiers
source                  1..32
                        mol_type = other RNA
                        organism = synthetic construct
SEQUENCE: 109
gccggagcag acgatatggc gtcgctccgg cc                                32

SEQ ID NO: 110          moltype = RNA  length = 112
FEATURE                 Location/Qualifiers
source                  1..112
                        mol_type = other RNA
                        organism = synthetic construct
SEQUENCE: 110
gtttaagagc tatgctggaa acagcatagc aagtttaaat aaggctagtc cgttatcaac  60
ttgaaaaagt ggcaccgagt cggtgcctga atgcctgcga gcatcttttt tt          112

SEQ ID NO: 111          moltype = RNA  length = 19
FEATURE                 Location/Qualifiers
source                  1..19
                        mol_type = other RNA
                        organism = synthetic construct
SEQUENCE: 111
ctgaatgcct gcgagcatc                                               19

SEQ ID NO: 112          moltype = DNA  length = 18
FEATURE                 Location/Qualifiers
source                  1..18
                        mol_type = other DNA
                        organism = synthetic construct
SEQUENCE: 112
gaagaagctg caggaggt                                                18

SEQ ID NO: 113          moltype = DNA  length = 18
FEATURE                 Location/Qualifiers
source                  1..18
                        mol_type = other DNA
                        organism = synthetic construct
SEQUENCE: 113
gctggagggg aagtggtc                                                18

SEQ ID NO: 114          moltype = DNA  length = 36
FEATURE                 Location/Qualifiers
source                  1..36
                        mol_type = other DNA
                        organism = synthetic construct
SEQUENCE: 114
gaagaagctg caggaggtgc tggaggggaa gtggtc                            36

SEQ ID NO: 115          moltype = DNA  length = 346
FEATURE                 Location/Qualifiers
source                  1..346
                        mol_type = other DNA
                        organism = synthetic construct
SEQUENCE: 115
tgaagaagct gcaggaggtg ctggagggga agtggtccgg atcttgaaga agctgcagga  60
ggtgctggag gggaagtggt ccggatcttg aagaagctgc aggaggtgct ggaggggaag  120
tggtccggat cttgaagaag ctgcaggagg tgctggaggg gaagtggtcc ggatcttgaa  180
gaagctgcag gaggtgctgg aggggaagtg gtccggatct tgaagaagct gcaggaggtg  240
```

-continued

```
ctggagggga agtggtccgg atcttgaaga agctgcagga ggtgctggag gggaagtggt  300
ccggatcttg aagaagctgc aggaggtgct ggaggggaag tggtcc                 346

SEQ ID NO: 116         moltype =   length =
SEQUENCE: 116
000

SEQ ID NO: 117         moltype = DNA  length = 20
FEATURE                Location/Qualifiers
source                 1..20
                       mol_type = other DNA
                       organism = synthetic construct
SEQUENCE: 117
cggcgtagcc gatgtcgcgc                                              20

SEQ ID NO: 118         moltype =   length =
SEQUENCE: 118
000

SEQ ID NO: 119         moltype =   length =
SEQUENCE: 119
000

SEQ ID NO: 120         moltype = DNA  length = 18
FEATURE                Location/Qualifiers
source                 1..18
                       mol_type = other DNA
                       organism = synthetic construct
SEQUENCE: 120
aagggttcag cgtgggcg                                                18

SEQ ID NO: 121         moltype = DNA  length = 19
FEATURE                Location/Qualifiers
source                 1..19
                       mol_type = other DNA
                       organism = synthetic construct
SEQUENCE: 121
aagggttcag gcgtgggcg                                               19

SEQ ID NO: 122         moltype = DNA  length = 20
FEATURE                Location/Qualifiers
source                 1..20
                       mol_type = other DNA
                       organism = synthetic construct
SEQUENCE: 122
aagggttcag tgcgtgggcg                                              20

SEQ ID NO: 123         moltype = DNA  length = 26
FEATURE                Location/Qualifiers
source                 1..26
                       mol_type = other DNA
                       organism = synthetic construct
SEQUENCE: 123
gatccgccac aacatcgagg acggca                                       26
```

UNITED STATES PATENT AND TRADEMARK OFFICE
CERTIFICATE OF CORRECTION

| | | |
|---|---|---|
| PATENT NO. | : 12,404,525 B2 | Page 1 of 1 |
| APPLICATION NO. | : 18/351800 | |
| DATED | : September 2, 2025 | |
| INVENTOR(S) | : J. Keith Joung and Peter Cabeceiras | |

It is certified that error appears in the above-identified patent and that said Letters Patent is hereby corrected as shown below:

In the Claims

In Column 93, Line 5, Claim 12, delete "PDK1." and insert -- PDPK1. --

In Column 93, Line 19, Claim 16, delete "NO:" and insert -- NOs: --

In Column 93, Line 34, Claim 21, after "encoding" insert -- a --

In Column 94, Line 6, Claim 23, delete "claim 22," and insert -- claim 21, --

Signed and Sealed this
Twenty-third Day of December, 2025

John A. Squires
*Director of the United States Patent and Trademark Office*